US011466246B2

(12) United States Patent
Dyson et al.

(10) Patent No.: US 11,466,246 B2
(45) Date of Patent: *Oct. 11, 2022

(54) MICROBIAL CONVERSION OF CO₂ AND OTHER C1 SUBSTRATES TO VEGAN NUTRIENTS, FERTILIZERS, BIOSTIMULANTS, AND SYSTEMS FOR ACCELERATED SOIL CARBON SEQUESTRATION

(71) Applicant: Kiverdi, Inc., Hayward, CA (US)

(72) Inventors: Lisa Dyson, Hayward, CA (US); John Reed, Hayward, CA (US); Jil Geller, Hayward, CA (US); Sonali Hande, Hayward, CA (US)

(73) Assignee: Kiverdi, Inc., Pleasanton, CA (US)

( * ) Notice: Subject to any disclaimer, the term of this patent is extended or adjusted under 35 U.S.C. 154(b) by 183 days.

This patent is subject to a terminal disclaimer.

(21) Appl. No.: 16/481,458

(22) PCT Filed: Feb. 4, 2018

(86) PCT No.: PCT/US2018/016779
§ 371 (c)(1),
(2) Date: Jul. 29, 2019

(87) PCT Pub. No.: WO2018/144965
PCT Pub. Date: Aug. 9, 2018

(65) Prior Publication Data
US 2019/0390158 A1    Dec. 26, 2019

Related U.S. Application Data

(60) Provisional application No. 62/454,347, filed on Feb. 3, 2017.

(51) Int. Cl.
| | |
|---|---|
| *C12N 1/20* | (2006.01) |
| *C12P 1/04* | (2006.01) |
| *C12P 7/64* | (2022.01) |
| *C12P 13/04* | (2006.01) |
| *C12P 21/02* | (2006.01) |
| *A23J 3/20* | (2006.01) |
| *A23J 1/00* | (2006.01) |

(52) U.S. Cl.
CPC ............ *C12N 1/20* (2013.01); *A23J 1/008* (2013.01); *A23J 3/20* (2013.01); *C12P 1/04* (2013.01); *C12P 7/64* (2013.01); *C12P 13/04* (2013.01); *C12P 21/02* (2013.01)

(58) Field of Classification Search
CPC ... C12N 1/20; C12N 1/04; C12P 13/04; C12P 7/64; C12P 21/02; A23J 3/20
See application file for complete search history.

(56) References Cited

U.S. PATENT DOCUMENTS

| | | | |
|---|---|---|---|
| 3,420,739 A | 1/1969 | Bongers | |
| 3,442,620 A | 5/1969 | Huebler | |
| 3,852,492 A | 12/1974 | Brown | |
| 3,867,255 A * | 2/1975 | Newell | C12N 1/005 435/270 |
| 3,887,431 A | 6/1975 | Robbins | |
| 3,888,740 A | 6/1975 | Ishizaki | |
| 3,891,774 A | 6/1975 | Baker | |
| 4,007,088 A * | 2/1977 | Fencl | A23J 1/18 426/7 |
| 4,367,146 A | 1/1983 | Pollock | |
| 4,426,450 A | 1/1984 | Donofrio | |
| 4,607,011 A | 8/1986 | Kaplan | |
| 4,859,588 A | 8/1989 | Sublette | |
| 5,173,429 A | 12/1992 | Gaddy | |
| 5,186,731 A | 2/1993 | Parker | |
| 5,250,427 A | 10/1993 | Weaver | |
| 5,342,702 A | 8/1994 | MacGregor | |
| 5,593,886 A | 1/1997 | Gaddy | |
| 5,807,722 A | 9/1998 | Gaddy | |
| 5,821,111 A | 10/1998 | Grady | |
| 6,187,565 B1 | 2/2001 | Weaver | |
| 6,340,581 B1 | 1/2002 | Gaddy | |
| 7,285,402 B2 | 10/2007 | Gaddy | |
| 7,687,091 B2 | 3/2010 | Moen | |
| 7,776,124 B2 | 8/2010 | Binder | |
| 8,236,522 B2 | 8/2012 | Bauer | |
| 2002/0040871 A1 | 4/2002 | Garcia | |
| 2003/0003528 A1 | 1/2003 | Brzostowicz | |
| 2003/0022364 A1 | 1/2003 | Parent | |
| 2003/0087234 A1 | 5/2003 | Heumann | |
| 2003/0134822 A1 | 7/2003 | Maekawa | |
| 2004/0078846 A1 | 4/2004 | Desouza | |
| 2004/0203134 A1 | 10/2004 | Pyntikov | |

(Continued)

FOREIGN PATENT DOCUMENTS

| | | |
|---|---|---|
| CA | 02255212 A1 | 12/1998 |
| DE | 2160478 A | 12/1971 |
| EP | 131220 A2 | 7/1985 |
| EP | 1264895 A1 | 12/2002 |
| EP | 2135939 A1 | 12/2009 |
| JP | 54119091 A | 9/1979 |
| JP | 06169783 A | 6/1994 |
| JP | 7163363 A | 6/1995 |
| JP | 2516154 B2 | 7/1996 |
| JP | 2912684 B2 | 6/1999 |
| JP | 2004051920 A | 2/2004 |

(Continued)

OTHER PUBLICATIONS

Andréia Anschau, Nutrient Delivery: Nanotechnology in the Agri-Food Industry, 2017, Chapter 20, pp. 749-794 (Year: 2017).*

(Continued)

*Primary Examiner* — Thane Underdahl
(74) *Attorney, Agent, or Firm* — FisherBroyles, LLP; Jill A. Jacobson

(57) ABSTRACT

Microorganisms and bioprocesses are provided that convert gaseous substrates, such as renewable H₂ and waste CO₂ producer gas, or syngas into high-protein biomass that may be used directly for human nutrition, or as a nutrient for plants, fungi, or other microorganisms, or as a source of soil carbon, nitrogen, and other mineral nutrients. Renewable H₂ used in the processes described herein may be generated by electrolysis using solar or wind power. Producer gas used in the processes described herein may be derived from sources that include gasification of waste feedstock and/or biomass residue, waste gas from industrial processes, or natural gas, biogas, or landfill gas.

16 Claims, 16 Drawing Sheets

(56) References Cited

U.S. PATENT DOCUMENTS

| | | |
|---|---|---|
| 2006/0286205 A1 | 12/2006 | Fichtali |
| 2008/0022593 A1 | 1/2008 | Gur |
| 2008/0193987 A1 | 8/2008 | Mantelatto |
| 2009/0117194 A1 | 5/2009 | Burja |
| 2009/0130706 A1 | 5/2009 | Berzin |
| 2009/0142322 A1 | 6/2009 | Ye |
| 2009/0191593 A1 | 7/2009 | Burk |
| 2010/0093860 A1 | 4/2010 | Boon |
| 2010/0235934 A1 | 9/2010 | Friedman |
| 2011/0020884 A1 | 1/2011 | Latouf |
| 2012/0015413 A1 | 1/2012 | Sichwart |
| 2012/0084886 A1 | 5/2012 | Lopez-Cervantes |
| 2013/0089899 A1 | 4/2013 | Kurek |
| 2013/0149755 A1 | 6/2013 | Reed |
| 2015/0044327 A1 | 2/2015 | Feinberg |
| 2016/0073671 A1 | 3/2016 | Geistlinger |
| 2019/0000124 A1 | 1/2019 | Sefton |

FOREIGN PATENT DOCUMENTS

| | | | |
|---|---|---|---|
| KR | 2003020766 A | 3/2003 | |
| WO | 98/00558 A1 | 7/1996 | |
| WO | 02/08438 A2 | 1/2002 | |
| WO | 2005/001981 A2 | 1/2005 | |
| WO | WO-2007024255 A1 * | 3/2007 | ............... C12P 7/62 |
| WO | 2009/009388 A2 | 1/2009 | |
| WO | 2009/058028 A1 | 5/2009 | |
| WO | 2009/113853 A2 | 9/2009 | |
| WO | 2011/014953 A1 | 2/2011 | |
| WO | 2011/056183 A1 | 5/2011 | |
| WO | WO2011/112695 A1 | 9/2011 | |
| WO | 2011/139804 A2 | 11/2011 | |
| WO | 2013/090769 A2 | 6/2013 | |
| WO | 2013/148348 A1 | 10/2013 | |
| WO | 2014/145194 A2 | 9/2014 | |
| WO | 2015/027209 A2 | 2/2015 | |
| WO | 2015/177800 A2 | 11/2015 | |
| WO | 2016/044423 A1 | 3/2016 | |
| WO | 2017/015321 A1 | 1/2017 | |
| WO | 2017/165244 A1 | 9/2017 | |
| WO | 2018/144965 A1 | 8/2018 | |

OTHER PUBLICATIONS

Homan "Biogas from Manure" Penn State Extension 18 pgs Mar. 5, 2012 (Year: 2012).*
Valeriy Grytsay "Self-Organization and Fractality in a Metabolic Process of the Krebs Cycle" Ukrainskii Biokhimicheskii Zhurnal Oct. 2013, 11 pages (Year: 2013).*
Alvarez, H., et al., Formation of intracytoplasmic inclusions by Rhodococcus opacus strain PD630, Arch Microbiol 165:377-386, 1996.
Anderson, A.J., et al., Occurrence, Metabolism, Metabolic Role, and Industrial Uses of Bacterial Polyhydroxyalkanoates, Microbiological Reviews 54(4):450-472, 1990.
Barbir, F., PEM electrolysis for production of hydrogen from renewable energy sources, Solar Energy 78:661-669, 2005.
Barton, L.L., The Cell Wall Matrix, Structural and Functional Relationships in Prokaryotes, pp. 136-189, Springer, 2005.
Bligh, E.G., et al., A Rapid Method of Total Lipid Extraction and Purification, Canadian Journal of Biochemistry and Physiology 37(8):911-917, 1959.
Bogdahn, I., Agriculture-independent, sustainable, fail-safe and efficient food production by autotrophic single-cell protein, PeerJ PrePrints, https://dx.doi.org/10/7287/peerj.preprints. 1279v3, Sep. 17, 2015.
Bongers, L., Energy Generation and Utilization in Hydrogen Bacteria, Journal of Bacteriology 104(1):145-151, 1979.
Calloway, D.H., et al., Protein Quality of the Bacterium Hydrogenomonas eutropha, Applied Microbiology 17(1):176-178, 1969.
Calloway, D.H., et al., Investagation of the Nutritional Properties of Hydrogenomonas eutropha, Final Report to the National Aeronautics and Space Administration NGR 05-003-089, 1968.
Campbell, B.J., et al., Hydrogen isotopic fractionation in lipid biosynthesis by H2-consuming Desulfobacterium autotrophicum, Geochiica et Cosmochimica Acta 73:2744-2757, 2009.
Chang, C.C., et al., Hydrogenotrophic denitrification with immobilized Alcaligenes eutrophus for drinking water treatment, Bioresource Technology 69:53-58, 1999.
Chee, J.Y., et al., The Potential Applicataion of Cupriavidus necator as Polyhydroxy-alkanoates Producer and Single Cell Protein: A Review on Scientific, Cultural and Religious Perspectives, Applied Food Biotechnology 6(1):19-34, 2019.
Chung, S.Y., et al., Purification of form L2 RubisCO from a marine obligately autotrophic hydrogen-oxidizing bacterium, Hydrogenovibrio marinus strain MH-110, FEMS Microbiology Letters 109, 49-54, 1993.
Decicco, B.T., Removal of Eutrophic Nutrients from Wastewater and their Bioconversion to Bacterial Single Cell Protein for Animal Feed Supplements Phase I, Water Resources Research Center, Nov. 1977.
Decicco, B.T., Removal of Eutrophic Nutrients from Wastewater and their Bioconversion to Bacterial Single Cell Protein for Animal Feed Supplements Phase I, Water Resources Research Center, Apr. 1979.
Decicco, B.T., Removal of Eutrophic Nutrients from Wastewater and their Bioconversion to Bacterial Single Cell Protein for Animal Feed Supplements Phase III, Water Resources Research Center, Apr. 1980.
Farrell, A., et al., Ethanol Can Contribute to Energy and Environmental Goals, Science 311:506-508, Jan. 27, 2006.
Feisthauer, S., et al., Differences of heterotrophic 13CO2 assimilation by Pseudomonas knackmussii strain B13 and Rhodococcus opacus 1CP and potential impact on biomarker stable isotope probing, Environmental Microbiology 10(6):1641-1651, 2008.
Ghose, T.K., et al., Advances in Biochemical Engineering, Chapter 6, Novel Energy and Carbon Sources, Springer-Verlag Berlin—Heidelberg, 1971.
Greife, et al., Nitrogen Metabolism in Broiler Chickens Consuming the Bacterial Strain Alcaligenes eutrophus, Anima Feed Science and Technology 5:241-253, 1980.
Henstra, A.M., et al., Microbiology of synthesis gas fermentation for biofuel production, Current Opinions in Biotechnology 18:200-206, 2007.
Hugler, M., et al., Evidence for Autotrophic CO2 Fixation via the Reductive Tricarboxylic Acid Cycle by Members of the epsilon Subdivision of Proteobacteria, Journal of Bacteriology 187(9):3020-3027, 2005.
Huijgen, W., et al., Carbon dioxide sequestration by mineral carbonation, Preprints of Papers: American Chemical Society, Division Fuel Chemistry, 41:1403-1406, 1996.
Ishizaki, A., et al., Batch culture of Alcaligenes eutrophus ATCC 176971 using recycled gas closed circuit culture system. Journal of Fermentation and Bioengineering 69(3):170-174, 1990.
Jannasch, H.W., et al., Geomicrobiology of Deep-Sea Hydrothermal Vents, Science 229:717-725, Aug. 23, 1985.
Jones, J., The Cativa Process for the Manufacture of Acetic Acid, Platinum Metals Rev 44(3):94-105, 2000.
Kasparkova, K., et al., Characterization of Low-Molecular Weight Collagen Hydrolysates Prepared by Combination of Enzymatic and Acid Hydrolysis, Journal of American Leather Chemists Association 104(2):46-51, 2009.
King, G., Molecular and Culture-Based Analyses of Aerobic Carbon Monoxide Oxidizer Diversity, Applied and Environmental Microbiology 69(12):7257-7265, 2003.
Klatte, S., et al., *Rhodococcus opacus* sp. novl., An Unusual Nutritionally Versatile *Rhodococcus*-species, System Appl Microbiol 17:355-360, 1994.
Kunasundari, B., et al., Revisiting the Single Cell Protein Application of Cupriavidus necator H16 and Recovering Bioplastic Granules Simultaneously, PLOS One 8(10:e78528, Oct. 2013.

(56) References Cited

OTHER PUBLICATIONS

Lehmicke, L., et al., Organiztion of Genes Necessary fro Growth of the Hydrogen-Methanol Autotroph *Xanthobacter* sp. Strai H4-14 on Hydrogen and Carbon Dioxide, J Bacteriol 162(3):1244-1249, 1985.
Macler, B.A., et al., Hydrogen Formation in Nearly Stoichiometric Amounts from Glucose by a Rhodpseudomonas sphaeroides Mutant, Bacteriology 138(2):446-452, 1979.
Madigan, M., et al., Growth of the Photosynthetic Bacterium Rhodopsuedomonas capsulata Chemoautotrophically in Darkness with H2 as the Energy Source, Journal of Bacteriology 137(1):524-530, Jan. 1979.
Madigan, M., et al., Physiology of Dark Fermentative Growth of Rhodopseudomonas capsulata, Journal of Bacteriology 142(3):908-915, Jun. 1980.
Manninen, A.H., Protein Hydrolysates in Sports and Exercise: A Brief Review, Journal of Sports Science and Medicine, 3:60-63, 2004.
Matassa, S., et al., Resource recovery from used water: The manufacturing abilities of hydrogen-oxidizing bacteria, Water Research 68:467-478, 2015.
Mersmann, A., et al., Packungskolnnen, Chem.-Ing.-Tech. 58(1):19-31, 1986.
Miltner, A., et al., Non-phototrophic CO2 fixation by soil microorganisms, Plant and Soil 269:193-203, 2005.
Miura, A., et al., A Soluble NADH-Dependent Fumarate Reductase in the Reductive Tricarboxylic Acid Cycle of Hydrogenobacter thermophilus TK-6, Journal of Bacteriology 190(21)7170-7177, 2008.
Munoz, et al., Algal-bacterial processes for the treatment of hazardous contaminants: a review, Water Research 40(15):2799-1815, 2006.
Murugan, P., et al., A new biological recovery approach for PHA using mealwork, Tenebrio molitor, Journal of Biotechnology 239:98-105, 2016.
Nippon Nogeikagaku Kaishi 61(10):1322-1325, 1987.
Ong, S. Y., et al., An integrative study on biologically recovered polyhydroxyalkanaoates (PHAs) and simultaneous assessment of gut microbiome in yellow mealworm, Journal of Biotechnology 265:31-39, 2018.
Oren, A., Chemolithotrophy, Encylopedia of Life Sciences, John Wiley & Sons, Ltd., 2009.
Paoli, G.C., et al., Aerobic chemolithoautotrophic growth and RubisCO function in Rhodobacater capsulatus and a spontaneous gain of function mutant of Rhodobacter sphaeroides, Arch Microbiol 170:8-17, 1998.
Rapp, P., et al., Formation, Isolation and Characaterization of Trehalose Dimycolates from Rhodococcus erythropilis Grown in n-Alkanes, Journal of General Microbiology 115:491-503, 1979.
Repaske, R., et al., Dense Autotrphic Culutures of Alcaligenes eutrophus, Applied and Environmental Microbiology 32(4):592-597, 1976.
Roth, M.S., The engine of the reef: photobiology of coral-algal synbiosis, Frontiers in Microbiology 5: Article 422, Aug. 22, 2014.
Schlegel, H.G., et al., The Production of Biomass from Hydrogen and Carbon Dioxide, Advances in Biochemical Engineering, 1:143-168, 1971.
Searchinger, T., et al., The great balancing act, World Resources Institute Working Paper, Washington, DC, 2013.
Shively, J., et al., Something from Almost Nothing: Carbon Dioxide Fixation in Chemoautotrophs, Annu. Rev. Microbiol. 52:19-230, 1998.
Storebakken, et al., Bacterial protein grown on natural gas in diets for Atlantic salmon, *Salmo salar*, in freshwater, Aquaculture 241(1-4):413-425, 2004.
Takeshita, T., et al., Studies on Dissolved Hydrogen Behavior in Autotrophic Culture of Alcaligenes eutrophus ATCC 17697, J. Fac. Kyushu Univ. 38(1-2):55-64, 1993.
Tanaka, K., et al., Production of Poly(D-3-Hydroxybutyrate) from CO2 H2, and O2 by High Cell Denisty Autotrophic Cultivation of Alcaligenes eutrophus, Biotechnology and Bioengineering 45:268-275, 1995.
Taub, F.B., Closed Ecological Systems, Annu. Rev. Ecol. Syst. 5:139-160, 1974.
The Closed Life-Support System, NASA Ames Research Center, 1966.
Tokuda, H., et al., Effects of electrical pre-treatment on the hydrolysis of agricultural wastes, J. Brew. Soc . . . Japan 101(10):769-775, 2006.
Toyoda, K., et al., The role of two CbbRs in the transcriptional regulation of three ribulose-1,5-biphosphate carboxylase/oxygenase genes in Hydrogenovibrio marinus strain MH-110, Microbiology 151:3615-3625, 2005.
Turner, J., et al., Renewable hydrogen production, Int J Energy Res DOI:10.1002/er.1372, 2007.
Volova, T.G., et al., Autotrophic synthesis of polyhydroxyalkanoates by the bacteria Ralstonia eutropha in the presence of carbon monoxide, Appl Microbiol Biotechnol 58:675-678, 2002.
Voss, I., et al., High cell density cultivation of Rhodococcus opacus for lipid production at a pilot-plant scale, Appl Microbiol Biotechnol 55:547-555, 2001.
Wahlund, T.M., et al., Bioconversion of CO2 to Ethanol and Other Compounds, Preprints of Papers—American Chemical Society Division Fuel Chemistry 41:1408-1406, 1996.
Walterman, M., et al., Rhodococcus opacus strain PD630 as a new source of high-value single-cell oil? Isolation and characterization of triacylglycerols and other storage lipids, Microbiology 146:1143-1149, 2000.
Watanabe, Y., et al., Microbial CO2 Fixation, Journal of the Agricultural Chemical Society of Japan, 61(10):1322-1325, 1987.
Yamamoto, M., et al., Role of two 2-oxoglutarate:ferredoxin oxidoreuctases in Hydrogenobacter thermophilus under aerobic and anaerobic conditions, FEMS Microbiol Lett 263:189-193, 2006.
U.S. Appl. No. 16/716,398 Office Action, dated Oct. 14, 2020.
U.S. Appl. No. 16/716,398 Office Action, dated Jan. 29, 2021.

* cited by examiner

| ORGANISM | HETEROTROPHIC | GROWTH CONDITIONS<br>CHEMOAUTOTROPHIC |
|---|---|---|
| R. OPACUS<br>(DSM 44193) | 9.00 (6d) | 0.00 |
| R. OPACUS<br>(DSM 43205) | 9.00 (6d) | 1.00 (5d) |
| RHODOCOCCUS SP.<br>(DSM 3346) | 2.40 (3d) | 0.51 (5d) |
| CUPRIAVIDUS<br>NECATOR (DSM 531) | 2.20 (3d) | 0.23 (3d) |

FIG. 6

2 L REACTOR CONFIGURATION, GAS LINES

MICROBIAL CONVERSION OF CO₂ AND OTHER C1 SUBSTRATES TO VEGAN NUTRIENTS, FERTILIZERS, BIOSTIMULANTS, AND SYSTEMS FOR ACCELERATED SOIL CARBON SEQUESTRATION

CROSS-REFERENCE TO RELATED APPLICATIONS

This application is a U.S. national stage application under 35 U.S.C. § 371 of PCT/US2018/016779, filed on Feb. 4, 2018, which claims the benefit of U.S. Provisional Application No. 62/454,347, filed on Feb. 3, 2017, which is incorporated by reference herein in its entirety.

FIELD OF THE INVENTION

The invention relates to the field of chemistry applied to agriculture, specifically to organic plant and fungal nutrition, animal feeding, and human nutrition. In particular, the invention relates to a method for obtaining nutrients, and extracts from organic material produced out of C1 substrates and other inorganic inputs, which can be used as biostimulants and/or bio-fertilizers in agriculture, particularly organic farming, and/or as protein and nutritional supplements in animal feed, and/or as ingredients in human nutrition.

BACKGROUND

Sustainable and renewable sources of amino acids, proteins, vitamins, and other nutrients are needed to help meet growing food needs. There is also a need to reduce the amount of carbon dioxide and other greenhouse gas (GHG) emissions to the atmosphere, as well as to reduce water consumption and global energy consumption based upon the utilization of coal, oil, and natural gas in food production systems. Increased demand in the global economy has placed increasing pressure on land and water resources. Increased pressure has also been placed on traditional fossil hydrocarbon inputs for the production of food and other agriculturally derived products. Many industries, including modern agriculture, rely heavily on the availability of fossil hydrocarbon sources as an input for the production and processing of crops. Cost-effective alternatives to current incumbent practices could help mitigate the upward pressure on land use, natural habitats, water, fossil resource demand, raw material costs, and greenhouse gas emissions.

Biologic systems that fix gaseous carbon through natural biochemical metabolic processes are known. The current agricultural system, which is based on photosynthesis in higher plant crops, is one obvious example. Algal systems have also been developed to create food and other agriculturally derived products from $CO_2$ through photosynthetic reactions. There are also heterotrophic reactions and productions utilizing fixed carbon feedstocks, such as sugar, which in turn are produced from $CO_2$ via photosynthesis. And thus, these heterotrophic reactions and production indirectly depend upon photosynthesis. However, a number of problems and limitations are confronting current agricultural, animal husbandry, and aquaculture practices, and the photosynthetically derived nutrients and feeds which are currently utilized.

The world's agricultural systems confront challenges of meeting two contradictory needs: (A) increase the production of food to meet the demand created as the global population rises to over a projected 9.3 billion by 2050, and (B) reduce the deleterious impacts of agriculture upon human health and the environment [T. Searchinger, C. Hanson, J. Ranganathan, B. Lipinski, R. Waite, R. Winterbottom, A. Dinshaw, and R. Heimlich, "The great balancing act," World Resources Institute Working Paper, Washington, D.C., 2013.]. The emerging global middle class over the past half century has been fueling rising demand for higher protein diets. There are worries about increasing scarcity of food proteins, as well as environmental problems that impact or result from food production such as land use limitations, water scarcity, climate change and the long-term inflation of feed and food prices on the world market [S. Matassa, N. Boon, and W. Verstraete (2015) "Resource recovery from used water: the manufacturing abilities of hydrogen-oxidizing bacteria" Water Research 68:467-478 (http://view.ncbi.nlm.nih.gov/pubmed/25462753)].

Fertilizers in current use primarily are composed of inorganic and/or synthetic compounds. However, there is a growing interest in the use of organic fertilizers and conditioners. Such organic materials can be added to soils, with plant nutrients such as ammonium, nitrate and sulfate ions being released by the action of soil microflora [Wainwright, M., W. Nevell, and U. Skiba (1985) "Fertilizer potential of some commercially available forms of keratin microbial biomass" Enzyme Microb. Technol. 7:108-110].

In addition to providing a comprehensive source of plant and fungal nutrients, organic fertilizers contribute organic matter to the soil, which, for sandy soils or low-activity clay soils, for example, represents an improvement in the physical, chemical and biological properties due to a conditioner effect. Fertilizers useful for soil conditioning may contain micronutrients and beneficial microorganisms such as yeasts, bacteria or fungi. Chinese Patent CN1911870 describes a plant nutrient which enhances soil microorganisms, promotes plant growth, increases the rate of utilization of fertilizers and increases plant resistance to disease and stress. This nutrient comprises *Saccharomyces cerevisiae* yeast, *Lactobacillus plantarum* and *Lactobacillus acidophilus* bacteria, and other components such as potato or coffee derivatives, glucose, peptone, magnesium and manganese sulfate, dipotassium hydrogen phosphate and sodium chloride.

There are abundant microorganisms thriving in soil, especially in the rhizosphere of plants. It is well known that a considerable number of bacterial and fungal species possess a functional relationship and constitute a holistic system with plants. They are able to exert beneficial effects on plant growth. It has been revealed that the effect of nitrogen fixation induced by nitrogen fixers is not only significant for legumes, but also non-legumes. Moreover, some strains have multiple functions for plant growth. The beneficial effect of *Azospirillum* may derive both from its nitrogen fixation and stimulating effect on root development. Similarly, it has been reported that *Azotobacter* not only provides nitrogen, but also produces a variety of growth-promoting substances, among them indole acetic acid, gibberellins and B vitamins. These substances stimulate, at least to some degree, the production of root exudates. Root exudates in turn are reported to stimulate the excretion of ammonia into the rhizosphere by *Azotobacter*, thus increasing soil Nitrogen content. A similar effect to those imparted by plant exudates has been attributed to organic Carbon contained in organic fertilizer. It has been reported that the use of suitable farmyard manures, green manures and other organic manures and fertilizers may enhance the $N_2$-fixation by *Azotobacter*. This could be due to the fact that the Nitrogen-fixation reaction requires a good deal of energy from available organic Carbon in order to break the bonds between nitrogen atoms.

Phosphate (P) and potassium (K)-solubilizing bacteria may enhance mineral uptake by plants by solubilizing insoluble P and releasing K from silicate in soil.

In summary, soil microorganisms are important components in the natural soil subecosystem because not only can they contribute to nutrient availability in the soil, but they also help bind soil particles into stable aggregates, which improve soil structure and reduce erosion potential.

The majority of plants growing under natural conditions are associated with fungal mycorrhizae. The mycorrhizal symbiosis, by linking the biotic and geochemical portions of the ecosystem, can also be regarded as a bridge connecting the root with the surrounding soil microhabitats. Rhizobacteria can act as "mycorrhization helper bacteria," which improve the ability of mycorrhizal fungi to colonize plant roots.

Recently, new strategies have been proposed with the aim of improving the sustainability of agricultural crop production while also increasing productivity. One promising approach is the application of substances and/or microorganisms defined also as "biostimulants" and/or "biofertilizers" [P. Calvo, L. Nelson, and J. Kloepper (2014) "Agricultural uses of plant biostimulants," *Plant and Soil* 383(1-): 3-41, 2014. (http://dx.doi.org/10.1007/s11104-014-2131-8)].

The application of microbial products to plants has several advantages over conventional chemicals for agricultural purposes, including: (i) microbial products are considered safer than many of the chemicals now in use; (ii) neither toxic substances nor the microbes themselves are accumulated in the food chain.

Recently, in addition to application of fertilizers to the soil, a growing interest has focused on foliar plant fertilizers. Foliar feeding is a technique of feeding plants by applying liquid fertilizer directly to their leaves. In the application of foliar fertilizers, it is recognized that not only basic chemical elements such as nitrogen, potassium, phosphorus, calcium, and magnesium are required by plants. It is also recognized that accompanying compounds, which can enhance efficiency and acceptability of various elements, are of great importance as well. Such enhancing compounds include amino acids, adhesives, and surfactants, many of which are included in modern foliar fertilizer ["Amino acid and soluble protein cocktail from waste keratin hydrolysed by a fungal keratinase of *Paecilomyces marquandii*"; Veselá, M., and Friedrich (2009) *J., Biotechnology and Bioprocess Engineering* 14:84-90].

Plant "biostimulants" sometimes refers to components other than fertilizers that affect plant growth and/or metabolism upon foliar application or when added to soil. Some plant biostimulants operate by up-regulating or down-regulating plant hormones. Plant biostimulants generally fall within one of three categories: amino acids, peptide, and protein mixtures; hormones; and humic substances.

Biostimulants have been reported to enhance crop quality parameters and nutrient efficiency, increase growth rates, photosynthetic rate, crop yield, growth of plant roots and leaves, abiotic stress tolerance, and disease tolerance, improve cultivated soils, and counter weed growth. Exemplary plant biostimulants include compositions based on seaweed extract, yeast extract, humic acids, amino acids, salicylic acid, biosolids, hydrolyzed proteins, silicate, and/or synthetic compounds. Exemplary stressors include heat, cold, drought, wear, excess moisture, salinity, alkalinity or other adverse soil pH, nutrient deficiency, oxidative, heavy metal toxicity, disease, and others.

There is increased interest in microbially derived biostimulants and biofertilizers. For example, Kobayashi, et al. studied the effect of a *Saccharomyces cerevisiae* yeast extract combined with an inorganic fertilizer on the growth of pea plants ["Effect of yeast extracts on higher plants", Kobayashi et al, *Plant and Soil* (1980), 57 (1)4:1-7;]. Hungarian Patent HU9902060 describes an aqueous fertilizer composition for the leaves and roots of plants containing the yeast *Saccharomyces*, plus trace elements, complexing agents, buffering agents and a number of other nutrients such as amino acids, humic acids, enzymes, sugars, etc.

Protein hydrolysates (PHs) are an important category of plant biostimulants comprising a mixture of polypeptides, oligopeptides and amino acids, which are manufactured from proteinaceous feedstocks using partial hydrolysis [G. Schaafsma (2009) "Safety of protein hydrolysates, fractions thereof and bioactive peptides in human nutrition" *European journal of clinical nutrition* 63 (10):1161-1168 (http://view.ncbi.nlm.nih.gov/pubmed/19623200)]. PHs have been the subject of rising interest due to their beneficial impacts on horticultural crop productivity and quality, including for fruit trees, vegetables, flower crops and ornamentals, especially under environmental stress conditions. They have been found to increase shoot and root biomass and productivity [K. Edward, G. Aneta, S. Agnieszka, and W. Renata, "The effect of cultivar type, time of cultivation, and biostimulant treatment on the yield of spinach (*Spinacia oleracea* l.)," pp. 9+, 2013. [Online]. Available: http://dx.doi.org/10.2478/fhort-2013-0153; Lisiecka et al., 2011; N. Paradiković, T. Vinković, I. Vinković Vrček, I. untar, M. Bojić, and Medić-Šarić, "Effect of natural biostimulants on yield and nutritional quality: an example of sweet yellow pepper (*Capsicum annuum* l.) plants," J. Sci. Food Agric., vol. 91, no. 12, pp. 2146-2152, September 2011. [Online]. Available: http://dx.doi.org/10.1002/jsfa.4431; G. Colla, Y. Rouphael, R. Canaguier, E. Svecova, and M. Cardarelli, "Biostimulant action of a plant-derived protein hydrolysate produced through enzymatic hydrolysis," Frontiers in Plant Science, vol. 5, p. 448, 2014. [Online]. Available: http://journal.frontiersin.org/article/10.3389/fpls.2014.00448; A. Ertani, D. Pizzeghello, O. Francioso, P. Sambo, S. Sanchez-Cortes, and S. Nardi, "*Capsicum chinensis* l. growth and nutraceutical properties are enhanced by biostimulants in a long-term period: chemical and metabolomic approaches." Frontiers in plant science, vol. 5, 2014. [Online]. Available: http://view.ncbi.nlm.nih.gov/pubmed/25136346). They are effective tools for making horticulture more sustainable and many research studies have documented the benefits of PH applications on growth, yield, product quality, resource use efficiency and tolerance to environmental and chemical soil stresses of several horticultural crops.

Applications of PHs have been shown to promote the vegetative growth and macro- and micronutrient uptake in several horticultural crops, resulting in increased crop productivity. Seed coating with PHs to enhance germination and early growth of vegetable and flower crops, foliage plants, and turf grasses are also a promising application.

Amino acids and small peptides are absorbed by both roots and leaves and then translocated into the plant. Plants absorb amino acids through stomata. For certain plants, amino acids are the principal source of nitrogen [Chapin, F. S., L. Moilanen, and K. Kielland (1993) "Preferential use of organic nitrogen for growth by a non-mycorrhizal arctic sedge" *Nature* 361:150-153]. In nature, foliar nutrition is a very important mechanism of nitrogen uptake in bromeliads, especially for the epiphytic ones [Endres, L. and H. Mercier (2003) "Amino acid uptake and profile in bromeliads with different habits cultivated in vitro" *Plant Physiol. Biochem.* 41:181-187]. Foliar nutrition in the form of protein hydrolysate and foliar spray provides ready-made building blocks for protein synthesis.

Following root/foliar uptake, amino acids and peptides are transported from cell to cell and over long distances through the plant vascular system (xylem and phloem) in support of plant metabolism and development. Several classes of integral membrane proteins are involved in amino acid and peptide transport through cell membranes in plants. For instance, members of the lysine-histidine-like transporter family, amino acid permease family and proline transporter family play a direct role in amino acid uptake through the roots. Amino acids and amides represent in most plants the principal transport form for organic Nitrogen, and they can be used directly for protein synthesis and other essential Nitrogen compounds or metabolized.

Microorganisms living in the phyllosphere and rhizosphere can also affect crop response to PH application not only because they are competing with plants for amino acids and peptides but also because they secret enzymes that can hydrolyze peptides into small fragments that may act as signaling compounds, modulating crop response. Moreover, recent studies have showed that application of a plant-derived PH on lettuce stimulated desirable, naturally occurring microorganisms, such as $N_2$-fixing, P-solubilizing and indoleacetic acid-producing bacteria. The above findings suggest that PHs may also act as plant biostimulants through a microorganism-mediated enhancement of plant growth. Application of PHs to plant leaves and roots have been observed to improve Fe and N metabolism and nutrient uptake, reduce the concentration of undesirable compounds, such as nitrates, and improve the efficiency of macro- and microelement and water utilization [M. Cerdán, A. Sánchez-Sánchez, J. D. Jordá, M. Juárez, and J. Sánchez-Andreu (2013) "Effect of commercial amino acids on iron nutrition of tomato plants grown under lime-induced iron deficiency," *Z. Pflanzenernähr. Bodenk.* 176(6):859-866 (http://dx.doi.org/10.1002/jpln.201200525); A. Ertani, L. Cavani, D. Pizzeghello, E. Brandellero, A. Altissimo, C. Ciavatta, and S. Nardi (2009) "Biostimulant activity of two protein hydrolyzates in the growth and nitrogen metabolism of maize seedlings" *Z. Pflanzenernähr. Bodenk* 172(2):237-244 (http://dx.doi.org/10.1002/jpln.200800174); M. Halpern, A. Bar-Tal, M. Ofek, D. Minz, T. Muller, and U. Yermiyahu (2015), The Use of Biostimulants for Enhancing Nutrient Uptake. Elsevier, vol. 130, pp. 141-174 (http://dx.doi.org/10.1016/bs.agron.2014.10.001)]. The causes attributed to the elevated nutrient uptake in plants supplemented with PH include (A) an increase in soil enzymatic and microbial activities, (B) improved of micronutrient mobility and solubility, particularly for Cu, Fe, Mn, and Zn, (C) changes in the root architecture of plants such as in root density, lengths, and number of lateral roots and, (D) increased activities of Fe(III)-chelate reductase, nitrate reductase, and glutamine synthetase [M. Cerdán, et al. (2013) supra; A. Ertani, et al. (2009) supra; A. M. Garcia-Martinez, A. Diaz, M. Tejada, J. Bautista, B. Rodriguez, C. Santa Maria, E. Revilla, and J. Parrado (2010) "Enzymatic production of an organic soil biostimulant from wheat-condensed distiller solubles: Effects on soil biochemistry and biodiversity" *Process Biochemistry* 45(7):1127-1133 (http://dx.doi.org/10.1016/j.procbio.2010.04.005); G. Colla, Y. Rouphael, R. Canaguier, E. Svecova, and M. Cardarelli (2014) "Biostimulant action of a plant-derived protein hydrolysate produced through enzymatic hydrolysis" *Frontiers in Plant Science* 5:448 (http://journal.frontiersin.org/article/10.3389/fpls.2014.00448); L. Lucini, Y. Rouphael, M. Cardarelli, R. Canaguier, P. Kumar, and G. Colla (2015) "The effect of a plant-derived biostimulant on metabolic profiling and crop performance of lettuce grown under saline conditions" *Scientia Horticulturae* 182:124-133, January 2015 (http://dx.doi.org/10.1016/j.scienta.2014.11.022)]. When amino acids are applied together with micronutrients, the absorption and transportation of micronutrients inside the plant may be facilitated.

Protein hydrolysates have been shown to stimulate Nitrogen metabolism and assimilation. A possible explanation for the increased Nitrogen assimilation in plants may be the positive effects of PHs on production of Carbon skeletons and energy supply needed for amino acid biosynthesis.

Amino acids and peptides can play an important role as signaling compounds. Specific receptors on cell membranes interact with peptides (elicitors) for signal transduction, leading to morpho-physiological and biochemical changes in plants. PHs may influence the phytohormone balance of the plant, and impact development of the plant through the action of specific peptides and phytohormone biosynthesis precursors, such as tryptophan [G. Colla, et al. (2014) supra]. Bioactive peptides produced in a number of different plants have been found to have hormone-like activities [Y. Ito, I. Nakanomyo, H. Motose, K. Iwamoto, S. Sawa, N. Dohmae, and H. Fukuda (2006) "Dodeca-CLE peptides as suppressors of plant stem cell differentiation" *Science* 313 (5788):842-845, (http://dx.doi.org/10.1126/science.1128436); T. Kondo, S. Sawa, A. Kinoshita, S. Mizuno, T. Kakimoto, H. Fukuda, and Y. Sakagami (2006) "A plant peptide encoded by CLV3 identified by in situ MALDI-TOF MS analysis" *Science* 313(5788):845-848, August 2006 (http://dx.doi.org/10.1126/science.1128439)]. Plant-derived PHs have been reported to elicit auxin- and gibberellin-like activities that improved crop performance [M. Schiavon, A. Ertani, and S. Nardi (2008) "Effects of an alfalfa protein hydrolysate on the gene expression and activity of enzymes of the tricarboxylic acid (TCA) cycle and nitrogen metabolism in *Zea mays* 1" *Journal of agricultural and food chemistry* 56(24):11 800-11 808 (http://view.ncbi.nlm.nih.gov/pubmed/19053364); A. Ertani, et al. (2009) supra; G. Colla, et al. (2014) supra].

In grapevine, it has been reported that foliar application of PHs from casein and soybean up-regulated genes encoding the stilbene synthase enzyme responsible for the biosynthesis of resveratrol in leaves (i.e., resveratrol synthase). Both hydrolysates proved to act as elicitors to enhance grapevine immunity against *Plasmopara viticola*, the causal agent of grapevine downy mildew. Chinese Patent CN1966663 ("Composite Microorganism Foliage Fertilizer Bacteria Agent And Its Producing Method And Use") describes an antimicrobial agent consisting of *Saccharomyces cerevisiae, Lactobacillus plantarum, Mucor racemosus*, and *Aspergillus oryzae*.

The activation of secondary metabolism by plant derived PHs, such as increased gene expression of the phenylalanine (tyrosine) ammonia-lyase enzyme involved in the phenylpropanoid pathway can result in beneficial nutraceutical properties. Phytochemical compounds found in fruits and vegetables have generated significant interest among scientists, food nutritionists and producers due to their health-benefiting properties. Phytochemicals are natural antioxidant compounds able to reduce or prevent chronic diseases, such as cardiovascular problems, ischemic stroke, arthritis and inflammatory bowel, as well as some cancers. Several studies have found that application of PHs are able to modify the primary and secondary metabolism, stimulating the production and accumulation of antioxidant compounds (carotenoids, polyphenols, flavonoids, etc.).

PHs can be classified on the basis of protein source, and method of protein hydrolysis. PHs are mainly sourced at present from animal- or plant-derived raw materials, and are generally produced through chemical and/or enzymatic hydrolysis. [P. Maini (2006) "The experience of the first biostimulant, based on amino acids and peptides: a short retrospective review on the laboratory researches and the practical results" *Fertilitas Agrorum* 1(1):29-43, 2006; M. Schiavon, et al. (2008) supra; M. Halpern, A. Bar-Tal, M. Ofek, D. Minz, T. Muller, and U. Yermiyahu (2015) "The Use of Biostimulants for Enhancing Nutrient Uptake" Elsevier vol. 130, pp. 141-174 (http://dx.doi.org/10.1016/bs.agron.2014.10.001)]. Both the protein source and production process strongly affect the chemical characteristics of PHs. [Cavani, L., C. Ciavatta, and C. Gessa (2003) "Determination of free L- and D-alanine in hydrolysed protein fertilizers by capillary electrophoresis" *J. Chromatogr. A* 985: 463-469]. Amino acids have a chelating effect on micronutrients [Koksal, A. I., H. Dumanoglu, N. T. Gunes, and M. Aktas (1999) "The effects of different amino acid chelate foliar fertilizers on yield, fruit quality, shoot growth and Fe, Zn, Cu, Mn content of leaves in Williams pear cultivar (*Pyrus communis* L.)" *Turk. J. Agric. For.* 23: 651-658.].

PHs are often produced through enzymatic hydrolysis. This is where proteolytic enzymes, which may originate from animal organs (e.g., pancreatin, pepsin), plants (e.g., bromelain, ficin, papain) or microorganisms (e.g., alcalase, flavourzyme, keratinases), catalyze protein hydrolysis. Proteolytic enzymes often target specific peptide bonds (e.g., pancreatin cuts the amino acid chain at bonds adjacent to arginine, lysine, tyrosine, tryptophan, phenylalanine and leucine bonds; papain cuts adjacent to arginine, lysine and phenylalanine; pepsin cuts where there is a phenylalanine or leucine bond; keratinases are mostly serine or metallo proteases). Chinese Patent CN19191800 describes a nutrient for plants and animals which is prepared by diluting *Saccharomyces cerevisiae* yeast sludge in water to obtain an emulsion, mixing this with papain, neutral proteinase and sodium chloride, then hydrolyzing the mixture, inactivating the enzymes, and finally, concentrating or drying the product obtained. The final product contains a high content of fast-absorption-rate nutrients.

Combined chemical and enzymatic hydrolytic processes have been developed which can help preserve the structure of amino acids and conserve energy relative to pure chemical hydrolysis.

In addition to amino acids and peptides, PHs contain other compounds that can contribute to the biostimulant action. These compounds include fats, carbohydrates, phenols, mineral elements, phytohormones and other organic compounds (e.g., polyamines).

PHs generated from agro-industrial byproducts represent an option for sustainable waste disposal, which is interesting from both environmental and economical points of view [V. Kasparkova, K. Kolomaznik, L. Burketova, V. Sasek, and L. Simek (2009) "Characterization of low-molecular weight collagen hydrolysates prepared by combination of enzymatic and acid hydrolysis" *The Journal of the American Leather Chemists Association* 104(2):46-51, 2009; J. Pecha, T. Fürst, K. Kolomaznik, V. Friebrová, and P. Svoboda (2012) "Protein biostimulant foliar uptake modeling: The impact of climatic conditions" *AIChE J.* 58(7):2010-2019 (http://dx.doi.org/10.1002/aic.12739); A. Baglieri, V. Cadili, C. Mozzetti Monterumici, M. Gennari, S. Tabasso, E. Montoneri, S. Nardi, and M. Negre (2014) "Fertilization of bean plants with tomato plants hydrolysates. effect on biomass production, chlorophyll content and n assimilation" *Scientia Horticulturae* 176:194-199 (http://dx.doi.org/10.016/j.scienta.2014.07.002)]. Celus, et al. (2007) "Enzymatic Hydrolysis Of Brewer's Spent Grain Proteins And Technofunctional Properties Of The Resulting Hydrolysates" *J. Agric. Food Chem.* 55(21):8703-8710) describe the enzymatic hydrolysis of proteins from brewery spent grain or bagasse (BSG), which is the insoluble residue from barley malt resulting from must production prior to alcoholic fermentation, and which constitutes the main byproduct of the brewing industry. The resulting hydrolysates, due to their ideal foaming and emulsifier properties, are used in the food and beverage industries. Spanish patent ES2329750 A1 ("Procedure For Obtaining Fertilizer Products From Brewing Waste") describes a multi-step process for making a fertilizer from brewing waste after the alcoholic fermentation of the must. This process includes various phases in which the waste is alkalinized, separated to obtain a liquid phase, which is then subjected to an acid treatment and from which in turn, a solid phase is separated, and which is finally subjected to enzymatic hydrolysis or acid hydrolysis.

There is an increased worry about the implications of animal-derived PHs in terms of food safety, as manifested by the European Regulation No. 354/2014, which prohibited the application of these products on the edible parts of organic crops. The peptide molecular weight of animal-derived PHs should be lower than 10 kDa to prevent any risk of BSE/TSE prion transmission to humans.

In addition to a biostimulant effect on plants, PHs and proteinaceous materials more generally can also have a nutritional and biostimulant effect on mushrooms and fungi and improve mushroom yield [Kurbanoglu, E. B. and O. F. Algur (2002) "The influence of ram horn hydrolyzate on the crop yield of the mushroom *Agaricus bisporus*" *Sci. Hortic.* 94: 351-357.]. A number of the major cultivated mushrooms, *Agaricus bisporus, Coprinus quadrifidus, Lepista nuda*, and *Pleurotus ostreatus*, are known to be capable of directly lysing and consuming bacteria. *A. bisporus* (viz. button, crimini, and portabella) and *P. ostreatus* (viz. oyster mushrooms) are the two most widely cultivated mushrooms for food. *A. bisporus* is typically grown on compost, where the microbial biomass component of the compost serves as a source of nitrogen, carbon and minerals, and as a water reserve. Protein-rich supplements have been found to stimulate mushroom yields (49-61%) when added to mushroom compost (i.e., growth substrate). Such protein-rich supplements include: Pro-Fam® H200 FG hydrolyzed soy protein, Remo's commercial supplement, 1-isoleucine (ile), egg white protein, amino blend HLA-198 hydrolyzed whey, cottonseed meal, soybean meal, dried skim milk, fish meal, malt sprouts, brewer's yeast products, casein, wheat germ, sunflower seed, corn gluten, and peanut protein. [L C. Schisler and J. W. Sinden (1962) in articles entitled, "Nutrient Supplementation of Mushroom Compost at Spawning," *Mushroom Science* 5:150-164 and "Nutrient Supplementation of Mushroom Compost at Casing" *Mushroom Science* 5:267-280]. Increases in yield using these materials are attributed to their relatively high nitrogen concentrations. U.S. Pat. No. 3,942,969 describes a nutrient composition for mushrooms using a denatured proteinaceous material (i.e., extract). The natural lignocelluloses used to grow many mushrooms have limited nutrient content, and generally require supplementations in the form of chemical and biological supplements. Addition of the supplements with basal substrate has been a common practice in mushroom cultivation to enhance the yield, nutritional and medicinal values. Oyster mushroom (*P. ostreatus*) can be grown on various lignocellulosic substrates including paddy straw, maize stalks/cobs, vegetable plant residues, bagasse, etc. However, it has been found that the ideal substrate should contain nitrogen (supplement) for rapid mushroom growth. Growth of *P. ostreatus* in substrates with nitrogen nutrient supplementation have increased productivity and nutritional value. Other research on mushroom supplementation have also reported, in addition to nitrogenous materials, that there is benefit to the addition of vegetable lipids (fatty materials) to mushroom compost [Schisler, L C. and J. W. Sinden (1966) "Nutrient Supplementation of Mushroom Compost at Casing—Vegetable Oils" *Can. J. BOL* 44:1063-1069; Schisler, L C. (1967) "Stimulation of Yield 15 in the Cultivated Mushroom by Vegetable Oils" *Appl Microbiol* 15:844-850; Schisler, L. C. and T. G. Patton, Jr. (1970) "Stimulation of Yield in the Cultivated Mushroom by Vegetable Oils: Effect of Sterols and Ethyl Linoleate" *Agric Food Chem* 18:1102-1103 20].

Despite the numerous fertilizers, bio-fertilizers, and plant biostimulants commercially available, there continues to be a demand for improved products capable of serving a variety of needs. There is a need for plant biostimulants that increase the tolerance of plants to stressors. There is a need to increase the reproductive rate of plants of economic interest. There is a need for plant biostimulants that are effective when applied on a less frequent basis than commercial products that are presently available and for plant biostimulants that offer a reduced risk of plant injury if over-applications occur. There is also a need to increase the nutrient use efficiency of food crops and to reduce nutrient leaching into the environment.

A need remains for a fungi and/or mushroom growth enhancer usable on a large, commercial scale. Growth stimulants are needed that are able to add nutrients to the growing mushroom crop without stimulating the growth of competing microorganisms, including bacteria and molds. There is a need for nutrient supplements that do not raise the temperature of the compost to undesirably high levels that may inhibit the growth of spawn and mushroom mycelium.

There is a need to augment current animal and plant derived protein hydrolysates, with PHs that are not derived from animals or plants. There is also a need for accelerated sequestration of carbon in the soil, and there is a need for carbon waste processing where most or all of the carbon is sequestered, as opposed to composting where generally half or more of the carbon is lost as $CO_2$ emissions during the composting process [S. M. Tiquia, T. L. Richard, and M. S. Honeyman (2002) "Carbon, nutrient, and mass loss during composting" *Nutrient Cycling in Agroecosystems* 62(1):15-24].

In addition to providing microbial protein, vitamins, and other biomolecules as a nutrient to plants and/or fungi, direct consumption of these microbial-derived nutrients by humans is also an option. However, one possible area of concern with respect to direct human consumption is the nucleic acid content of the nutrients. For human nutrition, the nucleic acid content of single-cell protein, such as derived from yeast, may need to be reduced to a lower level, if the SCP comprises a significant portion of the diet. The Recommended Daily Allowance of the Food and Nutrition Board, National Research Council for protein is 65 grams per day for a 70 kilogram adult male, and the Protein Advisory Group of the United Nations System recommends that the amount of nucleic acid ingested per day from microbial protein should be less than two grams per day. Therefore, according to these criteria the ratio of nucleic acid content to protein should be less than three percent, if SCP is the only source of dietary protein. The nucleic acid content of some sources of SCP, such as yeast cells from species *Candida utilis* and *Saccharomyces cerevisiae* may be about 12 to 15 grams of nucleic acid per 100 grams of crude protein. Thus, to enable utilization of a substantial amount of these sources of SCP for human nutrition, methods have been developed to reduce nucleic acid content several fold.

Bacteria, yeast, and other microbial cells have been applied to process sugar feedstocks into useful organic compounds such as proteins and amino acids in heterotrophic fermentation systems. However, there are significant drawbacks for these systems. Heterotrophic fermentations are vulnerable to contamination because other heterotrophic microorganisms that can grow on organic carbon nutrients and compete with a production strain are ubiquitous in the surrounding environment. Heterotrophic technologies also generally suffer limitations in terms competition with current modes of food production. In many heterotrophic systems, one is essentially using a food source to make another food source. This can lead to numerous negative environmental impacts and inefficiencies.

Autotrophic microbial systems for the production of proteins or amino acids from $CO_2$ were originally proposed in the human space flight program [G. L. Drake, C. D. King, W. A. Johnson, and E. A. Zuraw, "Study of life support systems for space missions exceeding one year in duration," NASA, Tech. Rep. SP-134, April 1966].

There is now a renewed interest in developing microbiological technologies for protein synthesis, as well as the synthesis of other nutrients, on different gaseous and liquid substrates, particularly waste substrates and substrates generated in a sustainable way.

Chemoautotrophic microorganisms represent a little explored alternative to photosynthetic organisms for the production of proteins, protein-derived products, and other nutrients from C1 feedstocks. The chemosynthetic reactions performed by chemoautotrophs for the fixation of $CO_2$, and other forms of inorganic carbon, to organic compounds, is powered by potential energy stored in inorganic chemicals, rather than by the radiant energy of light [J. M. Shively, G. van Keulen, and W. G. Meijer (1998) "Something from almost nothing: carbon dioxide fixation in chemoautotrophs." *Annual review of microbiology* 52:191-230 (http://dx.doi.org/10.1146/annurev.micro.52.1.191); A. J. Smith, J. London, and R. Y. Stanier, "Biochemical basis of obligate autotrophy in Blue-Green algae and thiobacilli" (1967) *Journal of Bacteriology* 94(4):972-983 (http://jb.asm.org/content/94/4/972.abstract); M. Hugler, C. O. Wirsen, G. Fuchs, C. D. Taylor, and S. M. Sievert (2005) "Evidence for autotrophic CO2 fixation via the reductive tricarboxylic acid cycle by members of the ε subdivision of proteobacteria" *Journal of Bacteriology* 187(9):3020-3027, (http://dx.doi.org/10.1128/jb.187.9.3020-3027.2005); K. M. Scott and C. M. Cavanaugh, "CO2 uptake and fixation by endosymbiotic chemoautotrophs from the bivalve solemya velum" (2007) *Applied and Environmental Microbiology* 73(4): 1174-1179 (http://dx.doi.org/10.1128/aem.01817-06)]. Carbon fixing biochemical pathways that occur in chemoautotrophs include the reductive tricarboxylic acid cycle, the Calvin-Benson-Bassham cycle [Jessup Shively, Geertje van Kaulen, Wim Meijer (1998) *Annu. Rev. Microbiol.* 191-230], and the Wood-Ljungdahl pathway [L. G. Ljungdahl, "The autotrophic pathway of acetate synthesis in acetogenic bacteria," Annual Review of Microbiology, vol. 40, no. 1, pp. 415-450, 1986. [Online]. Available: http://dx.doi.org/ 10.1146/annurev.mi.40.100186.002215].

Chemoautotrophic organisms are particularly well suited for hybrid chemical/biological processes for the conversion of $CO_2$-to-organic chemicals where the biological step is limited to $CO_2$ fixation alone. This $CO_2$-fixation step corresponds roughly to the dark reaction that occurs in photosynthesis. This hybrid chemical/biological approach has received far less attention than more traditional heterotrophic or photosynthetic bioprocesses for the production of bio-based products. However, there are a number of potential advantages of such a hybrid approach including the ability to efficiently combine enzymatic capabilities gained through billions of years of evolution in fixing $CO_2$ with a wide array of abiotic energy conversion technologies, such as solar PV, solar thermal, wind, geothermal, hydroelectric, or nuclear, in order to efficiently and cleanly power the overall biochemical production process from $CO_2$ carbon source.

A similar range of bio-products (single cell protein (SCP), polyhydroxybutyrate (PHB)) can be also obtained from methane and natural gas feedstocks using methane-oxidizing bacteria. These are relatively well-studied microorganisms, which in the past have been implemented in full scale SCP production systems, and tested as protein-rich feed additive for cattle and fish. The microorganisms may be applied to utilize biogas produced at sewage and manure treatment plants. Methane-oxidizing bacteria can enable technologies for upgrading low value methane to microbial biomass used as source of bioproducts.

Certain applications of chemoautotrophic or methanotrophic microorganisms in the capture and conversion of $CO_2$ or methane containing gases to fixed carbon products are known. However, many of the previously reported approaches have suffered shortcomings that have limited their effectiveness, economic feasibility, practicality and commercial adoption.

There is a need to break the bottleneck associated with significant increase in agricultural outputs sustainably, on a very large scale. There is a need for biological production with compact, vertical scaling as opposed to traditional agricultural operations that scale horizontally and are highly land and water intensive. There is a need to mitigate the food versus nature conflict, and conflicts over land use, and the disruption of natural habitats.

There is a need for a bioprocess that converts low cost syngas, $CO_2$ and/or methane into higher value organic chemicals, including but not limited to, amino acids, proteins, vitamins, fertilizers, biostimulants, and other biological nutrients.

There is a need to identify a set of microorganisms that can grow in conventional and scalable contained reaction vessels and that produce commercially viable sets of organic carbon chains, in particular over four carbon atoms long in a commercially feasible method. There is a need to identify microorganisms that are not limited metabolically by typical organic carbon inputs such as sugar. There is a need for microorganisms and systems that can additionally utilize syngas, producer gas, natural gas, biogas or a wide array of abiotic sources of carbon and energy, directed through a $H_2/CO_2$ gas mix intermediate, for the synthesis of amino acids, proteins, and other biological nutrients. This will result in a feedstock flexibility that far exceeds comparable heterotrophic systems. There is a need to identify and use microorganisms that can utilize electron donors such as hydrogen, present in syngas, producer gas, or readily generated through a wide array of abiotic renewable and/or low-$CO_2$ emission energy technologies, for growth and carbon fixation.

SUMMARY OF THE INVENTION

Systems, methods, and compositions are provided for the production of organic chemicals, including but not limited to amino acids, proteins, vitamins and other biological nutrients, from low-cost and sustainable feedstocks. In some embodiments, the efficient production of these high value organic compounds is coupled with the disposal of waste sources of carbon and/or with the capture of $CO_2$, which can generate additional revenue and/or social value.

Naturally occurring or engineered microorganisms are used to convert $CO_2$ gas, syngas, producer gas, and/or methane to higher value mid- to long-carbon chain length molecules, including but not limited to amino acids, proteins, vitamins, and other biological nutrients. Technology described herein allows the development of new natural or classically bred, and/or genetically enhanced, strains of microorganisms that can be used for syngas bioprocessing within biological gas-to-chemical (GTC) processes to produce and/or secrete various relatively long carbon chain organic compounds that are drop-in, and are currently only produced in bulk from higher plant agricultural crops or animal sources.

Methods are provided for the selection, breeding, and/or engineering of microorganisms, including but not limited to hydrogen-oxidizing, carbon monoxide-oxidizing, and knallgas microorganisms, with a natural capability to grow and synthesize biomass on gaseous carbon sources such as syngas and/or $CO_2$, such that the production microorganisms synthesize targeted chemical products under gas cultivation. The microorganisms and methods described herein can enable low cost synthesis of biochemicals, which can compete on price with petrochemicals and/or higher-plant derived amino acids, proteins, and other biological nutrients. In certain embodiments, these amino acids, proteins, vitamins, and other biological nutrients are predicted to have a substantially lower price than amino acids, proteins, vitamins and other biological nutrients produced through heterotrophic or microbial phototrophic synthesis.

Microorganisms are provided that convert syngas, and/or gaseous $CO_2$, and/or a mixture of $CO_2$ gas and $H_2$ gas, and/or methane, along with a nitrogen source, including but not limited to ammonia, ammonium, and/or urea, into one or more amino acids, proteins, vitamins, and/or other biological nutrients. In some embodiments, the microorganism is one or more of the following group: a hydrogen-oxidizing chemoautotrophic microorganism, a carbon monoxide-oxidizing microorganism, a knallgas microorganism, and/or a methanotrophic microorganism. Knallgas microbes, hydrogenotrophs, carboxydotrophs, and chemoautotrophs more broadly, are able to capture $CO_2$ or CO as their sole carbon source to support biological growth. Methanotrophs are able to capture $CH_4$ as their sole carbon source. In some embodiments, this microbial growth includes the biosynthesis of amino acids and proteins. Knallgas microbes and other hydrogenotrophs can use $H_2$ as a source of reducing electrons for respiration and biochemical synthesis. In some embodiments, knallgas microorganisms, hydrogenotrophs, carboxydotrophs, other chemoautotrophic microorganisms, and/or methanotrophs are grown on a stream of gasses, including but not limited to one or more of the following: $CO_2$; CO; $H_2$; $CH_4$; along with inorganic minerals dissolved in aqueous solution. In some embodiments, knallgas, hydrogenotrophic, carboxydotrophic, chemoautotrophic, and/or methanotrophic microorganisms are utilized to convert greenhouse gases (GHG's) into biomolecules, including but not limited to one or more of the following: amino acids and proteins, and vitamins.

Compositions are also provided that include any of the microorganisms disclosed herein. Compositions may include the microorganisms in a growth medium that includes nutrients for growth and/or bioproduct production. For example, the composition may be within a bioreactor into which gaseous substrates as described herein are introduced.

In some embodiments, the microorganism is chosen from the genera *Rhodococcus* or *Gordonia*. In some embodiments, the microorganism is *Rhodococcus opacus*. In some embodiments, the microorganism is *Rhodococcus opacus* (DSM 43205) or *Rhodococcus* sp. (DSM 3346). In some embodiments, the microorganism is chosen from the genera *Ralstonia* or *Cupriavidus*. In some embodiments, the microorganism is *Cupriavidus* necator. In some non-limiting embodiments, the strain of *Cupriavidus necator* is DSM 531 or DSM 541.

In one aspect, a natural or engineered microorganism is provided that is capable of converting a gaseous substrate such as producer gas or synthesis gas or another gas mixture that contains $H_2$ and $CO_2$, and/or CO, and/or $CH_4$ into amino acids, proteins, and other biological nutrients. The gaseous substrate is used by the microorganism as a carbon and/or energy source. In some embodiments, microorganisms that are capable of growing on a gaseous substrate are transformed with a polynucleotide that encodes a gene that is required for biosynthesis of an amino acid, protein, or other biological nutrient. In some embodiments, an amino acid, protein, other biological nutrient, or a whole cell product is recovered from the microbial cells or from a microbial growth medium. Producer gas, which may be used in the microbial growth processes described herein, may come from sources that include gasification of waste feedstock and/or biomass residue feedstock, or waste gas from industrial processes or steam reforming of natural gas or biogas.

In one aspect, a non-naturally occurring microorganism is provided that is capable of growing on a gaseous substrate as a carbon and/or energy source, and wherein the microorganism includes at least one exogenous nucleic acid. In some embodiments, the microorganism is a bacterial cell. For example, in some embodiments, the bacterial cell is a *Cupriavidus* sp. or *Ralstonia* sp., for example, but not limited to, *Cupriavidus* necator. In some non-limiting embodiments, the microorganism is *Cupriavidus necator* DSM 531 or DSM 541.

In some embodiments, the gaseous substrate includes $CO_2$ as a carbon source. In some embodiments, the gaseous substrate includes $H_2$ and/or $O_2$ as an energy source. In some embodiments, the gaseous substrate includes producer gas, syngas, or pyrolysis gas. In some embodiments, the gaseous substrate includes a mixture of gases, comprising $H_2$ and/or $CO_2$ and/or CO and/or $CH_4$. In some embodiments, the microorganism produces amino acids, proteins, and other biological nutrients when cultured in the presence of the gas substrate under conditions suitable for growth of the microorganism and production of bioproducts.

In another aspect, methods are provided for producing amino acids, proteins, and other biological nutrients using a microorganism as described herein that is capable of growing on a gaseous substrate as a carbon and/or energy source. In some embodiments, a microorganism as described herein is cultured in a bioreactor that includes a gaseous substrate and a culture medium (e.g., a liquid growth medium) that includes other nutrients for growth and bioproduct production, under conditions that are suitable for growth of the microorganism, wherein the microorganism produces amino acids, proteins, and other biological nutrients.

In some embodiments, the gaseous substrate in the bioreactor includes $H_2$ and/or $CO_2$. In some embodiments, the gaseous substrate is producer gas, syngas, or pyrolysis gas. In some embodiments, the gaseous substrate is natural gas or biogas. In some embodiments, the gaseous substrate is derived from municipal solid waste, black liquor, agricultural waste, wood waste, stranded natural gas, biogas, sour gas, methane hydrates, tires, pet coke, sewage, manure, straw, lignocellulosic energy crops, lignin, crop residues, bagasse, saw dust, forestry residue, food waste, waste carpet, waste plastic, landfill gas, and/or lignocellulosic biomass.

In some embodiments, amino acids, proteins, vitamins and/or other biological nutrients are recovered from the culture medium.

In another aspect, microorganisms and methods for producing amino acids, proteins, vitamins and/or other biological nutrients are provided. In some embodiments, a natural or non-naturally occurring microorganism is provided, wherein the microorganism includes zero or at least one exogenous nucleic acid, respectively, and is capable of growing on a gaseous substrate as a carbon and/or energy source, and wherein said microorganism biosynthesizes amino acids, proteins, vitamins and/or other biological nutrients. In some embodiments, the natural or non-naturally occurring microorganism is a *Cupriavidus* sp. or *Ralstonia* sp. In some embodiments, the microorganism is *Cupriavidus necator* or *Cupriavidus metallidurans*. In some embodiments, a method is provided for producing amino acids, proteins, vitamins and/or other biological nutrients utilizing a naturally or non-naturally occurring microorganism as described herein, wherein the microorganism includes zero or at least one exogenous nucleic acid, respectively, and that is capable of growing on a gaseous substrate as a carbon and/or energy source, and that biosynthesizes amino acids, proteins, vitamins and/or other biological nutrients, including culturing the naturally or non-naturally occurring microorganism in a bioreactor that includes a gaseous substrate and a culture medium (e.g., a liquid growth medium), that also includes other nutrients for growth and/or bioproduct production, under conditions that are suitable for growth of the microorganism and production of amino acids, proteins, vitamins, and/or other biological nutrients, and wherein the microorganism produces the amino acids, proteins, vitamins and/or other biological nutrients.

In some embodiments, the microorganisms described herein are used to capture $CO_2$ from industrial flue gases and produce a protein-rich biomass. In some embodiments this protein-rich biomass is a commodity. In some embodiments the protein-rich biomass is used as a single cell protein (SCP). In some embodiments, the protein-rich biomass is used in one or more of the following applications: fertilizer; biostimulant; biofertilizer; fungal growth enhancer or supplement; nutrient; ingredient; animal feed or within an animal feed formulation; human food or within a human food formulation. In some embodiments, the protein-rich biomass is used as a high-protein substitute for fishmeal and/or other animal protein, and/or is used in plant fertilizer products and/or mushroom and fungal growth enhancers. In some non-limiting embodiments, the present invention is used both for GHG reduction and to produce high-protein products for applications including but not limited to plant fertilizers and/or biostimulants and/or fungal fertilizers and/or nutritional supplements and/or human food ingredients.

In some embodiments, the high protein product is subjected to hydrolysis. In some embodiments, the hydrolysis yield is improved by the application of steam treatments to the protein-rich biomass. Some insoluble proteins are converted into a less refractory form upon heating in the presence of moisture [Kida, K., S. Morimura, J. Noda, Y. Nishida, T. Imai, and M. Otagiri (1995) "Enzymatic hydrolysis of the horn and hoof of cow and buffalo" *J. Ferment. Bioeng.* 80:478-484.].

Certain embodiments of this disclosure relate to a microbial protein isolate with lowered nucleic acid content. In certain embodiments, the nucleic acid content of the isolate is below 9% by weight. In certain non-limiting embodiments, the Protein Equivalence Ratio (PER) of the isolate is greater than 1.

In certain embodiments, similar methods to those developed to reduce the nucleic content of yeast SCP are applied to prokaryotic cells as described herein. The nucleic acid of yeast is mainly ribonucleic acid or RNA. In certain embodiments, the nucleic acid of cells is primarily RNA as well, and in this application the terms RNA and nucleic acid will sometimes be used interchangeably. In certain embodiments, the ratio of nucleic acid content to protein is reduced to less than three percent. In certain embodiments, the ratio of nucleic acid to protein is reduced to a level considered safe for providing a substantial proportion, or all of the protein requirement in a human diet, by one of average skill in the art and knowledge in the field.

Certain embodiments of this disclosure relate to microbial hydrolysates used as a feedstock or nutrient source in other industrial fermentations. Ummadi, M. and Curic-Bawden, M. (2010) "Use of Protein Hydrolysates in Industrial Starter Culture Fermentations." *Protein Hydrolysates In Biotechnology* 91-114, which is incorporated herein by reference in its entirety.

Certain embodiments of this disclosure relate to microbial protein isolates and/or hydrolysates with application in sport medicine and specifically, in certain non-limiting embodiments, consumption of said hydrolysate allows amino acids to be absorbed by the body more rapidly than intact proteins, thus maximizing nutrient delivery to muscle tissues. Manninen, Anssi H., "Protein Hydrolysates In Sports And Exercise: A Brief Review" (2004) *Journal of Sports Science and Medicine,* 3:60-63, (2004), which is incorporated herein by reference in its entirety.

In one aspect, methods are provided for producing plant and fungus biostimulants and nutrients. Biostimulants and nutrients produced by such a process are also provided. In some embodiments, methods of producing plant biostimulants and/or fertilizer are provided, including hydrolyzing bacterial cells to obtain a hydrolysate, and formulating the hydrolysate as a plant biostimulant and/or fertilizer for foliar application, application as a soil adjuvant, and/or application as a soil fertilizer. Plant biostimulants and/or fertilizers obtained by the methods described herein are also provided. Methods of growing plants or fungi by applying such plant or fungi biostimulants and nutrients are also provided. Processes for preparing products from such plants or fungi are also provided. Methods of raising heterotrophic organisms by feeding such plants or fungi to the organism are also provided. Methods of producing products from such heterotrophic organisms are also provided.

In another aspect, mushroom growth enhancers capable of increasing the yield and/or viability of commercial mushrooms are provided. Mushroom growth enhancers that are less accessible to competing foreign microorganisms as a food source, while fostering the propagation of commercial mushrooms, are also provided. Mushroom growth enhancers that are economical to manufacture and use are also provided. Mushroom growth enhancers that are effective at low concentration levels are also provided. Mushroom growth enhancers that are manufactured from readily available, low cost and/or waste materials are also provided. Mushroom growth enhancers that are easily manufactured using renewable power sources are also provided.

In one aspect, a biological and chemical method is provided for the biological conversion of inorganic and/or organic molecules containing one or more carbon atoms, into organic molecules comprising amino acids, proteins, and/or vitamins produced through a carbon fixing reaction or anabolic biosynthesis, comprising: introducing inorganic and/or organic molecules containing one or more carbon atom, into an environment that comprises microorganism cells in a culture medium that is suitable for maintaining the microorganism cells; wherein the inorganic and/or organic molecules containing one or more carbon atom are used as a carbon source by the microorganism cells for growth and/or biosynthesis; converting the inorganic and/or organic molecules containing one or more carbon atoms into the organic molecule products comprising amino acids, proteins, and/or vitamins within the environment via at least one carbon-fixing reaction or at least one anabolic biosynthetic pathway contained within the microorganism cells; wherein the carbon fixing reaction or anabolic biosynthetic pathway is at least partially driven by chemical and/or electrochemical energy provided by electron donors and/or electron acceptors that have been generated chemically and/or electrochemically and/or thermochemically and/or are introduced into the environment from at least one source external to the environment, and wherein the microorganism cells comprise biomass that comprises said amino acids, proteins, and/or vitamins. In some embodiments, the organic molecule products comprise compounds with carbon backbones that are five carbons or longer. In some embodiments, the amino acids and/or protein and/or vitamins and/or biomass produced in the environment are recovered from the culture medium.

In some embodiments, the carbon source contains only one carbon atom, and wherein said electron donors and/or molecules containing only one carbon atom are generated through a thermochemical process acting upon organic matter comprising at least one of: gasification; pyrolysis; steam reforming; and autoreforming. In some embodiments, the carbon source contains only one carbon atom, and the electron donors and/or organic molecules containing only one carbon atom are generated through methane steam reforming. In some embodiments, a gaseous substrate is derived from a gas stream comprising $H_2$, CO, and $CO_2$ that are generated from gasification and/or pyrolysis and/or autoreforming and/or steam reforming, wherein the ratio of hydrogen to carbon monoxide in the gas output from gasification and/or pyrolysis and/or autoreforming and/or steam reforming is adjusted using the water gas shift reaction prior to the gas stream being delivered to the microorganisms.

In some embodiments, the carbon source comprises a C1 molecule captured or directed from one or more sources comprising: the gasification of organic matter; the calcination of limestone, $CaCO_3$, to produce quicklime, CaO; methane steam reforming; combustion, incineration, or flaring; anaerobic or aerobic fermentation of sugar; a methanotrophic bioprocess; respiration of other organisms, waste water treatment; landfill gas, sodium phosphate production;

geologically or geothermally produced or emitted gases; acid gas, sour gas, or natural gas; sea water or other bodies of surface or underground water; and the atmosphere.

In some embodiments, one or more electron donors are selected from: ammonia; ammonium; carbon monoxide; dithionite; elemental sulfur; hydrocarbons; hydrogen; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, phosphates, sulfates, or carbonates, in dissolved or solid phases; and conduction or valence band electrons in solid state electrode materials. In some embodiments, one or more electron acceptors are selected from: carbon dioxide; oxygen; nitrites; nitrates; ferric iron or other transition metal ions; sulfates; and valence or conduction band holes in solid state electrode materials.

In some embodiments, the biological conversion is preceded by one or more chemical preprocessing steps in which electron donors and/or electron acceptors and/or carbon sources and/or mineral nutrients required by the microorganism, are generated and/or refined from at least one input chemical and/or are recycled from chemicals emerging from the carbon-fixing step and/or are generated from, or are contained within, waste streams from other industrial, mining, agricultural, sewage or waste generating processes.

In some embodiments, the electron donors and/or electron acceptors are generated or recycled using renewable, alternative, or conventional sources of power that are low in greenhouse gas emissions, and wherein said sources of power are selected from at least one of photovoltaics, solar thermal, wind power, hydroelectric, nuclear, geothermal, enhanced geothermal, ocean thermal, ocean wave power, and tidal power. In some embodiments, the electron donors and/or electron acceptors are generated using grid electricity during periods when electrical grid supply exceeds electrical grid demand, and wherein storage tanks buffer the generation of said electron donors and/or electron acceptor, and their consumption in the said carbon-fixing reaction.

In some embodiments, the electron donors comprise $H_2$ and/or CO and/or methane derived from a tail gas from one or more of: methane steam reforming; petroleum refining; steel production; aluminum production; manganese production; the chloroalkali process; carbon black manufacture; methanol synthesis; ammonia synthesis; metallurgical processes; chemical processes; and electrochemical processes.

In some embodiments, molecular hydrogen is utilized as an electron donor, wherein said hydrogen is generated via a method using at least one of the following: electrolysis of water; thermochemical splitting of water; electrolysis of brine; electrolysis and/or thermochemical splitting of hydrogen sulfide. In some embodiments, electrolysis of water for the production of hydrogen is performed using one or more of: Proton Exchange Membranes (PEM); liquid electrolytes such as KOH; alkaline electrolysis; Solid Polymer Electrolyte electrolysis; high-pressure electrolysis; and high temperature electrolysis of steam (HTES). In some embodiments, thermochemical splitting of water for the production of hydrogen is performed using one or more of: the iron oxide cycle; cerium(IV) oxide-cerium(III) oxide cycle; zinc zinc-oxide cycle; sulfur-iodine cycle; copper-chlorine cycle; calcium-bromine-iron cycle; hybrid sulfur cycle.

In one embodiment, the microorganism cell is a bacterial cell. In some embodiments, the microorganism is a *Cupriavidus* sp. or *Ralstonia* sp. In some embodiments, the microorganism is *Cupriavidus necator* or *Cupriavidus metallidurans*. In some embodiments, the microorganism cells comprise microorganisms selected from one or more of the following genera: *Cupriavidus* sp., *Rhodococcus* sp., *Hydrogenovibrio* sp., *Rhodopseudomonas* sp., *Hydrogenobacter* sp., *Gordonia* sp., *Arthrobacter* sp., *Streptomycetes* sp. *Rhodobacter* sp., and/or *Xanthobacter*.

In some embodiments, the microorganism cells produce amino acids and/or protein and/or vitamins and/or biomass when cultured in the presence of a gaseous substrate under conditions suitable for growth of the microorganism and production of bioproducts. In some embodiments, the gaseous substrate comprises $CO_2$ and/or CO and/or $CH_4$ as a carbon source. In one embodiment, the gaseous substrate comprises $H_2$. In one embodiment, gaseous substrate comprises $H_2$ and/or $O_2$ as an energy source. In some embodiment, the gaseous substrate comprises electron donors including one or more of $H_2$ and/or CO and/or $CH_4$. In some embodiments, the gaseous substrate comprises pyrolysis gas or producer gas or syngas or natural gas or biogas. In some embodiments, the gaseous substrate comprises a mixture of gases, comprising $H_2$ and/or $CO_2$ and/or CO. In some embodiments, the gaseous substrate is derived from municipal solid waste, black liquor, agricultural waste, wood waste, stranded natural gas, biogas, sour gas, methane hydrates, tires, pet coke, sewage, manure, straw, lignocellulosic energy crops, lignin, crop residues, bagasse, saw dust, forestry residue, food waste, waste carpet, waste plastic, landfill gas, kelp, seaweed, and/or lignocellulosic biomass.

In one embodiment, a method is provided for producing amino acids and/or protein and/or vitamins and/or biomass, comprising culturing a microorganism as described herein in a bioreactor that comprises a gaseous substrate and a culture medium that comprises other nutrients for growth and bioproduct production, under conditions that are suitable for growth of the microorganism and production of amino acids and/or protein and/or vitamins and/or biomass, wherein said microorganism produces amino acids and/or protein and/or vitamins and/or biomass.

In some embodiments, the microorganisms are knallgas microorganisms. In one embodiment, the gaseous substrate comprises $H_2$ and/or $CO_2$. In some embodiments, the gaseous substrate is pyrolysis gas or producer gas or syngas.

In one embodiment, microorganism cells produce said amino acids, proteins, and/or vitamins via a chemosynthetic reaction that comprises molecular hydrogen as an electron donor, wherein said hydrogen is generated via electrochemical or thermochemical processes known to produce hydrogen with low- or no-carbon dioxide emissions comprising one or more of: carbon capture and sequestration (CCS) enabled methane steam reforming; CCS enabled coal gasification; the Kværner-process and other processes generating a carbon-black product; CCS enabled gasification or pyrolysis of biomass; and pyrolysis of biomass producing a biochar co-product.

In some embodiments, at least one carbon-fixing reaction and at least one anabolic biosynthetic pathway results in the formation of bioproducts including at least one of: amino acids; peptides; proteins; lipids; polysaccharides; and/or vitamins. In one embodiment, the at least one carbon-fixing reaction and at least one anabolic biosynthetic pathway comprises the Calvin Cycle and an amino acid biosynthesis pathway.

In some embodiments, biomass and/or organic molecules produced by the microorganisms in a method as described herein are used to feed or provide nutrition to one or more other organisms. In some embodiments, the amino acids and/or proteins and/or vitamins produced in a method as described herein are used to produce a plant biostimulant or mushroom growth enhancer.

In another aspect, a plant biostimulant is provided, comprising biomass, amino acids, proteins, and/or vitamins produced according a method as described herein. In one embodiment, a method is provided for treating a crop, comprising applying a plant biostimulant as described herein to a plant, and/or to soil in which a plant is grown and/or to liquid medium used to grow a plant; and harvesting the plant. In one embodiment, a method is provided that comprises applying the biomass, amino acids, proteins, and/or vitamins produced through a carbon fixing reaction or anabolic biosynthesis as described herein to a plant and/or to soil in which a plant is grown and/or to liquid medium used to grow a plant; and harvesting the plant. In some embodiments, the plant is an agricultural crop.

In another aspect, microorganism cells grown in a method as described herein are lysed, thereby producing a lysate. In some embodiments, the lysate is used to produce an emulsion or suspension. In some embodiments, the lysate is separated into insoluble and soluble fractions, either or both of which may optionally be concentrated or dried. In some embodiments, a plant biostimulant is provided, comprising a lysate, emulsion, suspension, or fraction thereof produced as described herein.

In another aspect, proteins produced in a method as described herein are hydrolyzed, thereby producing a hydrolysate. In one embodiment, hydrolyzing comprises performing acid hydrolysis. In one embodiment, hydrolyzing comprises at least one enzyme that is capable of hydrolyzing proteins into at least one of free amino acids and oligopeptides. In one embodiment, hydrolyzing comprises performing alkali hydrolysis. In some embodiments, the hydrolysate is used to produce an emulsion or suspension. In some embodiments, the hydrolysate is separated into insoluble and soluble fractions, either or both of which may optionally be concentrated or dried. In some embodiments, the hydrolysate is filtered, thereby producing a filtrate (permeate) and a filtride (retentate; residue). In some embodiments, a plant biostimulant is provided, comprising a hydrolysate, emulsion, suspension, fraction, filtrate, or filtride thereof produced as described herein.

In another aspect, biomass produced in a method as described herein is used for production of a plant biostimulant, comprising: hydrolyzing said biomass to obtain a hydrolysate; and formulating the hydrolysate as a plant biostimulant for foliar application and/or application as a soil adjuvant or additive and/or for use in a liquid medium for plant growth. In one embodiment, the method further includes applying the plant biostimulant to a plant and/or to soil in which a plant is grown and/or to liquid medium used to grow a plant; and harvesting the plant. In one embodiment, hydrolyzing comprises at least one enzyme that is capable of hydrolyzing proteins into at least one of free amino acids and oligopeptides. In one embodiment, hydrolyzing comprises performing acid hydrolysis. In one embodiment, hydrolyzing comprises performing alkali hydrolysis. In some embodiments, a plant biostimulant is provided, comprising a biomass hydrolysate as described herein.

In another aspect, a method is provided for producing a lysate, comprising culturing a microorganism as described herein in a bioreactor under conditions that are suitable for growth of the microorganism, wherein biomass produced in said bioreactor is harvested and removed from the bioreactor, wherein said biomass removed from the bioreactor is subsequently lysed, thereby producing a lysate. In some embodiments, the cells are ruptured by homogenization. In some embodiments, the lysate comprises proteins, and the method further comprising hydrolyzing proteins in said lysate, thereby producing a hydrolysate.

In another aspect, a protein concentrate is provided that is isolated from a microorganism grown in a method as described herein. In one embodiment, the protein concentrate contains less than about 5% nucleic acid. In one embodiment, the protein concentrate contains less than about 3% nucleic acid.

In another aspect, a method as described herein for the biological conversion of inorganic and/or organic molecules containing one or more carbon atoms, into organic molecules comprising amino acids, proteins, and/or vitamins produced through a carbon fixing reaction or anabolic biosynthesis, further comprises producing a concentrated protein product, comprising the steps of: a. rupturing said microorganism cells, wherein said cells comprise one or more nuclease enzyme, thereby producing a mixture comprising soluble nucleic acid, nuclease, and protein and comprising insoluble cell wall debris; b. separating the soluble nucleic acid, nuclease, and protein from the insoluble cell wall debris under conditions in which the nucleic acid is hydrolyzed with the nuclease, thereby producing hydrolyzed nucleic acid; d. rendering the protein insoluble; and e. separating the insoluble protein from the remaining soluble materials that comprise the hydrolyzed nucleic acid. In some embodiments, the cells are ruptured by homogenization. In one embodiment, the insoluble protein comprises less than about 5% nucleic acid. In one embodiment, the insoluble protein comprises less than about 3% nucleic acid.

In another aspect, biomass and/or organic molecules produced as described herein have application as at least one of: an organic carbon and/or nitrogen source for fermentations; a nutrient source for the growth of other microbes or organisms; a prebiotic; a nutrient source or food ingredient for humans; a feed for animals; as a raw material or chemical intermediate for manufacturing or chemical processes; sources of pharmaceutical, medicinal or nutritional substances; a fertilizer; soil additive; a soil stabilizer; soil adjuvant; plant biostimulant; and/or a mushroom growth enhancer. In one embodiment, the fertilizer and/or soil additive; and/or soil stabilizer; and/or soil adjuvant; and/or plant biostimulant; and/or mushroom growth enhancer, adds carbon and/or nitrogen to the soil, resulting in an increase in the carbon and/or nitrogen content of the soil to which it is applied. In one embodiment, the carbon source is a gaseous C1 molecule, and wherein the carbon added to the soil represents sequestered carbon, and the end-to-end process from gaseous C1 carbon source to soil carbon represents a carbon sequestration process. In one embodiment, the fertilizer and/or biostimulant is applied to a crop which is grown hydroponically, aeroponically, aquaponically, or in a vertical farm system. In one embodiment, the fertilizer and/or biostimulant is used in fertigation. In one embodiment, the fertilizer and/or biostimulant is applied to a crop which is grown in a greenhouse, indoors, and/or using artificial lighting. In one embodiment, a method is provided for growth of microbes and other organisms, wherein said microbes and organisms are grown in soil on a nutrient source produced as described herein. In one embodiment, a fermentation method is provided, using said organic carbon and/or nitrogen sources to produce one or more bioproducts comprising: a commercial enzyme; an antibiotic; an amino acid; a protein; a plant biostimulant; a mushroom growth enhancer; a probiotic; a prebiotic; a biofertilizer; a food; a food ingredient; a vitamin; a lipid; a bioplastic; a polysaccharide; a neutraceutical; and/or a pharmaceutical.

In another aspect, a method is provided for obtaining an organic enzyme extract from C1 feedstock, comprising a method for the biological conversion of inorganic and/or organic molecules containing one or more carbon atoms, into organic molecules comprising amino acids, proteins, and/or vitamins produced through a carbon fixing reaction or anabolic biosynthesis as described herein, wherein said carbon source comprises only one carbon atom, wherein said method further comprises subjecting the said microorganism cells to one or more of: mechanical lysis; enzymatic lysis; a pH adjustment; an increase or decrease in pressure; an increase or decrease in temperature; electrical or electromagnetic fields; ultrasound; a change in osmolarity; and enzymatic hydrolysis, thereby producing an organic enzyme extract.

In another aspect, a mushroom growth enhancer is provided comprising biomass and/or protein produced in a method as described herein. In one embodiment, a method is provided for enhancing mushroom growth, comprising combining the mushroom growth enhancer with mushroom compost. In one embodiment a mushroom growth composition is provided, comprising the combined mushroom compost and mushroom growth enhancer.

Various objects, features, aspects, and advantages of the methods, systems, microorganisms, and compositions described herein will become more apparent from the following detailed description of some exemplary embodiments of the invention.

BRIEF DESCRIPTION OF THE DRAWINGS

Non-limiting embodiments of the present invention will be described by way of example with reference to the accompanying figures, some of which are schematic and are not intended to be drawn to scale. For purposes of clarity, not every component is labeled in every figure, nor is every component of each embodiment of the invention shown where illustration is not necessary to allow those of ordinary skill in the art to understand the invention.

FIG. 6 demonstrates the growth of chemotrophic and oleaginous microorganisms on different carbon sources. Bacterial growth was measured using optical density (OD) detection at 650 nm after the indicated days (in parentheses). Media and growth conditions are described in the Examples section, infra. ND, not done.

DETAILED DESCRIPTION

Figure 1:
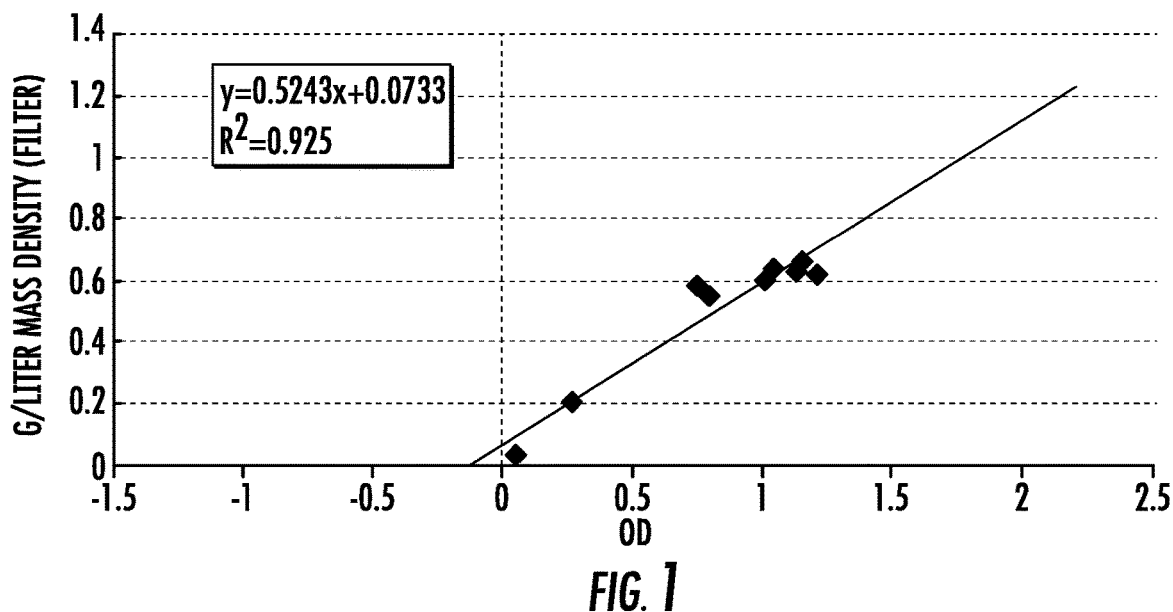
FIG. 1 depicts the correlation between OD and biomass density.

The disclosure herein relates to the biological production of amino acids and proteins and other biomass constituents, in a microbial system, using a gaseous substrate such as synthesis gas or producer gas or pyrolysis gas or $H_2$ and $CO_2$ gas mixtures, as a carbon and energy source. The disclosure also relates to the use of microbial amino acids, proteins, and other biomass constituents to feed or provide nutrients to other organisms, or humans. Amino acids, proteins, and other biomass constituents produced according to the disclosed methods can be consumed and used as nutrients by other organisms for the production of food and other bio-based products.

This disclosure also relates to compositions and methods for producing amino acids, proteins, and other biomass constituents through cultivating bacteria or other microorganisms that grow on carbon-containing gases such as syngas, producer gas, pyrolysis gas, $CO_2$, carbon monoxide and mixtures of the same containing hydrogen gas. It also relates to gas mixtures containing methane such as biogas, or natural gas. This disclosure further relates to methods of fixing carbon from gaseous input into useful organic molecules such as amino acids, proteins, vitamins and other nutrients. The bacteria and/or microorganisms disclosed herein can be genetically engineered for use in the methods or other aspects described herein. In some other aspects described herein, the microorganisms are not genetically engineered, i.e., are wild-type.

This disclosure further relates to methods of fixing carbon from gas into useful organic molecules such as amino acids, proteins, vitamins, and other nutrients. The disclosure further describes mechanisms to confer to an organism the ability to produce, and/or to enhance production by an organism of carbon-based products, through the conversion of carbon dioxide, or other inorganic carbon sources, and inorganic energy, including chemical energy from an inorganic chemical, or directly from an electrical source, into carbon-based products of commercial value, and in particular amino acids, proteins, vitamins, and other nutrients of commercial value.

This disclosure further relates to artificial ecologies, engineered trophic systems, closed ecological systems, microcosms, continuous culture systems, bioregenerative and closed-loop life-support systems (Freda B. Taub (1974) *Closed Ecological Systems Annual Review of Ecology and Systematics* 5:139-160; and E. A. Zuraw (1966) "Study of life support systems for space missions exceeding one year in duration" NASA, Tech. Rep. SP-134, which are incorporated herein by reference in their entireties).

This disclosure further relates to uses of hydrogen gas. Hydrogen has generally been regarded as a sustainable alternative to fossil fuels or as a means of electrical energy storage. However, it can also be used as a feedstock and primary energy source for the cultivation of hydrogen-oxidizing microorganisms.

This disclosure further relates to the technological application of chemoautotrophic microorganisms, and particularly hydrogen-oxidizing bacteria. These are a special group of bacteria that have been studied in the past, as potential producers of single cell protein (SCP) (G. L. Drake, C. D. King, W. A. Johnson, and E. A. Zuraw, "Study of life support systems for space missions exceeding one year in duration," NASA, Tech. Rep. SP-134, April 1966; R. Repaske and R. Mayer, "Dense autotrophic cultures of *Alcaligenes eutrophus*" (1976) *Applied and environmental microbiology* 32(4):592-597 (http://aem.asm.org/cgi/content/abstract/32/4/592)), and polyhydroxybutyrate (PHB).

This disclosure further relates to microbial extracts and protein hydrolysates. (U.S. Pat. Nos. 3,887,431; 9,416,062; U.S. Patent application 2012/0129695; European Patent application EP2,752,399; are incorporated herein by reference in their entireties) The disclosure is also directed to obtaining extracts with high bio-stimulant and/or bio-fertilizer capacity and high bioabsorption capacity for heterotrophic microorganisms, fungi, animals and plants, so they are especially useful for organic farming, fermentations, animal feed, and direct human nutrition.

This disclosure further relates to biostimulants, and biofertilizers. The disclosure also is directed to methods of producing plant and fungal nutrients, biostimulants, biofertilizers, and the biostimulants and/or biofertilizers thereby produced. The disclosure also relates to mushroom growth enhancing materials. The disclosure also relates to methods of growing plants and fungi by applying such biostimulants, biofertilizers, and/or growth enhancing materials. The disclosure further relates to processes for preparing products from such plants and fungi, raising livestock by feeding such plants or fungi to livestock, and producing products from such livestock. (Colla, G. et al. (2015) "Protein hydrolysates as biostimulants in horticulture" *Scientia Horticulturae* 196: 28-38 (http://dx.doi.org/10.1016/j.scienta.2015.08.037); U.S. Application No. US20120129695; European Application No. EP2752399A1; and U.S. Pat. No. 4,776,872, which are incorporated herein by reference in their entireties).

Provided herein are methods and systems for biosynthetic production of amino acids, proteins, vitamins and other biological nutrients. In certain embodiments, natural or engineered microorganisms are provided that produce amino acids, proteins, and other biological nutrients, on a gaseous substrate, including, but not limited to producer gas, syngas, tail gas, pyrolysis, knallgas, natural gas, biogas, and gas mixtures containing $H_2$ and $CO_2$, and/or CO and/or $CH_4$. The gaseous substrate may serve as a carbon and/or energy source and/or a source of electron donors and/or electron acceptors for growth of the microorganisms and biosynthesis of bioproducts. In certain embodiments, amino acids, peptides, proteins, vitamins and/or other nutrients are synthesized from simple C1 and inorganic precursors including but not limited to one or more of the following: syngas, producer gas, $H_2$, $CO_2$, CO, $H_2O$, $NH_3$, $CH_4$, $CH_3OH$, HCOH, urea.

Microorganisms are also provided, such as a wild-type or engineered microorganism capable of growing on syngas, or producer gas, and/or $H_2$, and/or $CO_2$, and/or CO, and/or $CH_4$, and/or other waste gases, which are capable of producing amino acids including but not limited to lysine and/or methionine.

In certain embodiments, amino acids, and/or peptides, and/or proteins and/or vitamins are synthesized from simple C1 and inorganic precursors including but not limited to one or more of the following: $H_2$, $CO_2$, CO, $H_2O$, $NH_3$, $CH_4$, $CH_3OH$, HCOH, urea. In other non-limiting embodiments amino acids, and/or peptides, and/or proteins and/or vitamins are produced heterotrophically from multi-carbon organic molecules such as, but not limited to sugars.

In some embodiments, the disclosure relates to a method of producing one or more amino acids or proteins or vitamins, comprising exposing a bacterial cell to syngas and/or producer gas and/or gaseous $CO_2$ and/or $H_2$ and/or CO and/or $CH_4$, e.g., $H_2$ and $CO_2$, and/or CO, and/or $CH_4$; wherein the bacterial cell is capable of fixing gaseous $CO_2$ and/or other C1 molecules into one or more amino acids or proteins or vitamins, and wherein the microorganism does not comprise an exogenous nucleic acid or comprises at least a first exogenous nucleic acid. In some embodiments, the cell utilizes the gaseous substrate(s) as a source of reducing equivalents and/or metabolic energy for the synthesis of one or more amino acids or proteins or vitamins. In some embodiments, the microorganism through its native machinery produces amino acids and/or proteins and/or vitamins.

In some embodiments, the disclosure relates to a method for producing amino acids and/or proteins and/or proteinaceous biomass and/or vitamins, wherein the method comprises culturing a natural microorganism strain or an engineered microorganism in a bioreactor or solution with a feedstock comprising syngas and/or producer gas and/or $CO_2$ and/or $H_2$ gas and/or CO and/or $CH_4$ and/or biogas and/or natural gas, e.g., $H_2$ and $CO_2$, and/or CO, and/or $CH_4$. In some embodiments, the disclosure relates to a bioreactor comprising the composition or bacterial or microbial cells described herein. In some embodiments, the disclosure relates to a system for the production of one or more amino acids, proteins, or nutrients, comprising a bioreactor, which comprises: (a) a microorganism population comprising a cell described herein; and (b) an inlet connected to a feedstock source allowing delivery of a feedstock comprising syngas or producer gas and/or gaseous $CO_2$ and/or $H_2$ and/or CO and/or $CH_4$ and/or methanol, e.g., $H_2$ and $CO_2$, and/or CO, and/or $CH_4$, and/or methanol.

In some embodiments the disclosure relates to a method of producing amino acids, or proteins, or other nutrients in a microorganism population comprising the cell of the composition described herein, wherein the method comprises: culturing a population of microorganisms comprising the cell or the composition described herein in a feedstock comprising syngas or producer gas and/or gaseous $CO_2$ and/or $H_2$ and/or CO and/or $CH_4$ and/or methanol, e.g., $H_2$ and $CO_2$, and/or CO, and/or $CH_4$, and/or methanol.

In some embodiments, the disclosure relates to a method of manufacturing one or more amino acids, or proteins, or other nutrients, comprising (a) culturing a cell described herein in a reaction vessel or bioreactor in the presence of syngas or producer gas and/or gaseous $CO_2$ and/or $H_2$ and/or CO and/or $CH_4$, e.g., $H_2$ and $CO_2$, and/or CO, and/or $CH_4$, wherein the cell produces and/or secretes one or more amino acids, or proteins, or other nutrients in a quantity equal to or greater than at least 10% of the cell's total dry cellular mass; and (b) separating the one or more amino acids, or proteins, or other nutrients, or a whole cell product from the reaction vessel. In some embodiments, the method further comprises purifying the one or more amino acids, or proteins, or other nutrients, or whole cell products after separation from the reaction vessel or bioreactor. In some embodiments, the one or more amino acids, or proteins, or other nutrients, or whole cell products are components of, or precursors to, or are included within a feed or nutrient supply or fertilizer provided to another organism. In some embodiments, the disclosure relates to a method of producing one or more amino acids, comprising exposing a bacterial cell, archaeal cell, and/or other microbial cell to syngas and/or gaseous $CO_2$ and/or $H_2$ and/or CO and/or $CH_4$, e.g., $H_2$ and $CO_2$, and/or CO, and/or $CH_4$; wherein the cell is capable of fixing gaseous $CO_2$ and/or other C1 carbon sources into one or more amino acids and/or proteins and/or vitamins; wherein the compounds are recovered from the bioreactor and fed to a second or more additional reactors and/or process steps wherein the compounds are post-processed to generate products including but not limited to one or more of the following: fertilizer, biostimulant, growth supplement, human nutrition, or vitamins.

Compositions and methods are provided for the capture of carbon dioxide from carbon dioxide-containing gas streams and/or atmospheric carbon dioxide or carbon dioxide in dissolved, liquefied or chemically-bound form through a chemical and biological process that utilizes obligate or facultative chemoautotrophic microorganisms, and particularly chemolithoautotrophic organisms, in one or more carbon fixing process steps. The disclosure also provides compositions and methods for the recovery, processing, and use of the chemical products of chemosynthetic reactions performed by chemoautotrophs to fix inorganic carbon into organic compounds that are intermediate or finished chemicals, including but not limited to amino acids and/or protein and/or vitamins and/or biomass. The disclosure also provides compositions and methods for the generation, processing and delivery of chemical nutrients needed for chemosynthesis and maintenance of chemoautotrophic cultures, including but not limited to the provision of electron donors and electron acceptors needed for chemosynthesis. The disclosure also provides compositions and methods for the maintenance of an environment conducive for chemosynthesis and chemoautotrophic growth, and the recovery and recycling of unused chemical nutrients and process water.

One feature of certain embodiments herein is the inclusion of one or more process steps that utilize chemotrophic microorganisms as a biocatalyst for the conversion of C1 chemicals into longer carbon chain organic molecules (i.e., C2 or longer, and in some embodiments, C5 or longer, carbon chain molecules), within an overall process for the conversion of C1 carbon sources, including but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks and/or methane feedstocks. In some such embodiments C1 containing syngas, or process gas, or C1 chemicals in a liquid form or dissolved in solution are pumped or otherwise added to a vessel or enclosure containing nutrient media and chemotrophic microorganisms. In some such cases, chemotrophic microorganisms perform biochemical synthesis to elongate C1 chemicals into longer carbon chain organic chemicals using the carbon and electrons stored in the C1 chemical, and/or electrons and hydrogen from molecular hydrogen and/or valence or conduction electrons in solid state electrode materials and/or one or more of the following list of electron donors pumped or otherwise provided to the nutrient media, including but not limited to: ammonia; ammonium; carbon monoxide; dithionite; elemental sulfur; hydrocarbons; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; thionite; transition metals or their sulfides, oxides, chalcogenides, halides, hydroxides, oxyhydroxides, sulfates, or carbonates, in soluble or solid phases. The electron donors can be oxidized by electron acceptors in a chemosynthetic respiratory reaction. In certain embodiments, electron acceptors that are used for respiration by the microorganisms described herein include but are not limited to one or more of the following: oxygen, carbon dioxide, ferric iron or other transition metal ions, nitrates, nitrites, oxygen, or holes in solid state electrode materials. In certain non-limiting embodiments, the said chemotrophic microorganism is a knallgas or oxyhydrogen microorganism.

In certain embodiments, the disclosure relates to chemotrophic bacterial strains that do not comprise an exogenous nucleic acid or that comprise one or more exogenous nucleic acid sequences. The present invention arises in part from the discovery that chemotrophic bacteria and particular related microorganisms provide unforeseen advantages in the economic and large-scale production of chemicals, proteins, feeds, fertilizers, monomers, oils, fuels, and other biological substances from gaseous and waste carbon feedstocks.

The proteins, lipids and other biochemicals synthesized by the microorganisms described herein can be applied to uses including but not limited to: feedstock for the production of biostimulants, biofertilizers, or mushroom growth supplements; and as ingredients in biostimulants, biofertilizers, fertilizers, animal feed, food, personal care, and cosmetic products. In some embodiments, enzymatic and chemical processes can be utilized to produce vitamins, amino acids, and/or proteins. Some embodiments provide methods for the production of biostimulants and/or fertilizers. In addition, the disclosure provides methods for culturing and/or modifying chemotrophic bacteria for improved amino acid and/or protein yield and/or lower production costs.

The disclosure relates to methods and mechanisms to confer production and/or secretion of carbon-based products of interest, including but not limited to chemicals, monomers, polymers, amino acids, proteins, polysaccharides, vitamins, and nutraceutical or pharmaceutical products or intermediates thereof, in obligate or facultative chemotrophic organisms such that these organisms convert carbon dioxide and/or other forms of inorganic carbon and/or syngas and/or other C1 compounds such as methanol and/or the liquid, gaseous, and solid products of pyrolytic reactions such as pyrolysis gas and/or oil, into carbon-based products of interest, and in particular the use of such organisms for the commercial production of chemicals, monomers, polymers, amino acids, proteins, polysaccharides, vitamins, animal feeds, biostimulants, fertilizers, and nutraceutical or pharmaceutical products or intermediates thereof. However, this disclosure also related to methods of producing said products heterotrophically from multi-carbon organic molecular carbon sources such as but not limited to sugars.

In some embodiments the disclosure also provides compositions and methods for chemical process steps that occur in series and/or in parallel with the chemosynthetic reaction steps that: convert unrefined raw input chemicals to more refined chemicals that are suited for supporting the chemosynthetic carbon fixing step; that convert energy inputs into a chemical form that can be used to drive chemosynthesis, and specifically into chemical energy in the form of electron donors and electron acceptors; that direct inorganic carbon captured from industrial or atmospheric or aquatic sources to the carbon fixation step or steps of the process under conditions that are suitable to support chemosynthetic carbon fixation; that further process the output products of the chemosynthetic carbon fixation steps into a form suitable for storage, shipping, and sale, with said products including but not limited to amino acids and/or proteins and/or vitamins and/or biomass. The fully chemical, abiotic, process steps combined with the biological chemosynthetic carbon fixation steps constitute the overall carbon capture and conversion process of the present invention. The present invention utilizes the unique ease of integrating chemoautotrophic microorganisms within a chemical process stream as a biocatalyst, as compared to other lifeforms.

Unless defined otherwise herein, all technical and scientific terms used herein have the same meaning as commonly understood by one of ordinary skill in the art to which this invention belongs. Singleton, et al., Dictionary of Microbiology and Molecular Biology, second ed., John Wiley and Sons, New York (1994), and Hale & Markham, The Harper Collins Dictionary of Biology, Harper Perennial, N.Y. (1991) provide one of skill with a general dictionary of many of the terms used in this invention. Any methods and materials similar or equivalent to those described herein can be used in the practice or testing of the methods, systems, and compositions described herein.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, Molecular Cloning: A Laboratory Manual, second edition (Sambrook et al., 1989); Oligonucleotide Synthesis (M. J. Gait, ed., 1984; Current Protocols in Molecular Biology (F. M. Ausubel et al., eds., 1994); PCR: The Polymerase Chain Reaction (Mullis et al., eds., 1994); and Gene Transfer and Expression: A Laboratory Manual (Kriegler, 1990).

Numeric ranges provided herein are inclusive of the numbers defining the range.

Unless otherwise indicated, nucleic acids are written left to right in 5' to 3' orientation; amino acid sequences are written left to right in amino to carboxy orientation, respectively.

Definitions

"A," "an" and "the" include plural references unless the context clearly dictates, thus the indefinite articles "a", "an,", and "the" as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

The term "about" as used herein when referring to a measurable value such as an amount, a temporal duration, and the like, is meant to encompass variations of ±20%, ±10%, ±5%, ±1%, or ±0.1% from the specified value, as such variations are appropriate to perform the disclosed methods or in connection with a disclosed composition.

The term "amino acid" refers to a molecule containing both an amine group and a carboxyl group that are bound to a carbon, which is designated the alpha-carbon. Suitable amino acids include, without limitation, both the D- and L-isomers of the naturally occurring amino acids, as well as non-naturally occurring amino acids prepared by organic synthesis or other metabolic routes. In some embodiments, a single "amino acid" might have multiple sidechain moieties, as available per an extended aliphatic or aromatic backbone scaffold. Unless the context specifically indicates otherwise, the term amino acid, as used herein, is intended to include amino acid analogs.

"Anabolism" refers to the process by which living organisms synthesize complex molecules of life from simpler ones. Anabolic processes produce peptides, proteins, polysaccharides, lipids, and nucleic acids. The energy required for anabolism is supplied by intracellular energy carriers such as adenosine triphosphate (ATP).

"Auxins" are a class of plant hormones (or plant growth substances) with some morphogen-like characteristics. Auxins have a central role in coordination of many growth and behavioral processes in the plant's life cycle and are essential for plant body development.

"Bioabsorption" refers to the process whereby substances are absorbed by tissues and organs of organisms.

"Bio-stimulants" or "Biostimulant" refers to compounds capable of stimulating the growth and development of plants, e.g., agricultural crops, as well as increasing and enhancing microbiological activity of the soil.

The term "biomass" refers to a material produced by growth and/or propagation of cells. Biomass may contain cells and/or intracellular contents as well as extracellular material, including, but not limited to, compounds secreted by a cell.

The term "bioreactor" or "fermenter" refers to a closed or partially closed vessel in which cells are grown and maintained. The cells may be, but are not necessarily held in liquid suspension. In some embodiments, rather than being held in liquid suspension, cells may alternatively be grown and/or maintained in contact with, on, or within another non-liquid substrate including but not limited to a solid growth support material.

The term "carbon-fixing" reaction or pathway refers to enzymatic reactions or metabolic pathways that convert forms of carbon that are gaseous under ambient conditions, including but not limited to $CO_2$, CO, and $CH_4$, into carbon-based biochemicals that are liquid or solid under ambient conditions, or which are dissolved into, or held in suspension in, aqueous solution.

"Carbon source" refers to the types of molecules from which a microorganism derives the carbon needed for organic biosynthesis.

"Carboxydotrophic" Microorganisms that can tolerate or oxidize carbon monoxide. In preferred embodiments a carboxydotrophic microorganism can utilize CO as a carbon source and/or as a source of reducing electrons for biosynthesis and/or respiration.

The term "catalyst" refers to a chemical actor, such as a molecule or macromolecular structure, which accelerates the speed at which a chemical reaction occurs where a reactant or reactants is converted into a product or products, while the catalyst is not turned into a product itself, or otherwise changed or consumed at the completion of the chemical reaction. After a catalyst participates in one chemical reaction, because it is unchanged, it may participate in further chemical reactions, acting on additional reactants to create additional products. To accelerate a chemical reaction a catalyst decreases the activation energy barrier across the reaction path allowing it to occur at a colder temperature, or faster at a given temperature. In this way, a more rapid approach of the system to chemical equilibrium may be achieved. Catalysts subsume enzymes, which are protein catalysts.

The term "cellulosic material" refers to any material with a high amount of cellulose, which is a polysaccharide having the formula $(C_6H_{10}O_5)_n$, that generally consists of a linear chain of hundreds to thousands of β (1→4) linked D-glucose monomers. Sources of cellulosic material include, but are not limited, to cardboard, cotton, corn stover, paper, lumber chips, sawdust, sugar beet pulp, sugar cane bagasses, and switchgrass.

"Chemoautotrophic" refers to organisms that obtain energy by the oxidation of chemical electron donors by chemical electron acceptors and synthesize all the organic compounds needed by the organism to live and grow from carbon dioxide.

The term "CoA" or "coenzyme A" refers to an organic cofactor for condensing enzymes involved in fatty acid synthesis and oxidation, pyruvate oxidation, acetyl or other acyl group transfer, and in other acetylation.

The term "cofactor" subsumes all molecules needed by an enzyme to perform its catalytic activity. In some embodiments, the cofactor is any molecule apart from the substrate.

In the claims, as well as in the specification, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively.

The term "culturing" refers to growing a population of cells, e.g., microbial cells, under suitable conditions for growth, in a liquid or solid medium.

The term "derived from" encompasses the terms "originated from," "obtained from," "obtainable from," "isolated from," and "created from," and generally indicates that one specified material finds its origin in another specified material or has features that can be described with reference to another specified material.

"Elicitors" are extrinsic or foreign molecules often associated with plant pests, diseases or synergistic organisms. Elicitor molecules can attach to special receptor proteins located on plant cell membranes.

"Energy source" refers to either the electron donor that is oxidized by oxygen in aerobic respiration or the combination of electron donor that is oxidized and electron acceptor that is reduced in anaerobic respiration.

"Edaphic" means of or relating to soil, especially as it affects living organisms and/or that which is associated with a particular type of soil.

The term "lignocellulosic material" is any material composed of cellulose, hemicellulose, and lignin where the carbohydrate polymers (cellulose and hemicelluloses) are tightly bound to lignin. Lignocellulosic materials subsume agricultural residues (including corn stover and sugarcane bagasse), most biomass energy crops, wood residues (including sawmill and paper mill discards), and a substantial fraction of municipal waste.

The terms "lipids" refers to category of molecules that can be dissolved in nonpolar solvents (such as chloroform and/or ether) and which also have low or no solubility in water. The hydrophobic character of lipids molecules typically results from the presence of long chain hydrocarbon sections within the molecule. Lipids subsume the following molecule types: hydrocarbons, fatty acids (saturated and unsaturated), fatty alcohols, fatty aldehydes, hydroxy acids, diacids, monoglycerides, diglycerides, triglycerides, phospholipids, sphingolipids, sterols such as cholesterol and steroid hormones, fat-soluble vitamins (such as vitamins A, D, E and K), polyketides, terpenoids, and waxes.

The term "lysate" refers to the liquid containing a mixture and/or a solution of cell contents that result from cell lysis. In some embodiments, the methods described herein comprise a purification of chemicals or mixture of chemicals in a cellular lysate. In some embodiments, the methods comprise a purification of amino acids and/or protein in a cellular lysate.

The term "lysis" refers to the rupture of the plasma membrane and if present, the cell wall of a cell such that a significant amount of intracellular material escapes to the extracellular space. Lysis can be performed using electrochemical, mechanical, osmotic, thermal, or viral means. In some embodiments, the methods described herein comprise performing a lysis of cells or microorganisms as described herein in order to separate a chemical or mixture of chemicals from the contents of a bioreactor. In some embodiments, the methods comprise performing a lysis of cells or microorganisms described herein in order to separate an amino acid or mixture of amino acids and/or proteins from the contents of a bioreactor or cellular growth medium.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

"Titer" refers to amount of a substance produced by a microorganism per unit volume in a microbial fermentation process. For example, biomass titer may be expressed as grams of biomass produced per liter of solution.

"Yield" refers to amount of a product produced from a feed material (for example, sugar) relative to the total amount of the substance that would be produced if all of the feed substance were converted to product. For example, amino acid yield may be expressed as % of amino acid produced relative to a theoretical yield if 100% of the feed substance were converted to amino acid.

"Productivity" refers to the amount of a substance produced by a microorganism per unit volume per unit time in a microbial fermentation process. For example, biomass productivity may be expressed as grams of biomass produced per liter of solution per hour.

"Wild-type" refers to a microorganism as it occurs in nature.

A "gene" refers to a DNA segment that is involved in producing a polypeptide and includes regions preceding and following the coding regions as well as intervening sequences (introns) between individual coding segments (exons).

The terms "recovered," "isolated," "purified," and "separated" as used herein refer to a material (e.g., a protein, nucleic acid, or cell) that is removed from at least one component with which it is naturally associated. For example, these terms may refer to a material that is substantially or essentially free from components which normally accompany it as found in its native state, such as, for example, an intact biological system.

"Lithoautotrophic" refers to a specific type of chemoautotrophy where the organism utilizes the oxidation of inorganic chemical electron donors by inorganic chemical electron acceptors as an energy source.

The term "knallgas" refers to the mixture of molecular hydrogen and oxygen gas. A "knallgas microorganism" is a microbe that can use hydrogen as an electron donor and oxygen as an electron acceptor in respiration for the generation of intracellular energy carriers such as Adenosine-5'-triphosphate (ATP). The terms "oxyhydrogen" and "oxyhydrogen microorganism" can be used synonymously with "knallgas" and "knallgas microorganism," respectively. Knallgas microorganisms generally use molecular hydrogen by means of hydrogenases, with some of the electrons donated from $H_2$ that is utilized for the reduction of $NAD^+$ (and/or other intracellular reducing equivalents) and some of the electrons from $H_2$ that is used for aerobic respiration. Knallgas microorganisms generally fix $CO_2$ autotrophically, through pathways including but not limited to the Calvin Cycle or the reverse citric acid cycle ["Thermophilic bacteria", Jakob Kristjansson, Chapter 5, Section III, CRC Press, (1992)].

"Heterotrophic" refers to organisms that cannot synthesize all the organic compounds needed by the organism to live and grow from carbon dioxide, and which must utilize organic compounds for growth. Heterotrophic organisms cannot produce their own food and instead obtain food and energy by taking in and metabolizing organic substances, such as plant or animal matter, i.e., rather than fixing carbon from inorganic sources such as carbon dioxide.

"Nicotinamide adenine dinucleotide" is a coenzyme found in all living cells that is involved in redox reactions, carrying electrons from one reaction to another. Nicotinamide adenine dinucleotide exists in two forms: oxidized and reduced forms abbreviated as $NAD^+$ and NADH, respectively.

"Hydrogen-oxidizer" refers to a microorganism that utilizes reduced $H_2$ as an electron donor for the production of intracellular reducing equivalents and/or in respiration.

"Acetogen" refers to a microorganism that generates acetate and/or other short chain organic acids up to C4 chain length as a product of anaerobic respiration.

"Methanogen" refers to a microorganism that generates methane as a product of anaerobic respiration.

"Methylotroph" refers to a microorganism that can use reduced one-carbon compounds, such as but not limited to methanol or methane, as a carbon source and/or as an electron donor for their growth.

"Extremophile" refers to a microorganism that thrives in physically or geochemically extreme conditions (e.g., high or low temperature, pH, or high salinity) compared to conditions on the surface of the Earth or the ocean that are typically tolerated by most life forms found on or near the earth's surface.

"Thermophile" refers to a type of extremophile that thrives at relatively high temperatures for life, typically about 45° C. to about 122° C.

"Hyperthermophile" refers to a type of extremophile that thrives in extremely hot environments for life, typically about 60° C. (140° F.) or higher.

"Acidophile" refers to a type of extremophile that thrives under highly acidic conditions (usually at pH 2.0 or below).

"Halophile" refers to a type of extremophile that thrives in environments with very high concentrations of salt.

"Psychrophile" refers to a type of extremophile capable of growth and reproduction in cold temperatures, typically about 10° C. and lower.

"Producer gas" refers to a gas mixture containing various proportions of $H_2$, CO, and $CO_2$, and having heat value typically ranging between one half and one tenth that of natural gas per unit volume under standard conditions. Producer gas can be generated various ways from a variety of feedstocks, including gasification, steam reforming, or autoreforming of carbon-based feedstocks. In addition to $H_2$, CO, and $CO_2$, producer gases can contain other constituents including but not limited to methane, hydrogen sulfide, condensable gases, tars, and ash depending upon the generation process and feedstock. The proportion of $N_2$ in the mixture can be high or low depending whether air is used as an oxidant in the reactor or not and if the heat for the reaction is provided by direct combustion or through indirect heat exchange.

"Flavonoids" (or bioflavonoids) (from the Latin word *flavus* meaning yellow, their color in nature) are a class of plant and fungus secondary metabolites. Chemically, flavonoids have the general structure of a 15-carbon skeleton, which consists of two phenyl rings (A and B) and heterocyclic ring (C). This carbon structure can be abbreviated C6-C3-C6.

"Fertilizer" is an organic or inorganic, natural or synthetic substance which is used to enrich the soil and to provide plants with one or more essential nutrients for ordinary vegetative growth. In certain embodiments, the term fertilizer also refers to nutrients for fungi and the production of mushrooms.

"Fertigation" is the injection of fertilizers, soil amendments, and other water-soluble products into an irrigation system.

The term "gasification" refers to a generally high temperature process that converts carbon-based materials into a mixture of gases including hydrogen, carbon monoxide, and carbon dioxide called synthesis gas, syngas or producer gas. The process generally involves partial combustion and/or the application of externally generated heat along with the controlled addition of oxygen and/or steam such that insufficient oxygen is present for complete combustion of the carbon-based material.

"Gibberellins" (GAs) are plant hormones that regulate growth and influence various developmental processes, including stem elongation, germination, dormancy, flowering, sex expression, enzyme induction, and leaf and fruit senescence.

"Glucosinolates" are natural components of many pungent plants such as mustard, cabbage, and horseradish. The pungency of those plants is due to mustard oils produced from glucosinolates when the plant material is chewed, cut, or otherwise damaged.

The terms "microorganism" and "microbe" mean microscopic single celled life forms.

The term "molecule" means any distinct or distinguishable structural unit of matter comprising one or more atoms, and includes for example hydrocarbons, lipids, polypeptides and polynucleotides.

The term "oleaginous" refers to something that is rich in oil or produces oil in high quantities.

"Oligopeptide" refers to a peptide that contains a relatively small number of amino-acid residues, for example, about 2 to about 20 amino acids.

The term "organic compound" refers to any gaseous, liquid, or solid chemical compound that contains carbon atoms, with the following exceptions that are considered inorganic: carbides, carbonates, simple oxides of carbon, cyanides, and allotropes of pure carbon such as diamond and graphite.

"Papain", also known as papaya proteinase I, is a cysteine protease (EC 3.4.22.2) enzyme present in papaya (*Carica papaya*) and mountain papaya (*Vasconcellea cundinamarcensis*).

"Pepsin" is an enzyme that breaks down proteins into smaller peptides (i.e., a protease). It is produced in the stomach and is one of the main digestive enzymes in the digestive systems of humans and many other animals, where it helps digest the proteins in food.

"Peptide" a compound consisting of two or more amino acids linked in a chain, the carboxyl group of each acid being joined to the amino group of the next by a bond of the type R—OC—NH—R', for example, about 2 to about 50 amino acids.

The term "precursor to" or "precursor of" is an intermediate towards the production of one or more of the components of a finished product.

The term "producing" includes both the production of compounds intracellularly and extracellularly, including the secretion of compounds from the cell.

"Phyllosphere" is a term used in microbiology to refer to the total above-ground portions of plants as habitat for microorganisms.

"Phytotoxicity" is a toxic effect of a compound on plant growth. Such damage may be caused by a wide variety of compounds, including trace metals, salinity, pesticides, phytotoxins, or allelochemicals.

As used herein, "polypeptide" refers to a composition comprised of amino acids and recognized as a protein by those of skill in the art. The conventional one-letter or three-letter code for amino acid residues is used herein. The terms "polypeptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also, included within the definition are, for example, polypeptides containing one or more analogs of an amino acid (including, for example, unnatural amino acids, etc.), as well as other modifications known in the art.

"Rhizosphere" is the narrow region of soil that is directly influenced by root secretions and associated soil microorganisms.

"Sulfur-oxidizer" refers to microorganisms that utilize reduced sulfur containing compounds including but not limited to $H_2S$ as electron donors for the production of intracellular reducing equivalents and/or in respiration.

"Syngas" or "Synthesis gas" refers to a type of gas mixture, which like producer gas contains $H_2$ and CO, but which has been more specifically tailored in terms of $H_2$ and CO content and ratio and levels of impurities for the synthesis of a particular type of chemical product, such as but not limited to methanol or fischer-tropsch diesel. Syngas generally contains $H_2$, CO, and $CO_2$ as major components, and it can be generated through established methods including: steam reforming of methane, liquid petroleum gas, or biogas; or through gasification of any organic, flammable, carbon-based material, including but not limited to biomass, waste organic matter, various polymers, peat, and coal. The hydrogen component of syngas can be increased through the reaction of CO with steam in the water gas shift reaction, with a concomitant increase in $CO_2$ in the syngas mixture.

"Trypsin" (EC 3.4.21.4) is a serine protease from the PA clan superfamily, found in the digestive system of many vertebrates, where it hydrolyses proteins. Trypsin is formed in the small intestine when its proenzyme form, the trypsinogen produced by the pancreas, is activated. Trypsin cleaves peptide chains mainly at the carboxyl side of the amino acids lysine or arginine, except when either is followed by proline. It is used for numerous biotechnological processes. The process is commonly referred to as trypsin proteolysis or trypsinisation, and proteins that have been digested/treated with trypsin are said to have been trypsinized. Certain embodiments herein utilize trypsinisation of proteins produced as described herein.

As used herein, the term "polynucleotide" refers to a polymeric form of nucleotides of any length and any three-dimensional structure and single- or multi-stranded (e.g., single-stranded, double-stranded, triple-helical, etc.), which contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. The terms "polynucleotide," "nucleic acid," and "oligonucleotide" are used herein interchangeably. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR.sub.2 ("amidate"), P(O)R, P(O)OR', CO or CH.sub.2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Polynucleotides may be linear or circular or comprise a combination of linear and circular portions.

As used herein, the term "host cell" refers to a cell or cell line into which a recombinant expression vector for production of a polypeptide may be transfected for expression of the polypeptide. Host cells include progeny of a single host cell, and the progeny may not necessarily be completely identical (in morphology or in total genomic DNA complement) to the original parent cell due to natural, accidental, or deliberate mutation. A host cell includes cells transfected or transformed in vivo with an expression vector.

The term "recombinant," refers to genetic material (i.e., nucleic acids, the polypeptides they encode, and vectors and cells comprising such polynucleotides) that has been modified to alter its sequence or expression characteristics, such as by mutating the coding sequence to produce an altered polypeptide, fusing the coding sequence to that of another gene, placing a gene under the control of a different promoter, expressing a gene in a heterologous organism, expressing a gene at a decreased or elevated levels, expressing a gene conditionally or constitutively in manner different from its natural expression profile, and the like. Generally recombinant nucleic acids, polypeptides, and cells based thereon, have been manipulated by man such that they are not identical to related nucleic acids, polypeptides, and cells found in nature. A recombinant cell may also be referred to as "engineered."

As used herein, a "vector" refers to a polynucleotide sequence designed to introduce nucleic acids into one or more cell types. Vectors include cloning vectors, expression vectors, shuttle vectors, plasmids, phage particles, cassettes and the like.

As used herein, the term "expression" refers to the process by which a polypeptide is produced based on the nucleic acid sequence of a gene. The process includes both transcription and translation.

As used herein, "expression vector" refers to a DNA construct containing a DNA coding sequence (e.g., gene sequence) that is operably linked to one or more suitable control sequence(s) capable of effecting expression of the coding sequence in a host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. The plasmid is the most commonly used form of expression vector. However, the invention is intended to include such other forms of expression vectors that serve equivalent functions and which are, or become, known in the art.

A "promoter" refers to a regulatory sequence that is involved in binding RNA polymerase to initiate transcription of a gene. A promoter may be an inducible promoter or a constitutive promoter. An "inducible promoter" is a promoter that is active under environmental or developmental regulatory conditions.

The term "operably linked" refers to a juxtaposition or arrangement of specified elements that allows them to perform in concert to bring about an effect. For example, a promoter is operably linked to a coding sequence if it controls the transcription of the coding sequence.

"Under transcriptional control" is a term well understood in the art that indicates that transcription of a polynucleotide sequence depends on its being operably linked to an element which contributes to the initiation of, or promotes transcription.

The term "heterologous" or "exogenous," with reference to a polynucleotide or protein, refers to a polynucleotide or protein that does not naturally occur in a specified cell, e.g., a host cell. It is intended that the term encompass proteins that are encoded by naturally occurring genes, mutated genes, and/or synthetic genes. In contrast, the term "homologous," with reference to a polynucleotide or protein, refers to a polynucleotide or protein that occurs naturally in the cell.

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. The methods and techniques of the present disclosure are generally performed according to conventional methods well-known in the art. Generally, nomenclatures used in connection with, and techniques of biochemistry, enzymology, molecular and cellular biology, microbiology, genetics and protein and nucleic acid chemistry and hybridization described herein are those well-known and commonly used in the art. The methods and techniques of the present disclosure are generally performed according to conventional methods well known in the art and as described in various general and more specific references that are cited and discussed throughout the present specification unless otherwise indicated.

Production of Amino Acids, Proteins, and Other Biological Nutrients from Gaseous Energy and Carbon Substrates In some embodiments, natural or engineered microorganisms are provided that are capable of converting producer gas or a gas mixture containing $H_2$ and/or CO and/or $CO_2$ and/or $CH_4$, e.g., $H_2$ and $CO_2$, and/or CO, and/or $CH_4$, into amino acids, proteins, and other biological nutrients. In some embodiments, natural or engineered microorganisms are provided that are capable of converting producer gas or a gas mixture containing $H_2$ and/or CO and/or $CO_2$ and/or $CH_4$, e.g., $H_2$ and $CO_2$, and/or CO, and/or $CH_4$, into amino acids, proteins, vitamins and/or other biological nutrients. In certain embodiments one or more B vitamin is produced, including but not limited to one or more of the following: vitamin B1, B2, and/or B12.

In some embodiments, a natural microorganism is provided that is capable of growing on syngas, and/or $H_2$ and $CO_2$, and/or CO, and/or $CH_4$, and/or other waste gases and which is capable of producing amino acids, proteins, vitamins, including but not limited to B vitamins, and/or other biological nutrients using said gases as a growth substrate.

In some embodiments, a method is provided for producing amino acids, proteins, and other biological nutrients including but not limited to vitamins, such as but not limited to B vitamins, by combining, in a bioreactor or solution, a carbon-containing gas, and a natural or engineered strain microorganism that converts a carbon-containing gas such as syngas, producer gas, $CO_2$, carbon monoxide and mixtures of the same containing hydrogen gas; $H_2$ and $CO_2$, and/or CO, and/or $CH_4$; and/or C1 compounds, gaseous or liquid, including but not limited to methanol or methane, into amino acids, proteins, and/or other biological nutrients including but not limited to vitamins, such as but not limited to B vitamins.

Producer gas used in the process may come from sources that include gasification of waste feedstock and/or biomass residue feedstock, or waste gas from industrial processes, or reforming of methane containing gases including by not limited to natural gas, biogas, landfill gas, stranded natural gas and/or flared natural gas.

In some embodiments, methane may be converted to amino acids, proteins, and/or other biological nutrients including but not limited to vitamins, using engineered or natural microorganisms and methods described herein.

Microorganisms

In some embodiments, microorganisms utilized in the methods described herein are chemoautotrophs. Chemoautotrophs are capable of performing chemosynthetic reactions that fix $CO_2$, and/or other forms of inorganic carbon, to organic compounds, using the potential energy stored in inorganic chemicals to drive the reaction, rather than radiant energy from light as in microorganisms performing photosynthesis [J. M. Shively, G. van Keulen, and W. G. Meijer, "Something from almost nothing: carbon dioxide fixation in chemoautotrophs" (1998) *Annual review of microbiology* 52:191-230 (http://dx.doi.org/10.1146/annurev.micro.52.1.191); A. J. Smith, J. London, and R. Y. Stanier" (1967) "Biochemical basis of obligate autotrophy in Blue-Green algae and thiobacilli" *Journal of Bacteriology* 94(4): 972-983 (http://jb.asm.org/content/94/4/972.abstract); M. Hugler, C. O. Wirsen, G. Fuchs, C. D. Taylor, and S. M. Sievert (2005) "Evidence for autotrophic $CO_2$ fixation via the reductive tricarboxylic acid cycle by members of the ε subdivision of proteobacteria" *Journal of Bacteriology* 187 (9):3020-3027 (http://dx.doi.org/10.1128/jb.187.9.3020-3027.2005); K. M. Scott and C. M. Cavanaugh (2007) "$CO_2$ uptake and fixation by endosymbiotic chemoautotrophs from the bivalve solemya velum" *Applied and Environmental Microbiology* 73(4):1174-1179 (http://dx.doi.org/10.1128/aem.01817-06)]. Carbon fixing biochemical pathways that occur in chemoautotrophs include the reductive tricarboxylic acid cycle, and the Calvin-Benson-Bassham cycle [J. M. Shively, G., et al. (1998), supra], and the Wood-Ljungdahl pathway [L. G. Ljungdahl (1986) "The autotrophic pathway of acetate synthesis in acetogenic bacteria" *Annual Review of Microbiology* 40(1):415-450 (http://dx.doi.org/10.1146/annurev.mi.40.100186.002215)].

Compositions comprising any of the microorganisms described herein (e.g., one or more microorganisms described herein) are also provided.

In some embodiments, the microorganism is selected from the genus *Hydrogenobacter*. In some embodiments, the microorganism is *Hydrogenobacter thermophilus*. In some embodiments, the microorganism contains the reverse tricarboxylic acid cycle (rTCA), also known as the reverse citric acid cycle or the reverse Krebs cycle. [Miura, A., Kameya, M., Arai, H., Ishii, M. & Igarashi, Y. (2008) "A soluble NADH-dependent fumarate reductase in the reductive tricarboxylic acid cycle of *Hydrogenobacter thermophilus* TK-6" J Bacteriol 190, 7170-7177, doi: JB.00747-08 [pii] 10.1128/JB.00747-08; Shively, J. M., van Keulen, G. & Meijer, W. G. (1998) "Something from almost nothing: carbon dioxide fixation in chemoautotrophs" *Annu Rev Microbiol* 52:191-230, doi:10.1146/annurev.micro.52.1.191; incorporated herein by reference in their entireties.].

In some embodiments, the microorganism is *Rhodococcus opacus* or *Rhodococcus jostii* or *Rhodococcus* sp. In some non-limiting embodiments, the microorganism is *Rhodococcus opacus* DSM 43205, DSM 43206, DSM 44193, and/or *Rhodococcus* sp. DSM 3346.

In some embodiments, the natural or engineered strain includes but is not limited to hydrogen utilizing microbes including but not limited to the genera *Rhodococcus, Gordonia, Ralstonia* or *Cupriavidus*. In some embodiments, the composition comprises a microorganism that can naturally grow on $H_2/CO_2$ and/or syngas, and wherein the microorganism can naturally accumulate lipid to 50% or more of the cell biomass by weight. In some embodiments, the microorganisms have a native ability to send a high flux of carbon down the fatty acid biosynthesis pathway. In some embodiments, the microorganism exhibiting these traits is *Rhodococcus opacus* (DSM 43205 or DSM 43206 or DSM 44193).

In some embodiments, the microorganism is of the class Actinobacteria comprising no exogenous genes or one or more exogenous gene(s). In some embodiments, the microorganism is of the class Actinobacteria or the family Nocardiaceae. In some embodiments, the microorganism is a *Corynebacterium, Gordonia, Rhodococcus, Mycobacterium*, or *Tsukamurella* microorganism comprising no exogenous genes or one or more exogenous gene(s). In some embodiments, microorganism of the family Nocardiaceae comprising no exogenous genes or one or more exogenous gene(s), wherein the microorganism is not of the genus *Mycobacterium*. In some embodiments, the microorganism is of the genus *Rhodococcus* comprising no exogenous genes or one or more exogenous gene(s), and in some embodiments the microorganism is a strain of the species *Rhodococcus* sp., *Rhodococcus opacus, Rhodococcus aetherivorans, Rhodococcus aurantiacus; Rhodococcus baikonurensis; Rhodococcus boritolerans; Rhodococcus equi; Rhodococcus coprophilus; Rhodococcus corynebacterioides; Nocardia corynebacterioides* (synonym: *Nocardia corynebacterioides*); *Rhodococcus erythropolis; Rhodococcus fascians; Rhodococcus globerulus; Rhodococcus gordoniae; Rhodococcus jostii; Rhodococcus koreensis; Rhodococcus kroppenstedtii; Rhodococcus maanshanensis; Rhodococcus marinonascens; Rhodococcus opacus; Rhodococcus percolatus; Rhodococcus phenolicus; Rhodococcus polyvorum; Rhodococcus pyridinivorans; Rhodococcus rhodochrous; Rhodococcus rhodnii*; (synonym: *Nocardia rhodnii*); *Rhodococcus ruber* (synonym: *Streptothrix rubra*);

*Rhodococcus* sp. RHA1; *Rhodococcus triatomae*; *Rhodococcus tukisamuensis*; *Rhodococcus wratislaviensis* (synonym: *Tsukamurella wratislaviensis*); *Rhodococcus yunnanensis*; *Rhodococcus zopfii*. In some embodiments, a *Rhodococcus* microorganism is provided that is non-infectious or non-pathogenic to animals and/or plants and/or humans. In some embodiments, the microorganism is *Rhodococcus equi* or *Rhodococcus fascians* that is non-infectious to animals and/or plants. In some embodiments, the microorganism is strain *Rhodococcus opacus* DSM number 43205 or 43206; or *Rhodococcus* sp. DSM number 3346. In some embodiments, the microorganism is *Rhodococcus* that is not a species selected from *Rhodococcus equi* and/or *Rhodococcus fascians*.

In some embodiments the microorganism is from the suborder corynebacterineae or the family burkholderiaceae. In some embodiments, the microorganism is not *E. coli*.

In some embodiments, a microorganism as described herein is not pathogenic to animals and/or plants and/or humans.

In some embodiments, a microorganism as described herein can accumulate protein to over 60% of the total cell mass. In some embodiments, the microorganism can accumulate protein to over 70% of the total cell mass. In some embodiments, the microorganism can accumulate protein to over 80% of the total cell mass. In some non-limiting embodiments, the microorganism is *Cupriavidus necator* DSM number 531 or 541.

In some embodiments, a microorganism as described herein can naturally grow on $H_2/CO_2$ and/or syngas, and the microorganism can naturally accumulate polyhydroxybutyrate (PHB) or polyhydroxyalkanoate (PHA) to 50% or more of the cell biomass by weight. In some embodiments, the microorganism has a native ability to direct a high flux of carbon through the acetyl-CoA metabolic intermediate, which can lead into fatty acid biosynthesis, along with a number of other synthetic pathways including PHA and PHB synthesis, as well as amino acids. In some embodiments, the microorganism exhibiting these traits is *Cupriavidus necator* (DSM 531 or DSM 541).

In some nonlimiting embodiments, the natural or engineered microorganism strain is *Corynebacterium autotrophicum*. In some nonlimiting embodiments, the natural or engineered microorganism is *Corynebacterium autotrophicum* and/or *Corynebacterium glutamicum*. In some embodiments, the microorganism is *Hydrogenovibrio marinus*. In some embodiments, the microorganism is *Rhodopseudomonas capsulata, Rhodopseudomonas palustris*, or *Rhodobacter sphaeroides*.

In some embodiments, the microorganism is an oxyhydrogen or knallgas strain. In some embodiments the microorganisms, or a composition comprising microorganisms, comprises one or more of the following knallgas microorganisms: *Aquifex pyrophilus, Aquifex aeolicus*, or other *Aquifex* sp.; *Cupriavidus necator* or *Cupriavidus metallidurans* or other *Cupriavidus* sp.; *Corynebacterium autotrophicum* or other *Corynebacterium* sp.; *Gordonia desulfuricans, Gordonia polyisoprenivorans, Gordonia rubripertincta, Gordonia hydrophobica, Gordonia westfalica*, or other *Gordonia* sp.; *Nocardia autotrophica, Nocardia opaca*, or other *Nocardia* sp.; purple non-sulfur photosynthetic bacteria, including but not limited to, *Rhodobacter sphaeroides, Rhodopseudomonas palustris, Rhodopseudomonas capsulata, Rhodopseudomonas viridis, Rhodopseudomonas sulfoviridis, Rhodopseudomonas blastica, Rhodopseudomonas spheroides, Rhodopseudomonas acidophila*, or other *Rhodopseudomonas* sp.; *Rhodobacter* sp., *Rhodospirillum rubrum*, or other *Rhodospirillum* sp.; *Rhodococcus opacus* or other *Rhodococcus* sp.; *Rhizobium japonicum* or other *Rhizobium* sp.; *Thiocapsa roseopersicina* or other *Thiocapsa* sp.; *Pseudomonas facilis, Pseudomonas flava, Pseudomonas putida, Pseudomonas hydrogenovora, Pseudomonas hydrogenothermophila, Pseudomonas palleronii, Pseudomonas pseudoflava, Pseudomonas saccharophila, Pseudomonas thermophile*, or other *Pseudomonas* sp.; *Hydrogenomonas pantotropha, Hydrogenomonas eutropha, Hydrogenomonas facilis*, or other *Hydrogenomonas* sp.; *Hydrogenobacter thermophiles, Hydrogenobacter halophilus, Hydrogenobacter hydrogenophilus*, or other *Hydrogenobacter* sp.; *Hydrogenophilus islandicus* or other *Hydrogenophilus* sp.; *Hydrogenovibrio marinus* or other *Hydrogenovibrio* sp.; *Hydrogenothermus marinus* or other *Hydrogenothermus* sp.; *Helicobacter pylori* or other *Helicobacter* sp.; *Xanthobacter autotrophicus, Xanthobacter flavus*, or other *Xanthobacter* sp.; *Hydrogenophaga flava, Hydrogenophaga palleronii, Hydrogenophaga pseudoflava*, or other *Hydrogenophaga* sp.; *Bradyrhizobium japonicum* or other *Bradyrhizobium* sp.; *Ralstonia eutropha* or other *Ralstonia* sp.; *Alcaligenes eutrophus, Alcaligenes facilis, Alcaligenes hydrogenophilus, Alcaligenes latus, Alcaligenes paradoxus, Alcaligenes ruhlandii*, or other *Alcaligenes* sp.; *Amycolata* sp.; *Aquaspirillum autotrophicum* or other *Aquaspirillum* sp.; *Arthrobacter* strain 11/X, *Arthrobacter methylotrophus*, or other *Arthrobacter* sp.; *Azospirillum lipoferum* or other *Azospirillum* sp.; *Variovorax paradoxus* or other *Variovorax* sp.; *Acidovorax facilis*, or other *Acidovorax* sp.; *Bacillus schlegelii, Bacillus tusciae*, other *Bacillus* sp.; *Calderobacterium hydrogenophilum* or other *Calderobacterium* sp.; *Derxia gummosa* or other *Derxia* sp.; *Flavobacterium autothermophilum* or other *Flavobacterium* sp.; *Microcyclus aquaticus* or other *Microcyclus* sp.; *Mycobacterium gordoniae* or other *Mycobacterium* sp.; *Paracoccus denitrificans* or other *Paracoccus* sp.; *Persephonella marina, Persephonella guaymasensis*, or other *Persephonella* sp.; *Renobacter vacuolatum* or other *Renobacter* sp.; *Seliberia carboxydohydrogena* or other *Seliberia* sp., *Streptomycetes coelicoflavus, Streptomycetes griseus, Streptomycetes xanthochromogenes, Streptomycetes thermocarboxydus*, and other *Streptomycetes* sp.; *Thermocrinis ruber* or other *Thermocrinis* sp.; *Wautersia* sp.; cyanobacteria including but not limited to *Anabaena oscillarioides, Anabaena spiroides, Anabaena cylindrica*, or other *Anabaena* sp., and *Arthrospira platensis, Arthrospira maxima*, or other *Arthrospira* sp.; green algae including but not limited to *Scenedesmus obliquus* or other *Scenedesmus* sp., *Chlamydomonas reinhardii* or other *Chlamydomonas* sp., *Ankistrodesmus* sp., and *Raphidium polymorphium* or other *Rhaphidium* sp; as well as a consortium of microorganisms that includes oxyhydrogen microorganisms.

In some non-limiting embodiments compositions comprising and methods of using chemoautotrophic metabolism are provided to produce ATP for the support of ATP consuming biosynthetic reactions and cellular maintenance, without the co-production of methane or short chain organic acids such as acetic or butyric acid, by means of energy conserving reactions for the production of ATP, which use inorganic electron donors and electron acceptors, including but not limited to the oxyhydrogen reaction.

A number of different microorganisms have been characterized that are capable of growing on carbon monoxide as an electron donor and/or carbon source (i.e., carboxydotrophic microorganisms). In some cases, carboxydotrophic microorganisms can also use $H_2$ as an electron donor and/or grow mixotrophically. In some cases, the carboxydotrophic microorganisms are facultative chemolithoautotrophs [Biology of the Prokaryotes, edited by J Lengeler, G. Drews, H. Schlegel, John Wiley & Sons, Jul. 10, 2009, is incorporated herein by reference in its entirety.]. In some embodiments the microorganisms or compositions comprising the microorganisms comprise one or more of the following carboxydotrophic microorganisms: *Acinetobacter* sp.; *Alcaligenes carboxydus* or other *Alcaligenes* sp.; *Arthrobacter* sp.; *Azomonas* sp.; *Azotobacter* sp.; *Bacillus schlegelii* or other *Bacillus* sp.; *Hydrogenophaga pseudoflava* or other *Hydrogenophaga* sp.; *Pseudomonas carboxydohydrogena, Pseudomonas carboxydovorans, Pseudomonas compransoris, Pseudomonas gazotropha, Pseudomonas thermocarboxydovorans*, or other *Pseudomonas* sp.; *Rhizobium japonicum* or other *Rhizobium* sp.; and *Streptomyces* G26, *Streptomyces thermoautotrophicus*, or other *Streptomyces* sp. In certain embodiments, a carboxydotrophic microorganism is used. In certain embodiments, a carboxydotrophic microorganism that is capable of chemolithoautotrophy is used. In certain embodiments, a carboxydotrophic microorganism that is able to utilize $H_2$ as an electron donor in respiration and/or biosynthesis is used.

In some embodiments microorganisms are provided that are capable of growing on syngas as the sole electron donor, source of hydrogen atoms, and carbon source.

In some embodiments the microorganisms or compositions comprising the microorganisms comprise obligate and/or facultative chemoautotrophic microorganisms including one or more of the following: *Acetoanaerobium* sp.; *Acetobacterium* sp.; *Acetogenium* sp.; *Achromobacter* sp.; *Acidianus* sp.; *Acinetobacter*sp.; *Actinomadura* sp.; *Aeromonas* sp.; *Alcaligenes* sp.; *Alcaligenes* sp.; *Aquaspirillum* sp.; *Arcobacter* sp.; *Aureobacterium* sp.; *Bacillus* sp.; *Beggiatoa* sp.; *Butyribacterium* sp.; *Carboxydothermus* sp.; *Clostridium* sp.; *Comamonas* sp.; *Dehalobacter* sp.; *Dehalococcoide* sp.; *Dehalospirillum* sp.; *Desulfobacterium* sp.; *Desulfomonile* sp.; *Desulfotomaculum* sp.; *Desulfovibrio* sp.; *Desulfurosarcina* sp.; *Ectothiorhodospira* sp.; *Enterobacter* sp.; *Eubacterium* sp.; *Ferroplasma* sp.; *Halothibacillus* sp.; *Hydrogenobacter* sp.; *Hydrogenomonas* sp.; *Leptospirillum* sp.; *Metallosphaera* sp.; *Methanobacterium* sp.; *Methanobrevibacter* sp.; *Methanococcus* sp.; *Methanococoides* sp.; *Methanogenium* sp.; *Methanolobus* sp.; *Methanomicrobium* sp.; *Methanoplanus* sp.; *Methanosarcina* sp.; *Methanospirillum* sp.; *Methanothermus* sp.; *Methanothrix* sp.; *Micrococcus* sp.; *Nitrobacter* sp.; *Nitrobacteraceae* sp., *Nitrococcus* sp., *Nitrosococcus* sp.; *Nitrospina* sp., *Nitrospira* sp., *Nitrosolobus* sp.; *Nitrosomonas* sp.; *Nitrosospira* sp.; *Nitrosovibrio* sp.; *Nitrospina* sp.; *Oleomonas* sp.; *Paracoccus* sp.; *Peptostreptococcus* sp.; *Planctomycetes* sp.; *Pseudomonas* sp.; *Ralstonia* sp.; *Rhodobacter* sp.; *Rhodococcus* sp.; *Rhodocyclus* sp.; *Rhodomicrobium* sp.; *Rhodopseudomonas* sp.; *Rhodospirillum* sp.; *Shewanella* sp.; *Siderococcus* sp.; *Streptomyces* sp.; *Sulfobacillus* sp.; *Sulfolobus* sp.; *Thermothrix* sp., *Thiobacillus* sp.; *Thiomicrospira* sp.; *Thioploca* sp.; *Thiosphaera* sp.; *Thiothrix* sp.; *Thiovulum* sp.; sulfur-oxidizers; hydrogen-oxidizers; iron-oxidizers; acetogens; and methanogens; consortiums of microorganisms that include chemoautotrophs; chemoautotrophs native to at least one of hydrothermal vents, geothermal vents, hot springs, cold seeps, underground aquifers, salt lakes, saline formations, mines, acid mine drainage, mine tailings, oil wells, refinery wastewater. coal seams, deep sub-surface; waste water and sewage treatment plants; geothermal power plants, sulfatara fields, and soils; and extremophiles selected from one or more of thermophiles, hyperthermophiles, acidophiles, halophiles, and psychrophiles.

In some embodiments, microorganisms are provided that are extremophiles that can withstand extremes in various environmental parameters, such as temperature, radiation, pressure, gravity, vacuum, desiccation, salinity, pH, oxygen tension, and chemicals. They include hyperthermophiles, such as *Pyrolobus fumarii*; thermophiles, such as *Synechococcus lividis*; mesophiles and psychrophiles, such as *Psychrobacter*, and/or extremely thermophilic sulfur-metabolizers such as *Thermoproteus* sp., *Pyrodictium* sp., *Sulfolobus* sp., and *Acidianus* sp.; radiation tolerant organisms such as *Deinococcus radiodurans*; pressure tolerant organisms including piezophiles or barophiles; desiccant tolerant and anhydrobiotic organisms including xerophiles, such as *Artemia salina*; microbes and fungi; salt tolerant organisms including halophiles, such as *Halobacteriacea* and *Dunaliella salina*; pH tolerant organisms including alkaliphiles, such as *Natronobacterium, Bacillus firmus* OF4, *Spirulina* spp., and acidophiles such as *Cyanidium caldarium* and *Ferroplasma* sp; gas tolerant organisms, which tolerate pure $CO_2$ including *Cyanidium caldarium*; and metal tolerant organisms including metalotolerants such as *Ferroplasma acidarmanus* and *Ralstonia* sp.

In certain embodiments, microorganisms provided herein comprise a cell line selected from eukaryotic plants, algae, cyanobacteria, green-sulfur bacteria, green non-sulfur bacteria, purple sulfur bacteria, purple non-sulfur bacteria, extremophiles, yeast, fungi, proteobacteria, engineered organisms thereof, and synthetic organisms. In certain embodiments, *Spirulina* is utilized.

In certain embodiments green non-sulfur bacteria are utilized which include but are not limited to the following genera: *Chloroflexus, Chloronema, Oscillochloris, Heliothrix, Herpetosiphon, Roseiflexus*, and *Thermomicrobium*.

In certain embodiments green sulfur bacteria are used which include but are not limited to the following genera: *Chlorobium, Clathrochloris*, and *Prosthecochloris*.

In certain embodiments purple sulfur bacteria are used, which include but are not limited to the following genera: *Allochromatium, Chromatium, Halochromatium, Isochromatium, Marichromatium, Rhodovulum, Thermochromatium, Thiocapsa, Thiorhodococcus*, and *Thiocystis*.

In certain embodiments purple non-sulfur bacteria are used which include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio*, and *Roseospira*.

In some embodiments the microorganism is a methanotroph and/or a methylotroph. In some embodiments the microorganism is in the genus *Methylococcus*. In some embodiments the microorganism is *Methylococcus capsulatus*. In some embodiments the microorganism is a methylotroph. In some embodiments the microorganism is in the genus *Methylobacterium*. In some embodiments the microorganism is drawn from one or more of the following species: *Methylobacterium zatmanii; Methylobacterium extorquens; Methylobacterium chloromethanicum*. In some embodiments, compositions are provided wherein the microorganism is a hydrogen-oxidizing chemoautotroph and/or a carboxydotroph and/or a methylotroph and/or methanotroph.

In certain embodiments, of the microorganisms are naturally occurring and/or non-genetically modified (non-GMO) microorganisms and/or non-pathogenic and/or rely on specific environmental conditions provided by the bioprocesses that are absent from the surrounding environment.

In certain embodiments, the microorganisms or consortium of microorganisms are isolated from environmental samples and enriched with desirable microorganisms using methods known in the art of microbiology through growth in the presence of targeted electron donors, including but not limited to one or more of: hydrogen, CO, syngas and/or methane, and electron acceptors including but not limited to one or more of oxygen, nitrate, ferric iron, and/or $CO_2$, and environmental conditions (e.g., temperature, pH, pressure, dissolved oxygen (DO), salinity, the presence of various impurities and pollutants, etc.).

In some embodiments, electron donors utilized in biosynthesis and/or respiration by the microorganisms include but are not limited to one or more of the following reducing agents: ammonia; ammonium; carbon monoxide; dithionite; elemental sulfur; hydrogen; metabisulfites; nitric oxide; nitrites; sulfates such as thiosulfates including but not limited to sodium thiosulfate ($Na_2S_2O_3$) or calcium thiosulfate ($CaS_2O_3$); sulfides such as hydrogen sulfide; sulfites; thionate; and thionite.

In some embodiments, the microorganism is able to produce ATP from an inorganic electron donor such as, but not limited to, $H_2$ and/or CO without the synthesis of methane or short chain organic acids, such as but not limited to acetic acid and/or butyric acid (short chain organic acids comprising carbon chain lengths from two to four carbons long). In some non-limiting embodiments, the microorganism produces ATP from an inorganic electron donor such as, but not limited to, $H_2$ and/or CO, coupled in respiration with an electron acceptor other than $CO_2$. In certain such embodiments, the electron acceptor is a stronger electron acceptor than $CO_2$ in the sense of having a more negative Gibbs free energy of reaction with the electron donor used in respiration.

In some embodiments, the microorganism is capable of converting syngas, and/or gaseous $CO_2$, and/or a mixture of $CO_2$ gas and $H_2$ gas, and/or CO, and/or $CH_4$, into one or more organic compounds, wherein less than 10% by weight of the organic compounds produced by the microorganism is methane. In some embodiments, the microorganism is capable of converting syngas, and/or gaseous $CO_2$, and/or a mixture of $CO_2$ gas and $H_2$ gas, and/or CO, and/or $CH_4$, into one or more organic compounds, wherein less than 10% by weight of the organic compounds produced are free organic acids (i.e., not included in a polymer), and/or salts of free organic acids, having carbon chain length of four carbons or less, excluding amino acids. In some embodiments, the microorganism is capable of converting syngas and/or gaseous $CO_2$, and/or a mixture of $CO_2$ gas and $H_2$ gas, and/or CO, and/or $CH_4$, into one or more organic compounds, wherein less than 10% by weight of the organic compounds produced are free organic acids (i.e., not included in a polymer), and/or salts of free organic acids, having carbon chain length of four carbons or less, excluding one or more of the following amino acids: alanine; threonine; serine; glycine, asparagine; aspartic acid; cysteine.

Certain embodiments utilize hydrogen-oxidizing, and/or CO-oxidizing, and/or $CH_4$ oxidizing microorganisms that use more electronegative electron acceptors in energy conserving reactions for ATP production, such as but not limited to $O_2$.

In some embodiments, the microorganism is capable of growing on untreated crude glycerol and/or glucose and/or methanol and/or acetate as the sole electron donor and carbon source. In some embodiments, the microorganism is able to grow mixotrophically on an organic carbon source and using an inorganic electron donor or carbon source.

In certain embodiments, microorganisms provided herein comprise a cell line selected from eukaryotic plants, algae, cyanobacteria, green-sulfur bacteria, green non-sulfur bacteria, purple sulfur bacteria, purple non-sulfur bacteria, extremophiles, yeast, fungi, proteobacteria, engineered organisms thereof, and synthetic organisms.

In certain non-limiting embodiments of microorganisms herein, there is no detectable acidogenesis caused by cellular respiration.

Microbial Cultures

The liquid cultures used to grow microorganism cells described herein can be housed in culture vessels known and used in the art. In some embodiments, large scale production in a bioreactor vessel can be used to produce large quantities of a desired molecule and/or biomass.

In certain embodiments, bioreactor vessels are used to contain, isolate, and/or protect the culture environment. For example, culture vessels can be used in some non-limiting embodiments for the production of organic compounds including but not limited to one or more of the following: amino acids; peptides; proteins; vitamins, such as but not limited to vitamin B1, B2, and B12; and/or other nutrients. The culture vessels include those that are known to those of ordinary skill in the art of large scale microbial culturing. Such culture vessels include but are not limited to one or more of the following: airlift reactors; biological scrubber columns; bubble columns; stirred tank reactors; continuous stirred tank reactors; counter-current, upflow, expanded-bed reactors; digesters and in particular digester systems such as known in the prior arts of sewage and waste water treatment or bioremediation; filters including but not limited to trickling filters, rotating biological contactor filters, rotating discs, soil filters; fluidized bed reactors; gas lift fermenters; immobilized cell reactors; loop reactors; membrane biofilm reactors; pachuca tanks; packed-bed reactors; plug-flow reactors; static mixers; trickle bed reactors; and/or vertical shaft bioreactors.

Microbial culturing aimed at the commercial production of organic compounds and specifically amino acids, peptides, proteins, and other nutrients is typically performed in bioreactors at much greater scale (e.g., 500 L, 1,000 L 5,000 L, 10,000 L, 50,000 L, 100,000 L, 1,000,000 L bioreactor volumes and higher).

In certain embodiments, chemoautotrophic and/or heterotrophic and/or carboxydotrophic and/or methanotrophic and/or methylotrophic microorganisms are grown in a liquid media inside a bioreactor using methods described herein.

In some embodiments, the bioreactor containing the microorganisms is constructed of opaque materials that keep the culture in near or total darkness. Bioreactors constructed out of opaque materials such as steel and/or other metallic alloys and/or reinforced concrete and/or fiberglass and/or various high strength plastic materials can be designed to have large working volumes. In some embodiments, fermenters constructed of steel or other metallic alloys that are 50,000 liters and greater in volume are utilized. In some embodiments, bioreactors capable of containing positive headspace pressures above ambient pressure are utilized. In some embodiments, egg-shape or cylindrical digesters or vertical shaft bioreactors 3,000,000 liters and greater in volume are utilized. In some embodiments, the bioreactor comprising the microorganism does not allow light to penetrate part or most or all of its contained liquid volume. In certain non-limiting embodiments, the microorganism used in the $CO_2$-fixation step is not photosynthetic. In certain non-limiting embodiments, the bioreactor design does not confine the culture in thin layers or have transparent walls so as to have light available to all parts, as is generally necessary with photosynthesis. In some embodiments, the microorganism is cultured without significant or any exposure to light. In certain such embodiments, net $CO_2$ consumption still occurs in the absence of light due to chemoautotrophic metabolism and conditions. In certain embodiments, converting electricity to artificial light is not required in a biological system for $CO_2$ capture and conversion.

In certain embodiments, the lack of light dependence facilitates continuous $CO_2$ capture operations, day and night, year-round, in all weather conditions, without the need for any artificial lighting.

In some embodiments, the microorganisms are grown and maintained for the production of amino acids, or proteins, or other nutrients, or whole cell products in a medium containing a gaseous carbon source, such as but not limited to syngas, producer gas, tail gas, pyrolysis gas, or $H_2$ and $CO_2$ gas mixtures, in the absence of light; where such growth is known as chemoautotrophic growth.

In certain embodiments, an increase in system capacity is met by vertical scaling, rather than only scaling horizontally. This is in contrast to phototrophic approaches using algae, cyanobacteria, or higher-plants for $CO_2$ capture. Although various vertical farming schemes have been proposed for photosynthetic systems, practically and economically speaking, phototrophic systems must expand horizontally, for example in shallow ponds or photobioreactors in the case of algae. This results in large geographic footprints and many negative environmental impacts.

An algal or higher plant system grown with artificial lighting is challenged by inefficient utilization of light energy, and by inefficient conversion of electrical energy to light energy. In certain embodiments, a comparable algal or high-plant culture grown under artificial lighting will require more electrical power than the $CO_2$ capture and/or biomass production system described herein, in terms of $CO_2$ capture and/or biomass production. In certain embodiments, a comparable algal or higher-plant culture grown under artificial lighting will require at least ten times more electrical power than the $CO_2$ capture and/or biomass production system described herein, in terms of power per unit $CO_2$ capture and/or biomass production. For algae or higher-plants grown on artificial lighting, the heat rejection requirement is almost in direct proportion to the electrical input. In certain embodiments of the methods described herein, the heat rejection requirements are lower than for a comparable algal or higher plant system, in terms of $CO_2$ capture and/or biomass production when grown on artificial lighting. In certain embodiments, the heat rejection requirements are at least ten times lower than for a comparable algal or higher plant system, in terms of $CO_2$ capture and/or biomass production when grown on artificial lighting.

In an exemplary but nonlimiting embodiment, a bioreactor containing nutrient medium is inoculated with production cells. Generally, there will follow a lag phase prior to the cells beginning to double. After the lag phase, the cell doubling time decreases and the culture goes into the logarithmic phase. The logarithmic phase is eventually followed by an increase of the doubling time that, while not intending to be limited by theory, is thought to result from either a mass transfer limitation, depletion of nutrients including nitrogen or mineral sources, or a rise in the concentration of inhibitory chemicals, or quorum sensing by the microbes. The growth slows down and then ceases when the culture enters the stationary phase. In certain embodiments, there is an arithmetic growth phase preceding the stationary phase. In order to harvest cell mass, the culture in certain embodiments is harvested in the logarithmic phase and/or in the arithmetic phase and/or in the stationary phase.

The bioreactor or fermenter is used to culture cells through the various phases of their physiological cycle. A bioreactor is utilized for the cultivation of cells, which may be maintained at particular phases in their growth curve. The use of bioreactors is advantageous in many ways for cultivating chemoautotrophic growth. For certain embodiments, protein-rich cell mass, which is used to produce proteins or protein hydrolysates, is grown to high densities in liquid suspension. Generally, the control of growth conditions, including control of dissolved carbon dioxide, oxygen, and other gases such as hydrogen, as well as other dissolved nutrients, trace elements, temperature and pH, is facilitated in a bioreactor. For certain embodiments, protein-rich cell mass, which is used to produce amino acids, peptides, proteins, hydrolysates, extracts, or whole cell products, is grown to high densities and/or grown at high productivities, in liquid suspension within a bioreactor.

Nutrient media, as well as gases, can be added to the bioreactor as either a batch addition, or periodically, or in response to a detected depletion or programmed set point, or continuously over the period the culture is grown and/or maintained. For certain embodiments, the bioreactor at inoculation is filled with a starting batch of nutrient media and/or one or more gases at the beginning of growth, and no additional nutrient media and/or one or more gases are added after inoculation. For certain embodiments, nutrient media and/or one or more gases are added periodically after inoculation. For certain embodiments, nutrient media and/or one or more gases are added after inoculation in response to a detected depletion of nutrient and/or gas. For certain embodiments, nutrient media and/or one or more gases are added continuously after inoculation.

For certain embodiments, the added nutrient media does not contain any organic compounds.

In certain embodiments, a small amount of microorganism cells (i.e., an inoculum) is added to a set volume of culture medium; the culture is then incubated; and the cell mass passes through lag, exponential, deceleration, and stationary phases of growth.

In batch culture systems, the conditions (e.g., nutrient concentration, pH, etc.) under which the microorganism is cultivated generally change continuously throughout the period of growth. In certain non-limiting embodiments, to avoid the fluctuating conditions inherent in batch cultures, and to improve the overall productivity of the culture system, the microorganisms that are used for the production of protein and/or vitamins and/or other nutrients are grown in a continuous culture system called a chemostat. In such systems. the culture may be maintained in a perpetual exponential phase of growth by feeding it with fresh medium at a constant rate [F] while at the same time maintaining the volume [V] of the culture constant. In certain embodiments, a continuous culture system ensures that cells are cultivated under environmental conditions that remain roughly constant. In certain embodiments, the cells are maintained in a perpetual exponential phase through the use of a chemostat system. In such a case the dilution rate (D) of the culture equals the growth rate of the microorganism, and is given by: $D=F/V$. The growth rate of a microorganism in continuous culture may be changed by altering the dilution rate. In certain embodiments, the growth rate of the microorganism is changed by altering the dilution rate.

In certain non-limiting embodiments, cells are grown in a chemostat at a dilution rate of around 0.2 h$^{-1}$.

In certain embodiments, inoculation of the culture into the bioreactor is performed by methods including but not limited to transfer of culture from an existing culture inhabiting another bioreactor, or incubation from a seed stock raised in an incubator. In certain embodiments, the seed stock of the strain may be transported and stored in forms including but not limited to a powder, liquid, frozen, or freeze-dried form as well as any other suitable form, which may be readily recognized by one skilled in the art. In certain non-limiting embodiments, the reserve bacterial cultures are kept in a metabolically inactive, freeze-dried state until required for restart. In certain embodiments, when establishing a culture in a very large reactor, cultures are grown and established in progressively larger intermediate scale vessels prior to inoculation of the full-scale vessel.

For certain embodiments, the bioreactors have mechanisms to enable mixing of the nutrient media that include, but are not limited to, one or more of the following: spinning stir bars, blades, impellers, or turbines; spinning, rocking, or turning vessels; gas lifts, sparging; recirculation of broth from the bottom of the container to the top via a recirculation conduit, flowing the broth through a loop and/or static mixers. The culture media may be mixed continuously or intermittently.

In certain embodiments the microorganism-containing nutrient medium may be removed from the bioreactor partially or completely, periodically or continuously, and in certain embodiments is replaced with fresh cell-free medium to maintain the cell culture in an exponential growth phase, and/or to replenish the depleted nutrients in the growth medium, and/or remove inhibitory waste products.

The ports that are standard in bioreactors may be utilized to deliver, or withdraw, gases, liquids, solids, and/or slurries, into and/or from the bioreactor vessel enclosing the microbes. Many bioreactors have multiple ports for different purposes (e.g., ports for media addition, gas addition, probes for pH and DO, and sampling), and a given port may be used for various purposes during the course of a fermentation run. As an example, a port might be used to add nutrient media to the bioreactor at one point in time, and at another time might be used for sampling. Preferably, the multiple uses of a sampling port can be performed without introducing contamination or invasive species into the growth environment. A valve or other actuator enabling control of the sample flow or continuous sampling can be provided to a sampling port. For certain embodiments, the bioreactors are equipped with at least one port suitable for culture inoculation that can additionally serve other uses including the addition of media or gas. Bioreactor ports enable control of the gas composition and flow rate into the culture environment. For example, the ports can be used as gas inlets into the bioreactor through which gases are pumped.

For some embodiments, gases that may be pumped into a bioreactor include, but are not limited to, one or more of the following: syngas, producer gas, pyrolysis gas, hydrogen gas, CO, $CO_2$, $O_2$, air, air/$CO_2$ mixtures, natural gas, biogas, methane, ammonia, nitrogen, noble gases, such as argon, as well as other gases. In some embodiments the $CO_2$ pumped into the system may come from sources including, but not limited to: $CO_2$ from the gasification of organic matter; $CO_2$ from the calcination of limestone, $CaCO_3$, to produce quicklime, CaO; $CO_2$ from methane steam reforming, such as the $CO_2$ byproduct from ammonia, methanol, or hydrogen production; $CO_2$ from combustion, incineration, or flaring; $CO_2$ byproduct of anaerobic or aerobic fermentation of sugar; $CO_2$ byproduct of a methanotrophic bioprocess; $CO_2$ from waste water treatment; $CO_2$ byproduct from sodium phosphate production; geologically or geothermally produced or emitted $CO_2$; $CO_2$ removed from acid gas or natural gas. In certain non-limiting embodiments, the $CO_2$ has been removed from an industrial flue gas, or intercepted from a geological source that would otherwise naturally emit into the atmosphere. In certain embodiments, the carbon source is $CO_2$ and/or bicarbonate and/or carbonate dissolved in sea water or other bodies of surface or underground water. In certain such embodiments the inorganic carbon may be introduced to the bioreactor dissolved in liquid water and/or as a solid. In certain embodiments, the carbon source is $CO_2$ captured from the atmosphere. In certain non-limiting embodiments, the $CO_2$ has been captured from a closed cabin as part of a closed-loop life support system, using equipment such as but not limited to a $CO_2$ removal assembly (CDRA), which is utilized, for example, on the International Space Station (ISS).

In certain non-limiting embodiments, geological features such as, but not limited to, geothermal and/or hydrothermal vents that emit high concentrations of energy sources (e.g. $H_2$, $H_2S$, CO gases) and/or carbon sources (e.g. $CO_2$, $HCO_3^-$, $CO_3^{2-}$) and/or other dissolved minerals may be utilized as nutrient sources for the microorganisms herein.

In certain embodiments, one or more gases in addition to carbon dioxide, or in place of carbon dioxide as an alternative carbon source, are either dissolved into solution and fed to the culture broth and/or dissolved directly into the culture broth, including but not limited to gaseous electron donors and/or carbon sources (e.g., hydrogen and/or CO and/or methane gas). In certain embodiments, input gases may include other electron donors and/or electron acceptors and/or carbon sources and/or mineral nutrients such as, but not limited to, other gas constituents and impurities of syngas (e.g., hydrocarbons); ammonia; hydrogen sulfide; and/or other sour gases; and/or $O_2$; and/or mineral containing particulates and ash.

In certain embodiments, one or more gases are dissolved into the culture broth, including but not limited to gaseous electron donors such as, but not limited to, one or more of the following: hydrogen, carbon monoxide, methane, hydrogen sulfide or other sour gases; gaseous carbon sources such as, but not limited to one or more of the following: $CO_2$, CO, $CH_4$; and electron acceptors such as, but not limited to, oxygen, either within air (e.g., 20.9% oxygen) or as pure $O_2$ or as an $O_2$-enriched gas. In some embodiments, the dissolution of these and other gases into solution is achieved using a system of compressors, flowmeters, and flow valves known to one skilled in the art of fermentation engineering, that feed into one of more of the following widely used systems for dispersing gas into solution: sparging equipment; diffusers including but not limited to dome, tubular, disc, or doughnut geometries; coarse or fine bubble aerators; venturi equipment. In certain embodiments, surface aeration and/or gas mass transfer may also be performed using paddle aerators and the like. In certain embodiments, gas dissolution is enhanced by mechanical mixing with an impeller or turbine, as well as hydraulic shear devices to reduce bubble size. Following passage through the reactor system holding microorganisms which uptake the gases, in certain embodiments the residual gases may either be recirculated back to the bioreactor, or burned for process heat, or flared, or injected underground, or released into the atmosphere. In certain embodiments herein utilizing $H_2$ as electron donor, $H_2$ may be fed to the culture vessel either by bubbling it through the culture medium, or by diffusing it through a hydrogen permeable-water impermeable membrane known in the art that interfaces with the liquid culture medium.

In certain embodiments, the microorganisms grow and multiply on $H_2$ and $CO_2$ and other dissolved nutrients under microaerobic conditions. In certain embodiments, a C1 chemical such as but not limited to carbon monoxide, methane, methanol, formate, or formic acid, and/or mixtures containing C1 chemicals including but not limited to various syngas compositions generated from various gasified, pyrolyzed, or steam-reformed fixed carbon feedstocks, are biochemically converted into longer chain organic chemicals (i.e., C2 or longer and, in some embodiments, C5 or longer carbon chain molecules) under one or more of the following conditions: aerobic, microaerobic, anoxic, anaerobic, and/or facultative conditions.

A controlled amount of oxygen can also be maintained in the culture broth of some embodiments, and in certain embodiments, oxygen will be actively dissolved into solution fed to the culture broth and/or directly dissolved into the culture broth. In certain aerobic or microaerobic embodiments that require the pumping of air or oxygen into the culture broth in order to maintain targeted DO levels, oxygen bubbles may be injected into the broth at an optimal diameter for mixing and oxygen transfer.

In some embodiments, the microorganisms convert a fuel gas, including but not limited to syngas, producer gas, pyrolysis gas, biogas, tailgas, fluegas, CO, $CO_2$, $H_2$, natural gas, methane, and mixtures thereof. In some embodiments, the heat content of the fuel gas is at least 100 BTU per standard cubic foot (scf). In some embodiments, a bioreactor that is used to contain and grow the microorganisms is equipped with fine-bubble diffusers and/or high-shear impellers for gas delivery.

Introducing and/or raising the gas flow rate into a bioreactor can enhance mixing of the culture and produce turbulence if the gas inlet is positioned beneath the surface of the liquid media such that gas bubbles or sparges up through the media. In certain embodiments, mixing is enhanced through turbulence provided by gas bubbles and/or sparging and/or gas plugging up through the liquid media. In some embodiments, a bioreactor comprises gas outlet ports for gas escape and pressure release. In some embodiments, gas inlets and outlets are preferably equipped with check valves to prevent gas backflow.

In certain embodiments where chemosynthetic reactions occur within the bioreactor, one or more types of electron donor and one or more types of electron acceptor are pumped or otherwise added as either a bolus addition, or periodically, or continuously to the nutrient medium containing chemoautotrophic organisms in the reaction vessel. The chemosynthetic reaction, driven by the transfer of electrons from electron donor to electron acceptor in cellular respiration, fixes inorganic carbon dioxide and/or other dissolved carbonates and/or other carbon oxides into organic compounds and biomass.

In certain embodiments a nutrient media for culture growth and production is used, comprising an aqueous solution containing suitable minerals, salts, vitamins, cofactors, buffers, and other components needed for microbial growth, known to those skilled in the art [Bailey and Ollis, Biochemical Engineering Fundamentals, 2nd ed; pp 383-384 and 620-622; McGraw-Hill: New York (1986)].

In certain embodiments, the chemicals used for maintenance and growth of microbial cultures as known in the art are included in the nutrient media. In certain embodiments, these chemicals may include but are not limited to one or more of the following: nitrogen sources such as ammonia, ammonium (e.g., ammonium chloride ($NH_4Cl$), ammonium sulfate (($NH_4)_2SO_4$)), nitrate (e.g., potassium nitrate ($KNO_3$)), urea or an organic nitrogen source; phosphate (e.g., disodium phosphate ($Na_2HPO_4$), potassium phosphate ($KH_2PO_4$), phosphoric acid ($H_3PO_4$), potassium dithiophosphate ($K_3PS_2O_2$), potassium orthophosphate ($K_3PO_4$), dipotassium phosphate ($K_2HPO_4$)); sulfate; yeast extract; chelated iron; potassium (e.g., potassium phosphate ($KH_2PO_4$), potassium nitrate ($KNO_3$), potassium iodide (KI), potassium bromide (KBr)); and other inorganic salts, minerals, and trace nutrients (e.g., sodium chloride (NaCl), magnesium sulfate ($MgSO_4$ $7H_2O$) or magnesium chloride ($MgCl_2$), calcium chloride ($CaCl_2$)) or calcium carbonate ($CaCO_3$), manganese sulfate ($MnSO_4$ $7H_2O$) or manganese chloride ($MnCl_2$), ferric chloride ($FeCl_3$), ferrous sulfate ($FeSO_4$ $7H_2O$) or ferrous chloride ($FeCl.sub.2$ $4H.sub.2O$), sodium bicarbonate ($NaHCO_3$) or sodium carbonate ($Na_2CO_3$), zinc sulfate ($ZnSO_4$) or zinc chloride ($ZnCl_2$), ammonium molybdate ($NH_4MoO_4$) or sodium molybdate ($Na_2MoO_4$ $2H_2O$), cuprous sulfate ($CuSO_4$) or copper chloride ($CuCl_2$ $2H_2O$), cobalt chloride ($CoCl_2$ $6H_2O$), aluminum chloride ($AlCl_3.6H_2O$), lithium chloride (LiCl), boric acid ($H_3BO_3$), nickel chloride $NiCl_2$ $6H_2O$), tin chloride ($SnCl_2H_2O$), barium chloride ($BaCl_2$ $2H_2O$), copper selenate ($CuSeO_4$ $5H_2O$) or sodium selenite ($Na_2SeO_3$), sodium metavanadate ($NaVO_3$), chromium salts). In certain embodiments, the mineral salts medium (MSM) formulated by Schlegel et al may be used ["Thermophilic bacteria", Jakob Kristjansson, Chapter 5, Section III, CRC Press, (1992)].

Aspects described herein relate to the growth and/or expression of bioproducts with microorganisms (e.g., bacterial cells). Microorganisms (e.g., bacterial cells) described herein can be cultured in some embodiments in media of any type (rich or minimal), including fermentation medium, and any composition. As would be understood by one of ordinary skill in the art, routine optimization would allow for use of a variety of types of media. The selected medium can be supplemented with various additional components. Some non-limiting examples of supplemental components include glucose, antibiotics, IPTG for gene induction, and ATCC Trace Mineral Supplement. Similarly, other aspects of the medium and growth conditions of the microorganisms described herein may be optimized through routine experimentation. For example, pH and temperature are non-limiting examples of factors which can be optimized. In some embodiments, factors such as choice of media, media supplements, and temperature can influence production levels of a desired molecule. In some embodiments, the concentration and amount of a supplemental component may be optimized. In some embodiments, how often the media is supplemented with one or more supplemental components, and the amount of time that the media is cultured before harvesting the desired molecule is optimized.

In certain embodiments, all pathogenic microorganisms present in raw waste feedstocks entering the process are killed through a gasification and/or pyrolysis and/or incineration step or steps leading into one or more C1 capture and bioconversion steps.

In certain embodiments, the concentrations of nutrient chemicals (e.g., electron donors, electron acceptors, carbon sources, and/or various mineral nutrients), are maintained within the bioreactor close to or at their respective optimal levels for optimal carbon uptake and/or fixation and/or conversion and/or production of organic compounds, which varies depending upon the microorganism utilized but is known or determinable without undue experimentation to one of ordinary skill in the art of culturing microorganisms.

In certain embodiments, one or more of the following parameters are monitored and/or controlled in the bioreactor: waste product levels; pH; temperature; salinity; dissolved oxygen; dissolved carbon dioxide gas; liquid flow rates; agitation rate; gas pressure. In certain embodiments, the operating parameters affecting chemoautotrophic growth are monitored with sensors (e.g., dissolved oxygen probe or oxidation-reduction probe to gauge electron donor/acceptor concentrations), and/or are controlled either manually or automatically based upon feedback from sensors through the use of equipment including but not limited to actuating valves, pumps, and agitators. In certain embodiments, the temperature of the incoming broth as well as of incoming gases is regulated by systems such as, but not limited to, coolers, heaters, and/or heat exchangers.

In certain embodiments, the microbial culture and bioreaction is maintained using continuous influx and removal of nutrient medium and/or biomass, in steady state where the cell population and environmental parameters (e.g., cell density, pH, DO, chemical concentrations) are targeted at a constant level over time. In certain embodiments, the constant level is an optimal level for feedstock conversion and/or production of targeted organic compounds. In certain embodiments, cell densities can be monitored by direct sampling, by a correlation of optical density to cell density, and/or with a particle size analyzer. In certain embodiments, the hydraulic and biomass retention times can be decoupled so as to allow independent control of both the broth chemistry and the cell density. In certain embodiments, dilution rates can be kept high enough so that the hydraulic retention time is relatively low compared to the biomass retention time, resulting in a highly replenished broth for cell growth and/or feedstock conversion and/or production of organic compounds. In certain embodiments, dilution rates are set at an optimal technoeconomic trade-off between culture broth and nutrient replenishment and/or waste product removal, and increased process costs from pumping, increased inputs, and other demands that rise with dilution rates.

In certain embodiments, the pH of the microbial culture is controlled. In certain embodiments, pH is controlled within an optimal range for microbial maintenance and/or growth and/or conversion of feedstock and/or production of organic compounds and/or survival. To address a decrease in pH, in certain embodiments a neutralization step can be performed directly in the bioreactor environment or prior to recycling the media back into the culture vessel through a recirculation loop. Neutralization of acid in the broth of certain embodiments can be accomplished by the addition of bases, including but not limited to one or more of the following: limestone, lime, sodium hydroxide, ammonia, ammonium hydroxide, caustic potash, magnesium oxide, iron oxide, alkaline ash.

In certain embodiments, an aqueous suspension of chemoautotrophic microorganisms converts one or more electron donors and $CO_2$ into protoplasm. In certain embodiments, an aqueous suspension of hydrogen-oxidizing microorganisms can be used to convert hydrogen and carbon dioxide into microbial protoplasm. In certain embodiments, an aqueous suspension of carbon monoxide-oxidizing microorganisms can be used to convert carbon monoxide and hydrogen and/or water into protoplasm. In certain embodiments, an aqueous suspension of methane-oxidizing microorganisms can be used to convert methane into protoplasm. In certain embodiments, the microorganism in suspension is a bacterium or an archaeon. In certain non-limiting embodiments, an aqueous suspension or biofilm of $H_2$-oxidizing chemoautotrophic microorganisms converts $H_2$ and $CO_2$, along with some other dissolved mineral nutrients, into biochemicals and protoplasm. In certain embodiments, the other dissolved mineral nutrients include, but are not limited to, a nitrogen source, a phosphorous source, and a potassium source. In certain embodiments, the protoplasm produced is of food value to humans and/or other animals and/or other heterotrophs. In certain embodiments, certain biochemicals may be extracted from the protoplasm and/or extracellular broth, which have nutrient value, and/or value in a variety of organic chemistry or fuel applications. In certain embodiments, the intracellular energy to drive this production of protoplasm is derived from the oxidation of an electron donor by an electron acceptor. In certain non-limiting embodiments, the electron donor includes, but is not limited to, one or more of the following: $H_2$; CO; $CH_4$. In certain non-limiting embodiments, the electron acceptor includes but is not limited to $O_2$ and/or $CO_2$. In certain non-limiting embodiments, the product of the energy generating reaction, or respiration, includes but is not limited to water. In certain embodiments, the intracellular energy derived from respiration used to drive this synthesis of biochemicals and protoplasm from $CO_2$ is stored and carried in biochemical molecules including, but not limited to, ATP. For the knallgas microbes used in certain embodiments herein, the electron acceptor is $O_2$ and the product of respiration is water.

In some embodiments the protein production and distribution of amino acid molecules produced is optimized through one or more of the following: control of bioreactor conditions, control of nutrient levels, and/or genetic modifications of the cells. In certain embodiments, pathways to amino acids, or proteins, or other nutrients, or whole cell products are controlled and optimized for the production of chemical products by maintaining specific growth conditions (e.g., levels of nitrogen, oxygen, phosphorous, sulfur, trace micronutrients such as inorganic ions, and if present any regulatory molecules that might not generally be considered a nutrient or energy source). In certain embodiments, dissolved oxygen (DO) may be optimized by maintaining the broth in aerobic, microaerobic, anoxic, anaerobic, or facultative conditions, depending upon the requirements of the microorganisms. A facultative environment is considered to be one having aerobic upper layers and anaerobic lower layers caused by stratification of the water column. The biosynthesis of amino acids, or proteins, or other nutrients, or whole cell products by the microbes disclosed herein can happen during the logarithmic phase or afterwards during the stationary phase when cell doubling has stopped, provided there is sufficient supply of carbon and energy and other nutrient sources.

The specific examples of bioreactors, culture conditions, heterotrophic and chemotrophic growth, maintenance, and amino acids, or proteins, or other nutrients, or whole cell product production methods described herein can be combined in any suitable manner to improve efficiencies of microbial growth and amino acid, or protein, or other nutrient, or whole cell production.

Electron Donors and Acceptors

In certain non-limiting embodiments, the biosynthetic reduction of $CO_2$ utilizes $O_2$ electron acceptor and/or $H_2$ electron donor which are generated by the electrolysis of water. In certain non-limiting embodiments, part of the $O_2$ generated by electrolysis of water, and all of the $H_2$ is fed to an aqueous suspension of microorganisms as described herein. In certain non-limiting embodiments, the molar ratio of $H_2$ fed to an aqueous suspension of microorganisms to the moles of $O_2$ is greater than 2:1. In certain non-limiting embodiments where $O_2$ electron acceptor and $H_2$ electron donor are generated by the electrolysis of water, there is a surplus of $O_2$ remaining after all of the metabolic requirements for $H_2$ and $O_2$ of the microorganisms described herein have been met. In certain such embodiments the surplus $O_2$ may be supplied to humans and/or other aerobic lifeforms and/or to hydroponic systems for root aeration and/or is used in a gasification or partial oxidation or combustion process and/or is stored and sold as a chemical co-product.

In certain embodiments that utilize molecular hydrogen as an electron donor, there can be a chemical co-product formed in the generation of molecular hydrogen using a renewable and/or $CO_2$ emission-free energy input. In certain embodiments, the oxyhydrogen reaction used in respiration is enzymatically linked to oxidative phosphorylation. In certain embodiments, the ATP and/or other intracellular energy carriers thus formed are utilized in the anabolic synthesis of amino acids and/or proteins. In certain embodiments, the oxygen produced by water-splitting in excess of what is required for respiration in order to maintain optimal conditions for carbon fixation and organic compound production by the knallgas microorganisms, may be processed into a form suitable for sale through process steps known in the art and science of commercial oxygen gas production.

The production of organic molecules with carbon chain lengths longer than C4 is most commonly and efficiently accomplished biologically through anabolic biosynthesis pathways, such as fatty acid biosynthesis [C. R. Fischer, D. Klein-Marcuschamer, and G. Stephanopoulos (2008) "Selection and optimization of microbial hosts for biofuels production" *Metabolic Engineering* 10(6):295-304 (http://dx.doi.org/10.1016/j.ymben.2008.06.009)], and various amino acid biosynthetic pathways. Certain embodiments apply hydrogen-oxidizing and/or CO-oxidizing and/or $CH_4$ oxidizing microorganisms that use more electronegative electron acceptors than $CO_2$ in energy conserving reactions for ATP production (e.g., respiration), such as but not limited to $O_2$. For example, hydrogenotrophic oxyhydrogen or knallgas microbes that couple the oxyhydrogen reaction, $2H_2+O_2\rightarrow 2H_2O$, to ATP production, can produce more ATP per $H_2$ and/or other electron donor consumed for respiration, than acetogens or methanogens that use $CO_2$ as an electron acceptor in respiration. For example, knallgas microorganisms can produce at least two ATP per $H_2$ consumed in respiration [L. Bongers (1970) "Energy generation and utilization in hydrogen bacteria" *Journal of bacteriology* 104(1):145-151 (http://jb.asm.org/content/104/1/145.abstract), which is incorporated herein by reference in its entirety], which is eight times more ATP produced per $H_2$ consumed in respiration than what can be produced in microorganisms undergoing methanogenesis or acetogenesis, using $H_2$ as electron donor and $CO_2$ as electron acceptor in respiration. For this reason, using microorganisms that can utilize more electronegative electron acceptors in respiration and in the production of ATP, such as but not limited to knallgas microbes, for anabolic biosynthesis such as but not limited to amino acid or protein or fatty acid biosynthesis from syngas or $H_2$, can be more efficient than using acetogens or methanogens, such as those which are currently used in biological GTC technologies for the production of short chain acids or alcohols (e.g., acetic acid or ethanol). In certain embodiments, the oxyhydrogen reaction used in respiration is enzymatically linked to oxidative phosphorylation. In certain embodiments, aerobic respiration is utilized by the microorganism cells described herein for the production of ATP. In certain embodiments, the ATP and/or other intracellular energy carriers thus formed are utilized in the anabolic biosynthesis of amino acids and/or proteins. In some embodiments, a knallgas and/or carboxydotrophic and/or methanotrophic and/or heterotrophic microorganism or a compositions comprising these microorganisms is utilized, wherein the microorganism expresses one or more enzymes that enables biosynthesis of useful carbon-based products of interest including but not limited to chemicals, monomers, polymers, proteins, polysaccharides, vitamins, nutraceuticals, antibiotics, or pharmaceutical products or intermediates thereof from a carbon-containing gas feedstock, including but not limited to syngas or producer gas or natural gas or biogas or waste $CO_2$ combined with renewable $H_2$ or CO or methane containing gases. In some embodiments, these said carbon-based products of interest can be biosynthesized heterotrophically from an organic multi-carbon feedstock, such as, but not limited to glucose, fructose, and other sugars. In some non-limiting embodiments, a microorganism, or a composition comprising a microorganism is utilized, wherein the microorganism requires less than $4H_2$ or NADH to produce one ATP through respiration. In other non-limiting embodiments, a microorganism or a compositions comprising a microorganism it utilized, wherein the microorganism produces more than one ATP per $H_2$ or NADH consumed through respiration. In other non-limiting embodiments a microorganism or a composition comprising a microorganism is utilized, wherein the microorganism produces at least two ATP per $H_2$ or NADH consumed through respiration, or at least 2.5 ATP per $H_2$ or NADH consumed through respiration.

An additional feature of certain non-limiting embodiments regards the source, production, or recycling of the electron donors used by the chemoautotrophic microorganisms to fix carbon dioxide and/or other C1 feedstocks into organic compounds. The electron donors used for carbon dioxide capture and carbon fixation can be produced or recycled in certain embodiments electrochemically or thermochemically using power from a number of different renewable and/or low carbon emission energy technologies including but not limited to: photovoltaics, solar thermal, wind power, hydroelectric, nuclear, geothermal, enhanced geothermal, ocean thermal, ocean wave power, tidal power. Many of the reduced inorganic chemicals upon which chemoautotrophs can grow (e.g. $H_2$, CO, $H_2S$, ferrous iron, ammonium, $Mn^{2+}$) can be readily produced using electrochemical and/or thermochemical processes well known in the art and science of chemical engineering that can be powered by a variety carbon dioxide emission-free or low-carbon emission and/or renewable sources of power including but not limited to photovoltaics, solar thermal, wind power, hydroelectric, nuclear, geothermal, enhanced geothermal, ocean thermal, ocean wave power, or tidal power.

The production of hydrogen from renewable energy sources is gradually replacing the generation from fossil feedstock systems, and the technical advances in the energy sector are expected to lower the prices of green hydrogen production in the near future. For instance, electrical energy efficiencies up to 73% are already achieved by commercial and industrial grade electrolyzers, and researches on new materials and electrolyzer configurations have shown possible efficiencies as high as 96%. Certain embodiments utilize a commercially available electrolysis technology with electrical energy efficiency of over 70% for the generation of $H_2$ electron donor and/or $O_2$ electron acceptor.

Certain embodiments use electrolysis technologies with 73% or higher energy efficiency, and/or up to 96% energy efficiency, or higher.

In certain embodiments that use molecular hydrogen as electron donor, the $H_2$ is generated by methods well known to art and science of chemical and process engineering, including but not limited to one or more of the following: through electrolysis of water including but not limited to approaches using Proton Exchange Membranes (PEM), liquid electrolytes such as KOH, alkaline electrolysis, Solid Polymer Electrolyte electrolysis, high-pressure electrolysis, high temperature electrolysis of steam (HTES); and/or through the thermochemical splitting of water through methods including but not limited to the iron oxide cycle, cerium(IV) oxide-cerium(III) oxide cycle, zinc zinc-oxide cycle, sulfur-iodine cycle, copper-chlorine cycle, calcium-bromine-iron cycle, hybrid sulfur cycle; and/or electrolysis of hydrogen sulfide; and/or thermochemical splitting of hydrogen sulfide; and/or other electrochemical or thermochemical processes known to produce hydrogen with low- or no-carbon dioxide emissions including but not limited to: carbon capture and sequestration (CCS) enabled methane reforming; CCS enabled coal gasification; the Kværner-process and other processes generating a carbon-black product; CCS enabled gasification or pyrolysis of biomass. In certain embodiments, the approach to generating $H_2$ includes but is not limited to electrolysis powered by renewable electrical energy and/or electricity from a low-GHG source. In certain embodiments, electrolysis is powered by one or more of the following: solar, including but not limited to, photovoltaics and/or solar thermal; wind power, hydroelectric; nuclear; geothermal; enhanced geothermal; ocean thermal; ocean wave power; tidal power.

Worldwide there are enormous wind energy resources, of which only a tiny percentage is utilized. The low current utilization is mainly attributed to the intermittent nature of wind resources, resulting in varying electricity generation over time, and underutilization of capacity to meet energy demand at most hours. The common mismatch between wind power supply and grid demand is manifested in examples from around the world, such as in Scotland where wind farms have been paid to shut down turbines due to oversupply [http://www.mnn.com/earth-matters/energy/blogs/blown-away-wind-turbines-generate-enough-energy-to-power-every-home-in], and in parts of Texas where electricity has been provided for free at night when wind power is high and grid demand is low [http://www.nytimes.com/2015/11/09/business/energy-environment/a-texas-utility-offers-a-nighttime-special-free-electricity.html?_r=2]. This challenge may be resolvable by utilizing wind power produced during off-peak demand hours to produce $H_2$ feedstock for the process in certain embodiments herein.

Currently, hydrogen is increasingly regarded as a possible energy storage system in the so-called "power-to-gas" approach. The inherent instability of renewable energy production (particularly solar and wind energy), and excess grid electricity (off-peak energy) may be mitigated by the production of hydrogen through water electrolysis. According to most current schemes, the produced hydrogen gas may then be converted back to electricity, by fuel cells and/or gas turbines, during periods of peak demand. Or alternatively the $H_2$ may be fed into the gas grid, or converted to methane via methanation. Furthermore, the hydrogen may be used as a raw material in the chemical, petrochemical, metallurgy and food industries. Certain embodiments provide new options within the power-to-gas framework, by enabling the $H_2$ to be used in a wider range of products, including biochemicals and in particular proteins, amino acids, fertilizers, and biostimulants. In certain embodiments, hydrogen produced using excess grid electricity and/or off-peak energy is used as an electron donor for one or more metabolic pathways occurring in hydrogen-utilizing microorganisms. In certain embodiments, the hydrogen and/or the oxygen needed for the microbial biosynthesis by hydrogen-oxidizing bacteria and/or aerobic bacteria is generated by water electrolysis using renewable energy, and in particular off-peak electricity, i.e., electrical power available when the energy supply exceeds demand, and which, in the current situation, is often wasted.

In certain embodiments, onsite storage of $H_2$ and $CO_2$ gases enables diversion of power from the grid only during periods when renewable generation exceeds electrical demand. In certain embodiments, power is allowed to flow as usual into the grid during periods of higher demand. In certain embodiments, the process does not disrupt renewable power supply, but rather enables more complete utilization of renewable generation capacity such as, but not limited to, wind and solar. Certain embodiments allow continued renewable operation and generation even during periods when electrical generation exceeds grid demand (e.g., off-peak wind or solar generation).

In certain embodiments, hydrogen electron donors are not necessarily generated with low- or no-carbon dioxide emissions. However, in certain such embodiments the hydrogen is generated from waste, sustainable, or low value sources of energy and/or carbon using methods known in to art of chemical and process engineering. Such methods include but are not limited to gasification, pyrolysis, steam-reforming, or autothermal reforming of feedstock such as but not limited to one or more of the following: municipal solid waste, black liquor, agricultural waste, wood waste, stranded natural gas, biogas, sour gas, methane hydrates, liquid petroleum gas, pet coke, tires, sewage, manure, straw, sea weed and kelp, and low value, highly lignocellulosic biomass in general. In certain embodiments, a synthesis gas or producer gas containing $H_2$ and/or $CO$ and/or $CO_2$ is utilized as an electron donor and/or as a carbon source. In certain embodiments, the $H_2$ and/or $CO$ and/or $CO_2$ contained in a syngas or producer gas is supplemented by $H_2$ generated using a renewable and/or low-GHG energy source and conversion process such as one or more of those described herein.

In certain non-limiting embodiments, reduction of waste $CO_2$ occurs and/or synthesis of cellular material that can be utilized as a food or nutrition source, and/or the disposal and utilization of waste urea occurs and/or other biological wastes.

In certain embodiments, the ratio of hydrogen to carbon monoxide in the syngas or producer gas may be adjusted through the water gas shift reaction and/or carbon capture, prior to the gas being delivered to the microbial culture. In certain embodiments, C1 compounds are generated through methane steam reforming of methane or natural gas, and particularly stranded natural gas, or natural gas that would be otherwise flared or released to the atmosphere, or biogas, or landfill gas, and provided as a syngas and/or producer gas or liquid stream of C1 compounds to the culture of microorganisms, where in certain embodiments the ratio of hydrogen to carbon monoxide in the syngas or producer gas may be adjusted through the water gas shift reaction and/or carbon capture, prior to the gas being delivered to the microbial culture.

The electron donors in certain embodiments may also be sourced or refined from pollutants or waste products including but not limited to one or more of the following: process gas; tail gas; enhanced oil recovery vent gas; stranded natural gas; biogas; landfill gas; and sour gases. In certain embodiments, a tail gas containing $H_2$ and/or $CH_4$ and/or CO is used as a source of electron donor and/or carbon. In certain embodiments tail gases from an oil refinery are used as a source of electron donors and/or carbon.

Products

In some embodiments, the microorganisms described herein produce at least 1 mg of carbon-based product of interest per liter of liquid culture suspension. In some examples, the product is secreted by the microorganism into culture medium. In other examples, the product is retained in the microorganism in the course of fermentation. In some cases, the product may be recovered by lysing the cells and separating the product. In other cases, the product may have commercial value in the intact microorganism without significant preparation or purification of the product from the microorganism.

In certain embodiments, separation of cell mass from liquid suspension is performed. In certain embodiments, this separation is performed by methods known in the art of microbial culturing. Examples of cell mass harvesting techniques are provided, for example, in PCT Application No. WO08/00558; U.S. Pat. Nos. 5,807,722; 5,593,886; and 5,821,111, Separation may be performed by one or more methods including, but not limited to: centrifugation; flocculation; flotation; filtration using a membranous, hollow fiber, spiral wound, or ceramic filter system; vacuum filtration; tangential flow filtration; clarification; settling; hydrocyclone. In certain embodiments where the cell mass may be immobilized on a matrix, it may be harvested by methods including but not limited to gravity sedimentation or filtration, and separated from the growth substrate by scraping or liquid shear forces.

In certain embodiments, the liquid left over following the removal of cell mass can be pumped to a system for removal and/or recovery of dissolved chemical products of the bioprocess and/or unreacted nutrients. In certain embodiments, unreacted nutrients and/or water are recovered and recycled to the extent possible and/or in certain embodiments sold as a co-product and/or properly disposed of. In certain embodiments, the removal of waste products and/or contaminants and/or any inhibitory and/or deleterious compounds, using methods and technologies known in the art, is performed prior to returning water and/or unreacted nutrients to the bioreactor/s.

In certain embodiments, free and/or dissolved organic molecules can be released into the process stream solution from the microorganisms through methods including, but not limited to, cellular excretion or secretion or cell lysis.

In certain embodiments, recovery and/or recycling of chemical products and/or unreacted nutrients from the aqueous solution can be accomplished using equipment and techniques known in the art of process engineering, and targeted towards the chemical products of particular embodiments, including but not limited to: solvent extraction; water extraction; distillation; fractional distillation; cementation; chemical precipitation; alkaline solution absorption; absorption or adsorption on activated carbon, ion-exchange resin or molecular sieve; modification of the solution pH and/or oxidation-reduction potential; evaporators; fractional crystallizers; solid/liquid separators; nanofiltration; reverse osmosis; and all combinations thereof.

In certain embodiments, chemical products and/or unreacted nutrients flow into an environment that supports the growth of other organisms. In certain embodiments, effluent water and unreacted nutrients are used to irrigate and fertilize higher plants and/or seaweed, and/or algae, and/or to feed heterotrophic organisms such as fungi, yeast, and/or bacteria. In certain embodiments, inorganic nutrients from the bioreactor effluent function as an inorganic fertilizer which may increase primary production of a pond and/or or other enclosures used in aquaculture and/or hydroponics.

The high growth rate attainable by certain chemoautotrophic species can allow them to match or surpass the highest rates of carbon fixation and/or biomass production per standing unit biomass that can be achieved by photosynthetic microbes. In certain embodiments, surplus biomass can be produced. In certain embodiments, surplus growth of cell mass can be removed from the system to produce a biomass product. In some embodiments, surplus growth of cell mass can be removed from the system in order to maintain a desirable (e.g., an optimal) microbial population and cell density in the microbial culture for continued high carbon capture and fixation rates and/or feedstock conversion rates.

To assist in the processing of the biomass product into useful products, harvested microbial cells in certain embodiments can be broken open using well known methods including but not limited to one or more of the following: ball milling, cavitation pressure, sonication, homogenization, or mechanical shearing.

The harvested biomass in some embodiments may be dried in a process step or steps. Biomass drying can be performed in certain embodiments using well known technologies, including but not limited to, one or more of the following: centrifugation, drum drying, evaporation, freeze drying, heating, spray drying, vacuum drying, and/or vacuum filtration. In certain embodiments, waste heat can be used in drying the biomass. In certain embodiments, heat waste from the industrial source of flue gas used as a carbon source can be used in drying the biomass. In certain embodiments, the heat co-product from the generation of electron donors and/or C1 carbon source as discussed above can be used for drying the biomass.

In an exemplary but non-limiting embodiment, a bioreactor containing nutrient medium is inoculated with production cells; generally, there will follow a lag phase prior to the cells beginning to double. After the lag phase, the cell doubling time decreases and the culture goes into the logarithmic phase. The logarithmic phase is eventually followed by an increase of the doubling time that, while not intending to be limited by theory, is thought to result from either a depletion of nutrients including dissolved gases, nitrogen source, or mineral sources, or a rise in the concentration of inhibitory chemicals, or quorum sensing by the microbes. In certain cases, and particularly in aerobic bioprocesses, a prolonged linear or arithmetic growth phase can follow the logarithmic phase, prior to the onset of stationary phase. This arithmetic growth phase is characteristic of $O_2$ limitation. In order to harvest cell mass, the culture in certain embodiments is harvested late in the logarithmic phase, or during the arithmetic phase, or in the stationary phase. In some embodiments, the cells are harvested in logarithmic phase. The accumulation of carbon storage such as lipids or PHB can generally be triggered by the depletion of the nitrogen source or another key nutrient, excepting the carbon or the electron source (e.g., hydrogen). This signals the cells to store reduced carbon produced from the excess carbon and energy sources.

In an exemplary but non-limiting embodiment, a closed culture vessel is used and hydrogen, oxygen, and $CO_2$ are supplied under pressure to the vessel at the base of the liquid working volume; the flow of gases to the chamber is controlled by gas sensors to maintain fixed $H_2$, $O_2$, and $CO_2$ concentrations in the chamber headspace; the gases and culture medium are mixed by mechanical agitation in the vessel to maximize gas diffusion into the liquid; the hydrogen and oxygen gases are supplied by a water electrolysis cell and the $CO_2$ is captured from a waste source or from cabin air or from a point source normally emitted into the atmosphere; the process stream flows from the culture vessel to a protein and/or proteinaceous biomass harvest unit; a centrifugal action is used to separate the solids from the liquid; the separated liquid flows to a water reclamation unit; any undesirable substances which might otherwise build up in the system are removed at the water reclamation unit; the reclaimed water is re-used in the water electrolysis cell; nutrient makeup is supplied to the culture vessel to maintain a targeted culture medium composition; in certain such embodiments urine is provided as one of the nutrient source; recovered dewatered biomass is further processed into nutrients and/or fertilizer and/or ingredients and/or food. In certain such embodiments, unused gases that bubble into the bioreactor headspace, are recirculated back to the base of the liquid working volume and introduced there back into the liquid working volume. In certain other embodiments, newly input $H_2$ and/or $CO_2$ is fed directly into the headspace of the bioreactor, instead of at the base of the working volume, and then is recirculated along with other headspace gases through the recirculation system, to the base of the liquid working volume, where the gases are dissolved and/or bubbled into the liquid working volume.

In certain embodiments, the biomass is further processed following drying, or, without a preceding drying step, in order to aid the separation and production of useful biochemicals. In certain embodiments, this additional processing involves the separation of the protein or lipid content or vitamins or other targeted biochemicals from the microbial biomass. In certain embodiments, the separation of the lipids can be performed by using nonpolar solvents to extract the lipids, such as, but not limited to one or more of: hexane, cyclohexane, ethyl ether, alcohol (isopropanol, ethanol, etc.), tributyl phosphate, supercritical carbon dioxide, trioctylphosphine oxide, secondary and tertiary amines, or propane. In certain embodiments, other useful biochemicals can be extracted using solvents, including but not limited to, one or more of: chloroform, acetone, ethyl acetate, and tetrachloroethylene. In certain embodiments cell lysis is performed.

In some embodiments, methods are provided for producing amino acids and/or proteins and/or vitamins by combining, in a bioreactor or solution, one or more biosynthetic pathways including but not limited to, an amino acid biosynthetic pathway, a vitamin biosynthetic pathway, a carbon-containing gas, and an engineered or natural microorganism that converts a carbon-containing gas such as syngas, producer gas, natural gas, biogas, $CO_2$, carbon monoxide and mixtures of the same containing hydrogen gas; and/or C1 compounds, gaseous or liquid, including but not limited to methanol or methane, into amino acids and/or proteins and/or vitamins. In some embodiments, the amino acids and/or proteins and/or vitamins are included in one or more of a fertilizer, biostimulant, biofertilizer, microbial nutrient media, mushroom growth enhancer, an animal feed formulation, and/or human food product, using processes known in the art and science of chemistry, chemical engineering, microbiology, agronomy, and/or food science. In some non-limiting embodiments, the microorganism is *Cupriavidus necator* DSM 531 or DSM 541. In some non-limiting embodiments, the vitamin is a B vitamin and more particularly vitamins B1, B2, and/or B12.

In certain embodiments, methods are provided for producing one or more amino acids, comprising exposing a bacterial cell and/or archaeal cell and/or other microbial cell to syngas and/or producer gas and/or gaseous $CO_2$ and/or natural gas and/or biogas and/or a mixture of gaseous $CO_2$ and/or gaseous $H_2$ and/or CO and/or $CH_4$ (e.g., $H_2$ and $CO_2$, and/or CO, and/or $CH_4$); wherein the microbial cell is capable of fixing gaseous $CO_2$ and/or other C1 carbon sources into one or more amino acids and/or protein and/or vitamins; wherein the compounds are recovered from the bioreactor and fed to a second, or more, additional reactors wherein the compounds are post-processed to generate products including but not limited to one or more of the following: fertilizer, biostimulant, biofertilizer, mushroom growth enhancer, aquaculture feed, animal feed, food ingredients, human nutrition (e.g., food or nutritional supplement), or vitamins. In some embodiments, the composition comprises a bacterial cell, wherein the bacteria are chosen from the genus *Rhodococcus*. In certain embodiments, the bacterial cell is *Rhodococcus opacus* (DSM 43205 or 43206 or 44193) or *Rhodococcus* sp (DSM 3346). In some embodiments, the bacterial cell is chosen from the genera *Ralstonia* or *Cupriavidus*. In some embodiments, the bacterial cell is *Cupriavidus necator* or *Cupriavidus metallidurans*. In some embodiments the bacterial cell is from the suborder corynebacterineae or the family burkholderiaceae.

In one embodiment, a wild-type or engineered microorganism is utilized that is capable of growing on syngas, and/or a mixture of $H_2$ and/or $CO_2$, and/or CO, and/or $CH_4$ (e.g., $H_2$ and $CO_2$, and/or CO, and/or $CH_4$), and/or other waste gases and is capable of producing amino acids including but not limited to lysine.

In some embodiments, methods are provided for manufacturing one or more amino acids, peptides, proteins, vitamins, or other nutrients, comprising (a) culturing a cell described herein in a reaction vessel or bioreactor in the presence of syngas and/or producer gas and/or natural gas and/or biogas and/or a mixture of gaseous $CO_2$ and/or gaseous $H_2$ and/or CO and/or $CH_4$ (e.g., $H_2$ and $CO_2$, and/or CO, and/or $CH_4$), wherein the cell produces and/or secretes one or more amino acids, or proteins, or other nutrients in a quantity equal to or greater than at least 10% of the cell's total dry cellular mass; and (b) separating the one or more amino acids, peptides, proteins, vitamins, or other nutrients, and/or a whole cell product from the reaction vessel (e.g., separating from the culture medium in the reaction vessel).

In some embodiments, the one or more amino acids, or proteins, or other nutrients, or whole cell products produced in a method described herein are used as an alternative or non-conventional protein and/or nutrient source. In some embodiments, the one or more amino acids, or proteins, or other nutrients, or whole cell products produced in a method as described herein are components of, or precursors to, or are included within a feed or nutrient supply provided to another organism. In certain non-limiting embodiments that other type of organism consuming said nutrient supply is one or more of the following: bacteria, archaea, yeast, microalgae, seaweed, kelp, zooplankton, fungus, mushroom, plant, shellfish or other invertebrate, fish, bird, or mammal.

In certain non-limiting embodiments, proteinaceous biomass produced as described herein is used as an alternative protein source. In certain embodiments, it is used as a replacement for fish meal and/or casein and/or whey and/or soy meal. In certain non-limiting embodiments, the protein products are not deficient in lysine and/or methionine. In certain embodiments, amino acids, peptides, and/or proteins produced as described herein are used in fertilizer, biostimulant, biofertilizer, mushroom growth enhancer, feed formulations, and/or human food ingredients in place of fish meal, casein, whey, and/or soy meal and/or other plant proteins. In certain non-limiting embodiments, the protein products are not deficient in any essential amino acids. In certain non-limiting embodiments, the protein products are not deficient in lysine and/or methionine. In certain non-limiting embodiments, the proteinaceous biomass does not contain significant amounts of anti-nutritional factors. In certain embodiments, the proteinaceous biomass does not contain significant amounts of one or more of the following: gossypol, glucosinolates, saponins, or trypsin inhibitors.

A number of current sources of protein and nutrients including but not limited to fish meal can be contaminated with heavy metals such as mercury (Hg) and or lead (Pb), as well as other toxic chemicals and organics, because, for example, the water from which the fish are harvested is contaminated. Certain embodiments relate to protein products with especially low levels of toxic contaminants, such as but not limited to heavy metal and/or toxic organics, compared to current sources of protein and other nutrients, including but not limited to fish meal.

A significant fraction of higher plants is inedible to many different animals including but not limited to humans and other non-ruminants. This can result in numerous disadvantages including the channeling of energy and carbon into undesirable byproducts or waste products, lowering the yield of desired products, and adding additional burdens for waste processing and disposal. In certain embodiments, a greater flux of carbon and/or energy is directed into targeted biomass products than for a comparable higher plant crop, in terms of $CO_2$ capture, biomass production, and/or protein production. In certain embodiments, the ratio of inedible fraction (e.g., to a human) versus edible fraction of the biomass produced as described herein is lower than for a comparable higher plant crop. In certain embodiments, there is lower amount of food wastage than for comparable higher plant crops.

Systems for Bioproduct and/or Biomass Production

Certain non-limiting embodiments relate to production facilities having a relatively small land-footprint, enabling collocation of the bioprocess with industrial facilities producing $CO_2$ and/or other carbon wastes. In certain non-limiting embodiments those industrial facilities include one or more of the following: fossil power plants; oil refineries; tar sands upgrading facilities; natural gas or petroleum drilling operations; ethanol distilleries; cement manufactures; aluminum manufactures, chloroalkali manufactures, steel foundries; geothermal power plants. In certain embodiments, a compact vertical design allows convenient collocation next to industrial flue-gas sources, and associated waste-heat that could be further utilized in the production process, including but not limited to in biomass drying.

Additional practical advantages are realized in certain embodiments via a relatively highly controlled and contained system compared to some alternative systems for biological $CO_2$ capture and conversion. In some embodiments, the bioreactors used are gas and liquid tight, structurally robust, highly isolated and insulated from the surrounding environment, with relatively tightly controlled internal parameters (e.g., Temperature, Pressure, etc.), inputs and outputs. This relatively closed system protects the culture, which in some embodiments comprises knallgas and/or hydrogenotrophic and/or carboxydotrophic and/or chemoautotrophic and/or methanotrophic microorganisms, to a far greater degree than the organisms in practical algal or traditional agricultural systems. Practical algal and traditional agricultural systems are by necessity extremely open systems, where the organisms are directly exposed to the surrounding environment and ecosystems. The relatively highly controlled and contained aspect of the process in certain embodiments greatly reduces risks of environmental contamination, disease, or pest and weed risks compared to practical algal or traditional agricultural systems. In certain embodiments, the process is more insulated from weather and climate variables than practical algal or traditional agricultural systems. In certain embodiments, the process has reduced batch loss and/or productivity variations compared to practical algal or traditional agricultural systems.

Because of the high containment provided by the gas and liquid tight bioreactors in certain embodiments, and strict control over inputs and outputs, water and nutrient recycling in certain embodiments is greatly facilitated. In certain embodiments, water recycling is achieved by adding the appropriate units downstream of the bioreactor outlets including but not limited to condensers. Such types of equipment and methods are well known in the art and science of water recovery and recycling. In certain embodiments, evaporative losses and/or water runoff and/or nutrient runoff and/or contamination of surrounding groundwater and waterways is prevented to a greater degree than open algal or traditional agricultural systems. In contrast, open algal systems and traditional agriculture have high evaporative water losses, and are prone to agricultural runoff, which leads to waste of fertilizer and water; eutrophication of lakes and water ways; and even the emergence of "dead zones" (highly $O_2$ depleted bodies of water). Higher plants lose water by transpiration. In certain embodiments, no water is lost by transpiration. Open algal and traditional agricultural systems also present a high risk for non-native organism 'escape' into the surrounding environment and genetic cross-contamination. In certain embodiments, there is a lower risk for non-native organism 'escape' into the surrounding environment or genetic cross-contamination than for open algal and traditional agricultural systems. In certain embodiments, there is no use of pesticides, herbicides, or antibiotics in the bioprocess. Certain embodiments represent a new type of agriculture where chemoautotrophic organisms replace photosynthetic plants, algae, or microorganisms; or heterotrophic fungi, bacteria, or animals; in the production of bio-based products. In certain embodiments these bio-based products supplement, augment, replace, or expand upon the products of conventional agriculture and/or animal husbandry.

Optimization of protein production and the targeting of specific amino acid distributions can be achieved by control of bioreactor conditions and/or nutrient levels and/or through genetic modifications of the cells. In some embodiments, the protein production and distribution of amino acid molecules produced is optimized through one or more of the following: control of bioreactor conditions, control of nutrient levels, genetic modifications of the cells. In certain embodiments, pathways to amino acids, proteins, vitamins, and/or other nutrients, and/or more generally spatially separate regions of a bioreactor system which are aerobic and anaerobic. The biosynthesis of amino acids, proteins, or other nutrients, or whole cell products by the microbes disclosed herein can happen during the logarithmic phase, linear phase, or afterwards during the stationary phase when cell doubling has stopped, provided there is sufficient supply of carbon and energy and other nutrient sources.

Use of chemoautotrophic microorganisms for the production of proteins, amino acids and other nutrients from gaseous feedstocks comprising $H_2$ and/or $CO_2$ and/or CO and/or $CH_4$ is described, for example, in an International Patent application received on Mar. 18, 2017 under No. PCT/US17/23110, and entitled MICROORGANISMS AND ARTIFICIAL ECOSYSTEMS FOR THE PRODUCTION OF PROTEIN, FOOD, AND USEFUL CO-PRODUCTS FROM C1 SUBSTRATES. This application is incorporated herein by reference in its entirety for all purposes.

Engineering of knallgas microorganisms is described, for example, in U.S. patent application Ser. No. 13/623,089, filed Sep. 19, 2012, and entitled "INDUSTRIAL FATTY ACID ENGINEERING GENERAL SYSTEM FOR MODIFYING FATTY ACIDS." This application is incorporated herein by reference in its entirety for all purposes.

Use of knallgas microorganisms for the conversion of syngas, producer gas, or other $H_2$ and $CO_2$ and/or CO containing gas mixes into mid- to high-carbon chain number or anabolic molecules is described, for example, in a patent application filed in the United States Patent and Trademark Office on Oct. 26, 2012 under Ser. No. 13/643,872, and entitled USE OF OXYHYDROGEN MICROORGANISMS FOR NON-PHOTOSYNTHETIC CARBON CAPTURE AND CONVERSION OF INORGANIC AND/OR C1 CARBON SOURCES INTO USEFUL ORGANIC COMPOUNDS. This application is incorporated herein by reference in its entirety for all purposes.

Use of chemotrophic microorganisms for the conversion of $CO_2$ into useful organic chemicals is described, for example, in PCT Application No. PCT/US2010/001402, filed May 12, 2010 and entitled BIOLOGICAL AND CHEMICAL PROCESS UTILIZING CHEMOAUTOTROPHIC MICROORGANISMS FOR THE CHEMOSYNTHETIC FIXATION OF CARBON DIOXIDE AND/OR OTHER INORGANIC CARBON SOURCES INTO ORGANIC COMPOUNDS, AND THE GENERATION OF ADDITIONAL USEFUL PRODUCTS. This application is incorporated herein by reference in its entirety for all purposes.

An additional feature of some embodiments includes modifying microorganisms described herein through artificial procedures including but not limited to accelerated mutagenesis (e.g., using ultraviolet light or chemical treatments), genetic engineering or modification, hybridization, synthetic biology or traditional selective breeding. Possible modifications of the microorganisms include but are not limited to those directed at producing increased quantity and/or quality of amino acids, and/or protein and/or enzymes and/or vitamins.

In certain embodiments, chemotrophic bacterial strains are utilized that comprise one or more exogenous nucleic acid sequences. The biochemicals synthesized by the microorganisms described herein can be applied to uses including but not limited to petrochemical substitutes, monomers, feedstock for the production of polymers, lubricants, as ingredients in fertilizers, animal feed, food, personal care, and cosmetic products. In some embodiments, enzymatic and chemical processes can be utilized to produce vitamins, amino acids, and/or proteins. Some embodiments enable the production of fertilizers, biostimulants, or animal feeds. In addition, methods are provided for culturing and/or modifying chemotrophic bacteria for improved amino acid and/or protein and/or vitamin yield and/or lower production costs. In some embodiments, a genetically modified microorganism (e.g., bacterium) produces more of a certain type or types of vitamin or amino acid molecule or protein or enzyme as compared to the same microorganism that is not genetically modified.

The specific examples of bioreactors, culture conditions, heterotrophic and chemotrophic growth, maintenance, and production methods for amino acids, proteins, vitamins, other nutrients, and/or whole cell products, described herein, can be combined in any suitable manner to improve efficiencies of microbial growth and amino acid, protein, vitamin, other nutrient, and/or whole cell production.

Post-Bioprocess Recovery of Products and Applications of Use

In certain non-limiting embodiments, a plant biostimulant and/or biofertilizer and/or organic fertilizer is obtained by a process herein. Certain embodiments comprise adding at least one of an amino acid fermentation liquid and/or microbial cells to a plant biostimulant formulation. In certain non-limiting embodiments, the microbial cells are gram negative and/or gram-positive bacteria. In certain non-limiting embodiments, microbial cells are obtained through the conversion of C1 carbon source as described herein. It is a further object of certain embodiments to provide a relatively inexpensive method for preparing a biostimulant and/or fertilizer and/or nutrients from waste and/or low-cost feedstocks. In certain embodiments, amino acids and/or oligopeptides and/or low-molecular-weight peptides are produced from waste and/or low-cost feedstocks including but not limited to C1 carbon sources. In certain embodiments, nutrients produced from waste and/or low-cost feedstocks, including but not limited to C1 carbon sources, are easily absorbed and assimilated by plants, through leaves and/or roots. In certain embodiments, the absorbed nutrients are transported to the plant organs such as buds, flowers or fruits, for instance (Gjalakshimi et al. (2004) Bioresource Technology (92):291-296; Parrado et al. (2008) Bioresource Technology 99:2312-2318). In certain embodiments, amino acids and/or oligopeptides and/or low-molecular-weight peptides can be used by a plant to develop its own proteins. In certain embodiments, this saves metabolic energy that would otherwise be expended in one or more of energy-consuming metabolic processes within the plant (Higgings, C. F., Payne, J. W. (1982) Plant peptides. In: Boulder, D., Parthier, B., (Eds). Encyclopedia of Plant Physiology, 14A. Springer. 438-458). In certain embodiments, nutrients produced as described herein can be used by micro-fauna in the edaphic environment, including but not limited to, as a carbon and/or nitrogen source. In certain embodiments, the micro-fauna converts nutrients into forms beneficial for plant growth and activity. Likewise, amino acids, oligopeptides, low-molecular-weight peptides, and other nutrients produced as described herein are also readily absorbed and assimilated by animals when incorporated into their diet.

In certain embodiments, the microbial cells are obtained as a by-product of an industrial process that generates microbial cell mass. For example, the industrial process may be selected from production of amino acids, ethanol, other alcohols, organic acids, lipids, and/or hydrocarbons, and/or waste-water treatment. In certain non-limiting embodiments, cells are provided in spent media from production of at least one amino acid, for example, selected from lysine, threonine, tryptophan, glutamic acid, arginine, histidine, isoleucine, leucine, methionine, phenylalanine, valine, glycine, serine, cysteine, tyrosine, alanine, aspartic acid, proline, asparagine and/or glutamine.

In Integrated Multi-Trophic Aquaculture, several species are raised together in a way that allows one species' byproducts to be recycled as feed for another species. In integrated agriculture (especially hydroponic) and aquaculture, ponds or recirculating systems are used to raise both seafood and other organisms (for example, fish and lettuce). In certain embodiments, the protein and/or other nutrients produced as described herein are used in techniques and technologies for the raising of lettuce and/or fish within one or more of the following: recirculating systems; integrated multi-trophic aquaculture; integrated agriculture and aquaculture.

In some embodiments, bioreactors comprise a microorganism, which comprises at least one endogenous or exogenous nucleic acid sequence that encodes a pathway enzyme to an amino acid, or protein, vitamin, or other nutrient of interest. In some embodiments, the system comprises two or more, three or more, or four or more bioreactors, at least one of which comprise a microorganism, which comprises at least one endogenous or exogenous nucleic acid sequence that encodes a pathway enzyme to an amino acid, or protein, or vitamin, or other nutrient of interest. In some embodiments, the system of bioreactors comprises at least a first and second bioreactor, wherein the first bioreactor comprises a microorganism, which comprises at least one endogenous or exogenous nucleic acid sequence that encodes a pathway enzyme to an amino acid, or protein, or vitamin, or other nutrient of interest; and wherein the second bioreactor comprises a microorganism derived from a different species, wherein the microorganism from a different species may comprise at least one exogenous nucleic acid sequence. In some embodiments, the system of bioreactors comprises a first bioreactor that comprises a microorganism as described herein and a second bioreactor comprising a zooplankton, fungi, microalgae, yeast, or bacterial cell. In some embodiments, the system comprises a first bioreactor that comprises a microorganism as described herein and a second tank or vessel comprising a multicellular animal and/or an aquaculture and/or a hydroponic system.

Figure 23:
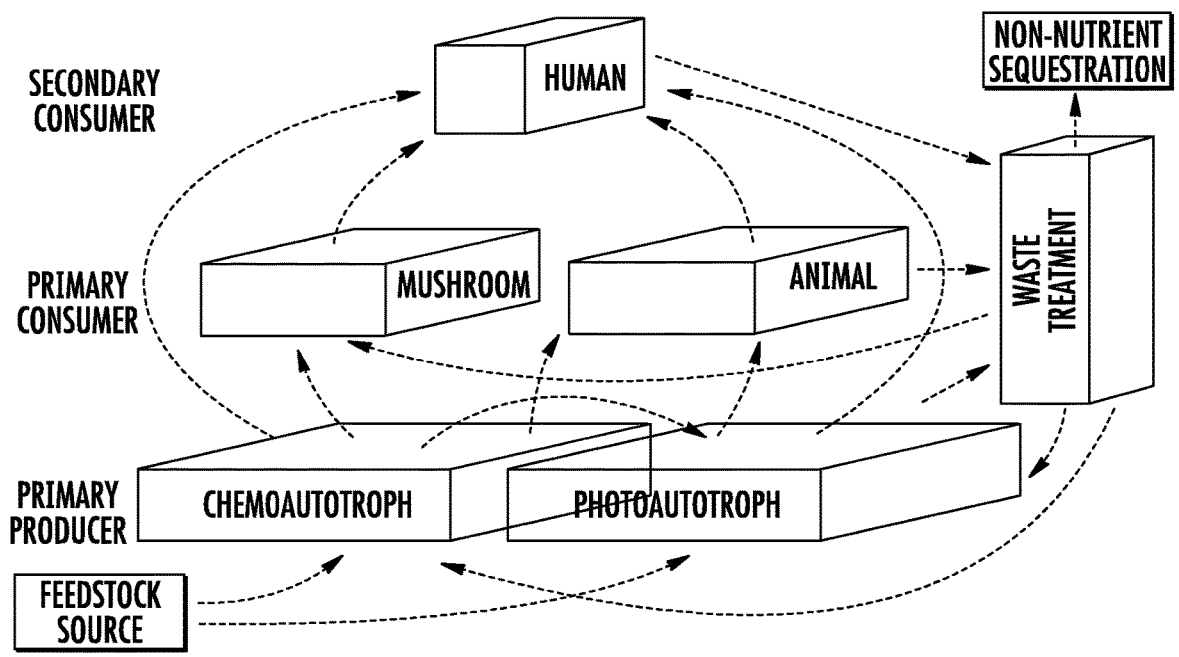
FIG. 23 schematically shows a composite multi-stage life-support system or ecological system with chemoautotrophic primary producer.

In certain non-limiting embodiments, the microorganisms described herein are maintained in a symbiotic relationship and/or a trophic relationship with other living organisms. An example of such a relationship is illustrated in FIG. 23.

In certain embodiments, recovery of biosynthetic chemical products and/or spent nutrients from the aqueous broth solution can be accomplished using equipment and techniques known in the art of process engineering, and targeted towards the chemical products of particular embodiments described herein, including but not limited to: solvent extraction; water extraction; distillation; fractional distillation; cementation; chemical precipitation; alkaline solution absorption; absorption or adsorption on activated carbon, ion-exchange resin or molecular sieve; modification of the solution pH and/or oxidation-reduction potential, evaporators, fractional crystallizers, solid/liquid separators, nanofiltration, and all combinations thereof.

In some embodiments biomass produced as described herein is converted to a high protein and/or high vitamin and/or high nutrient product for fertilizer, biostimulant, biofertilizer, mushroom growth enhancer, animal feed, and/or human nutrition applications, using methods and processes well known in the art and science of chemistry, chemical engineering, and/or food science.

In certain embodiments the biomass produced as described herein is used as a supplementary feeding nutrient. In certain embodiments, the biomass is used as an organic fertilizer material to restore chemical and microbial properties in soils and/or to increase crop productivity.

In some embodiments, over 90% of the nitrogen from the amino acids and/or peptides and/or protein produced by the microorganisms are subsequently absorbed by other microorganisms, plants, fungi, animal, or people that consume the amino acids, and/or peptides, and/or proteins and/or proteinaceous biomass produced as described herein. In some embodiments, the microbial cells are boiled prior to feeding to another organism. In other embodiments, the cells are sonicated, or otherwise lysed or ruptured prior to feeding to another organism.

In certain embodiments formulations are made combining biomass from one or more of the following groups: high-protein strains; high oil/fat strains; high carbohydrate/polysaccharide strains. In certain such embodiments the resulting formulation has a more appropriate balance of protein, oils and fats, and carbohydrates for the diet of nutritional requirements of another organism, than any subgroup of the collection of the strain utilized alone.

In certain embodiments, the biomass recovered from the bioreactor is water washed, and in certain such embodiments dilute alkali may be incorporated in the wash to remove adhering color and taste bodies. In certain embodiments, there is a pasteurization step. In certain embodiments, the pasteurization occurs at about 220° F. for about five minutes. In some embodiments, the microbial cells are boiled prior to fertilizing or feeding another organism.

To assist in the processing of the biomass product into useful products, harvested microbial cells in certain embodiments can be broken open using well known methods including but not limited to one or more of the following: ball milling, cavitation pressure, sonication, mechanical shearing, high pressure homogenization, sand or colloid mill, repeated freeze-thaw cycles, lytic enzymes. In some embodiments the cells are subjected to one or more of the following: ball milling, cavitation pressure, sonication, mechanical shearing, high pressure homogenization, sand or colloid mill, repeated freeze-thaw cycles, lytic enzymes prior to fertilizing or feeding another organism.

Most proteins and other large biomolecules are found within the cell, and in certain embodiments, these biomolecules are extracted from the intracellular environment [Doelle, H. W. Microbial Process Development (World Scientific, 1994). URL https://books.google.com/books?id=_qDabLa-0ukC]. Some proteins are structurally associated with insoluble parts of the cell, including internal membranes and/or ultrastructure. Often, to recover these products first requires that the cell be ruptured or broken. In certain embodiments, the cells are ruptured or broken. There are many methods for cell disruption and particular cell types may be best suited to one or more of these. Microorganisms (e.g., bacteria) vary from fairly fragile to highly resilient. In certain embodiments, a method of cell disruption known to one skilled in the art to be well suited to a particular cell type is utilized to break open the cells produced as described herein.

Homogenizers or presses are a common device used to lyse microorganisms, such as bacteria. The presses lyse cells by pressurizing the cell suspension and suddenly releasing the pressure. This creates a liquid shear capable of lysing cells. In certain embodiments, a pressure homogenizer is used in the cell disruption process. The French pressure cell press, or French press, is an apparatus used to disrupt the plasma membrane of cells by passing them through a narrow valve under high pressure. The Gaulin Homogenizer is a machine used to create stable emulsions and dispersions in many industries including food and dairy, pharmaceutical, petroleum, and chemical. Typical operating pressures for the French press and Manton-Gaulin homogenizer, are 6000-10,000 psi. Multiple (e.g., ~2-3) passes are generally required to achieve adequate lysis. The high operating pressures, however, result in a rise in operating temperatures. Therefore, pressure cells are often cooled (e.g., ~4° C.) prior to use. The Hughes Press forces a frozen suspension of cells through a small gap in a receiving chamber at pressures from 700 to 5,500 bar. Slit widths down to 25 m may be used. The X-Press is a modification of the Hughes Press in that it also works on frozen cells. In this case, cells are passed through a cylindrical hole in a disk. A dual plunge arrangement allows the cells to be passed back and forward several times to increase cell damage. X-presses operate above 2,000 to 6,000 bar.

In certain embodiments, one or more of the following homogenizers or presses is used for cell disruption: Gaulin; Manton-Gaulin; French; Chaikoff; Hughes; X-press; and/or Sorvall-Ribi Fractionator. The Sorvall-Ribi Fractionator is a modification or the French Press in which the needle valve has facility for cooling with chilled nitrogen. In certain embodiments, the cells are subjected to pressure greater than 1,000 bar, or greater than 1,700 bar, or greater than 2,400 bar in a Sorvall-Ribi fractionator. Some more modern homogenizers are often continuous and can be operated at higher pressures than older models. An Avestin Emulsiflex-05 is reported to efficiently lyse $E.$ $coli$ cells in one passage at 15,000 psi (100 Mpa). In certain non-limiting embodiments, an Avestin Emulsiflex-05 is used to lyse cells. In certain non-limiting embodiments, cell lysis is accomplished in a single pass through a homogenizer. In certain non-limiting embodiments, the cells are exposed to around 15,000 psi, or higher, in a homogenizer. In certain non-limiting embodiments, homogenization occurs under the following conditions: pressure 5000 to 15000 psig.; I to 5 passes through the homogenizer; temperature 32° F. to 122° F.; pH 4.5-6.5.

Ultrasound and sonication have been found to be a suitable technique for cell disruption of almost every cell type, with the possible exception of fungi. Cells are lysed by liquid shear and cavitation. A challenge is controlling the temperature. This is addressed by keeping the suspension on ice and using a number of short pulses (5-10 sec) with pauses (10-30 sec) to re-establish a low temperature. DNA is also sheared during sonication. In certain embodiments it is not necessary to add DNase to the cell suspension for the hydrolysis of DNA. In certain embodiments, ultrasound is used in the disruption of bacterial and/or archaea cells.

In certain embodiments, cell disruption is accomplished by grinding of cell material against solid surfaces. Efficient disruption of most cell types has been demonstrated with bead mills, including plant, yeast and bacterial cells. Systems up to 20 liters are available with reported yields of greater than 90% for yeast disruption at throughputs of 40-70 kg/h and up to 80% at 200 kg/h [Doelle, H. W. Microbial Process Development (World Scientific, 1994). URL https://books.google.com/books?id=_qDabLa-0ukC]. In certain embodiments, one or more milling methods is used for cell disruption including but not limited to: pestle and mortar (with or without abrasive powders); Potter-Elvehjiem homogenizer; Braun homogenizer; bead mills and/or colloid mills. In certain embodiments one or more factor is optimized for the most efficient and/or cost-effective cell disruption including but not limited to: residence time in the system; size and density of beads, as well as quantity and composition; rotor speed; design of blades and/or rotor axis; cell concentration; viscosity; and temperature.

In certain embodiments, non-mechanical methods may be used for cell lysis, in addition to mechanical methods, or without additional mechanical methods, comprising physical and/or chemical and/or enzymatic lysis of cells.

Osmotic shock occurs when a cell is suspended in hypotonic solution; water will diffuse into the cell, forcing it to swell and ultimately burst. The technique is relatively gentle and controllable. Typical solutions include, for example, 1 M glycerol, 1 M sucrose, distilled water, or simply the dilution of the supernatant. In certain non-limiting embodiments, osmotic shock is used as part of a cell lysis process.

In certain non-limiting embodiments, pressure release is used as part of a cell lysis process. In certain embodiments, the cell suspension is pressurized under a gas, and left to equilibrate. The gas tension increases in the broth and cell cytoplasm. On suddenly releasing the pressure, the gas desorbs from the solution and the expansion within the cells causes them to explode. In certain such embodiments, the cell suspension is pressurized up to 60 bar. In certain non-limiting embodiments, the cell suspension is equilibrated under 35 bar, or higher, of nitrous oxide for 3 minutes or more. In other non-limiting embodiments, the cell suspension is equilibrated under 35 bar, or higher, of nitrogen for 3 minutes or more.

In certain non-limiting embodiments freezing and thawing is used as part of a cell lysis process. Freezing cells followed by thawing often ruptures membranes through the action of ice crystals, which pierce the cell. In certain embodiments, one or more freeze-thaw cycles is utilized.

In certain embodiments, a combination of freezing and grinding is used as part of a cell lysis process. In certain embodiments, the cells are frozen using, for example, but not limited to, liquid nitrogen, and the frozen cells are then ground to a powder using one or more of the grinding and milling approaches described above. In certain embodiments, a mortar and pestle are used which have also been cooled with liquid nitrogen. In certain embodiments, a cell lysate is prepared by adding said frozen ground powder to 5 volumes of buffer.

Drying or desiccation is commonly used to disrupt microbial cells, often rendering them susceptible to buffer action. In certain non-limiting embodiments, drying or desiccation and/or the action of buffers is used as part of a cell lysis process. In certain embodiments vacuum may be applied to expedite the process. In certain embodiments freeze drying maybe employed, and in other embodiments slow air drying. In certain embodiments, drying with volatile chemicals may be used. Reagents such as acetone, ethanol, and ether can improve product solubility in buffer. In certain non-limiting embodiments, acetone and/or ethanol and/or ether is used as part of a cell lysis process.

In certain non-limiting embodiments, enzymatic lysis is used as part of a cell lysis process. One or more enzyme(s) can be used to lyse cell walls by attacking specific bonds. Enzymatic lysis may be based, for example, on the digestion of the peptidoglycan layer of a bacterial cell. The enzyme is generally lost in each disruption batch, although it is possible in certain situations to conjugate the enzyme to a macromolecule and recover it by ultrafiltration. In certain non-limiting embodiments, the lytic enzyme(s) are conjugated to a macromolecule and/or recovered by ultrafiltration. A commonly used enzyme is lysozyme, which is obtained from egg white. It attacks muramic peptides in cell walls and has been found effective with gram-positive and gram-negative bacteria. Gram-negative bacteria, however, have an outer membrane that is external to the cell wall and needs to be permeabilized to expose the peptidoglycan layer. Tris, often used as a buffer in lysis methods, effectively permeabilizes outer membranes. This effect can be enhanced by the addition of ethylenediamine tetraacetate (EDTA) (e.g., ~1 mM). EDTA chelates the magnesium ions that stabilize membranes. In certain non-limiting embodiments, one or more lysozyme(s) are used as part of a cell lysis process. In certain non-limiting embodiments Tris is used as a buffer in lysis. In certain non-limiting embodiments, EDTA is used as a chelating agent in lysis. In certain non-limiting embodiments, enzymatic lysis is performed in conjunction with sonication.

In certain non-limiting embodiments, detergents and/or solvents and/or other chemicals are used as part of a cell lysis process. Cationic and anionic detergents, alkalis, acids, and solvents such as chloroform and toluene, are effective in damaging the lipid or lipoprotein of the cell membrane. In certain non-limiting embodiments, cationic and/or anionic detergent(s) and/or alkali(s) and/or acid(s) and/or solvent(s), such as, but not limited to, chloroform or toluene, are used as part of a cell lysis process. In certain such embodiments, the chemical agent is chosen so as to result in no residues that are toxic or harmful to plants and/or fungi and/or animals and/or the environment in the final product downstream from the cell lysis process. In certain such embodiments, a process for the removal to safe levels of any chemicals that may have harmful effects to plants and/or fungi and/or animals and/or the environment, such as are well known in the art, are implemented downstream from the cell lysis process.

Antibiotics, such as polymyxins, amphotericin B, and/or nystatin increase the permeability of bacterial membranes and may induce lysis. Penicillin-based antibiotics are effective inhibitors of bacterial cell wall synthesis, but are only of value for cell disruption where cells are still in active growth. In certain non-limiting embodiments, antibiotics including but not limited to one or more of polymyxins, amphotericin B, nystatin, and/or penicillin are used as part of a cell lysis process. In certain such embodiments, the antibiotic is chosen so as to result in no residues in the final product downstream from the cell lysis process that are toxic or harmful to plants and/or fungi and/or animals and/or the environment and/or that might exacerbate the medical problem of antibiotic resistant microorganisms.

In certain non-limiting embodiments, a bacteriophage is used as part of a cell lysis process. Most groups of bacteria are sensitive to bacteriophage. Phages carry an enzyme that hydrolyzes cell membranes for nucleic acid penetration. A heavy infection can result in lysis. In such embodiments recycling such a phage contamination into the fermentation vessel is a great risk, and steps to prevent such contamination as are known to one skilled in the art are implemented to prevent such contamination.

When cells are ruptured by any method, a cellular debris fraction and a soluble cytoplasmic constituent fraction are generally obtained. These fractions may be separated by methods such as, but not limited to, centrifugation or filtration. Among the soluble cytoplasmic constituents are the nucleic acid and the protein, either individually or in conjugation. Substantial amounts of DNA may be liberated by cell lysis, increasing viscosity. In certain non-limiting embodiments DNase (e.g., ~1 mg/ml) is added to reduce the viscosity of the lysed preparation. Following cell lysis, recovery of the protein by isoelectric precipitation may result in a proteinaceous product having a content of nucleic acids that is undesirable in certain embodiments. In certain embodiments, measures well known in the art to reduce or eliminate the nucleic acid content of proteinaceous material are undertaken.

In certain embodiments, extracts from cell material are obtained. In certain such embodiments, the extracts are organic extracts. In certain such embodiments, the extracts are enzyme extracts. Cell extracts obtained or obtainable by such methods are provided. In some embodiments, the cell extracts (e.g., organic extracts) are used in agriculture, animal feeding, and/or direct human nutrition.

As described herein, the expression culture and/or broth refers to the cell suspension obtained through the bioprocesses disclosed herein, which may use C1 carbon sources and/or organic carbon sources for microbial growth and production. More particularly culture and/or broth include microorganism cells and/or the products of their metabolism and/or unconsumed nutrients which may include, but are not limited to, one or more of the following: protein, water-soluble B-complex vitamins, other vitamins, phosphates, minerals such as but not limited to potassium, sulfur, magnesium, calcium and/or sodium, saturated and/or unsaturated fatty acids, lecithin, cephalins, carbohydrates such as glycogen, trehalose, glucan and/or mannan, ethyl alcohol, carbon dioxide, esters, aldehydes, ketones, and higher alcohols, etc. These residues may be suspended and/or dissolved in the aqueous solution, exactly as they come out of the bioreactor, without drying or concentration, or in a concentrated liquid or solid form after water has been removed. The remnant water can be separated by any conventional method, such as, but not limited to filtration, sedimentation or centrifugation, for instance.

U.S. Patent Application No. 2003/022357 describes a biological fertilizer based on yeast cells of the *Saccharomyces* genus and sludge from wastewater storage or treatment plants, for whose manufacture yeast cells are activated by applying a magnetic field. In certain non-limiting embodiments herein, microorganism cells grown on C1 feedstocks are activated by applying a magnetic field. U.S. Patent Application No. US2002/187900 describes a biological fertilizer comprising electromagnetically activated yeast cells of the *Saccharomyces* genus combined with cattle manure, and U.S. Patent Application No. US2002/187552 discloses a biological fertilizer that also comprises electromagnetically activated *Saccharomyces* cells, combined with bird manure. In certain non-limiting embodiments herein, microorganism cells that have been grown on gaseous substrates including, but not limited to, one or more of $H_2$, $CO_2$, CO, and $CH_4$, are activated electromagnetically. In certain embodiments, the cells are combined with one or more other ingredients, including but not limited to, cattle and/or bird manure and/or other manures and/or extracts from plants, seaweed, and/or kelp, and/or animal waste products.

Protein Hydrolysis

In certain non-limiting embodiments, organic extracts from microorganism (microbial) cells as described herein contain nearly all protein content in a hydrolyzed state, comprising one or more of free amino acids, oligopeptides, and/or other peptides of higher molecular weight, as well as substantially all of the nutrients of the starting whole cell material. In certain such embodiments, the extracts have high bio-fertilizer and/or bio-stimulant capacity, as well as a greater bio-absorption capacity for fungi and/or animals and/or plants. In certain embodiments, these extracted products are useful in organic farming, and/or in animal feed, and/or in hydroponic farming, and/or as additives with a high nutritional value for livestock and/or aquaculture, and/or as nutrients for the growth of heterotrophic microorganisms and/or macroorganisms, and/or as nutrients for direct human consumption.

In certain non-limiting embodiments, the microbial cells as described herein are hydrolyzed to obtain a hydrolysate. In various exemplary embodiments, methods of producing plant biostimulants include hydrolyzing microbial cells to obtain a hydrolysate, and formulating the hydrolysate as a plant biostimulant and/or plant nutrient and/or fertilizer for foliar application and/or application as a soil adjuvant and/or application as a soil fertilizer. In certain non-limiting embodiments, the hydrolysate is used in seed coatings to enhance germination and early growth of vegetable and flower crops, foliage plants, and turf grasses. Certain non-limiting embodiments include a method of producing a plant biostimulant and/or fertilizer comprising: hydrolyzing microbial cells, e.g., grown as described herein, to obtain a hydrolysate; and formulating the hydrolysate as the plant biostimulant for foliar application or application as a soil adjuvant or application in seed coatings. In certain non-limiting embodiments, hydrolyzing the microbial cells comprises hydrolyzing a cell cream having a solids content of about 1 to about 30 weight percent. In certain non-limiting embodiments, hydrolyzing the microbial cells comprises hydrolyzing a cell cream having a nitrogen content of about 0.12 to about 4 weight percent. Microbial cells may be processed by hydrolysis to yield shorter chain compounds with much reduced viscosity compared with intact cells or partially lysed cells. While it is possible to use other cells, microbial cells (preferably prokaryotic cells and more preferably bacterial or eubacterial cells) are employed to prepare plant biostimulants and/or fungal nutrients according to certain embodiments as described herein. Amine-containing compounds may be obtained by hydrolyzing plant or animal cells. Exemplary methods herein in which microbial cells are hydrolyzed may also yield bio-active compounds such as peptidoglycans, lipopolysaccharides, fats, lipids, vitamins, carbohydrates, phenols, mineral elements, phytohormones, amine-containing compounds, and polyamines that may act as plant biostimulants.

Hydrolysis of microbial cells may be carried out by any known method which substantially lyses cell components into short chain or single compounds. Alternatively, a partial hydrolysis can be utilized to produce a plant biostimulant and/or fertilizer from cells by utilizing a less energy intensive and shorter hydrolysis period.

Enzymatic hydrolysis may be employed in embodiments in which the microbial cells are amenable to such enzymatic hydrolysis. In certain non-limiting embodiments, hydrolyzing microbial cells comprises performing enzymatic hydrolysis. After final enzymatic hydrolysis, a product is obtained that may be referred to as an "organic enzyme extract." The organic enzyme may be used as such for agricultural, livestock, and/or human nutrition purposes. In some embodiments, the organic enzyme extract described herein is used in applications of agriculture, animal feeding, and/or heterotrophic fermentations. In certain embodiments, the organic enzyme extract can be used as a bio-stimulant and/or as a bio-fertilizer in organic farming, given its special composition of amino acids, oligopeptides and peptides having a low molecular weight, which enable absorption of these molecules by plants and/or soil organisms. In certain embodiments, biostimulants produced according to the methods described herein and applied to crops deliver one or more of the following outcomes: enhanced crop quality parameters and/or nutrient efficiency; increased growth rate; increased photosynthetic rate; increased crop yield; increased growth of plant roots and leaves; increased abiotic stress tolerance; increased disease tolerance; improved soil quality; less weed growth. In certain embodiments, biostimulants produced according to the methods described herein increase the efficiency of nutrient use by crops to which the said biostimulant has been applied, and/or reduce nutrient leaching into the environment from fields where the crops are planted. In certain non-limiting embodiments, biostimulants produced according to the methods described herein increase the tolerance of plants to stressors and/or increase the reproductive rate of plants and/or have greater efficacy per dose than presently available commercial products and/or offer a reduced risk of plant injury if over-applications occur compared to presently available commercial products. In certain embodiments, the protein hydrolysate or organic extract described herein stimulates desirable, naturally occurring soil microorganisms, such as $N_2$-fixing, P-solubilizing, and indoleacetic acid-producing bacteria. In certain non-limiting embodiments, the stimulated microorganisms include *Azospirillum* sp. and/or *Azotobacter* sp. In certain embodiments, the organic enzyme extract can be used as a nutrient or supplement for fungi (e.g., mushrooms). In certain embodiments, the organic enzyme extract can be used as a nutritional additive with a high added value as animal feed, more particularly, for livestock feed (cattle, sheep, goats, etc.), and/or for aquaculture, and/or for insects (e.g., bees) or other invertebrates (e.g., red worms), and/or for heterotrophic fermentations, and/or for domestic animals or pets, and/or for direct human consumption.

In certain embodiments, the extract contains substantially all of the starting protein in a hydrolyzed form. In certain non-limiting embodiments, more than 90% of the starting protein by weight is in a hydrolyzed form, e.g., in the form of free amino acids, oligopeptides and other peptides having a higher molecular weight. In certain non-limiting embodiments, substantially all the nutrients from the cells in the culture entering the hydrolysis process are contained in the hydrolysate. In certain embodiments, extracellular nutrients from the liquid solution or suspension of organic matter are also included in the product. In some embodiments, a hydrolysate and/or organic enzyme extract obtained or obtainable by a method as described herein is provided. In certain embodiments, the extract is rich in proteins, for example, mostly in the form of peptides (e.g., oligopeptides and peptides having a low molecular weight under 10,000 Daltons) and free amino acids. In certain embodiments, the free amino acids have a high bioabsorption. In certain embodiments, the extract contains carbohydrates. By employing such enzymes as described herein, it is possible to obtain plant biostimulants using alternatives to strong acid or base in hydrolysis. In various exemplary embodiments, enzymatic hydrolysis of microorganism (e.g., bacterial) cells may be carried out using any suitable enzyme or enzymatic composition.

In certain non-limiting embodiments, the microorganisms are hydrolyzed with at least one enzyme that is capable of hydrolyzing microbial (e.g., bacterial) proteins into free amino acids and/or short peptides. In certain embodiments, enzymatic hydrolysis comprises hydrolyzing with a purified enzyme. In certain embodiments, enzymatic hydrolysis comprises hydrolyzing with a mixture of an enzyme and a medium in which the enzyme was prepared. In certain embodiments, enzymatic hydrolysis comprises hydrolyzing with an enzyme of plant and/or animal and/or bacterial and/or archaea and/or fungal origin. In certain embodiments, enzymatic hydrolysis comprises hydrolyzing with a mixture of one or more enzyme(s) of plant, animal, bacterial, archaea, and/or fungal origin. In certain embodiments, the hydrolytic enzyme is produced by a microorganism strain as described herein. In certain embodiments, the hydrolytic enzyme is produced from C1 substrates and/or $H_2$ and/or syngas feedstock. In exemplary embodiments, bacterial cells may be hydrolyzed with one or more of proteases, lipases and amylases. In certain embodiments, enzymatic hydrolysis comprises one or more proteolytic enzyme(s) of microbial, plant, fungal, and/or animal origin. In certain embodiments, the method includes use of an alkaline protease. In certain embodiments, enzymatic hydrolysis comprises hydrolyzing with at least one enzyme selected from pancreatin, papain, bromelain, ficin, bacterial protease, fungal protease, a neutral protease produced by *Bacillus* sp. Alcalase 2.4 L, *Bacillus B. licheniformis*, and/or *Subtilisin carlesberg*, Esperase from *B. lentus*, Nutrase from *B. amyloliquifacus*, Protamex from *Bacillus* sp., Therolysin/therolase from *B. thermoproteolyticus*, Flavouzyme from *Aspergillus oryzae*, Protease N from *B. subtilis*, trypsin, chymotrypsin, keratinase, pepsin, subtilisin, and/or rennin. As would be well understood by one of ordinary skill in the art, pancreatin includes a mixture of digestive enzymes, proteases, lipases and amylases.

Enzymatically hydrolyzing microbial (e.g., bacterial) cells may include combining an enzyme and bacterial cells in any suitable amount under any suitable conditions. Generally, quantities of reactants, reaction conditions, and sequences of reaction steps are selected to achieve ideal enzyme activity. In certain embodiments the conditions of pressure, temperature, pH and time of the enzymatic hydrolysis are those in which maximum or a suitable level of enzyme activity is achieved. In certain embodiments performing enzymatic hydrolysis comprises combining an enzyme and the bacterial cells in a weight ratio ranging from about 0.1 to about 10 g of enzyme per 100 g of nitrogen content of microbial (e.g., bacterial) cells. In another particular embodiment, the enzymatic hydrolysis is performed using a concentration of 0.05%-0.5% by volume of enzyme stock solution with an activity of around 70,000 units using the azocasein assay. In various exemplary embodiments, any suitable method may be employed to improve the efficiency of the enzymatic hydrolysis of the microbial (e.g., bacterial) cells. In certain embodiments, enzymatic hydrolysis comprises combining an enzyme and the microbial cells and agitating the combined enzyme and microbial cells by any suitable method. The enzymatic treatment can be performed in any suitable device known to one skilled in the art, such as a reactor with temperature control and stirring, for example.

As indicated above, hydrolysis may be carried out under any suitable conditions, however in various exemplary embodiments, hydrolysis may be carried out at pH's ranging from 2 to about 10. In certain embodiments, enzymatic hydrolysis is performed under pH conditions falling within the range of pH 4 to 12. In other embodiments, hydrolysis is performed within the pH range of 5 to 9.5 or between pH 6 and 8, or at pH 7. It should be appreciated that each type of enzyme hydrolyzes at its own optimum pH, and the optimum pH may vary depending on the rate and extent of hydrolysis desired. In certain particular embodiments, the pH value is maintained constant during the enzymatic hydrolysis by adding a base, such as, for example, ammonium hydroxide or potassium hydroxide, and in other embodiments pH is maintained by adding an acid. In various exemplary embodiments, hydrolysis may be carried out at a temperature of from 15.5° C. to 55° C. and for a period ranging from 2 to 120 hours. In certain embodiments, enzymatic hydrolysis is performed under temperature conditions ranging from 10° C. to 80° C., and in other embodiments under temperatures ranging from 10 to 65° C. or 10 to 55° C.

In certain embodiments, performing enzymatic hydrolysis comprises reacting an enzyme and the microbial cells in the presence of a catalyst. Any catalyst that improves the efficiency of the enzyme or enzymes may be employed, such as heterogeneous catalysts, homogeneous catalysts and/or electrocatalysts. In certain such embodiments, the catalyst comprises at least one of iron, copper, cobalt, nickel, boron, magnesium, calcium and rare earth metals, such as but not limited to lanthanum. In certain embodiments, enzymatic hydrolysis comprises reacting an enzyme and the microbial cells while electric current is applied. In certain embodiments, enzymatic hydrolysis comprises treating the microbial cells with electrical current before and/or during enzymatically hydrolyzing the microbial cells. Electrical current may be applied to cells by any suitable method and under any suitable conditions. Exemplary methods and conditions for applying electrical current are described, for example, in Tokuda, et al. (2006) "Effects of electrical pre-treatment on the hydrolysis of agricultural Wastes," *J. Brewing Soc. Jap.*, 101(10): 769-775, which is incorporated herein by reference in its entirety. In various exemplary embodiments, electrical current is applied in an amount of from 2 V to 120 V for periods of from 1 to 60 minutes.

Various exemplary embodiments of the methods herein may further include a pretreatment before enzymatically hydrolyzing microbial (e.g., bacterial) cells. The efficiency of microbial protein hydrolysis using enzymes can be improved by using various pre-treatment methods. Such pretreatment methods are believed to degrade the structure of the cells and, thus, increase the rate and extent of hydrolysis by an enzyme. By increasing the efficiency of protein hydrolysis, it is possible to perform hydrolysis using less enzyme or to perform hydrolysis in less time than would ordinarily be required with a given amount of enzyme. It is particularly desirable to perform hydrolysis using less enzyme, as a reduction in the amount of enzyme used can substantially reduce production costs.

In certain embodiments, performing enzymatic hydrolysis comprises treating the microbial (e.g., bacterial) cells with a mild acid or a mild base before enzymatically hydrolyzing the microbial cells. In various exemplary embodiments, a mild acidic pretreatment is carried about by adjusting the pH of the broth to a range falling from 3 to 5 using an acid such as, but not limited to, hydrochloric acid or sulfuric acid. In certain embodiments, mild acidic pretreatment may be carried out at a temperature of from 100° C. to 130° C. for a period of from 0.25 hours to 10 hours. In various exemplary embodiments, a mild basic pretreatment is carried about by adjusting the pH of the bacterial cells to from 9 to 12 using a base such as, but not limited to, sodium hydroxide, potassium hydroxide, or ammonia. In certain embodiments, mild basic pretreatment may be carried out at a temperature of from 100° C. to 130° C. for a period of from 0.25 hours to 10 hours. In certain embodiments, enzymatic hydrolysis comprises treating the microbial cells with ultrasonic vibration before and/or during enzymatically hydrolyzing the microbial cells. In certain embodiments, enzymatic hydrolysis comprises treating the microbial cells with supercritical water and/or supercritical carbon dioxide before enzymatically hydrolyzing the microbial cells.

Certain embodiments include a method for obtaining a hydrolysate or organic enzyme extract through a "one-pot" synthesis. In the context of the invention the expression "one-pot" means that the procedure is carried out without intermediate separation steps. In certain embodiments, the physical treatment of the cell broth occurs, without phase separation, at a super-atmospheric pressure and high temperature, where the cell broth is treated with a concentrated base prior to undergoing enzymatic hydrolysis. In certain embodiments, cell broth is subjected to a type of "one-pot" synthesis which, in certain non-limiting embodiments, comprises the steps of: (a) adding a concentrated base to the broth comprising a cell suspension to adjust the pH thereof; (b) subjecting the mixture obtained in step (a) to a super-atmospheric pressure and high temperature; and (c) subjecting the mixture obtained in step (b) to an enzymatic hydrolysis to obtain an organic enzyme extract. In certain embodiments the alkaline treatment of step (a) uses a suitable base selected from one or more of ammonium hydroxide, potassium hydroxide and/or calcium hydroxide. In certain embodiments the base is used in concentrated form to avoid increasing the reaction volume in excess, something that would increase energy costs by heating, concentrating, etc., as well as the equipment costs. In certain embodiments this concentration is selected according to the desired pH range for the subsequent enzymatic hydrolysis. In certain non-limiting embodiments ammonium hydroxide at around 28% by weight is used and in others roughly 10M potassium hydroxide is used.

In certain embodiments, after alkaline treatment of the broth, the physical treatment of the mixture is conducted at a super-atmospheric pressure and/or high temperature. In one particular non-limiting embodiment a pressure of 102 kPa-141 kPa is applied in step (b) at an elevated temperature. In some particular embodiments a temperature of 90° C.-140° C. is used in the physical treatment. In some particular embodiments, a pressure of 102 kPa-141 kPa is applied at a temperature of 90° C.-140° C. in step (b). This physical treatment is carried out in any suitable device selected by one skilled in the art, such as an autoclave, for instance.

In certain embodiments, enzymatic treatment is performed after the physical treatment. In certain embodiments, after the physical treatment and before the enzymatic treatment, a concentrated base and/or acid is added so that the mixture to be treated has the optimum pH value for the enzyme to be used. In certain embodiments one or more enzymes used in the enzymatic hydrolysis of step (c) is a proteolytic enzyme of microbial, plant, fungal, or animal origin. In a particular embodiment, the enzymatic hydrolysis of step (c) is conducted at a temperature of 40° C.-70° C. and a pH of 8-11 for a period of 2 hr-48 hr. In certain embodiments, one-pot synthesis increases process simplicity and/or decreases expense and/or is less polluting than comparable multi-pot processes.

Hydrolysis of microbial (e.g., bacterial) cells, with or without the assistance of enzymes, may be accomplished through the application of acid or alkali hydrolysis in combination with sufficient heat and pressure conditions. In certain non-limiting embodiments, hydrolyzing the microbial cells comprises performing acid hydrolysis. In certain such embodiments, acid hydrolysis comprises adjusting a pH of a composition comprising the microbial cells with at least one agent selected from sulfuric acid, hydrochloric acid, phosphoric acid, carbonic acid, boric acid, acetic acid, propionic acid, and citric acid. In various exemplary embodiments, acid hydrolysis is carried out by adjusting pH of a microbial cell cream to a pH of about 0.5 to about 5. In certain such embodiments, acid hydrolysis comprises adjusting a pH of a composition comprising the microbial (e.g., bacterial) cells and heating the pH-adjusted composition to a temperature of 30° C. to 200° C. for periods of time from about 10 minutes to about 48 hours. In certain such embodiments, acid hydrolysis comprises adjusting the pH of a composition comprising the microbial (e.g., bacterial) cells and heating the pH-adjusted composition under pressure. In certain non-limiting embodiments, hydrolyzing the microbial cells comprises performing alkali hydrolysis. In certain such embodiments, performing alkali hydrolysis comprises adjusting the pH of a composition comprising the microbial cells to a pH of about 8 to about 14. In certain such embodiments alkali hydrolysis comprises adjusting the pH of a composition comprising the microbial cells with at least one agent selected from potassium hydroxide, sodium hydroxide, calcium oxide, magnesium oxide, and ammonia. In certain such embodiments, alkali hydrolysis comprises adjusting the pH of a composition comprising the microbial (e.g., bacterial) cells and heating the pH-adjusted composition to a temperature of 30° C. to 200° C. for periods from about 10 minutes to about 48 hours. In certain such embodiments, alkali hydrolysis comprises adjusting the pH of a composition comprising the microbial (e.g., bacterial) cells and heating the pH-adjusted composition under pressure. Such acid or alkali hydrolysis techniques as described herein generally yield a hydrolysate including solubles and cell wall debris.

Single Cell Protein, and Microbial Protein Isolates

Certain embodiments of this disclosure relate to a single cell protein (SCP) and/or microbial protein isolate with lowered nucleic acid content. In some embodiments, a protein product is provided that is relatively free of nucleic acid, but that still provides good nutritional value and acceptable eating (i.e., consumption) quality. In certain embodiments, the nucleic acid content is reduced below 9% by weight. In certain embodiments, the RNA content is reduced to meet World Health Organization [WHO] guidelines for human consumption. In certain embodiments, the RNA content of the SCP is below 2% dry weight; in some embodiments it is below 1% dry weight. In certain embodiments, a nucleic acid reduction process is included which produces cell material containing two to three grams of nucleic acid, or less, per 100 grams of protein. In certain non-limiting embodiments, the Protein Equivalence Ratio (PER) of the cell isolate is greater than 1. In certain non-limiting embodiments, the composition of the cell isolate in terms of weight percentage is 65%-85% protein, or higher; 0.5%-9% nucleic acid; 7%-15% lipid; 1%-5% ash; and 5%-20% carbohydrate and/or other N-free, non-lipid organic matter.

In certain embodiments, the cells are subjected to a temperature which inactivates proteases and stops them from breaking down proteins, but which still allows RNase (RNA-digesting enzymes) to break down ribosomal RNA. In certain such embodiments, this temperature is at least about 64° C. In certain such embodiments the small products of this RNA digestion diffuse through the cell walls into the culture broth and so are removed from the final SCP product. In certain such embodiments, this RNA removal step occurs in a RNA reduction vessel in fluid connection with the bioreactor. In certain such embodiments, the culture is harvested continuously from the bioreactor. In certain such embodiments, after the RNA content has been reduced, the cell mass is spread over a large moving filter through which most of the liquid is drawn off by vacuum. In certain such embodiments, this leaves behind a thin sheet of high protein material, for example, a thin sheet of high protein material that is low in nucleic acid content.

The cell isolate of certain embodiments herein may be made by a process which involves rupturing the cells and removing the cell wall residue. In certain such embodiments, this cell rupturing is performed in an alkaline medium. In certain embodiments, the reduction of the nucleic acid content can be accomplished by the hydrolysis of the nucleic acid within the cell to fragments of such size that the fragments can be diffused from the cell away from the protein.

It is known that nuclease enzyme, which is present in a number of different microorganisms, including yeast, hydrolyzes or breaks up nucleic acid molecules to smaller fragments. Hydrolysis of the nucleic acids by enzymatic methods allows the use of much milder conditions in terms of pH and temperature than those generally needed for chemical methods of hydrolysis, where milder is taken to be pH closer to 7, and temperature closer to ambient, respectively. In certain embodiments, the mild conditions obviate the need for acid or alkali resistant equipment. In certain embodiments, an enzymatic process and mild conditions are utilized which better preserve the nutritional quality of proteins than comparable chemical methods of hydrolysis. Several sources of nuclease have been described in the literature. Certain embodiments herein utilize nuclease(s) for the hydrolysis of nucleic acid polymers that are well known to one of average skill in the art. In certain embodiments, such nuclease(s) are free of secondary enzyme systems such as protease, which could cause a decrease in protein recovery by the co-diffusion of amino acids and/or small peptides out of the cell along with the hydrolyzed nucleic acids. In certain embodiments, the nuclease preparation does not contribute an undesirable flavor to products derived from the nucleic acid reduction process. In certain embodiments, the nuclease preparation used is commercially available. In certain embodiments, the nuclease is food grade. In certain embodiments, a nuclease from yeast is used to break up nucleic acid molecules to small fragments. In certain embodiments, an endogenous and/or exogenous nuclease is utilized to break up nucleic acid molecules to small fragments.

In some embodiments, a process is provided for making a protein isolate in which endogenous nuclease is used to hydrolyze the nucleic acid so that the nucleic acid fragments can be separated from the protein, e.g., by precipitation of the protein. It also is known in the art that the hydrolysis of nucleic acids within a cell can be accomplished by a multi-step heating process to activate a self-contained and/or endogenous nuclease to convert insoluble nucleic acid polymer to soluble nucleic acids. In certain embodiments, a multi-step heating process is used to activate a self-contained and/or endogenous nuclease to convert insoluble nucleic acid polymer to soluble nucleic acids. In certain embodiments, the cell lysate is incubated in such a manner that an endogenous nuclease contained in the soluble portion degrades the nucleic acid present in the cell to a soluble form.

Nucleic acid also can be hydrolyzed by exposing the cell to an external nuclease. In certain embodiments, the cell and/or cell lysate is exposed to an external (exogenous) nuclease.

Nucleases are known to be extractable into the soluble fraction above a certain pH. In certain embodiments, the nuclease is soluble at a pH greater than 4. In certain embodiments, the nuclease is soluble at a pH greater than 5.5. In certain embodiments, the pH for nuclease extraction is optimized for minimum alkali addition and/or salt content at adequate soluble nuclease yield. In certain embodiments, the nuclease is extracted at a pH where the nuclease is soluble but inactive, and is maintained in an inactive state until its activity is required, at which point the pH is lowered to regain nuclease activity.

In certain embodiments, a cell strain is improved and/or engineered for increased nuclease activity. In certain embodiments, the nuclease content of the cells is increased by genetic and/or environmental manipulation. In certain embodiments, strains require additional nuclease beyond the endogenous nuclease to adequately reduce the RNA. In certain embodiments, this additional nuclease is provided either from an outside source and/or by selective development of strains for increased internal nuclease.

Nucleases are known to generally have an optimum pH and temperature for maximum aggregate activity (i.e., conversion rate per individual active enzyme multiplied by the number of active enzymes). The reaction rate increases with temperature; however, the fraction of enzymes that are inactivated also generally increases with increasing temperature. These two counteracting effects generally result in the enzyme exhibiting maximum activity within a certain temperature range. In certain embodiments, this optimum is identified and used following standard experimental methods known to one skilled in the art.

In certain embodiments, the incubation time for RNA breakdown by nucleases is optimized.

Nucleic acid polymers and proteins are known to co-precipitate below a certain pH, producing a nucleoprotein mixture. In certain embodiments, the pH to which the lysate is exposed is kept above this pH so as to avoid the formation of a nucleoprotein mixture.

Chargaff, in Vol. I, The Nucleic Acids, states that ribonucleic acid (RNA) can be hydrolyzed by the action of 1N HCl for one hour at 100° C., or by the action of 0.1N NaOH at 100° C. In certain embodiments, the application of acidic or alkaline conditions to the microbial cytoplasmic constituents released by cell rupture results in the hydrolysis of the nucleic acid. In certain embodiments, HCl or NaOH is utilized for the hydrolysis of RNA. In certain non-limiting embodiments RNA is hydrolyzed using about 1N HCl or about 0.1N NaOH at about 100° C. for around 1 hour.

Figure 22:
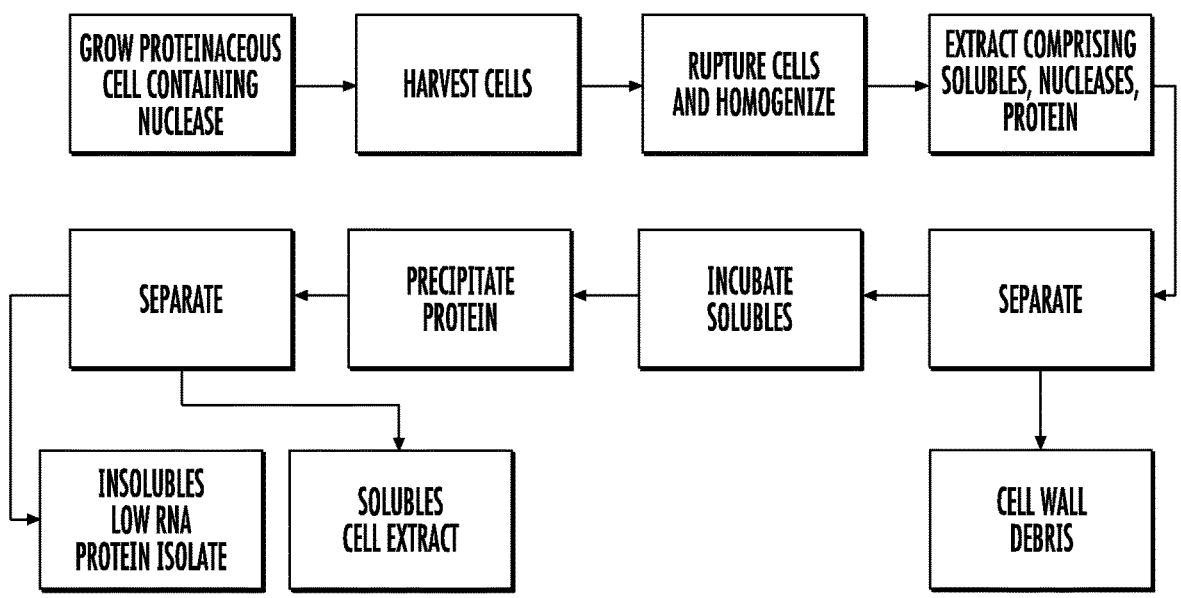
FIG. 22 shows a block diagram of an embodiment a method described herein, whereby a high protein, low nucleic acid isolate is derived from the cells as described herein.

In certain embodiments, following hydrolysis of nucleic acid polymers, two fractions are obtained: one fraction comprises solids containing a reduced content of nucleic acid; and the other fraction is the surrounding medium containing dissolved nucleic acid fragments and other diffusible material. In certain embodiments, the protein is made insoluble, so as to separate it from the hydrolyzed and dissolved nucleic acid. In certain embodiments, an insoluble protein fraction is separated from a fraction containing soluble nucleic acid. In certain embodiments reaction conditions, including but not limited to, pH, time, temperature, and/or concentration, are optimized to recover a protein product having a low content of nucleic acid and an acceptable protein yield, and/or are optimized to maximize protein yield at an acceptable nucleic acid content. Certain embodiments also comprise a method of making protein of low nucleic acid content and free of cell wall debris. In certain such embodiments, a nuclease is used to solubilize nucleic acid including but not limited to an endogenous nuclease. The drawing provided in FIG. 22 is a block diagram of an embodiment of the process of this particular aspect.

Protein Hydrolysates and Uses Thereof

Hydrolysates have been used in the biotechnology industry as a supplement to cell cultures [M. S. Ummadi and M. Curic-Bawden (2010) "Use of protein hydrolysates in industrial starter culture fermentations," in Protein Hydrolysates in Biotechnology, V. K. Pasupuleti and A. L. Demain, Eds. Springer Netherlands, pp. 91-114 (http://dx.doi.org/10.1007/978-1-4020-6674-0_6)]. Certain embodiments of this disclosure relate to microbial hydrolysates produced as described herein, used as a feedstock or nutrient source in other industrial fermentations and bioprocesses. In certain embodiments, hydrolysates produced as described herein are used as a supplement in cell cultures.

Protein hydrolysate has found special application in sports medicine because its consumption allows amino acids to be absorbed by the body more rapidly than intact proteins, thus maximizing nutrient delivery to muscle tissues [Manninen, Anssi H. (2004) "Protein Hydrolysates In Sports And Exercise: A Brief Review" *Journal of Sports Science and Medicine* 3:60-63]. Certain embodiments of this disclosure herein relate to microbial protein isolates and/or hydrolysates and/or extracts with application in sport medicine and specifically, in certain non-limiting embodiments, consumption of said isolate and/or hydrolysate and/or extract allows amino acids to be absorbed by the body more rapidly than intact proteins, thus maximizing nutrient delivery to muscle tissues. In certain embodiments, the hydrolysate and/or isolate and/or extract is rich in antioxidants and/or L-aspartic acid and/or manganese and/or selenium. Certain embodiments relate to using the microbial protein isolates and/or hydrolysates and/or extracts in pet food, including but not limited to food for mammals, such as dogs or horses.

The method of applying the organic enzyme extract and/or hydrolysate described herein to an agricultural crop can be performed by any conventional technique such as, for example, direct application to the soil or via the leaves or by fertigation. In certain embodiments, the application of hydrolysate biostimulant produced according to the methods described herein results in modification of the primary and/or secondary metabolism of the plants receiving the said biostimulant. In certain embodiments, the application of hydrolysate biostimulant produced according to the methods described herein stimulates the production and accumulation of antioxidant compounds such as but not limited to carotenoids, polyphenols, and/or flavonoids in the plants receiving the said biostimulant. In addition to amino acids and peptides, hydrolysates made according to certain embodiments described herein contain other compounds that can contribute to the biostimulant action including fats, lipids, vitamins, carbohydrates, phenols, mineral elements, phytohormones, polyamines, and other organic compounds.

Furthermore, a hydrolysate described herein can alternatively undergo further step/s of concentration and/or separation for stabilization. In certain embodiments, the method described herein comprises further steps after hydrolysis wherein the hydrolysate is subjected to concentration to obtain a concentrated hydrolysate. The concentrated hydrolysate in certain embodiments has at least 40% by weight of dry matter, in other embodiments at least 50% by weight of dry matter, and in other embodiments 50-55% by weight of dry matter, or higher. This concentration may be achieved by any conventional method known in the art, such as, for example, by heating and using a rotary evaporator with a thermostatic bath or reverse osmosis, or any other suitable device.

In another particular embodiment, the method comprises further step(s) following protein hydrolysis, wherein the protein hydrolysate obtained after hydrolysis is subjected to separation to obtain: (i) a soluble hydrolysate fraction, and (ii) a solid phase, insoluble hydrolysate fraction. This separation can be done by any conventional solid-liquid separation method known in the art, such as, for example, by filtration or centrifugation using a decanter or other suitable industrial equipment. In various embodiments of the methods described herein, formulating the hydrolysate includes collecting both liquid and solid fractions of the hydrolysate. In certain embodiments, the hydrolysate may be applied as is, as a biostimulant and/or fertilizer. For example, formulating the hydrolysate may include simply collecting all fractions of the hydrolysate and applying the combined liquid or solid fractions of the hydrolysate to crops as a plant biostimulant and/or fertilizer. In other embodiments, formulating the hydrolysate comprises separating liquid and solid fractions of the hydrolysate and retaining the liquid fraction and/or the solid fraction as the plant biostimulant and/or fertilizer. In other embodiments, the hydrolysate may be separated into soluble and insoluble fractions for foliar and soil applications, respectively. In certain embodiments, the soluble hydrolysate fraction contains virtually all the hydrolyzed starting protein, and in certain embodiments more than 90% by weight. In certain embodiments the insoluble fraction is reduced through the action of heating in the presence of moisture or steam treatment.

In certain embodiments, the soluble hydrolysate fraction provides a composition suitable for agricultural and livestock purposes, and more particularly, as a bio-stimulant and/or bio-fertilizer in organic farming given its special composition of free amino acids, oligopeptides and peptides with a low molecular weight.

In certain embodiments, the hydrolysate can also be used as a nutritional additive with a high added value for animal feed, more particularly, animal feed for livestock (cattle, sheep, goats, etc.), or aquaculture, or insects (e.g., bees) or invertebrates (e.g., worms), or heterotrophic microorganisms (e.g., yeast; $E.\ coli$), or for domestic animals or pets, or for direct human consumption.

Optionally, the soluble hydrolysate fraction can undergo further concentration. In certain embodiments, following a liquid-solid separation step as described above, the soluble hydrolysate fraction is subject to a further concentration step in order to obtain a concentrated soluble hydrolysate fraction. The concentrated soluble hydrolysate fraction has at least 40% by weight of dry matter in certain embodiments, and in other embodiments at least 50% by weight of dry matter, or 50-55% by weight of dry matter, or higher. This concentration may be performed by any conventional method known in the art, such as, for example, by heating and vacuum using a rotary evaporator with a thermostatic bath or reverse osmosis, or any other suitable device. The concentrated soluble hydrolysate of certain embodiments has a composition making it suitable for agricultural and livestock purposes; in particular, in some embodiments, it may be used as a bio-stimulant and/or bio-fertilizer in organic farming given its special composition of amino acids, oligopeptides and peptides with a low molecular weight, which enable absorption of these molecules by plants and/or soil organisms. In certain embodiments the protein hydrolysate or organic extract described herein stimulates desirable, naturally occurring soil microorganisms, such as $N_2$-fixing, P-solubilizing, and indoleacetic acid-producing bacteria. In certain embodiments, the amino acids produced according to the methods described herein have a chelating effect on plant micronutrients. In certain embodiments, the concentrated soluble hydrolysate can be used as a nutrient or supplement for growing fungi (e.g., mushrooms). In certain embodiments, it can be used as a nutritional additive for animal feed, more particularly, animal feed for livestock (cattle, sheep, goats, etc.), or aquaculture (e.g., finfish, shellfish), or insects (e.g., bees) or invertebrates (e.g., red worms), or for heterotrophic microorganisms (e.g. yeast; $E.\ coli$), or for domestic animals or pets, or for direct human nutrition.

Plant Biostimulants and Fertilizers

The solid fraction of the hydrolysate obtained as described above may be applied to crops as a plant biostimulant and/or fertilizer, either in solid form or after being re-dissolved in a suitable solvent, such as an aqueous medium. In certain embodiments, the insoluble fraction of the hydrolysate can undergo a final drying process to obtain a solid in the form of a paste or a powder, with a moisture content of 10-15% by weight, or lower. Such a drying process may be performed by any conventional method, such as by using hot air circulating ovens, or by freeze drying, for example. The dried or undried insoluble hydrolysate can be used as a nutritional additive with a high added value for animal feed, more particularly, animal feed for livestock (cattle, sheep, goats, etc.) or aquaculture (e.g., fin fish, shellfish), or insects (e.g., bees) or invertebrates (e.g., red worms), or for heterotrophic microorganisms (e.g., yeast; $E.\ coli$), or for domestic animals or pets, or for direct human consumption.

In certain non-limiting embodiments, the solid faction of the hydrolysate is granulated, wherein granulating the solid fraction comprises using an apparatus selected from feed pelletizers, pin mixers, disc pelletizers, drum pelletizers, and compaction granulators. In certain embodiments granulating the solid fraction comprises obtaining granules with a size of from about 0.25 mm to about 5 mm. In certain embodiments the solid fraction is dispersed or dissolved in an aqueous medium.

The granulated product may be applied to crops as-is, or may be reconstituted as a liquid by adding a solvent and then applied to crops. In certain embodiments, formulating the hydrolysate includes collecting only one of the liquid and solid fractions of the hydrolysate. For example, formulating the hydrolysate may include separating the hydrolysate into solid and liquid fractions and retaining only one of such fractions. In such case, the liquid or solid fraction may be applied to crops as a plant biostimulant and/or fertilizer. Formulating the hydrolysate may also include collecting all of one of the solid fraction and the liquid fraction of the hydrolysate and only a portion of the other fraction. Alternatively, formulating the hydrolysate may include collecting only a portion of each of the solid fraction and the liquid fraction of the hydrolysate.

A plant biostimulant produced in the manner described herein could be categorized as an amino acid-containing plant biostimulant and/or fertilizer. It is understood that organic fertilizers or manure traditionally includes all plant and animal materials, and that their fertilizer value (neglecting biostimulant or biofertilizer aspects) is primarily dependent upon their respective carbon (C), nitrogen (N), phosphorous (P), and potassium (K) contents. Common organic fertilizers include fish meal, poultry, cow and pig dung, cottonseed meal, rice straw and other agricultural waste products. In certain embodiments herein, a new kind non-plant, non-animal based organic fertilizer is derived. In certain embodiments the organic fertilizer is additionally a biostimulant and/or biofertilizer. In certain embodiments, nutrients produced in the microbial process described herein are used to fertilize ponds where a polyculture is implemented. In certain embodiments, nutrients are used to fertilize plant crops including but not limited to rice.

In certain embodiments, the hydrolysate obtained as described herein is formulated as a liquid product for foliar application and/or as a dry product for soil application. In certain non-limiting embodiments, formulating the hydrolysate comprises formulating without chelating the hydrolysate and/or without separating amino acids from the hydrolysate. In certain non-limiting embodiments, the plant biostimulant has a total nitrogen content of about 0.5 wt. % to about 15 wt. % on a dry matter basis and/or a total solids content of about 2 wt. % to about 100 wt. %. In certain embodiments, the pH of the plant biostimulant is about 2 to about 10.

In certain embodiments, the nitrogen contained in the biostimulant and/or biofertilizer and/or hydrolysate produced as described herein is used by plants to which the material is applied in the production of one or more of the following: proteins, nucleic acids, chlorophylls, etc. In certain embodiments, this applied nitrogen source enhances the metabolic activity of plants and/or fungi and/or microorganisms.

In certain embodiments, the carbon contained in the biostimulant and/or biofertilizer and/or hydrolysate produced as described herein is used by soil microorganisms to produce cell mass and/or for respiration, and/or to fix-$N_2$, and/or to enhance the solubilization of phosphate, and/or to stimulate indoleacetic acid-producing bacteria. In certain embodiments, the carbon contained in the biostimulant and/or biofertilizer and/or hydrolysate produced as described herein is sequestered in the soil and/or increases the soil's carbon content. In such embodiments, where $CO_2$ is captured from a $CO_2$ source that would otherwise emit to the atmosphere, or where the $CO_2$ is captured from the atmosphere, the methods described herein can be considered a form of carbon capture and sequestration where the carbon is sequestered as soil carbon. Certain embodiments herein represent a sustainable conversion of waste carbon and other elements into valuable biomass, or bio-based products such as lysate, hydrolysate, proteins, peptides, vitamins and/or amino acids. In certain embodiments, a larger fraction of input carbon remains in the final fertilizer or biostimulant product, than in a conversion of organic carbon input into compost. In certain embodiments, less than half of the input carbon is lost as $CO_2$ emissions in the conversion to final fertilizer or biostimulant product. In certain embodiments, less than 10% of the input carbon is lost as $CO_2$ emissions in the conversion to final fertilizer or biostimulant product.

In certain embodiments, the methods herein include mixing in additional components to the obtained plant biostimulants and/or fertilizer. Such additional components may be added during hydrolysis, and/or during formulation, and/or after formulation. In certain embodiments, at least one preservative is added to the plant biostimulant, which comprises at least one member selected from citric acid, benzoic acid, propylene glycol, propionic acid, sorbic acid, zinc sulfate, iron sulfate, copper sulfate, and silver chloride. Certain embodiments comprise adding at least one fertilizer and/or plant macro-nutrient to the plant biostimulant, wherein the fertilizer or plant macro-nutrient comprises at least one element selected from nitrogen, potassium, phosphorous, iron, copper, zinc, boron, manganese, calcium, molybdenum, and magnesium. Certain embodiments comprise adding at least one composition selected from herbicides, pesticides and fungicides, to the plant biostimulant, wherein at least one composition is selected from thiophanate methyl, chlorothalonil, captan, piperalin, fenarimol, metalaxyl, triforine, ethoxy thialdiazole, pyretin, algicide, oryzalin, aldxylarypolyethoxyethanol, glyphosate, and naphthalene. Certain other embodiments comprise the addition of no herbicides, pesticides, fungicides, or synthetic fertilizers to the formulation, such that the formulation is considered an organic fertilizer and/or organic biostimulant and that crops to which the organic fertilizer and/or biostimulant are applied, are considered to be organically grown by relevant regulatory bodies.

In some embodiments, methods are provided for applying the plant biostimulants described herein to crops. The crops to which the plant biostimulants and/or fertilizers herein may be applied are not particularly limited; however exemplary crops may include food crops and ornamental crops. Exemplary food crops may include fruits, vegetables, tubers, and grains. Exemplary ornamental crops may include turfgrass, trees, shrubs and flowers. Certain embodiments represent a process for treating a crop, comprising applying a plant biostimulant produced as described herein to a crop. Certain non-limiting embodiments comprise a process wherein the plant biostimulant produced as described herein is applied in an amount of about 0.001 to about 3.0 lbs. of nitrogen per 1,000 square feet. In certain embodiments, a plant biostimulant and/or a fertilizer produced as described herein is applied to a crop. In certain embodiments, applying the plant biostimulant and/or fertilizer to the crop comprises applying the plant biostimulant and/or fertilizer and at least one composition selected from the herbicides, pesticides and fungicides to the crop. In other embodiments applying the plant biostimulant and/or fertilizer to the crop comprises applying the plant biostimulant and/or fertilizer and not applying any synthetic herbicides, pesticides and fungicides to the crop. In certain such embodiments, applying the plant biostimulant and/or fertilizer to the crop, is done in the context of growing crops according to requirements needed to qualify as organic food according to the relevant regulatory bodies.

In some embodiments, a process is provided for making an agricultural product and/or a consumer product and/or an industrial product, comprising: preparing plant biostimulants and/or fertilizers and/or fungal supplements by the methods described herein; applying the plant biostimulant and/or fertilizer and/or fungal supplement produced as described herein to a crop; and harvesting the crop to obtain the agricultural product; and in certain cases further processing the agricultural product to obtain the consumer or industrial product. In certain such embodiments, the crop is a food crop. In certain such embodiments, the food crop comprises at least one member selected from a fruit, a vegetable, a tuber, and a grain. Examples of agricultural products include but are not limited to vegetables such as broccoli, cauliflower, globe artichoke, peas, beans, kale, collard greens, spinach, arugula, beet greens, bok choy, chard, choi sum, turnip greens, endive, lettuce, mustard, greens, watercress, garlic chives, gai lan, leeks, brussels sprouts, capers, kohlrabi, celery, rhubarb, cardoon, chinese celery, lemon grass, asparagus, bamboo shoots, galangal, ginger, soybean, mung beans, urad, carrots parsnips, beets, radishes, rutabagas, turnips, burdocks, onions, shallots, leeks, garlic, green beans, lentils, and snow peas; fruits, such as tomatoes, cucumbers, squash, zucchinis, pumpkins, melons, peppers, eggplant, tomatillos, christophene, okra, breadfruit, avocado, blackcurrant, redcurrant, gooseberry, guava, lucuma, chili pepper, pomegranate, kiwifruit, grapes, cranberry, blueberry, orange, lemon, lime, grapefruit, blackberry, raspberry, boysenberry, pineapple, fig, mulberry, hedge apple, apple, rose hip, and strawberry; nuts such as almonds, pecans, walnuts, brazil nuts, candlenuts, cashew nuts, gevuina nuts, horse-chestnuts, macadamia nuts, malabar chestnuts, mongongo, peanuts, pine nuts, and pistachios; tubers such as potatoes, sweet potatoes, cassava, yams, and dahlias; and cereals or grains such as maize, rice, wheat, barley, sorghum, millet, oats, rye, triticale, fonio, buckwheat, and quinoa. In other embodiments, the crop is an ornamental crop. In certain such embodiments, the ornamental crop comprises at least one member selected from turfgrass, a tree, a shrub, and a flower. In other embodiments, the crop is a mushroom or fungus. Examples of fungal crops include but are not limited to: *Agaricus bisporus* (button, crimini, and portabella), *Coprinus quadrifidus*, *Lepista nuda*, and *Pleurotus ostreatus* (oyster mushrooms). In certain embodiments, a protein hydrolysate as described herein is applied to a mushroom or fungus. In certain embodiments, whole cell biomass (i.e., unlysed cells) as described herein is fed to mushrooms or fungi, which have the ability to lyse and consume bacteria. In certain such embodiments, the mushrooms which lyse and consume bacterial cells produced as described herein include one or more of the following: *Agaricus bisporus, Coprinus quadrifidus, Lepista nuda*, and *Pleurotus ostreatus*.

It is known that UV light exposure right before mushrooms are harvested, can create vitamin D2 content of more than twice the FDA daily value—i.e., a vegan dietary source of vitamin D. In certain embodiments, mushrooms produced as described herein are exposed to UV such that high vitamin D2 content results.

In certain embodiments, methods are provided to increase the yield of produce, crops, or other plants. In certain embodiments, the yield of the produce, crops, or other plants is increased by at least 5%, or by at least 10%, or by at least 40% over a growing season in plants receiving biostimulant or fertilizer produced as described herein compared to the same type of plant grown under the same conditions but without application of the biostimulant. In certain embodiments, the use of fertilizers and/or biostimulants produced as described herein increases crop yield by at least about 5%, 10%, 15%, 20%, 25%, 30%, 35%, 40%, 45%, 50%, or 55%, or greater than 55% over a growing season.

Certain embodiments herein enable the reduction or elimination in the use of conventional chemical nitrogen fertilizers such as, but not limited to, urea nitrate, ammonium nitrate, calcium ammonium nitrate, and/or other nitrate or ammonium fertilizers. In certain non-limiting embodiments, the use of such conventional chemical nitrogen fertilizers can be reduced or eliminated, while retaining the same yield of produce, crops, or other plants, through the application of fertilizer and/or biostimulant produced as described herein. In certain embodiments, the application of fertilizer and/or biostimulant as described herein may be accompanied by a reduction of conventional chemical nitrogen fertilizer by at least about 5%, 10%, 20%, 30%, 40%, or 50%. In certain such embodiments, reduction of conventional chemical nitrogen fertilizer may be over 50% or up to 100% (i.e., totally eliminated).

In certain embodiments, the compositions described herein may more than double soil organic matter or more. In another embodiment, the compositions described herein may increase soil organic matter by up to about 140% or about 150% or more. In other embodiment it may increase soil organic matter by about 40% to about 150%, depending on the initial level of soil organic matter.

Food Products

Examples of consumer products include but are not limited to processed foods, such as potato chips, corn chips, jams, jellies, breakfast cereals, breads, cookies, cakes, crackers, flour, protein powders, protein bars, sports and/or energy drinks, protein shakes and/or smoothies, animal feed, pet food etc. The ability to process agricultural products as described herein into such consumer products is well within the capabilities of those skilled in the art.

In some embodiments, processes are provided for making a nutritional product, and/or a food ingredient, and/or a food item. In certain embodiments, a high-protein and/or high vitamin ingredient is derived from the microorganism cells described herein. In certain embodiments, the product has no animal protein or fats. In certain embodiments, the high-protein and/or high vitamin ingredient is incorporation into food products including but not limited to dairy products, dairy replacement products, meat products, meat replacement and/or imitation meat products, bakery products, confections, health and protein bars, protein powders, sports and/or energy drinks, and/or protein shakes and/or smoothies. In certain embodiments, the high-protein and/or high vitamin ingredient is textured for incorporation into meat products and/or imitation meat products. In certain embodiments, the high protein ingredient can be used as a meat extender in beef patties.

In certain embodiments, the microorganism cells and/or organic matter as described herein are utilized in the production of a vegetarian or vegan food product. In certain embodiments, they are utilized in the production of an organic food product and/or pesticide-free and/or herbicide-free and/or fungicide-free and/or antibiotic-free and/or non-genetically modified (non-GMO) food product. In certain embodiments, they are utilized in a locally produced food product. In certain embodiments, they are utilized in a probiotic food product or in a prebiotic food or nutritional product.

In certain non-limiting embodiments, protein hydrolysis is not performed. In these non-limiting embodiments, a combination of pasteurization, relatively whole proteins, and/or preservative agent addition, provides for a mushroom growth product that exhibits delayed nutrient release properties and/or properties hindering competitive microorganisms and/or properties preventing undesirable temperature rise in the mushroom substrate, when applied as a mushroom growth enhancer.

This invention is not limited in its application to the details of construction and the arrangement of components set forth in the description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference, in particular for the teaching that is referenced hereinabove. However, the citation of any reference is not intended to be an admission that the reference is prior art.

Other features of the invention will become apparent in the course of the following descriptions of examples. The following examples are intended to illustrate, but not limit, the invention.

EXAMPLES

Example 1

*Cupriavidus necator* strain DSM 531 was grown on a mixture of $H_2$ and $CO_2$ and $O_2$ gases as the sole source of energy and carbon for growth.

The following protocol was followed for experiments performed using a mixture of gases in gas tight serum bottles.

Experimental inoculum: 5% by volume, taken from another $H_2$ grown serum bottle culture.

The initial $H_2$ grown serum bottle culture was in turn given 5% inoculation from a Lysogeny broth (LB) grown *Cupriavidus necator* inoculum, and grown ~72 hours on $H_2/CO_2/O_2$ gas mix following inoculation from original LB grown culture. Original LB grown inoculum was recovered from glycerol stock stored at −80° C.

Serum bottle growth on gas was performed in 160-ml stoppered and sealed Wheaton glass serum bottles (VWR product number 16171-385). Volume of liquid media was 20 ml. The bottles were plugged with a rubber stopper (VWR #100483-774) and aluminum seal (VWR #89047-008) using Wheaton Hand-Operated Crimper (VWR #80078-996). 20 ml working volume included 19 ml Minimal Salts Medium (MSM), as described in Thermophilic Bacteria, CRC Press, Boca Raton, Fla., Jacob K. Kristjansson, ed., 1992, p. 87, Table 4+1 ml inoculum (i.e., 5% inoculum).

The MSM was dispensed in the bottles and gaseous compounds were added as follows: Sterile MSM was transferred into bottles under sterile conditions. 5% gas cultured inoculum was inoculated into the bottles under sterile conditions, and the bottles were plugged with rubber stoppers and sealed. A gas mixture was added at 15 psig to the bottles through a manifold. After the gas mix was added, the seal was crimped with aluminum to seal the serum bottles. The bottles were then placed in a shake flask incubator.

The following experimental results were obtained from 16 serum bottles (14 experimental replicates, 2 controls) incubated at 30° C., 250 RPM. All 16 serum bottles were purged simultaneously with a 67% $H_2$, 24% air (4.8% $O_2$), 9% $CO_2$ gas mix using a manifold as described above. The gas composition run through the manifold was confirmed using gas chromatography (GC) before connecting the serum bottles. Bottles were sacrificed for analysis at 7 time points. The two negative controls were sacrificed at T0 and the last time point respectively. Negative control bottles had identical preparation as experimental bottles minus the inoculum, and were used to detect any contamination and/or abiotic loss or leakage of gas from the bottle headspace. Gas headspace pressure readings samples were taken on negative controls to observe any abiotic $CO_2$ & $H_2$ sorption into the liquid medium and/or gas loss due to leakage.

Sampling and Analytical Procedures

All samples were taken under sterile conditions using syringes and needles for bottle experiments. The optical density (OD) was measured using a Beckman Coulter DU720 UV/Vis spectrophotometer at 650 nm using 100 microliter samples.

At each time point one to three experimental replicate bottles were sacrificed for analysis. Gaseous consumption within the serum bottles was measured using a pressure gauge connected to a needle. The headspace gas pressure was measured for each sacrificed bottle, and a sample of headspace gas was taken by gas tight syringe for gas chromatography (GC) analysis. Analysis of gas headspace samples by GC used a 100-uL sample of headspace gas injected into the GC via gas tight syringe. Gas headspace content of $H_2$, $CO_2$, $O_2$, and $N_2$ in the serum bottles was quantified at each time point. For sampling the broth, the septum of serum bottle was wiped with EtOH and the entire liquid contents of bottle withdrawn into a 30 mL syringe, using bottle pressure. 100 µL of sample was pipetted out for OD measurement at 650 nm. Samples were centrifuged at 12,000 G for 15 min at 4° C. Pellets were resuspended in 10 mL sterile PBS, vortexed, and vacuum filtered through pre-weighed 0.45 μm filters. The filters were dried and filter+biomass retentate weighed to determine biomass dry weight. Dry weights were determined for cells collected on membrane filters (0.45 μm) by drying at 60° C. for 24 hours and cooling to room temperature in a desiccator and weighing. This cycle of drying and re-weighing was continued until the weight remained constant. A correlation was developed between OD and biomass density (dry cell weight per volume).

Figure 2:
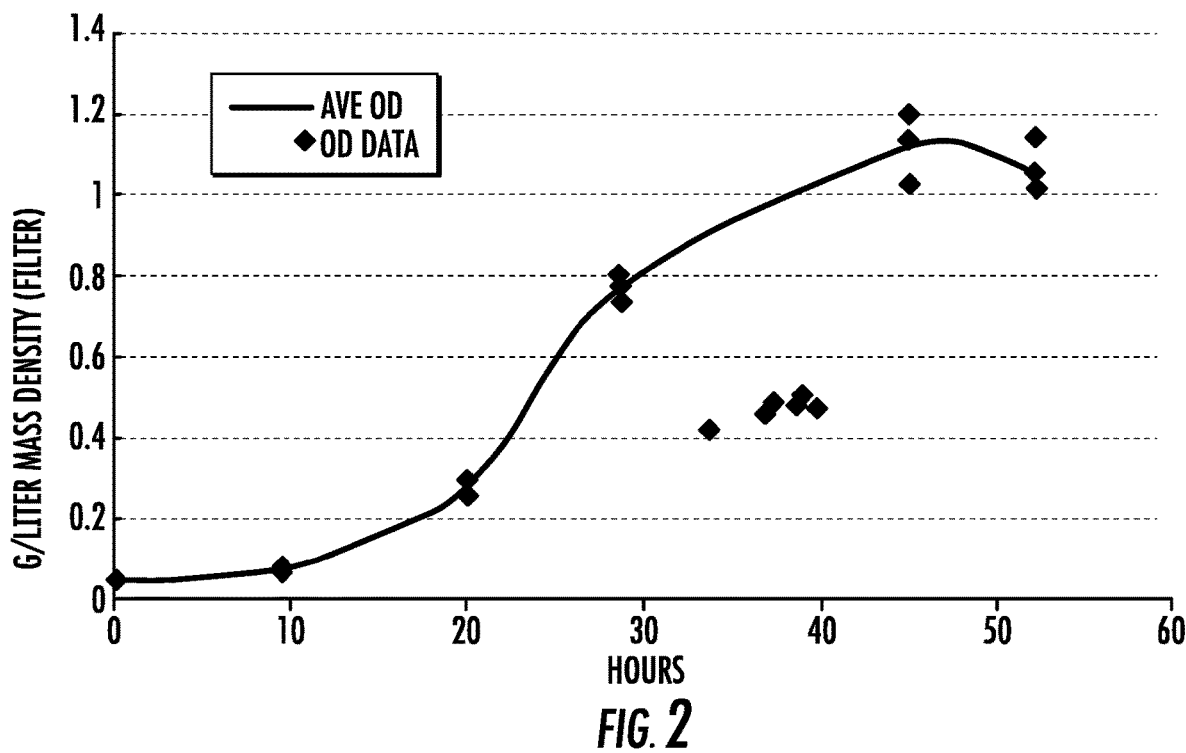
FIG. 2 depicts a growth curve for Cupriavidus necator in serum bottles on gas.
Figure 3:
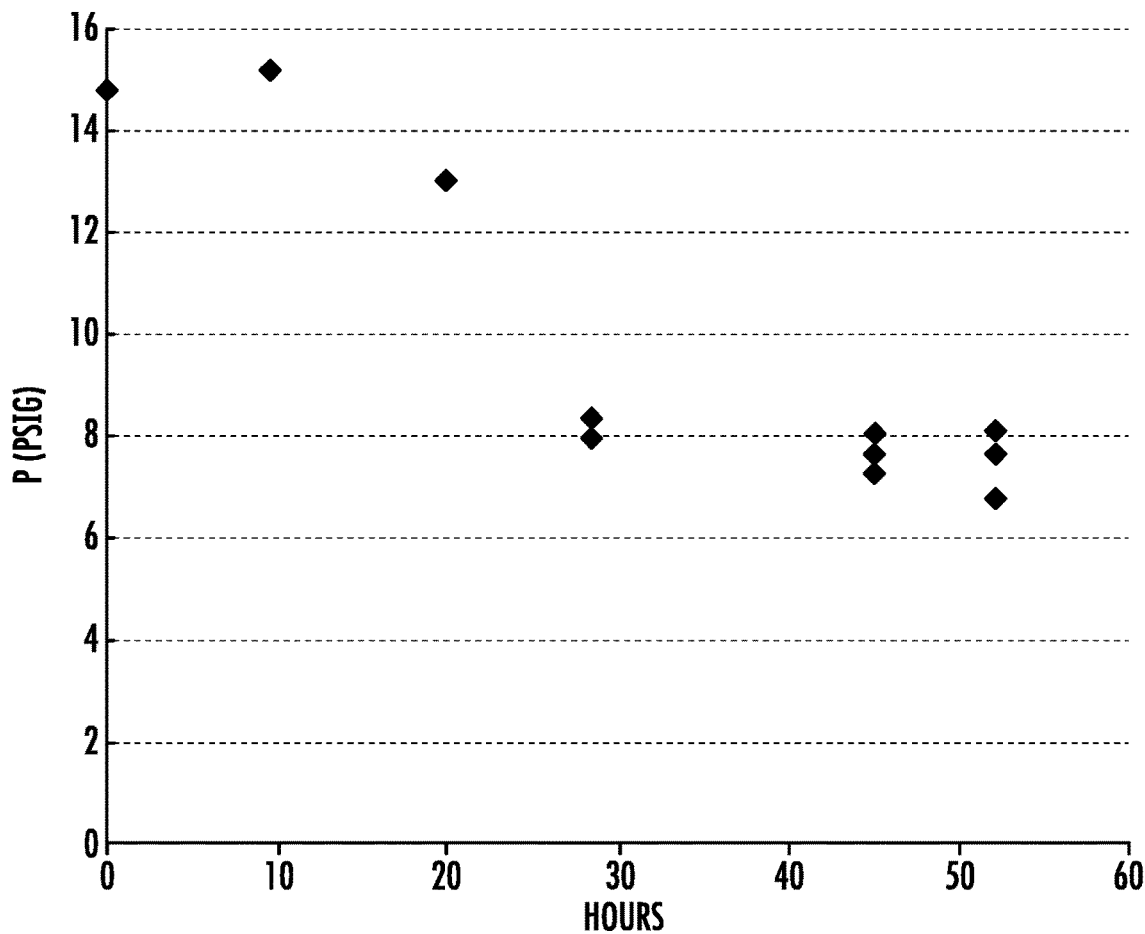
FIG. 3 depicts the change in headspace pressure over time for growth of Cupriavidus necator on gas in serum bottles.

The correlation between OD and biomass density is shown in FIG. 1. The growth curve for this experiment is shown in FIG. 2. The OD measured for individual experimental replicates is represented by the diamond symbols, and the average OD is represented by the solid line. Logarithmic growth occurred between 9 and 30 hours. Change in headspace gas pressure over time due to consumption of the gases by the growing culture is shown in FIG. 3.

Figure 4:
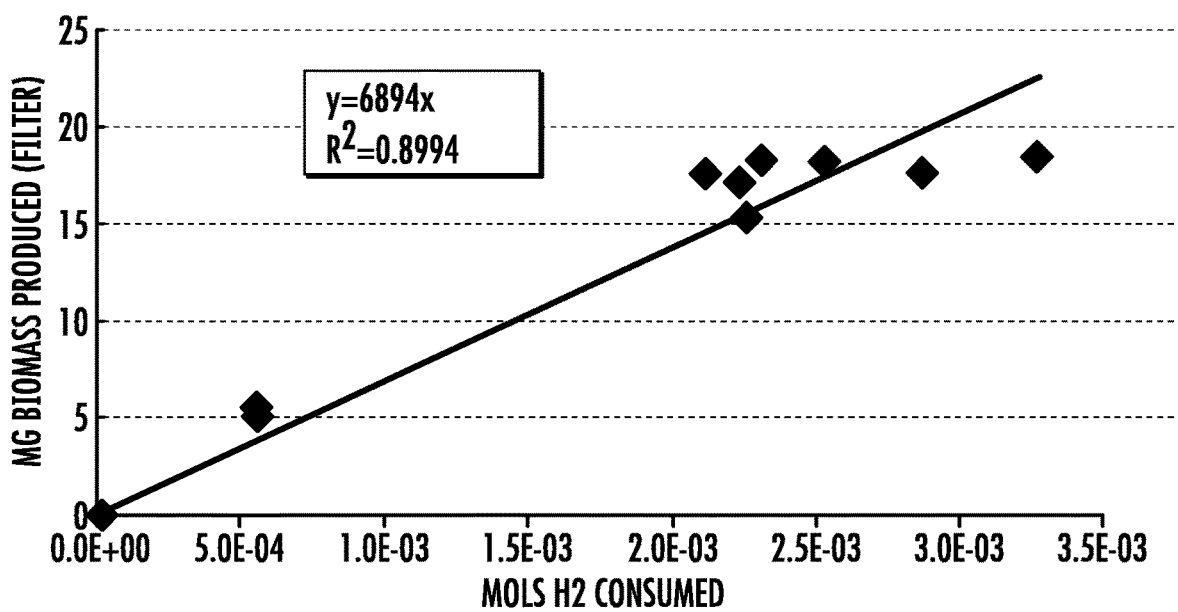
FIG. 4 depicts dry biomass produced per moles of $H_2$ consumed for Cupriavidus necator in serum bottles.

Assuming the ideal gas law (PV=nRT) for the headspace gases, the total moles of gases were calculated, accounting for temperature variation in sample points. The proportion of each respective gas in the headspace of each bottle was determined by GC. Using the gas headspace results and the measured dry weights, the proportionality of cell weight to moles of $H_2$ consumed was determined. FIG. 4 shows the measured dry biomass for each bottle sacrificed, plotted against the moles of $H_2$ consumed, as determined by headspace pressure measurement and GC analysis for each respective bottle. These results indicated that between 6.7 to 7.2 grams of dry cell mass were synthesized per mole of $H_2$ consumed, or 3.3-3.6 grams cell mass per gram of $H_2$.

Example 2

*Cupriavidus necator* strain DSM 531 was grown to 38 grams per liter dry cell density on a mixture of $H_2$, $CO_2$, and $O_2$ gases as the sole source of energy and carbon for growth.

The following protocol was followed for experiments performed using a mixture of gases including $H_2$, $CO_2$, and $O_2$ in a stirred-tank bioreactor.

Apparatus: Culture was grown in batch, using a custom-manufactured 500 mL glass fermenter with PEEK headplate. Temperature and pH were controlled and monitored with a commercial controller (Electrolab, Fermac 360, United Kingdom). A combination of magnetic stir bars and continuous recycle at 280 mL/min were used for mixing. Recycle could be either withdrawn from the bottom liquid section of the reactor and returned to the headspace through sprayers to control foaming or run in reverse to recycle the headspace gas and foam into the bottom of the broth. Gas supply was from compressed $H_2$, compressed $CO_2$ and house air, each regulated to 20 psi. $H_2$ and air were delivered to a flow proportioner (Matheson G2-4D151-E401/E401, 20 psi), which set the relative fraction of the gases. The $H_2$/air gas mix was then delivered to each fermenter through a variable area flow meter; the flow rate to each fermenter of the same $H_2$/air composition could be adjusted by the needle valve of the flow meter. $CO_2$ gas was split and delivered to individual variable area flow meters at each fermenter. The $CO_2$ and $H_2$/air lines tee into a single line delivered to the fermenter. A pressure gauge was used to monitor the gas delivery pressure to the fermenter. Gas was mixed into the fermenter broth via four 2-micron diffusion stones (p/n KEG592, http://morebeer.com/products/diffusion-stone-2-micron-oxygen.html), and vented from the reactor via a condenser to a foam-overflow bottle, then to an exhaust system.

Medium: The medium used for this experiment is described in Example 1. pH control was performed with 2N $NH_4OH$ or 2N NaOH. 2N $NH_4OH$ was prepared from 5M $NH_4OH$, Fluke 318612 (kept at 4° C.) (120 mL) and autoclaved milliQ-$H_2O$ (180 mL).

Autotrophically prepared inoculum: *Cupriavidus necator* DSM 531 inoculum was taken from $H_2$/$CO_2$/$O_2$ grown serum bottle culture. Inoculum for the serum bottles was in turn prepared from preserved 0.5 mL glycerol stocks stored at −80 C for the DSMZ 531 strain. Revival cultures were started on $H_2$/$CO_2$/$O_2$ gas mix per the serum bottle protocol described in Example 1, with 0.5 mL glycerol stock added to 20 mL minimal salts medium (MSM) in a gas tight serum bottle. This initial serum bottle was then subcultured, 1 mL to 20 mL fresh MSM, into 2 serum bottles under the standard $H_2$/$CO_2$/$O_2$ gas headspace. These serum bottles were incubated at 30° C., 250 RPM. The initial revival from the glycerol stock on gas took 2 days and the subculture took another day to grow. The two serum bottle cultures were provided as inoculum for the bioreactor. Optical density (OD) of inoculum was taken as well as a sample for DNA analysis. The gas grown inoculum had an OD ~1. The fermenter was inoculated to give an initial OD ~0.1. In other words, the serum bottle broth was diluted in the bioreactor at a 1:10 ratio. Inoculum was transferred from serum bottles to the bioreactor using a 60 mL syringe. After inoculation, a T0 OD was taken. Generally, all OD measurements were performed with a Beckman Coulter DU720 UV/Vis spectrophotometer.

Fermenter Operation:

Base addition—pH was controlled with 2N $NH_4OH$

Foam Control—If foaming filled more than ½ headspace, and was not controlled by headspace spraying or recirculation, then anti-foam was used. (A8011, Sigma Antifoam C Emulsion, http://www.sigmaaldrich.com/catalog/product/sigma/a8011?lang=en&region=US)

Nutrient amendment—In addition to nitrogen nutrient provided by base addition of $NH_4OH$, other mineral nutrients were added during the run so as to prolong growth and prevent any mineral nutrient limitations from occurring.

Figure 5:
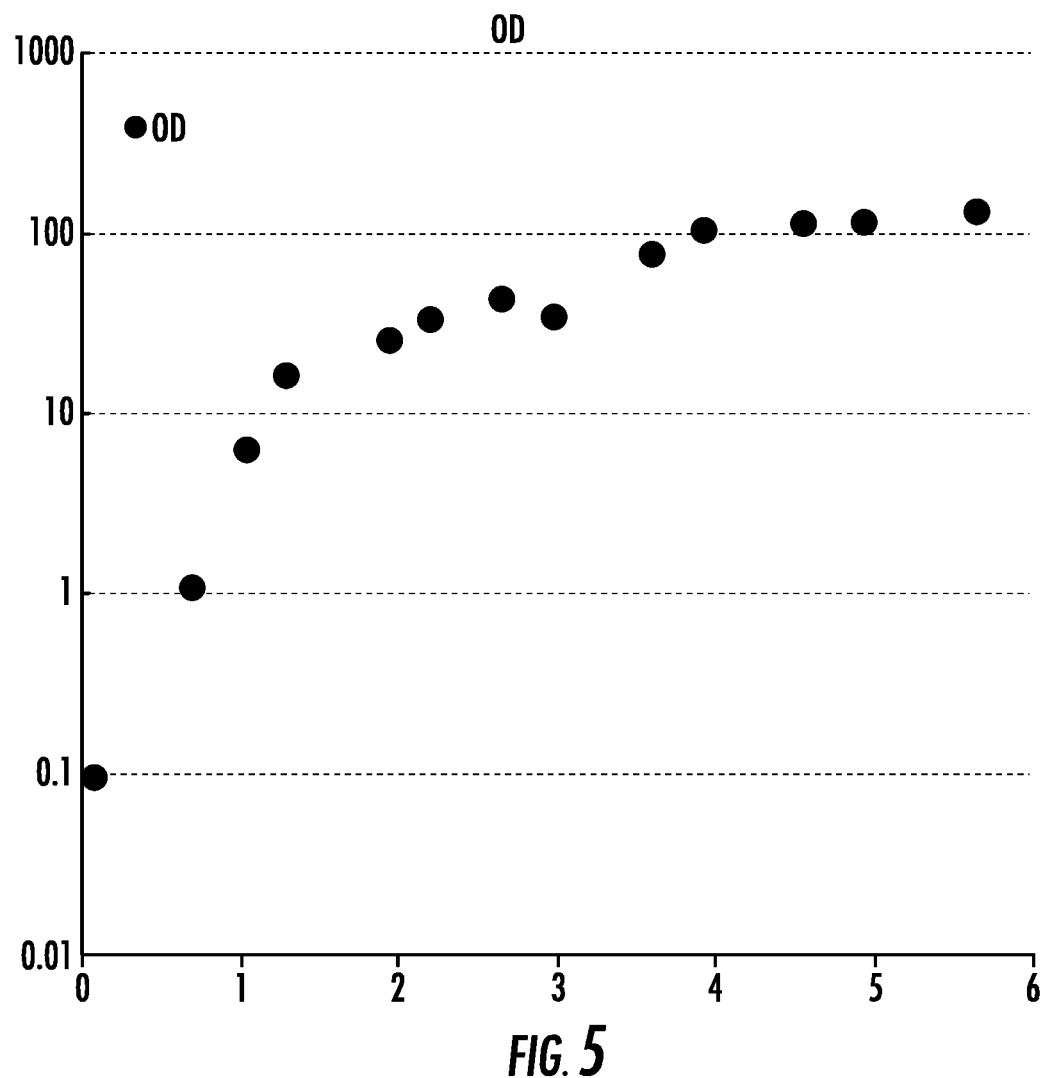
FIG. 5 depicts a growth curve for Cupriavidus necator grown on $H_2/CO_2/O_2$ in a bioreactor.

FIG. 5 gives an example of a growth curve for the knallgas microorganism *Cupriavidus necator* grown on $H_2$/$CO_2$/$O_2$ gas substrate according to this protocol. The y-axis unit is optical density (OD) measured at 650 nm and x-axis is time measured in days. The final OD measured at 650 nm was 132 and the final dry biomass density was 38 grams/liter from growth on $H_2$/$CO_2$/$O_2$ gas substrate. Log growth lasted the first day and a half, however the biomass was still accumulating at a linear rate at the termination of the run during day five.

Example 3

Inoculation and Growth Conditions

Organisms from the genus *Rhodococcus* and from the genus *Cupriavidus* were tested for their ability to grow on different carbon sources (FIG. 6). Colonies from strains grown on LB agar plates at 30° C. were transferred into flasks containing 10% (v/v) of the indicated media (i.e. heterotrophic or chemoautotrophic) for 3-20 days at 30° C. and 250 rpm. *R. opacus* strain DSM 44193 exhibited growth only under heterotrophic growth conditions as measured by optical density (OD) at 650 nm on MSM medium (1 L Medium A: 9 g $Na_2HPO_4 \cdot 12H_2O$, 1.5 g $H_2PO_4$, 1.0 g $NH_4Cl$ and 0.2 g MgSO$_4$.7H$_2$O per 1 L; 10 ml Medium B: 50 mg Ferric ammonium citrate and 100 mg CaCl$_2$) per 100 ml; 10 ml Medium C: 5 g NaHCO$_3$ per 100 ml; and 1 ml Trace Mineral Solution: 100 mg ZnSO$_4$.7H$_2$O, 30 mg MnCl$_2$.4H$_2$O, 300 mg H$_3$BO$_3$, 200 mg CoCl$_2$.6H$_2$O, 10 mg CuCl$_2$.2H$_2$O, 20 mg NiCl$_2$.6H$_2$O and 30 mg Na$_2$MoO$_4$.2H$_2$O per 1 L) supplemented with 40 g/L glucose. *R. opacus* strain DSM 43205 showed identical growth rates under heterotrophic conditions reaching O.D=9.0. Strain DSM 43205 was also able to grow on chemoautotrophic conditions (MSM medium supplemented with 66.7% H$_2$, 9.5% CO$_2$, 5% O$_2$ and 18.8% N$_2$). *Rhodococcus* sp. (DSM 3346) exhibited growth under heterotrophic conditions and chemoautotrophic conditions (DSMZ Medium 81: 1 L of Mineral Medium for chemolithotrophic growth: 2.9 g Na$_2$HPO$_4$.2H$_2$O, 2.3 g KH$_2$PO$_4$, 1.0 g NH$_4$Cl, 0.5 g MgSO$_4$.7H$_2$O, 0.5 g NaHCO$_3$, 0.01 g CaCl$_2$.H$_2$O and 0.05 g Fe(NH$_4$) citrate per 1 L; and 5 ml Trace Mineral Solution, supplemented with 80% H$_2$, 10% CO$_2$ and 10% O$_2$). *Cupriavidus necator* (DSM 531) was able to grow under heterotrophic and chemoautotrophic conditions (media described for Strain DSM 43205) (FIG. 6).

Example 4

In one group of experiments, colonies from *Rhodococcus* strains grown on LB agar plates at 30° C. were transferred into gas tight serum bottles containing the indicated growth media and gas mixtures. (Original LB grown inoculum was previously recovered from glycerol stock stored at −80° C.). Serum bottle growth on gas was performed in 160-ml stoppered and sealed Wheaton glass serum bottles (VWR product number 16171-385). Volume of liquid media was 10 to 20 ml. The bottles were plugged with a rubber stopper (VWR #100483-774) and aluminum seal (VWR #89047-008) using Wheaton Hand-Operated Crimper (VWR #80078-996). Sterile growth media was transferred into bottles under sterile conditions. Inoculum was introduced to bottles under sterile conditions, and the bottles were plugged with rubber stoppers and sealed. A gas mixture was added to the bottles. After the gas mix was added, the seal was crimped with aluminum to seal the serum bottles. The bottles were then placed in a shake flask incubator. The bottles were incubated at 30° C., 250 RPM. All samples were taken under sterile conditions using syringes and needles. Growth was assessed by measurement of optical density (OD) in a spectrophotometer at 650 nm.

Following the procedure described above, *Rhodococcus opacus* strain DSM 43205 exhibited growth under chemoautotrophic conditions in the following media: MSM medium (1 L Medium A: 9 g Na$_2$HPO$_4$.12H$_2$O, 1.5 g H$_2$PO$_4$, 1.0 g NH$_4$Cl and 0.2 g MgSO$_4$.7H$_2$O per 1 L; 10 ml Medium B: 50 mg Ferric ammonium citrate and 100 mg CaCl$_2$ per 100 ml; 10 ml Medium C: 5 g NaHCO$_3$ per 100 ml; and 1 ml Trace Mineral Solution: 100 mg ZnSO$_4$.7H$_2$O, 30 mg MnCl$_2$.4H$_2$O, 300 mg H$_3$BO$_3$, 200 mg CoCl$_2$.6H$_2$O, 10 mg CuCl$_2$.2H$_2$O, 20 mg NiCl$_2$.6H$_2$O and 30 mg Na$_2$MoO$_4$.2H$_2$O per 14 supplemented with a gas mixture that contained 66.7% H$_2$, 9.5% CO$_2$, 5% O$_2$ and 18.8% N$_2$. The liquid volume was 20 mL and the gas headspace volume was 140 mL.

*Rhodococcus* sp. DSM 3346 exhibited growth under chemoautotrophic conditions in the following media: DSMZ Medium 81 (1 L of Mineral Medium for chemolithotrophic growth: 2.9 g Na$_2$HPO$_4$.2H$_2$O, 2.3 g KH$_2$PO$_4$, 1.0 g NH$_4$Cl, 0.5 g MgSO$_4$.7H$_2$O, 0.5 g NaHCO$_3$, 0.01 g CaCl$_2$.2H$_2$O and 0.05 g Fe(NH$_4$) citrate per 1 L; and 5 ml Trace Mineral Solution), supplemented with a gas mixture that contained 80% H$_2$, 10% CO$_2$ and 10% O$_2$. The liquid volume was 10 mL and the gas headspace volume was 150 mL.

Cells were harvested after 72 hours, and profiles of fatty acids contained in neutral lipids, such as triacylglycerol (TAG), produced by each strain were determined by gas chromatography and mass spectrometry (GC/MS).

Example 5

In another experiment, *R. opacus* strain DSM 43205 was grown on a mixture of H$_2$ and CO$_2$ and O$_2$ gases as sole sources of energy and carbon for growth in a one-liter bottle. Inoculum was recovered from a water+MSM stock aliquot stored at −80 C. The medium used was MSM, as described above. An aliquot from stock stored at −80 C was inoculated into MSM (20 ml) in a small serum bottle. Serum bottle growth on gas was performed as described above in a 160-ml stoppered and sealed Wheaton glass serum bottle, with a gas mixture consisting of 67% H$_2$, 24% air (4.8% O$_2$), 9% CO$_2$. The bottle was placed in a shake flask incubator and incubated at 30° C., 250 RPM.

Following roughly 72 hours of growth, a high-density subculture inoculum was prepared from the gas serum bottle culture by centrifuging and resuspending in fresh MSM. The high-density inoculum was inoculated into 100 ml MSM in a 1 L glass bottle with a gas tight cap, having two valves which allowed inflow and outflow of gas. A gas mixture in the following ratio was provided to the headspace of the 1 L bottle: H$_2$: 71%; O$_2$: 4.2%; N$_2$: 15.8%; CO$_2$: 9.0%.

Following gas addition, the sealed one-liter bottle was placed in a shake flask incubator at 28° C. and 200 rpm. The gases were refreshed once per day. The culture grew on gas until a final OD at 650 nm was reached of OD=1.27.

DNA sequencing was performed on the final recovered cells following growth on gas in the 1 L bottle to confirm strain identity of the final culture. 16S rRNA sequences were determined using 27F and 800R primers. With both primers, the top BLAST hits were identified as *Rhodococcus* sp., *Rhodococcus opacus*, *Rhodococcus wrastislaviensis*, GenBank numbers EU127452.1, AB032565.1, and AY940038.1, respectively.

Example 6

Numerous oxyhydrogen species are publicly available or may be isolated using techniques that are described herein. For example, at least 238 different *Rhodococcus* strains and at least 55 different *Cupriavidus* strains are available from public DSMZ (Deutsche Sammlung von Mikroorganismen and Zellkulturen GmbH) strain depositories as well as strains from many other genera that include oxyhydrogen microorganisms including *Hydrogenovibrio*, *Rhodopseudomonas*, *Hydrogenobacter*, *Xanthobacter*, and *Hydrogenothermus*. Oxyhydrogen strains may also be obtained by routine processes, such as isolation from soil samples or geothermal fluid samples using enrichment methods. Testing of strains for oxyhydrogen growth and the ability to produce organic compound including those with carbon number C5 or greater including but not limited to amino acids and proteins under the claimed chemosynthetic conditions are routine in the art. For example, the ability of a *Rhodococcus* strain to grow under oxyhydrogen conditions using CO$_2$ as a carbon source could be performed as described above in the previous Examples. Other methods for growing under oxyhydrogen (knallgas) conditions using CO$_2$ as a carbon source are described in "Thermophilic bacteria," Jakob Kristjansson, Chapter 5, Section III, CRC Press, 1992, pp. 86-88 and have been found to work well with a wide variety of strains drawn from a wide range of genera. Assessment of production of organic compounds, such as those chemosynthetically produced by oxyhydrogen species, is also routine in the art. For example, gas chromatography and mass spectrometry (GC/MS) may be used, as described in Example 5. Other methods include lipid extraction, thin layer chromatography (TLC), gas chromatography (GC), high performance liquid chromatography (HPLC), and mass spectrometry (MS), as described in Waltermann et al. (2000) "*Rhodococcus opacus* strain PD630 as a new source of high-value single-cell oil? Isolation and characterization of triacylglycerols and other storage lipids" *Microbiology* 146:1143-1149.

Example 7

Approximately five kilograms of biomass (dry weight) was produced by *Cupriavidus necator* strain DSM 531 grown on a mixture of $H_2$, $CO_2$, and $O_2$ gases as the sole source of energy and carbon for growth. From this biomass a hexane soluble oil was extracted and analyzed. The following protocol was used in producing the biomass from $H_2$, $CO_2$, and $O_2$ feedstocks in stirred-tank bioreactors and then extracting the oil from the biomass.

Figure 7:
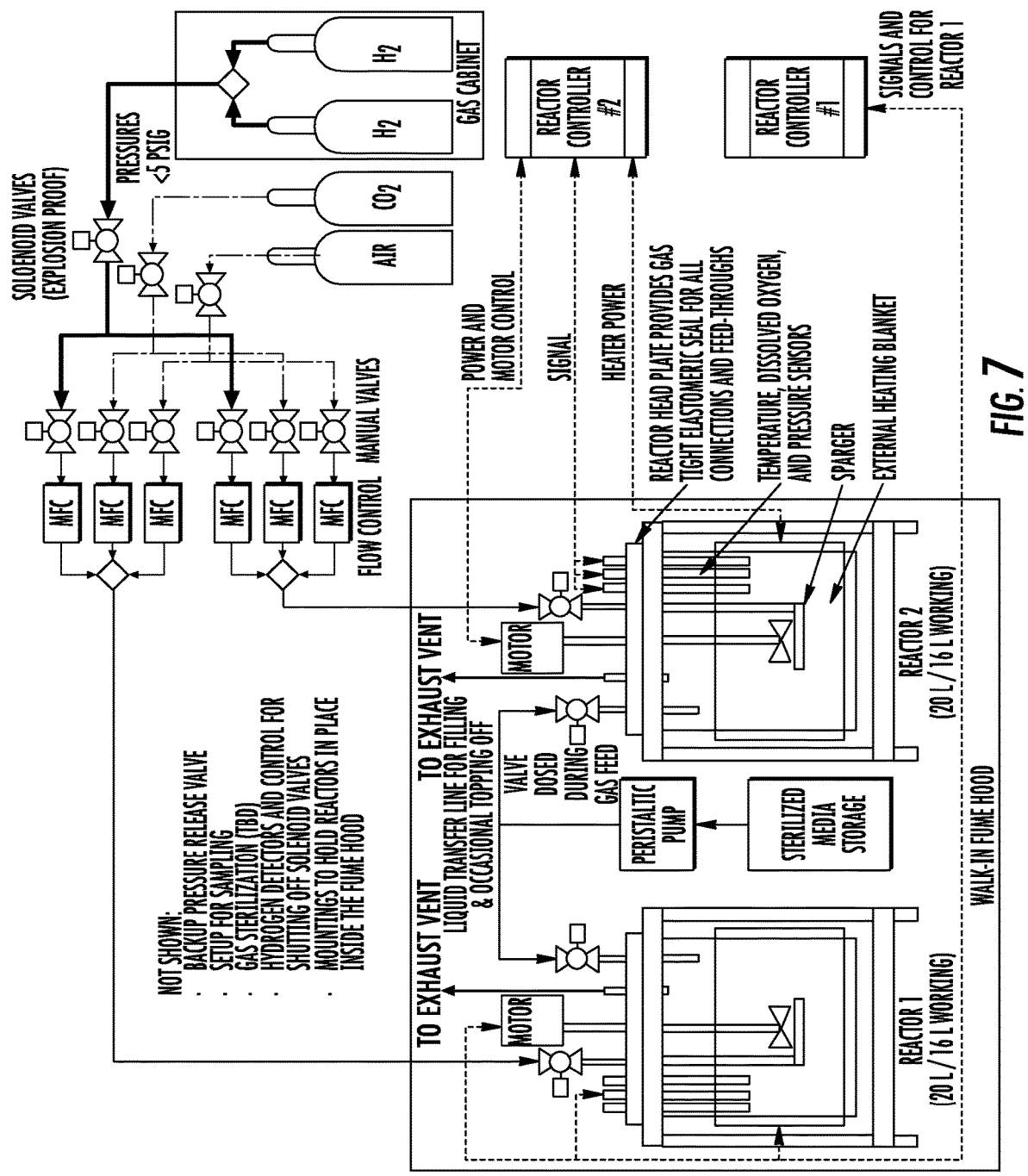
FIG. 7 shows a schematic diagram of bioreactors and supporting systems used to grow C. necator on gas.
Figure 8:
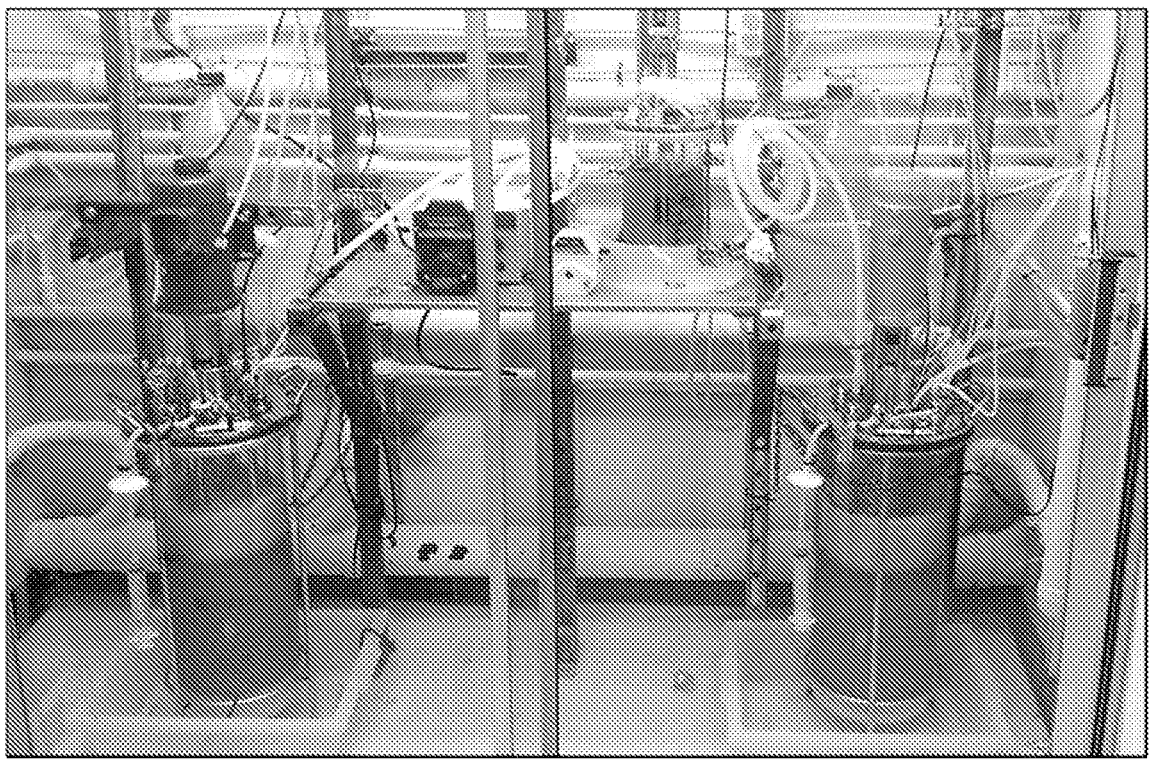
FIG. 8 shows two 20-L bioreactors growing C. necator on gas in a fume hood.

Apparatus: *C. necator* cultures were grown in batch, using two 20-liter reactors from Applikon Biotechnology (Applikon) (FIG. 7 and FIG. 8).

Bioreactor: Each bioreactor consisted of a glass vessel mounted on a support stand with a stainless-steel head plate having an elastomeric seal. The head plate had ports for numerous feed-throughs, all of which had an elastomeric seal to prevent the leakage of gas into or out of the reactor. These feed-throughs allowed for thermowells, pH probes, dissolved oxygen probes, gas inlets, liquid inlets, gas outlets, liquid sampling ports, and more to all be mounted on the head plate.

Bioreactor Sensors: A temperature probe located in a thermowell was used to monitor the temperature and to allow for control of a heater. A pH probe was used to monitor the pH and, if needed, control the addition of higher or lower pH buffered solutions to the reactor. A foam sensor was used to control the addition of anti-foam. A dissolved oxygen probe was used measure the oxygen levels in the reactor liquid and could be used to control agitation or open/close the gas flow to the reactor. All of the sensors were powered by, controlled by, and provided inputs to the bioreactor controller/console.

Stirring: A stirrer passed through the head plate with a complete seal and magnetic coupling. The stirrer had an external motor that was a separate item that fit around the external portion of the stir shaft. The motor speed was controlled by an external controller that allowed for precise control of the rotational speeds.

Heating/Cooling: The reactor was heated by an external electric heating blanket, which used a closed-loop proportional-integral-derivative controller (PID) controlled by the Pt 100 temperature probe via the bioreactor system controller. To maintain temperatures, a cooling finger was also plumbed to prevent overheating of the media by the stirrer motor.

Bioreactor Mounting: The bioreactor systems were mounted on metal tripod holders. Clamps or chains were used to attach this tripod to the strut mountings located inside of a fume hood to prevent the reactor from being knocked over. The whole tripod and reactor setup was placed in a shallow plastic container to provide secondary containment.

A schematic diagram of the bioreactors and supporting systems is shown in FIG. 7. The two 20-L bioreactors were located in a fume hood as shown in FIG. 8. The bioreactors were installed inside of a fume hood to contain releases of hydrogen gas. All of the controls and gas sources were located outside of the fume hood as well as the gas cylinders, reactor controllers, mass flow meters, hydrogen sensors, and gas control valves. Shown in FIG. 8 are the two 20-liter reactors in use during growth of *C. necator* on $H_2$, $CO_2$, and $O_2$ gases as the sole source of energy and carbon.

Figure 9:
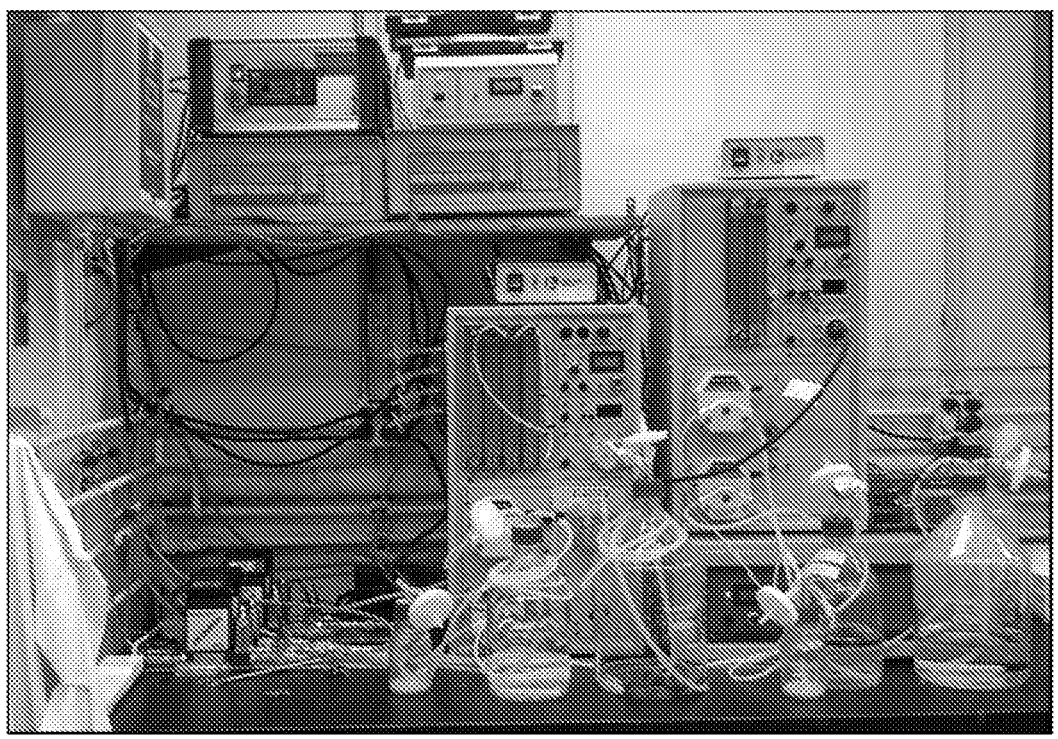
FIG. 9 shows Applikon controllers and consoles that were used to operate 20-L reactors along with explosive gas detection system, mass flow meters, level controllers, base control reservoirs, media addition reservoir, and foam control reservoir.

Controller/Console: The bioreactor system controller/console contained the components that controlled and operated the bioreactor system. These units provided the power, temperature control, stirring control, received inputs from the sensors, turned on and off the feed pumps (acid, base, anti-foam, and additional nutrients) based on sensor inputs, and were used to turn on/off the gas flows with solenoid valves and rotometers. Due to the lack of all stainless-steel components, these units were not used to control the hydrogen to minimize the risk of hydrogen leaks. The controller/console units were located outside of the hood away from the bioreactors to minimize exposure to hydrogen in case of a leak and to minimize the time operators spend working directly around the bioreactors. FIG. 9 shows the Applikon controllers and consoles that were used to operate the reactors. Included in FIG. 9 are the controllers, consoles, stirrer controls, explosive gas detection system, mass flow meters, level controllers, base control reservoirs, media addition reservoir, and foam control reservoir. All of the reactor controls were located outside of the hood.

Gas Delivery: The gas was delivered into the lower portion of the bioreactor though a sparger setup that passed through the head plate. A valve located just outside the reactor enabled the gas flow to be manually shut off at each reactor separately. The gas feed line plumbed to the reactor was a flexible stainless-steel line with a 0.2-micron filter installed at the reactor head to minimize possible contamination. Mass flow meters located outside of the hood were used to control the flow rates to the reactors. Lines between the cylinders and mass flow meters had both manual and solenoid valves for both manual and automatic shutoff of gases. The solenoid valves were connected to explosive gas sensors that automatically shut off gas flows when hydrogen was detected in lab or in the hood.

Gas Storage: A gas cabinet was used to store the hydrogen cylinders. The gas cabinet was mounted in place and included ventilation and sprinklers. The cabinet included enough room to store multiple cylinders to allow for easy switching between an old to a new cylinder.

Safety Controls: Explosive gas detectors were used to determine the presence of hydrogen in the lab. Multiple sensors were located in strategic positions around the lab and in the hood. These gas detectors were configured to shut off the solenoid valves on the gas delivery lines if hydrogen was detected, which shuts off the flow of gas to the reactors.

Peristaltic Pump: An additional peristaltic pump was located in the hood. This pump was used to transfer fresh media into the reactors at the start of a batch run and used to remove the media and biomass at the end of a batch run.

Media Storage: Plastic carboys or glass bottles were used to store the fresh media and the biomass recovered after a batch run.

Medium: The MSM medium used for this experiment is described in Thermophilic Bacteria, CRC Press, Boca Raton, Fla., Jacob K. Kristjansson, ed., 1992, p. 87, Table 4.

Inoculum: *Cupriavidus necator* inoculum was prepared from preserved 0.5 mL glycerol stocks stored at −80 C for the DSMZ 531 strain. Revival cultures were started on $H_2/CO_2/O_2$ gas mix per the serum bottle protocol described in Example 1, with 0.5 mL glycerol stock added to 20 mL minimal salts medium (MSM) in a gas tight serum bottle. The inoculum was provided in multiple containers, which were combined inside of a biosafety cabinet into a single sterile media bottle outfitted with a sterile transfer cap assembly. An OD and streak of the inoculum was taken. The inoculum was then transferred into the reactor using sterile transfer tubing and a peristaltic pump. After inoculating the reactor, a starting OD of the batch was taken using the sample assembly.

Media Preparation and Addition: All of the media was prepared using the recipes provided in Thermophilic Bacteria, CRC Press, Boca Raton, Fla., Jacob K. Kristjansson, ed., 1992, p. 87, Table 4, except at the larger quantities required for 20-liter scale. The main media component (A) was prepared in 20-liter Nalgene carboys outfitted with sterile liquid transfer cap and filter assemblies. The media was autoclaved in the carboys and transferred into the autoclaved reactors using sterile tubing and peristaltic pumps to avoid contamination. The smaller media components (B and D) were prepared in large reservoirs and were sterilized by syringing the solutions through a single-use, sterile 0.2-micron filter directly into the reactor using the septa. Using the septa minimized the risk of contamination as it allowed the opening of the reactor to be avoided. A fourth smaller media component (C) was handled in a manner similar to A, in that a larger reservoir outfitted with a sterile transfer cap was prepared with media, autoclaved, and the media was transferred using sterile tubing and a peristaltic pump.

Bioreactor Preparation and Start-up: Prior to starting freshly inoculated batches, the bioreactor was prepared for autoclaving. The reactor head plate was mounted in place. Transfer lines were connected, clamped, and the end was covered with foil and sealed with autoclave tape. A 0.2-micron filter was connected to the gas inlet of the sparger to sterilize the incoming gases. A vent line was clamped and sealed with foil. The thermowell, condenser, foam level probe, cooling coil, sampling apparatus, adjustable liquid draw tube, and dissolved oxygen probe were installed. The port for the pH probe was covered and sealed with foil. The reactor was then autoclaved for 60 minutes at 131° C. with a dry cycle. The pH probe was sterilized with a combination of quick flaming, ethanol, and UV light. After the bioreactor was autoclaved and cooled to room temperature, the pH probe was inserted into the reactor while both the reactor and probe were inside a biosafety cabinet. The reactor was then mounted in the hood; i.e. cooling lines, transfer lines, electronic controls, heater, stirring motor, etc. were all connected. As quickly as possible, media component A was transferred into the reactor to minimize the amount of time that the pH probe was dry. The temperature control and stirring were turned on, and if necessary, the cooling water as well. Once the temperature of the media reached the desired temperature, media components B, C, and D were transferred into the reactor via the methods described above. The pH control was then started.

Inoculating Bioreactor: Fresh inoculation was performed as described above. In a number of runs the media and biomass from the previous batch was removed via peristaltic pump except for a residual volume, typically less than one liter, which was used to inoculate the next batch. When inoculating with residual volume from the previous batch, after removal of the bulk of the culture, sterile media component A at room temperature was transferred into the bioreactor and the heating was turned on. The rest of the media components B, C, and D were then transferred in via the methods described above. Then the gas flow was turned on, stirring turned up, and pH control turned on. At this point, the run was considered to have started and a starting OD was taken. After the reactor reached the operational temperature the cooling was turned on.

Gas Composition And Flow Rates: The gas compositions used were those specified in section 5. The ratios were controlled using mass flow controllers. The gas flow rates ranged from 0.05 to 0.3 VVM of total gas flow. Typical flow rates were 0.05 VVM over the weekends and 0.2 VVM during the week when both reactors were in operation and had foam control. In the runs that did not use foam control, typical values of 0.05 to 0.075 VVM were used to reduce the foam to manageable levels.

pH Control: Ammonium hydroxide (2.0 M) was used to control the pH of the media in the bioreactor. The ammonium hydroxide solution was prepared by autoclaving 1200 mL of MilliQ water in a 2-liter media bottle outfitted with a sterile transfer cap and filter assembly and adding 800 mL of filter-sterilized 5.0 M ammonium hydroxide inside of a biosafety cabinet. The ammonium hydroxide was automatically transferred into the reactor via peristaltic pump, which was controlled by the bioreactor controller using the pH probe signal.

Nutrient Addition/Amendment: The nutrient amendment solutions used were the same as those used for the initial media, however with different quantities. Mineral nutrients were added during the run so as to prolong growth and prevent any mineral nutrient limitations from occurring. The amendment solutions were either added directly into the reactor using a syringe and sterilizing through a 0.2-micron filter or added through sterile tubing that remained connected to the reactor using a peristaltic pump. The total reactor volume was also manually adjusted on a regular basis (typically daily) by removing small portions of the reactor media and biomass to maintain a working volume of approximately 15.5 L. This was done to compensate for the water additions from the nutrient amendments and water generation by the cellular respiration in order to maintain stable mixing kinetics and prevent overflow.

Sampling: Small aliquots of the media solution were taken at regular intervals from the bioreactor via the liquid sample assembly. These were used to perform the OD600 measurements on an Eppendorf Biophotometer Plus as well as provide the microfuged samples for DNA analysis. The microfuged samples were spun at 10000 rpm for 10 min and, decanted, and stored at −20° C.

Foam Control: After reaching an OD of approximately 15, foam would start to fill the headspace and if not controlled the foam would easily fill up the 2-liter overflow reservoir overnight when gas flow rates of 0.2 VVM were used. A foam sensor was used to determine the presence of foam and turn on a pump that would deliver a solution of silicon-based antifoam emulsion. Gas flow rates and stirrer speeds were adjusted as necessary in batches 11 and 12 to prevent excessive foam build-up. At gas flow rates of 0.05 VVM to 0.075 VVM, the bioreactors were able to be operated without anti-foam. However, the foam would fill the headspace; causing a small amount to flow into the foam overflow container via the gas outlet.

During the batches temperature, pH, and OD were monitored and recorded. Cell purity was monitored using streak plates. A total of 9 batches at the 20-liter scale using *C. necator* were performed. The final optical densities (ODs) of the batches were typically between 30 and 50. The results of these 20-liter batches are summarized in Table 1.

TABLE 1

Results of a series of batch runs for *C. necator* at 3-liter and 20-liter scale.

| Batch # | Scale | Reactor | Start Date | End Date | Start OD | Final OD | Duration (Hrs) | Total gas flow range (VVM) | Stirring rate range (rpm) | Inoculant |
|---|---|---|---|---|---|---|---|---|---|---|
| 1 | 3 L | | 9/4 | 9/6 | 0.63 | 28 | 57.7 | 0.1-0.5 | 850 | 240 ml of gas grown *C. necator* from serum bottles |
| 2 | 3 L | | 9/9 | 9/13 | 2.96 | 32.4 | 103 | 0.2-1 | 900 | ~200 ml of batch 1 |
| 3 | 3 L | | 9/16 | 9/20 | 5 | 40 | 99.9 | 0.2-1 | 1000-1200 | ~200 ml of batch 2 |
| 4 | 20 L | A | 9/23 | 10/3 | 0.94 | 42 | 248 | 0.1-0.3 | 600-800 | ~600 ml of barch 3 |
| 5 | 20 L | B | 10/1 | 10/9 | 1.1 | 6.7 | 188 | 0.05-0.2 | 200 | ~650 ml of batch 4 |
| 6 | 20 L | A | 10/4 | 10/11 | 0.085 | 42 | 165 | 0.05-0.2 | 800-900 | ~400 ml of sugar grown *C. necator* from flasks |
| 7 | 20 L | B | 10/11 | 10/18 | 1.2 | 50 | 168 | 0.05-0.2 | 200-850 | ~500 ml of batch 6 |
| 8 | 20 L | A | 10/11 | 10/18 | 2.1 | 42.5 | 167 | 0.05-0.2 | 800-980 | <1 L of batch 6 |
| 9 | 20 L | B | 10/18 | 10/25 | 3.5 | 49.4 | 165 | 0.05-0.2 | 750-850 | <1 L of batch 7 |
| 10 | 20 L | A | 10/18 | 10/24 | 1.9 | 39.2 | 143 | 0.05-0.2 | 800-950 | <1 L of batch 8 |
| 11 (S1) | 20 L | A | 11/1 | 11/7 | 2.34 | 29.2 | 143 | 0.04-0.2 | 800-850 | ~750 ml of batch 12 |
| 12 | 20 L | B | 10/25 | 11/5 | 0.56 | 37.3 | 264 | 0.05-0.1 | 500-750 | <500 ml of batch 10 |

Eight of the batches reached a final OD of higher than 39, one that was run with lower gas flows (#11) achieved an OD of 30, and one batch that was limited to low stirring rates (#5) only reached an OD of 6.7. The highest OD achieved was 50 in batch #7. All biomass grown was centrifuged out of the culture broth.

Biomass Centrifuging and Storage: A Beckman Coulter Allegra X-12R centrifuge was used to centrifuge the broth harvested from a batch run to recover the biomass. The Allegra-12R has refrigeration down to −10° C. and is outfitted with a SX4750 swinging bucket rotor capable of 3,750 rpm and has a 3-L capacity. After a batch, the biomass and media were transferred out of a bioreactor using a peristaltic pump into 10-liter polypropylene jerry cans. The jerry cans of biomass and media were stored in a refrigerator until they were centrifuged. The biomass was centrifuged 3 liters at a time split between four 750-mL polycarbonate centrifuge bottles. The centrifuge was operated 3,750 rpm at 4° C. for 30 minutes. The supernatant was decanted off and sterilized with bleach prior to disposal. The dewatered biomass for a single batch was combined and stored in polypropylene bottles in a refrigerator.

Example 8

Cell Rupture and Extraction of Oils from Wet Biomass of Strain *Cupriavidus necator*

We determined that efficient oil extraction from samples of wet cell material can be obtained using a cell lysis followed by isopropanol/hexane oil extraction procedure described below. Using this procedure, a crude hexane extract was recovered from *C. necator* biomass grown of $CO_2$ as sole carbon source from which a microbial oil was obtained.

To estimate the moisture content of the wet biomass, two empty vials were labeled and their weights were recorded, and 1-gram of wet biomass was allocated into each of the vials and dried for 12 hours at 60° C. using vacuum oven (Binder Safety Vacuum Oven, Model VDL 115-9030-0040). In order to have statistically significant numbers, samples were runs in duplicate.

Figure 10:
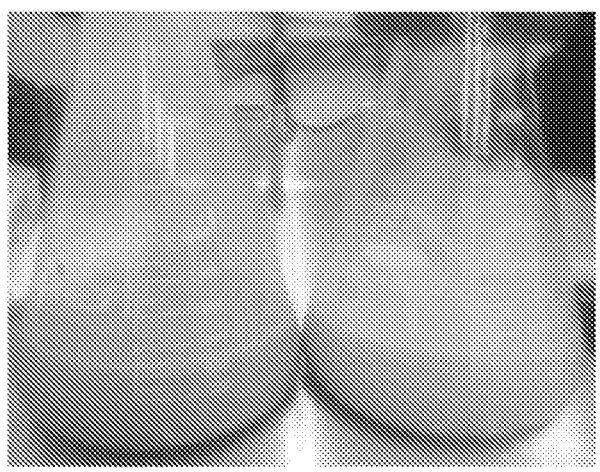
FIG. 10 shows a biomass slurry of C. necator before sonication (left) with a brown color, and after sonication, with complete cell disruption (right), with the color of the biomass turned from brown to cream.

To study the process parameters and operating conditions for lipids extraction using the solvents hexane and 2-propanol, 10 g (A1) and 9.4 g (A2) of wet biomass were mixed into 33.5 mL and 31.5 mL of 2-Propanol respectively. The cell suspension was then transferred into 250 mL beakers and the beakers were kept on an ice bath and were sonicated in a batch mode for 20 minutes. The wet biomass was sonicated with 2-propane for complete cell disruption, cell lysis and to recover oils from the microbial cells. A QSonica Q700 sonicator was used. A temperature probe was immersed in the beaker to record the change in temperature during sonication. Disruption of cells using sonicator or ultrasound waves is a very common method of cell lysis; ultrasound is a cyclic sound pressure wave with frequencies from 20 kHz up to several gigahertz. During the low-pressure cycle, high-intensity ultrasonic waves create small vacuum bubbles in the liquid. When the bubbles attain a volume at which they can no longer absorb energy, they collapse violently during a high-pressure cycle and the resulting shear forces to break the cell envelope. As shown in FIG. 10, after a complete cell disruption the color of the biomass turned from brown to cream. The biomass slurry before sonication is shown on the left in FIG. 10, and after sonication on the right. The initial biomass suspension was viscous but after sonication, the viscosity of the sample decreased, perhaps due to macromolecular shearing effect.

Following the cell lysis due to sonication in 2-propanol, 33.5 mL and 31.5 mL of hexane were added into A1 and A2 respectively and incubated at 60° C. for an hour. The mixture was agitated at 100 rpm. After an hour reaction time the samples were transferred into centrifuge tubes and centrifuged at 3200 g for 15 minutes using a tabletop centrifuge (Eppendorf centrifuge R). The supernatant, which is the mixture of hexane, 2-propanol, and dissolved oils, lipids and polymers was transferred into a Rotavap flask and distilled at 60° C. using a rotary evaporator (Rotavap R-210/215). The hexane and 2-propanol was evaporated at 60° C. and less than 200 mbar vacuum pressures. After evaporation of hexane and 2-propanol, around 4 grams of yellow oils were recovered.

200 g to 250 Gram Per Batch Wet Biomass Extraction

After the small-scale extraction results were confirmed, work on larger-scale extractions commenced. 4 kg of wet *C.*

*necator* biomass was divided into 20 batches (0.2 kg per batch) for extraction, and each batch was transferred into a shake flask. To each flask was added 650 ml isopropanol. 5 mL of 2-propanol solvent was used per 1.5 gram of wet biomass. The biomass was well mixed with 2-propanol to create a uniform suspension.

After creating a uniform suspension, sonication was used to lyse the cells. A QSonica Q700 sonicator was operated in continuous mode for complete cell disruption. The flowcell of the sonicator was attached to the horn and the tubes were connected to the inlet and outlet ports of the flocell. The inlet tubing on the flocell was passed through a peristaltic pump and it was immersed in the flask containing the biomass suspension, while the outlet tubing from the flocell was placed in the same flask to allow circulation. To perform a complete cell lysis, 1 to 1.2 kJ of energy per gram of wet biomass was dissipated. A temperature probe was immersed in the sample beaker to record the change in temperature during sonication.

Each of the 20 portions made from the 4 kg input was sonicated in batch mode at 100% amplitude for 30 minutes with 30 seconds intervals between each 1 minute sonication burst.

After sonication with 2-propanol, 5 mL of hexane per gram of wet biomass was added, then the samples were incubated using a Kuhner Shaker X at 60° C. for an hour. 650 ml of hexane was added to each batch, which was then incubated for 60 minutes at 60° C.

The samples were transferred into centrifuge tubes and were centrifuged using an Eppendorf centrifuge R at 3200 g for 15 minutes. Each batch of the biomass was distributed into 4×400 mL Eppendorf centrifuge R tubes. The centrifuge rotational speed was set at 4000 rpm, which is equivalent to 3200 g for the 18 cm rotor radius.

After separating the cell pellet, the organic extracts i.e. supernatant were transferred to a rotary evaporator (Rotavap) mixing flask. The Rotavap was used to separate the oils and polymers from hexane and 2-propanol. The hexane and 2-propanol were evaporated at 60° C. and 200-100 mbar, and the oil dried of solvent. The hexane and 2-propanol was heated by means of a heating bath at 60° C.

For the larger-scale extraction, optimal distillation conditions were reached at 100-mbar vacuum pressure and 60° C. water heating bath; however, after evaporating hexane and 2-propanol the yellow polymers/oils mixture was left inside the mixing flask. To separate the oils from the yellow polymers, hexane was reapplied and the polymers were then separated by centrifuge.

The polymer/oil/hexane mixture was reheated to 60° C. for 10 minutes, transferred to centrifuge tube and spun at 3200 rpm for 5 minutes. After reheating and centrifugation, oil separated and was isolated and analyzed. The oil extract was found to contain mostly saturated and mono-unsaturated C16 and C18 fatty acids including Palmitic acid—a primary constituent of palm oil. From 4 kg of wet *C. necator* biomass, which corresponded to around 1 kg of dry biomass, 80 grams of crude hexane extract (i.e. hexane soluble oils) was recovered.

In total about 230 ml of oil was extracted from various samples of *Cupriavidus necator* produced from $H_2$ and $CO_2$ as sole source of hydrogen, electrons, and carbons, according to the methods described in this section. This corresponds to around 210 grams of oil. Of this total, about 160 ml (140 grams) of the oil was extracted from samples generated by the 20-liter batch runs described in this section, and the remainder, was from other continuous and batch runs on $H_2/CO_2$ substrates.

The residual biomass left after oil extraction was found to be high in PHB and protein.

Example 9

Production of Amino Acids from Feedstock Consisting of a Syngas, or Components Thereof

*Cupriavidus necator* strains DSM 531 and DSM 541 were cultured using a $H_2/CO_2/O_2$ gas mixture and mineral salt fermentation medium. The culture was grown for 96 hrs. in 20 ml MSM medium (1 L Medium A: 9 g $Na_2HPO_4.12H_2O$, 1.5 g $H_2PO_4$, 1.0 g $NH_4Cl$ and 0.2 g $MgSO_4.7H_2O$ per 1 L; 10 ml Medium B: 50 mg Ferric ammonium citrate and 100 mg $CaCl_2$) per 100 ml; 10 ml Medium C: 5 g $NaHCO_3$ per 100 ml; and 1 ml Trace Mineral Solution: 100 mg $ZnSO_4.7H_2O$, 30 mg $MnCl_2.4H_2O$, 300 mg $H_3BO_3$, 200 mg $CoCl_2.6H_2O$, 10 mg $CuCl_2.2H_2O$, 20 mg $NiCl_2.6H_2O$ and 30 mg $Na_2MoO_4.2H_2O$ per 1 L) in a serum bottle supplemented with 66.7% $H_2$, 9.5% $CO_2$, 5% $O_2$ and 18.8% $N_2$ at 30° C. and 200 rpm.

For lysine detection in the growth media, 1 ml of the cells (O.D=0.1) were separated by centrifugation (10,000 rpm, 5 min at room temperature) and the supernatant (200 microliters) was further filtrated (0.22 micron). Samples of the supernatants were collected and analyzed for secretion of amino-containing compounds, such as amino acids including lysine, tyrosine, and phenylalanine, as shown in Table 2.

TABLE 2

Secreted amino-containing compounds from *C. necator*.

|  | Compound | Blank | DSMZ 531: *C. necator* umol/L | DSMZ 541: *C. necator* umol/L | fold difference |
| --- | --- | --- | --- | --- | --- |
| Glu | Glutamic acid | 0.1952 | 11.556 | 40.614 | 3.5 |
| Sar | Sarcosine | 1.7232 | 2.5708 | 36.4692 | 14.2 |
| Ser | Serina | 1.7688 | 7.9428 | 35.8164 | 4.5 |
| Gly | Glycine | 9.4757 | 10.3272 | 35.0351 | 3.4 |
| Ala | Alamine | 0.6504 | 5.996 | 32.3436 | 5.4 |
| Thr | Threonine | 0.216 | 5.4152 | 22.9456 | 4.2 |
| Val | Valine | 0.0984 | 4.182 | 21.5904 | 5.2 |
| Ile | Isoleucine | 0.0272 | 2.1476 | 14.0068 | 6.5 |
| Orn | Ornithine | 0.9324 | 10.4876 | 13.056 | 1.2 |
| His | Histidine | 0.99 | 2.3816 | 12.0852 | 5.1 |
| Arg | Arginine | 0.2988 | 0.4112 | 9.3428 | 22.7 |
| Phe | Phenylalanine | 0.1 | 3.4216 | 8.6652 | 2.5 |
| Lys | Lysine | 0.1012 | 0.063 | 7.9088 | 125.5 |
| Tyr | Tyrosine | 0.386 | 2.9448 | 7.3972 | 2.5 |

TABLE 2-continued

Secreted amino-containing compounds from *C. necator*.

| Compound | | Blank | DSMZ 531: C. necator umol/L | DSMZ 541: C. necator umol/L | fold difference |
|---|---|---|---|---|---|
| Cit | Citosine | 0.3332 | 0.6572 | 6.8248 | 10.4 |
| Asp | Aspartic acid | 2.1964 | 3.2776 | 4.6132 | 1.4 |
| Gln | Glutamine | 0.1412 | 1.2548 | 4.2944 | 3.4 |
| Pro | Proline | 0.0477 | 1.2567 | 4.1107 | 3.3 |
| Leu | Leucine | 0.054 | 2.5558 | 3.7205 | 1.5 |
| Trp | Tryptophan | 0.0352 | 0.9464 | 2.7072 | 2.9 |
| Met | Methionine | 0.0156 | 1.3944 | 1.614 | 1.2 |
| Tpr | Tpr | 0.034 | 0.5208 | 0.8052 | 1.5 |
| B-Ala | B-Alanine | 0 | 2.0904 | 0.6688 | 0.3 |
| SAM | S-Adenosylmethionine | 0 | 0 | 0.5604 | |
| SAH | S-Adenosylhomocysteine | 1.194 | 2.3232 | 0.2812 | 0.1 |
| MetSo | Methionine Sulfoxide | 0.0128 | 0.3696 | 0.2528 | 0.7 |
| Hcy-PCA | Hcy-PCA | 0.024 | 0.1944 | 0.2344 | 1.2 |
| a-AAA | a-AAA | 0.0096 | 0.2008 | 0.1492 | 0.7 |
| APA | APA | 0 | 0.0248 | 0.134 | 5.4 |
| Put | Putracine | 0.1912 | 15.0568 | 0.128 | 0.0 |
| Cys-PCA | Cys-PCA | 0.0392 | 0.7148 | 0.1272 | 0.2 |
| GSH-PCA | GSH-PCA | 0.0056 | 0.0052 | 0.0468 | 9.0 |
| Spd | Spd | 0.0652 | 0.0728 | 0.0444 | 0.6 |
| 3-His | 3-His | 0.0264 | 0.0384 | 0.0276 | 0.7 |
| Cy2 | Cy2 | 0.0364 | 0.0628 | 0.0128 | 0.2 |
| Cth | Cth | 0.0072 | 0.0072 | 0.0124 | 1.7 |
| CysGly-PCA | CysGly-PCA | 0.002 | 0.01 | 0.0112 | 1.1 |
| Erg | Erg | 0.0076 | 0.0512 | 0.0084 | 0.2 |
| Hcy2 | Hcy2 | 0.0116 | 0.008 | 0.0048 | 0.6 |

Lysine is a six carbon molecule, and tyrosine and phenylalanine are nine carbon molecules. It was observed that *C. necator* strain DSM541 secreted higher concentrations of lysine, tyrosine, and phenylalanine into the medium compared to *C. necator* strain DSM531. The analyses were performed on 200 µl of sterile filtered fermentation medium. Compounds were isolated and derivatized using a clean-up and derivatization kit (e.g. EZ-FaaST (Phenomenex) followed by liquid chromatography-mass spectrometry to separate and identify compounds that had been secreted by the bacterial strains into the medium (Table 2). The levels of lysine found in the media from DSM 541 were 125-fold higher than DSM 531.

Example 10

Figure 11:
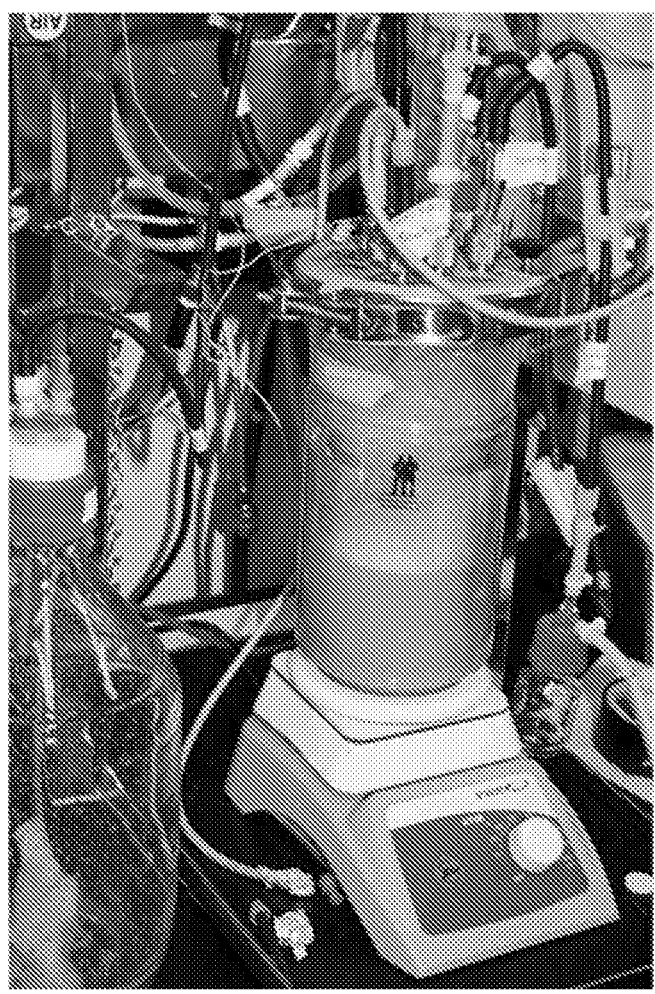
FIG. 11 shows Hydrogenovibrio marinus strain DSM 11271 growing in a bioreactor on a mixture of $H_2$, $CO_2$, and $O_2$ gases.

*Hydrogenovibrio marinus* strain DSM 11271 was grown to over eight grams per liter dry cell density on a mixture of $H_2$, $CO_2$, and $O_2$ gases as the sole source of energy and carbon for growth (FIG. 11). The following protocol was followed for experiments performed using a mixture of gases including $H_2$, $CO_2$, and $O_2$ in a stirred-tank bioreactor.

Apparatus: Culture was grown in batch, using custom-manufactured 500 mL glass fermenter with PEEK headplate; a sparge tube having one porous glass frit, connected to tubing for gas delivery with a 0.2 m filter; a septum port for amendment delivery; a dip-tube to bottom with aseptic sampling assembly, a condenser connected via tubing to an overflow vessel with a 0.2 m filter on the gas outlet; a port for base delivery and tubing for base-delivery with a luer fitting to a sterile syringe; a grounding probe; a port for antifoam delivery; a pH/temperature probe; an oxidation/reduction probe (ORP). Temperature was controlled to 37° C., and pH to 6.5, using a commercial controller (Electrolab, Fermac 360, United Kingdom). The target temperature was maintained by a heating pad on the bottom of the reactor, and an integral glass jacket for cooling water. The pH was maintained at 6.5 using 6N $NH_4OH$. The reactor sat on a stir-plate (VWR 12365-344) and a magnetic stir bar (cross shape, VWR 'spinplus' #58947-828) was used for mixing. The stirplate was set to 300-400 RPM. The gas flow rate into the bioreactor was 1 WM. Gas supply was from compressed $H_2$, compressed $CO_2$ and house air, each regulated to 20 psi. $H_2$ and $CO_2$ were delivered to a flow proportioner (Matheson G2-4D151-E401/E401, 20 psi), which set the relative fraction of the gases. Air was delivered to a variable area flow meter (Key Instruments 1G03_R5). The $H_2/CO_2$ gas mix from the flow proportioner was tee'd into the air, and then delivered to the fermenter through a variable area flow meter. A pressure gage was used to monitor the gas delivery pressure to the fermenter. Inlet gas flowed through a 0.2 m filter (Pall, p/n 4251), and then was dispersed into the fermenter broth via one porous pyrex frit (40-60 m, Sigma-Aldrich CLS3953312-C) and vented from the reactor via a condenser (jacketed and cooled) to a 2 L foam-overflow bottle, then through another 0.2 m filter (Pall, p/n 4251) and finally to an exhaust system. $CO_2$ flow was set to the minimum c.l.=5 (c.l.=centerline of float), and the other gases were set to achieve the targeted gas composition, calculating according to the flow meter tables, measuring composition by GC and adjusting and re-measuring. Used c.l. $H_2$=25, c.l. air=45 to give a gas mix having respective proportions of $CO_2/O_2/H_2$ of 11/6.3/59. Ongoing monitoring of $O_2$ in influent and effluent lines was done using a Foxy probe. Occasional gas samples were taken for GC analysis (in 1 L foil bags, skcinc.com p/n 262-01).

Medium: One liter of the basal medium contained 2.0 g $K_2HPO_4$, 1.0 g $KH_2PO_4$, 5.0 g $(NH_4)_2SO_4$, 29.3 g NaCl, 0.2 g $MgSO_4 \cdot 7H_2O$, 10.0 mg $CaCl_2$), 10.0 mg $FeSO_4 \cdot 7H_2O$, 0.6 mg $NiSO_4 \cdot 7H_2O$, and 2.0 ml of trace element solution. The trace element solution was taken from Thermophilic Bacteria, CRC Press, Boca Raton, Fla., Jacob K. Kristjansson, ed., 1992, p. 87, Table 4.

Autotrophic inoculum: A 10% inoculation gas-grown inoculum was prepared in two 500 ml bottles with stoppers containing 50 mL of liquid media. A volume of 61.5 mL inoculum, OD600 0.75, was injected into bioreactor via a dip-tube to below the liquid level to prevent dispersion in headspace. The line was flushed with filtered air after inoculation to remove trapped inoculum in the dip-tube.

Fermenter Operation: Base addition—pH was controlled with 6N $NH_4OH$; Nutrient amendment—In addition to nitrogen nutrient provided by base addition of $NH_4OH$, 0.2 grams $FeSO_4.7H_2O$ were added when the broth OD=3, and 2 grams $MgSO_4.7H_2O$ when the broth OD=10. The influent $O_2$ was measured to be around 5%, and effluent $O_2$ ranged from 3-4%. Samples were withdrawn from a tube extending to the bottom of the reactor using an aseptic sampling system with 25 mL bottles. The DNA sequencing results confirmed *H. marinus* and no contamination was observed to grow on agar plates that were streaked daily throughout the run.

Table 3 shows the cell dry weight (CDW) density measured at various time points during the run. The CDW density reached over eight grams/liter during day 5. The content of chloroform/methanol soluble lipid, and hexane soluble lipid, respectively, as a percentage of the biomass sampled at various time points, is also given in Table 3. The lipids were analyzed by GC/MS using the methods described above and were found to contain fatty acids ranging from 14 to 20 carbons in length.

resulted in a gas mixture of 10.5% $O_2$, 5% $CO_2$, and 84.5% $H_2$ as measured by GC (Shimadzu GC-8A, TCD detector, and Alltech CTR I column), which was deemed close enough to the target mixture for conducting the experiment.

Medium: 970 ml DI water; 20 mg $Na_2.EDTA$; 12 mg $FeSO_4.7H_2O$; 200 mg $MgSO_4.7H_2O$; 75 mg $CaCl_2.2H_2O$; 1 g NaCl; 1 g $(NH_4)_2SO_4$; 1 mg thiamine HCl; 15 g biotin; 1 ml trace element solution. Trace element solution: 250 mL DI water; 700 mg $H_3BO3$; 398 mg $MnSO_4.H_2O$; 188 mg $Na_2MoO_4.2H_2O$; 60 mg $ZnSO_4.7H_2O$; 10 mg $Cu(NO_3)_2$. pH was adjusted to 7.2 before autoclaving. After autoclaving added 30 ml sterile solution with 1.2 g $KH_2PO_4$ and 1.8 g $K_2HPO_4$. pH readjusted back to pH=7.2.

Inoculum: A 10% inoculum provided from *R. capsulata* culture grown photoheterotrophically in light with agitation of 250 rpm. The RCVB media given in: Wall, J. D., Johansson, B. C., Gest, H., 1977. A pleiotropic mutant of *Rhodopseudomonas capsulata* defective in nitrogen metabolism. Arch. Microbiol. 115:259-263; was used for photoheterotrophic growth of the inoculum which had a dark green color. This photoheterotrophically grown inoculum was in turn started from a glycerol stock of the strain stored at −80° C.

TABLE 3

| sample ID | days | vol (mL) | CDW (g/L) | OD | n | c/m extractable (%) average | Sd | hexane extractable (%) average | sd |
|---|---|---|---|---|---|---|---|---|---|
| T3 | 2.78 | 25 | 4.556 | 7.068 | 2 | 19.34 | 11.12 | 6.88 | 0.72 |
| T4 | 3.79 | 25 | 6.776 | 11.824 | 3 | 18.42 | 2.83 | 8.12 | 0.43 |
| T5 | 4.79 | 25 | 7.492 | 14.18 | 3 | 20.59 | 6.31 | 8.99 | 2.39 |
| T6 | 5.79 | 25 | 8.296 | 13 | 3 | 24.33 | 6.07 | 8.26 | 1.53 |

Cell dry weight (CDW) density measured at various time points during the growth of *H. marinus* on gas.
Content of chloroform/methanol soluble lipid, and hexane soluble lipid, respectively, as a percentage of the biomass sampled is also provided.

Example 11

*Rhodopseudomonas capsulata* strain DSM 1710 was grown to an OD of 4.5 on a mixture of $H_2$, $CO_2$, and $O_2$ gases as the sole source of energy and carbon for growth. The following protocol was followed for experiments performed using a mixture of gases including $H_2$, $CO_2$, and $O_2$ in a one-liter sealed bottle fed a continuous flow of gases.

Figure 12:
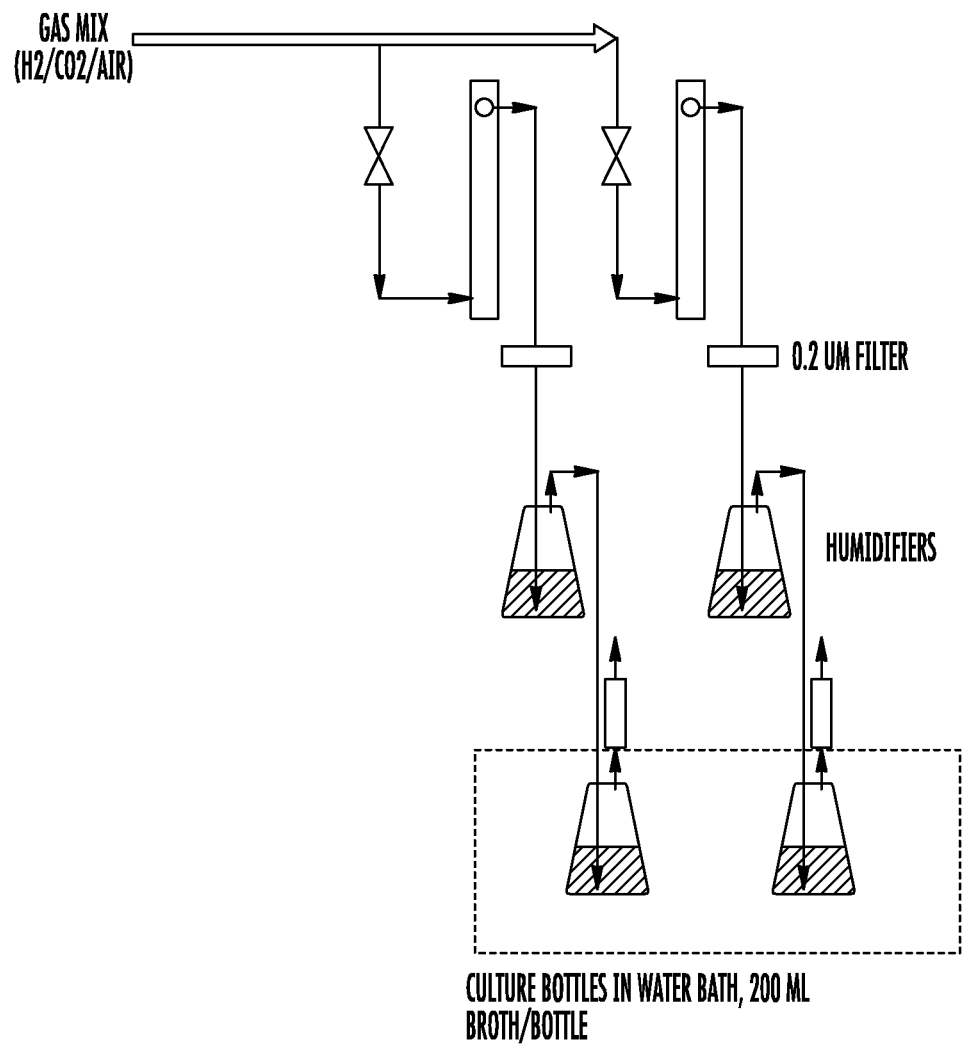
FIG. 12 shows a system of gas delivery and culture bottles used to grow Rhodopseudomonas capsulata strain DSM 1710, diagrammed schematically.
Figure 13:
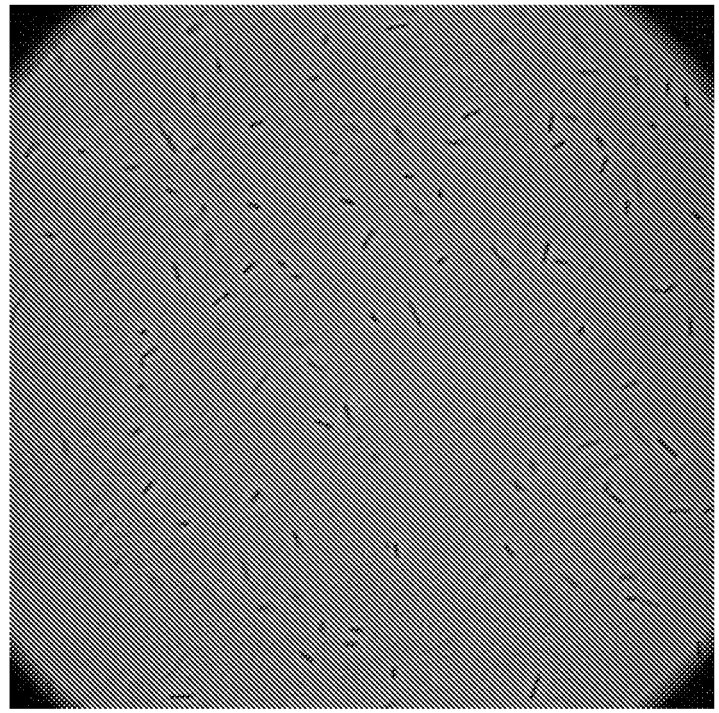
FIG. 13 shows a micrograph of the R. capsulata.
Figure 14:
FIG. 14 shows a pellet of R. capsulata biomass recovered after centrifugation.

Apparatus: Culture was grown in batch, using custom-manufactured system comprising one-liter high pressure liquid chromatography (HPLC) solvent delivery bottles, which were repurposed for use as culture bottles. These one-liter culture bottles were continuously fed gases from a system of gas tanks; gas mixers; filters (0.2 micron); flowmeters; and humidifiers. This system of gas delivery and culture bottles is illustrated schematically in FIG. 12. The gases were distributed and mixed into solution using a porous glass frit. The culture bottles contained 200 mL of liquid media and were wrapped in aluminum foil to prevent light from penetrating media. Temperature was controlled by immersing the culture bottles in a water bath. pH was not controlled beyond the including of chemical buffers into the media. The gas was outlet from the culture bottles through a 0.2 micron filter and the entire system was installed inside of a fume hood. Gas supply was from a compressed $H_2$ and $CO_2$ gas mixture, and a separate tank of compressed $O_2$. The target gas mix for the experiment was 10% $O_2$, 5% $CO_2$, and 85% $H_2$. The flowmeter from the $H_2/CO_2$ gas tank mix was set to 25 and that from the $O_2$ tank was set to 34. This Operation: The 10% inoculum resulted in a starting OD of 0.15. After eight days of growth on gas the OD reached 4.5. OD was measured using a Beckman Coulter DU720 UV/Vis spectrophotometer at 650 nm. The color of the chemoautotrophically grown culture was dark red. Wet mounts of the culture were observed using phase contrast optics with an Axioskop research microscope (Zeiss, Germany). Micrographs were generated with a MacroFIRE device (Optronics; Galeta, Calif.) using the PictureFrame (Optronics; Galeta, Calif.) software for imaging and data storage. A micrograph of the *R. capsulata* is shown in FIG. 13. Following chemoautotrophic growth, the culture was centrifuged at 10,000 G for 15 minutes and 4° C. The supernatant was then poured off and the biomass pellets were stored temporarily at −20° C. and then freeze dried. A picture of a pellet of *R. capsulata* biomass recovered after centrifugation is shown in FIG. 14. A total of 2.59 grams of wet biomass was recovered in this fashion from a single one-liter bottle of *R. capsulata* grown on $H_2$ and $CO_2$ as the sole source of hydrogen, electrons, and carbon for biosynthesis. The lipids were extracted and analyzed by GC/MS using the methods described above, and were found to contain fatty acids that were primarily 16 or 18 carbons in length.

Example 12

*Hydrogenobacter thermophilus* DSM 6534 was grown in a one-liter gas tight bottle on a mixture of $H_2$ and $CO_2$ and $O_2$ gases as sole sources of energy and carbon for growth. A live culture of *H. thermophilus* DSM 6534 in a serum bottle under a gas headspace was received from Deutsche Sammlung von Mikroorganismen and Zellkulturen (DSMZ). *Hydrogenobacter thermophilus* DSM 6534 is known to contain the rTCA $CO_2$ fixation cycle. This live culture was used to provide a 10% inoculum to a 160 ml serum bottle containing the MSM media given in "Thermophilic bacteria," Jakob Kristjansson, Chapter 5, Section III, CRC Press, 1992, pp. 86-88 under an $H_2:CO_2:O_2$ atmosphere of 8:1:1. The initial OD at 600 nm following inoculation was 0.03. The temperature of the serum bottle was kept at 70° C. by immersing the serum bottle in a heated water bath. No agitation was applied. The media was observed to become turbid, and after 65 hours the OD was measured to be 0.354—an over ten-fold increase. This serum bottle was then subcultured as a 10% inoculum into a one-liter gas-tight bottle containing 120 mL of MSM media and 8:1:1 atmosphere of $H_2:CO_2:O_2$. The culture bottle was kept at 70° C. using a water bath and was not agitated. Over the course of 64 hours the gas headspace was refreshed once and the OD increased to 0.25. Over the next 24 hours the OD increased to 0.42. The headspace gases were refreshed again and two days later the OD was measured at 0.56. 1 mL of culture broth was sampled for DNA extraction and sequencing. The 16S rRNA sequence was determined and the top BLAST hit was identified as *Hydrogenobacter thermophilus* TK-6 strain. Culture broth was then taken removed from the one-liter bottle and centrifuged at 10,000 g for 15 minutes at 4° C. The pellet of wet biomass resulting after centrifugation weighed 212 mg. A hexane extraction of the wet biomass was performed as described in the Example above. 15.2 mg of hexane soluble lipids were recovered from the wet biomass, or, 7.2% of the wet biomass weight was comprised of hexane soluble lipids. The lipids were extracted and analyzed by GC/MS using the methods described above, and were found to have a relatively high proportion of fatty acids with 20 carbon chain lengths.

Example 13

*Xanthobacter autotrophicus* strain DSM 432 was grown to 14 grams per liter dry cell density on a mixture of $H_2$, $CO_2$, and $O_2$ gases as the sole source of energy and carbon for growth. The following protocol was adhered to for an experiment performed using a mixture of gases including $H_2$, $CO_2$, and $O_2$ in a stirred-tank bioreactor.

Figure 15:
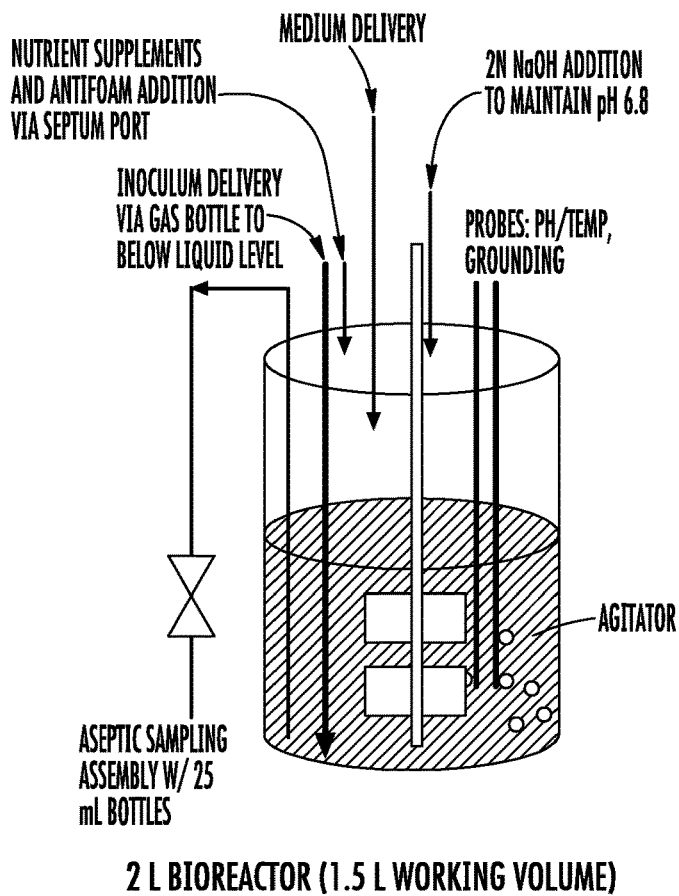
FIG. 15 shows a schematic diagram of a two-liter glass fermenter system used to grow Xanthobacter autotrophicus strain DSM 432 on a mixture of $H_2$, $CO_2$, and $O_2$ gases as the sole source of energy and carbon for growth.
Figure 16:
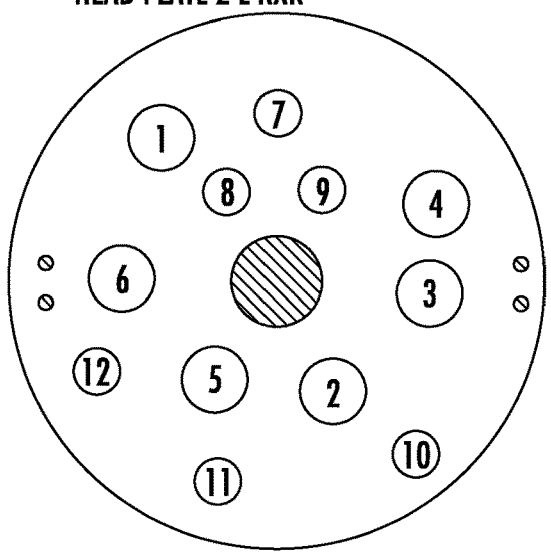
FIG. 16 shows a head plate of the two-liter bioreactor used to grow X. autotrophicus, schematically illustrated.
Figure 17:
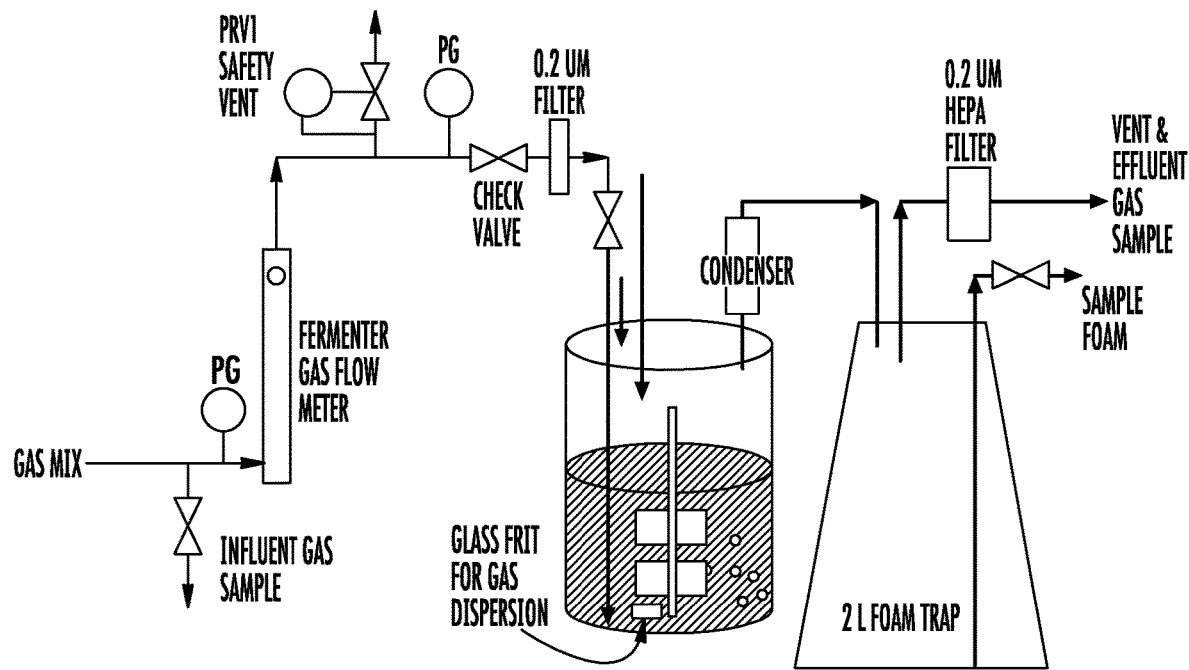
FIG. 17 shows a schematic diagram of a reactor system to grow Xanthobacter autotrophicus, including: pressure gauges; gas flow meters; safety and check valves; 0.2 micron filters; the bioreactor vessel, sensors, actuators, and controllers; a condenser and foam trap; and outlet vent.
Figure 18:
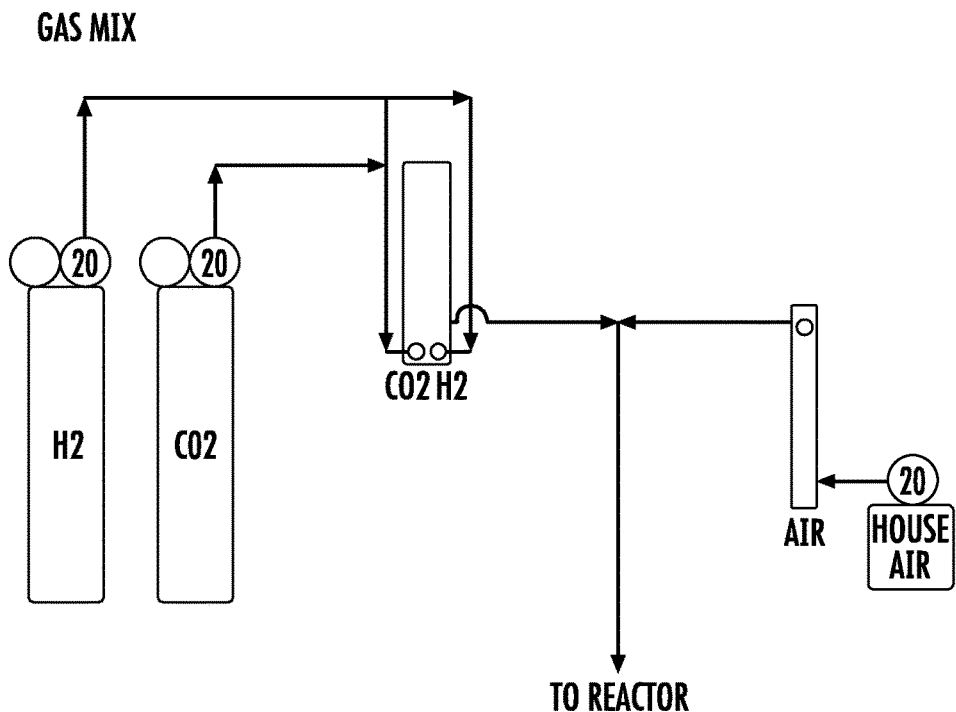
FIG. 18 shows a schematic diagram of the gas delivery system used to grow X. autotrophicus.

Apparatus: Culture was grown in batch, using a two-liter glass fermenter schematically illustrated in FIG. 15 with a headplate schematically illustrated in FIG. 16. Temperature and pH were controlled and monitored with pH and temperature probes and a commercial controller. pH was adjusted through automatic addition of 2N NaOH. Ports in the bioreactor were available for provision of nutrient supplements and anti-foam; inoculum delivery; base; fresh media; and aseptic sampling. Agitation was provided by a turbine and gases were sparged through a glass frit. The reactor system is illustrated schematically in FIG. 17. It comprised pressure gauges; gas flow meters; safety and check valves; 0.2 micron filters; the bioreactor vessel, sensors, actuators, and controllers; a condenser and foam trap; and outlet vent. Gas supply was from compressed $H_2$, compressed $CO_2$ and house air, each regulated to 20 psi. A schematic of the gas delivery system is shown in FIG. 18. $H_2$ and $CO_2$ were delivered to a flow proportioner (Matheson G2-4D151-E401/E401, 20 psi), which set the relative fraction of the gases. The settings used in the flow proportioner were c.l. $H_2=35$; c.l $CO_2=10$; and c.l air=55. This resulted in a gas mix being delivered to the bioreactor of 64% $H_2$, 11% $CO_2$, 5.4% $O_2$ as measured by GC (Shimadzu GC-8A, TCD detector, and Alltech CTR I column).

Medium: The MSM medium used for this experiment is described in Thermophilic Bacteria, CRC Press, Boca Raton, Fla., Jacob K. Kristjansson, ed., 1992, p. 87, Table 4.

Inoculum: *Xanthobacter autotrophicus* strain DSM 432 inoculum was started from a single glycerol stock vial stored at −80° C. which was transferred into 200 mL of MSM in a one-liter gas-tight bottle. Gas pressure of the $H_2/CO_2/O_2$ headspace was 10 psig. The culture bottle was agitated at 150 rpm at 30° C.

Fermenter Operation: Prior to inoculation 1.3 liters of MSM was transferred into the bioreactor vessel. The pH was adjusted to 6.8 using NaOH. The temperature was set at 30° C. and the agitation at 500 RPM. Samples were taken twice per day for OD and lipid analysis through an aseptic sampling assembly. All OD measurements were performed with a Beckman Coulter DU720 UV/Vis spectrophotometer. One time per day samples were examined under the microscope once per day to check cell morphology. All culture broth samples were centrifuged at 12,000 g. 1 mL of supernatant was stored for $NH_4^+$ analysis at −20° C. Wet biomass pellets were stored temporarily at −80° C. and then freeze dried.

Figure 19:
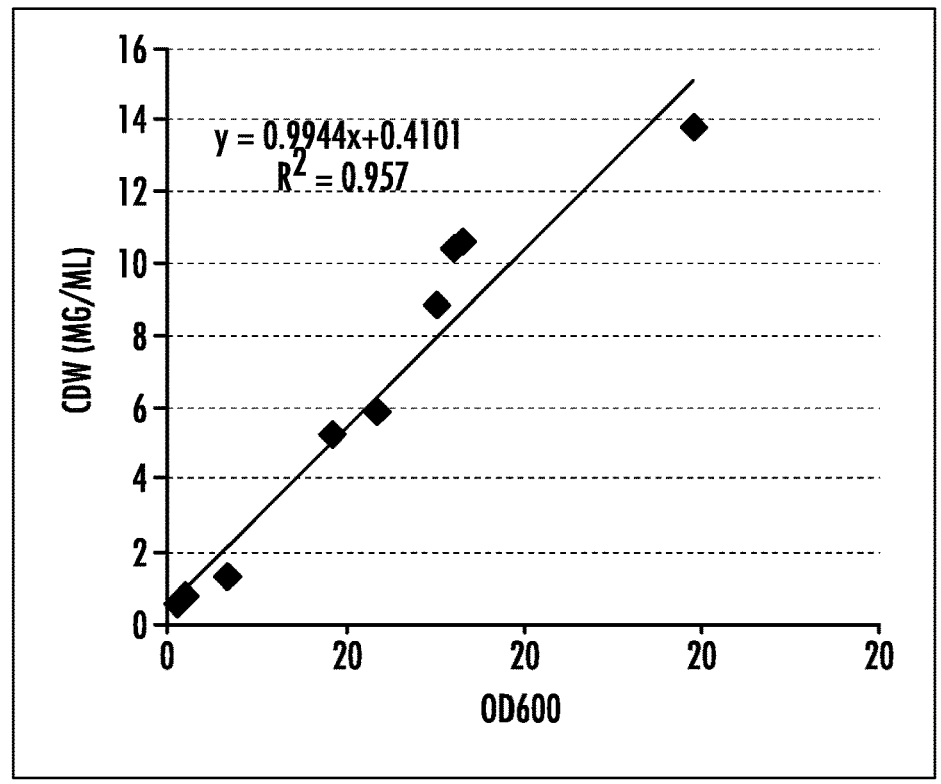
FIG. 19 depicts the correlation between OD600 and cell dry weight (CDW) for X. autotrophicus.
Figure 20:
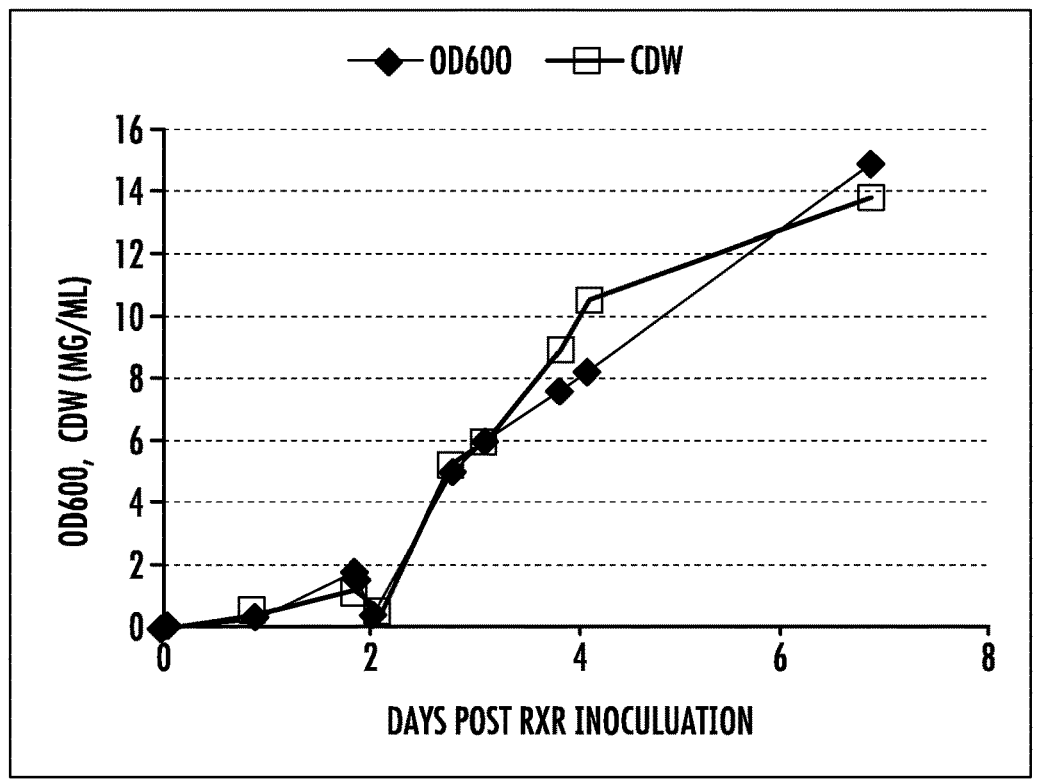
FIG. 20 depicts the growth curve for X. autotrophicus grown on $H_2/CO_2/O_2$.

The correlation between $OD_{600}$ and CDW (mg/ml) is shown in FIG. 19. The linear fit to this correlation was $CDW=0.9944*(OD_{600})+0.4101$ with an R2=0.957. FIG. 20 shows the growth curve for the knallgas microorganism *Xanthobacter autotrophicus* grown on $H_2/CO_2/O_2$ gas substrate according to this protocol. The final OD measured at 600 nm was 14.8 and the final CDW was 13.8 grams/liter from growth on $H_2/CO_2/O_2$ gas substrate. After a brief period of logarithmic growth at the onset of the run, the biomass accumulated at a roughly linear rate until the termination of the run on day six. The lipids were extracted and analyzed by GC/MS using the methods described above, and were found to have a relatively high proportion of fatty acids that are 18 carbons in length.

Example 14

Chemoautotrophic Strain Screening

Strains were first screen for chemoautotrophy on plates using Almore's Vacu-Quick jar system. Promising strains were then tested in liquid culture.

A minimal salts medium (MSM) was prepared as described above and combined and added in agarose (1.5%) plates aseptically. 162 candidate strains drawn from the following genera were tested: *Cupriavidus; Xanthobacter, Dietzia; Gordonia; Mycobacterium; Nocardia; Pseudonocardia; Arthrobacter, Alcanivorax; Rhodococcus; Streptomyces; Rhodopseudomonas; Rhodobacter*, and *Acinetobacter*. Each strain was streaked onto a minimal salts medium (MSM)+agarose (1.5%) plate. All the respective plates were then placed in an Almore's Vacu-Quick jar system. At the bottom of each chamber was laid a sterile paper towel soaked with sterile water in order to maintain humidity in the chamber and prevent the plates from drying during incubation. The gas tight chambers filled with plates were then evacuated; followed by supply of a $H_2:CO_2$:Air (70/10/20) gas mixture. The gases provided the sole source of energy and carbon for growth. The gas chambers were incubated at 30 C for 7-10 days, purging fresh gas mix every day. For plates that exhibited chemoautotrophic growth/ colonies, the colonies were picked and then streaked onto fresh minimal salts medium (MSM)+agarose (1.5%) plates followed by a second incubation in the Almore's Vacu-Quick jar system supplied with $H_2$ and $CO_2$ and air (70/10/20). Strains the exhibiting strong colony growth in this second incubation were then subjected to chemoautotrophic testing in liquid mineral salts medium (MSM). Experiments were performed in (Chemglass CLS-4209-10, anaerobic, 18×150 mm) Hungate tubes with working volume of 5 mL, capped with solid neoprene rubber stoppers (Wheaton Science Products, No.: 224100331), crimped with an aluminum cap. Tubes were purged with a gas mix of $H_2$:$CO_2$:Air (70/10/20) using a gas manifold designed for high throughput screening. Tubes were purged with fresh gas mix every day. Tubes were incubated in a Multitron Pro Infors HT shaker at a 45-angle, at 600 rpm and 30° C. for 96 hrs. Optical density at 600 nm was measured by spectrophotometer (Genesys 10S, UV-Vis spectrophotometer, Thermo Scientific) every 24 hours. The following bacterial strains were identified as being chemoautotrophic on the knallgas mix: *Arthrobacter methylotrophus* DSM 14008; *Rhodococcus opacus* DSM 44304; *Rhodococcus opacus* DSM 44311; *Xanthobacter autotrophicus* DSM 431; *Rhodococcus opacus* DSM 44236; *Rhodococcus ruber* DSM 43338; *Rhodococcus opacus* DSM 44315; *Cupriavidus metallidurans* DSM 2839; *Rhodococcus aetherivorans* DSM 44752; *Gordonia desulfuricans* DSM 44462; *Gordonia polyisoprenivorans* DSM 44266; *Gordonia polyisoprenivorans* DSM 44439; *Gordonia rubripertincta* DSM 46039; *Rhodococcus percolatus* DSM 44240; *Rhodococcus opacus* DSM 43206; *Gordonia hydrophobica* DSM 44015; *Rhodococcus zopfii* DSM 44189; *Gordonia westfalica* DSM 44215, *Xanthobacter autotrophicus* DSM 1618; *Xanthobacter autotrophicus* DSM 2267; *Xanthobacter autotrophicus* DSM 3874; *Streptomycetes coelicoflavus* DSM 41471; *Streptomycetes griseus* DSM 40236; *Streptomycetes* sp. DSM 40434; *Streptomycetes xanthochromogenes* DSM 40111; *Streptomycetes thermocarboxydus* DSM 44293; *Rhodobacter sphaeroides* DSM 158.

Fully proximate analysis was performed on knallgas strains grown in liquid MSM media with a knallgas mixture as the sole carbon and energy source. It was found that *C. necator* DSM 531 and DSM 541 accumulated over 70% and over 80% total protein by weight for samples taken during the arithmetic growth phase. Both *C. necator* DSM 531 and DSM 541 were also found to synthesize vitamins including vitamin B1, vitamin B2, and vitamin B12.

Example 15

*C. necator* DSM 531 Lysate Preparation

*Cupriavidus necator* strain DSM 531 was grown on a sterile MSMG media (Minimal Salts Medium+40 g/L D-Glucose) as the source of energy and carbon for growth and the cells were lysed.

The following protocol was followed for *C. necator* strain DSM 531 biomass production and lysate preparation.

Experimental strain biomass production: 1% by volume for 72-hour seeding, taken from strain glycerol stock, followed by 10% by volume for 120-hour culturing for the strain biomass production.

The initial growth of *C. necator* strain was seeded from 1.5 mL glycerol stock into 160 mL MSMG media in a 500 mL Erlenmeyer flask (VWR #10536-926) in a shaking incubator (New Brunswick Scientific, Series 25 Incubator Shaker, Floor Model) for 72 hours, 30° C., 250 rpm. The strain was checked by Nutrient Broth (NB) agar plate, optical density at 600 nm on SpectraMax M5 spectrophotometer, and morphology check on a microscope Labomed iVu3100 at 1000× lens magnification.

20 mL of the seeding stock was transferred to a 2 L Erlenmeyer flask (VWR #10545-844) containing 200 mL MSMG media, resulting a total of 8 2 L flasks from the 160 mL seeding stock. The 2 L flasks were incubated in the incubator shaker at 30° C., 250 rpm for 120 hours. The strain was monitored by streaking on Nutrient Broth (NB) agar plate, optical density at 600 nm on the spectrophotometer, pH measurement, and morphology check on the microscope at 1000× lens magnification upon harvest.

The culture broth was transferred to tare-weight, sterile 250 mL centrifuge bottles (Fisher Scientific #05 564 1) and spun down in a centrifuge (Sorvall Evolution RC) at 8000 rpm, 4° C., 20 minutes. The broth was decanted and the pellets were transferred to a tare-weight, sterile 50 mL falcon tube (VWR #89039-656). The pellets were stored at −80° C.

The cell dry weight measurement of *C. necator* DSM 531 strain was also explored at the harvest time. Prior to the harvest of 2 L flasks, 10 mL of culture broth from each flask was transferred to a tare-weight, sterile 50 mL falcon tubes. The tubes were put on a centrifuge (Eppendorf) at 12000 rpm, 4° C., 5 minutes. The broth was decanted and the wet pellets were frozen at −80° C. for 2 hours. The frozen pellets were put onto a lyophilizer (Virtis Benchtop, −62.6° C., 56 mTorr) for 18 hours.

After 75 hours of seeding of the glycerol stock in 160 mL MSMG media, OD600 was measured at 0.792, pH=7.34. The culture broth had milky appearance. Uninoculated MSMG media was also streaked on a NB agar plate serving as a negative control.

After 113 hours of subculturing into 2 L flasks from 20 mL of seeding stock in 200 mL MSMG media per flask. The cells from each 2 L flask was streaked on a NB agar plate and observed on 1000× magnitude of microscope. The strain purity visually was determined around 99.9%.

*C. necator* culture in 2 L flasks was harvested via centrifugation at 8000 rpm, 4 C, 20 minutes in sterile 250 mL centrifuge bottles with sealing caps. The broth was decanted and the wet pellets were combined and stored at −80° C. At harvest time average $OD^{600}$=19.9 and pH=6.2-6.3. Weight and concentration of wet pellets in the culture broth were measured.

Prior to harvest, 10 mL of culture broth from each 2 L flask was transferred tare-weight falcon tubes for cell dry weight measurements.

Lysed Cell Extract Preparation

A 30 g wet cell pellet was thawed out at room temperature for 15 min. 30 g of sterile MilliQ water was added. The tube was vortexed vigorously until a homogeneous solution was produced. The cell solution was split into 6-50 ml Falcon tubes containing 10 g each, and subjected to sonication in an ice water bath using a Branson Sonifier 250 with a ⅛ inch tapered microtip probe (#101-148-070). The probe was lowered to within 1 cm of the bottom of the tube. Power was dialed up slowly to 40-60% output with 1 min total sonication time. Both microtip and the cell solution were allowed to cool for about 10 min. Sonication was repeated with two more cycles of 1 min with 10 min cooling time in between.

Protein Measurement of Lysed Cell Extract

Bradford assay was used to determine protein concentrations in the whole lysed cell extract, clear lysate and permeates that passed through Molecular Weight Cutoff (MWCO) filter membranes.

5 uL samples and BSA standards (BIO-RAD #5000201) were added to a transparent 96-well flat bottom plate. BSA concentrations range from 150 ug/mL to 600 ug/mL. Subsequently, 250 uL 1× Dye reagent (Comassie Blue G250, BIO-RAD #5000201) was added to each well of the plate. The plate was placed on a plate shaker for 30 min at room temperature, 300 rpm, followed by absorbance reading at 595 nm on SpectraMax M5 spectrophotometer.

Hydrolysate Preparation

Cell lysate generated according to this protocol is subjected to chemical and enzymatic hydrolysis methods well known in the art.

Example 16

Protease Demonstration Experiment

The microorganism (e.g., fungus *P. marquandii*) is grown in a suitable medium under aerobic submerged conditions synthesizes a protease (e.g. keratinase).

The extracellular liquid is concentrated and partially purified to produce an enzyme powder. The average activity of the enzyme powder is determined.

For a keratinase, a hoof and horn substrate is ground and sieved, as a positive control, then hydrolysis of the keratin powder is performed by treatment with the keratinase in concentrations from 0.75 to 3.00 g/L at 50° C. and pH 8.0 (enzyme/substrate ratio from 1:67 to 1:17). This serves as a positive control for the activity of the keratinase enzyme.

For the experiment, a freeze dried microbial biomass powder from *Cupriavidus necator* or another microorganism grown on $H_2/CO_2$ is hydrolyzed by treatment with the keratinase in concentrations from 0.75 to 3.00 g/L at 50° C. and pH 8.0 (enzyme/substrate ratio from 1:67 to 1:17).

The hydrolysis reaction is followed for up to 6 h. During the incubation, keratin or protein degradation is measured and expressed as the fraction of solubilized nitrogen. Also, the increase in amount of soluble proteins and the increase of total free amino acids in the liquid phase is recorded. Free amino acid composition of the hydrolysate is also determined. The nitrogen content in the solution, measured by the Kjeldahl method, is expressed as a percentage of the total nitrogen content in the dry meal (keratin or microbial). The portion of the N-content in original biomass that is solubilized is determined. The enhancement of the protein solubilization compared to a blank sample (without the enzyme) is determined. The effect of differing concentrations of protease enzyme on protein solubilization is determined. The soluble protein increase as a function of time is measured and a time course of the enzymatic reaction determined.

Amino acids previously found to have a positive effect on plants are measured. A comparison of amino acid content (in % of the total) of the obtained hydrolysate is compared with the composition of protein hydrolysates described in literature.

As a positive control, applying the keratinase of *P. marquandii* to powdered hoof and horn substrate is expected to obtain 4 g/L to 5 g/L of soluble protein in 5 h, depending on the enzyme concentration, and a free amino acid concentration in the hydrolysate of over 4,000 mg/L.

In follow up experiments, the treatment of protein-rich biomass by steam followed by enzymatic hydrolysis, is tested. The solubilization of the nitrogen with and without steam pre-treatment are compared. The time course of hydrolysis by the protease of steam-pretreated protein-rich biomass versus non-steam treated material is compared. The amounts of protein, peptide, and amino acids released from substrate into the solution are compared between the steam treated and non-treated cases. In a positive control applying the keratinase of *P. marquandii* to powdered hoof and horn substrate that has been steam treated, 98% solubilization of keratin nitrogen is expected.

Analogous experiments are performed testing proteases from strains described herein, including but not limited to *Streptomyces* sp., grown on substrates including but not limited to C1 carbon sources.

Example 17

Enzymatic PH Process

Figure 21:
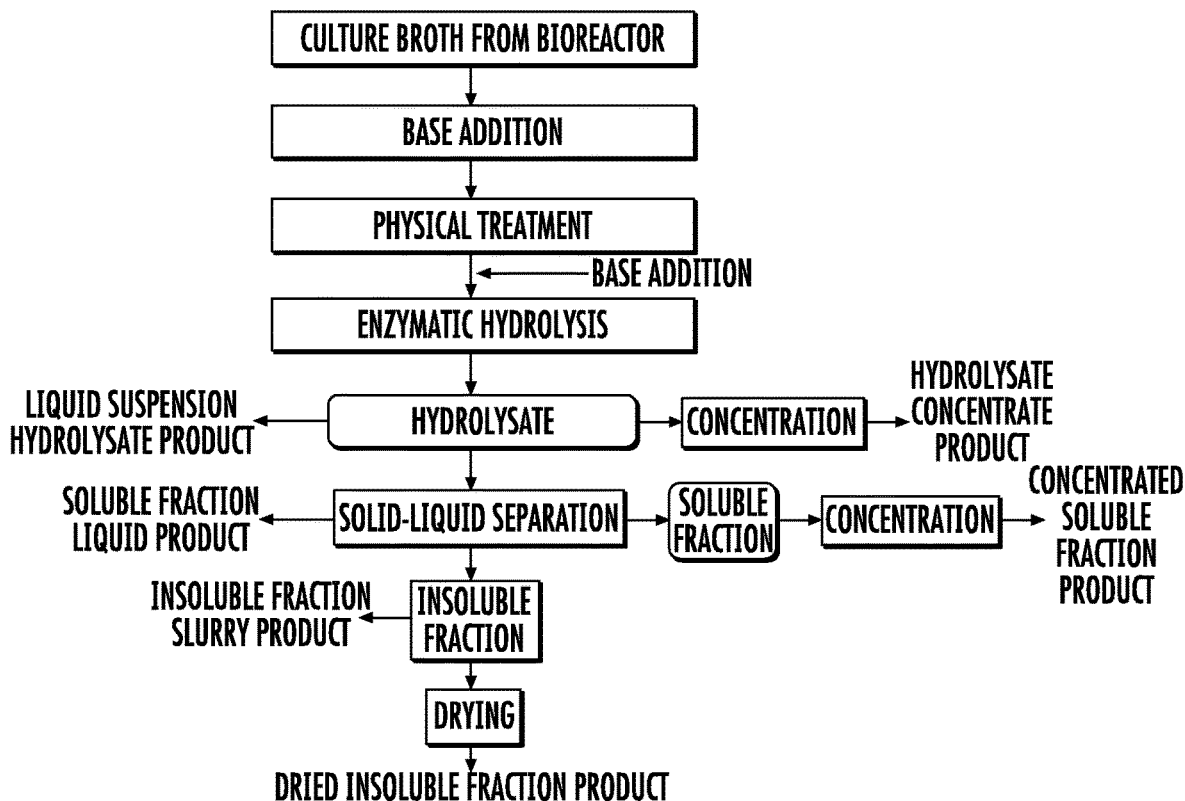
FIG. 21 shows a block diagram of an embodiment a method described herein, with alkaline treatment of fermentation broth in the form of an aqueous cell suspension, followed by a physical treatment and enzymatic hydrolysis to obtain an organic enzyme extract.

FIG. 21 shows the block diagram of one embodiment of the method described herein, wherein the culture broth in the form of an aqueous cell suspension undergoes alkaline treatment, followed by a physical treatment and enzymatic hydrolysis to directly obtain an organic enzyme extract. In some cases, further steps of concentration and/or separation and/or drying is performed providing a variety of organic enzyme extract products. In experimental tests of this approach, the peptide profile of the extracts obtained by the method of the invention is determined.

An experiment is performed according to the block diagram shown in FIG. 21. The percentage of dry matter in 500 ml of culture broth is determined with a target of 10-11% w/w and w/v. The chemical composition of cells in the broth is also determined (e.g. % C, H, O, N, P, K, S). The culture broth is treated in an open glass reactor with 28% $NH_3$ added to give a pH of 9.6, while stirring (60-80 rpm).

After the alkaline treatment the mixture is subjected to a pressure of 115 kPa and a temperature of 120° C. for 20 minutes in an autoclave. The solution thus obtained is adjusted to pH 9.2 with potassium hydroxide 10 M. This solution at pH 9.2 is maintained at 55° C. in a thermostat bath while stirring (60-80 rpm) and 0.3% v/v of Subtilisin is added (from a protease stock solution of 70,000 Units of activity per the azocasein assay). The pH is maintained with 28% ammonia. These hydrolysis conditions are maintained for 24 hours. The resulting hydrolysate is collected at 24 hours, and chemical composition determined (e.g. % C, H, O, N, P, K, S). The nitrogen and organic matter yield of the hydrolysis are determined.

A volume of the hydrolysate is measured, and then the hydrolysate is concentrated 5-fold in a rotary evaporator with a thermostat bath at 70° C., thereby obtaining a concentrated hydrolysate. The percent weight of dry matter is measured following concentration, with 50-55% by weight of dry matter targeted. The experiment tests whether this concentrated hydrolysate will take the form of a stable syrup.

Another volume of the hydrolysate is measured and centrifuged at 4000 G for 30 minutes. The volume of supernatant called soluble hydrolysate fraction, and the weight of pellet called insoluble hydrolysate fraction are obtained. The dry matter content of each is determined as well as the chemical compositions of the dry matter in both fractions (e.g. % C, H, O, N, P, K, S). The organic matter yield of each fraction is determined. The amino acid composition of each fraction is also established, as well as its peptide profile. Peptides with a size below 300 Da relate to free amino acids and small peptides. The content of such free amino acids and small peptides are determined.

Concentration of the soluble hydrolysate is determined and the volume and organic matter w/w % is measured. The soluble hydrolysate consistency is observed (e.g., whether like a syrup). The insoluble hydrolysate fraction is dried at 90° C., and the final weight measured and moisture content.

Example 18

Protein Extract with Reduced Nucleic Acid

High pressure homogenization is applied to cells grown according to the present invention. Conditions are tested to identify an optimum in terms of rupturing a majority of the cells while retaining activity of endogenous nuclease; preserving proteins to be harvested, and not imparting any off flavors. The following homogenization parameters are tested: pressures from 5,000 to 15,000 psig; temperatures from 32° F. to 122° F., and pH from 4.5 to 6.5; with 1 to 5 passes through the homogenizer. The ruptured cells (homogenate) may be diluted, warmed or cooled, and pH adjusted as necessary to enhance processing and nuclease and protein extractability. The homogenate is adjusted to a pH of above 5.5, and especially the pH range between 8 and 11 is tested; for 5 to 60 minutes and at a temperature of 40° F. to 140° F. The objective is to extract the nuclease, protein, and other alkali soluble materials. The homogenate is separated by centrifugation and/or filtration into an insoluble cell wall residue, and a soluble extract, referred to as the alkaline extract. Factors that affect the extraction and utilization of the endogenous nuclease are: nuclease content, pH, processing temperature, reaction time, substrate concentration, activators, and inhibitors. These factors can interact to affect the protein composition and yield and are optimized over to maximize protein yield and/or minimize nucleic acid contamination. An attempt to develop a glycan product from the cell wall residue is performed, analogous to the yeast glycan product described in the patent application entitled Yeast Glycan and Process of Making Same Ser. No. 310,452, filed Nov. 29, 1972. Baker's yeast glycan is the comminuted, washed, pasteurized, and dried cell walls of the yeast, *Saccharomyces cerevisiae*. It is composed principally of long chain carbohydrates, not less than 85 percent on a dry solids basis. The carbohydrate is composed of glycan and mannan units in approximately a 2:1 ratio. It can be used as an emulsifier and emulsifier salt and stabilizer and thickener and texturizer in salad dressings, frozen dessert analogues, sour cream analogs, cheese-flavored and sour-cream flavored snack dips.

Following separation of the cell wall residue, the soluble remainder is incubated allow the endogenous nuclease to break down nucleic acid polymers. Incubation conditions tested will range from 40° to 60° C., a pH of 5 to 8, and for a time of 15 to 120 minutes. The protein is separated by centrifugation. At the end of the nuclease reaction stage, the system is treated in various ways to attempt to increase the rate of centrifugation of the protein sludge. 0.1 to 1.0% by weight of solids of $CaCl_2$) is tested to expedite recovery of the protein. The centrifugation conditions tested range from pH of 4 to 7 and a temperature of 4° to 90° C. It is tested whether the addition of calcium chloride after completion of the endogenous nuclease reaction, and before the centrifugation, significantly improves the rate of centrifugation or throughput. A block diagram of one possible embodiment is provided in FIG. 22.

The nuclease reaction mixture is separated by centrifugation into a low RNA-protein sludge fraction, and a soluble cytoplasmic constituents fraction. The soluble cytoplasmic constituents fraction are tested for composition. It is expected to contain the nucleic acid fragments, some protein and protein fragments, glycogen, and many metabolic intermediates including vitamins. The soluble cytoplasmic constituents are expected to constitute a valuable fraction of the total microbial fraction and is expected to have similar applications as yeast extract or acid whey.

Water washing of the insoluble protein fraction is tested for effect on flavor. An additional vacuum dewatering step is tested followed by drying to a powder. Vacuum conditions tested range from 20 to 28 inches Hg, at T=120° F. to 200° F., for 10 to 60 minutes. Solid contents entering the final drying step are tested over a range from 5% to 25% solids. Drying methods tested comprise: spray drying, drum drying, freeze drying, and the like.

The composition of the powder is tested. The cell-free composition and absence of viable cells are confirmed. Proximate analysis is performed to establish the composition by weight on a dry solids basis of: protein; nucleic acid (targeting less than about 3%); lipid; ash; carbohydrate; fiber; other biomass. The vitamin and mineral content are determined as well.

Example 19

Preparation of Protein from *Cupriavidus necator*

Biomass grown on $H_2$ and $CO_2$ according to the methods of the present invention is given three water washes and thickened if necessary by centrifugation to 11% solids by weight.

Fifty gallons of this suspension containing 45 pounds of *C. necator* solids is cooled to 45° F. and subjected to homogenization at a pressure of 8,000 PSIG and immediately cooled to 45° F. The homogenization is repeated for a total of three passes. The homogenate is diluted to a volume of 150 gallons with water, and a food grade alkaline reagent Sodium hydroxide is added until pH 9.5 is reached. The material is agitated for 15 minutes and then centrifuged. The insoluble residue (cell wall debris) is removed. The initial amount of homogenate solids is weighed, along with recovery after homogenization, extraction, and separation, of alkali extract soluble biomass and insoluble biomass. The alkali extract is adjusted to pH 6.0 by the addition of one normal hydrochloric acid, and warmed to 122° F. The extract is subjected to mild agitation for one hour at pH 6.0 to allow the endogenous nuclease to digest the nucleic acid.

A parallel run for comparison involves treating an alkaline extract with an exogenous nuclease at pH 7; 50° C.; for 2 hours. The exogenous nuclease is extracted from malt sprouts and used at the rate of 9 lbs. malt sprout extract solids per 18 lbs. of *C. necator* extract solids.

Other parallel runs for comparison: 1) use a low temperature, high alkali process to reduce RNA. In this process the alkali extract from the homogenate is adjusted to pH 12 with NaOH and heated for 2 hours at 60° C. The protein is isolated after adjustment of the system to pH 4.5. 2) use a high temperature low alkali process to reduce RNA. In this process the alkali extract from the homogenate is adjusted to pH 10.5 and heated for 4 hours at 80° C. The protein is isolated after adjusting the system to pH 4.5.

At the end of the incubation, 37.5 grams of calcium chloride is added. The protein suspension is warmed to 175° F. and centrifuged to yield the protein sludge and the acid whey. The weight of dry solids in each respective fraction is measured. The protein sludge is washed by diluting with two volumes of water, and again centrifuging while the temperature is maintained at 175° F., and the pH is maintained at 6.0. On a dry solids basis, the amount of washed protein sludge is measured, along with the amount of wash solids. The washed protein sludge is concentrated in vacuo (28 inches of Hg) at 175° F., pH 6, to 20% solids and spray dried. The composition of the spray dried product is determined including: % moisture, % crude protein (N×6.25), % nucleic acid, % lipid, % ash, % carbohydrate (by difference).

The nutritional quality of unfractionated *C. necator* and of isolated *C. necator* protein, in which the nucleic acid content has been reduced by various methods described above, is compared. The unfractionated biomass is washed three times with water and spray dried.

The essential amino acid content is determined for all samples. The contents are compared against those cited by the FAO Committee on Protein Requirements (1957b) "FAO Nutritional Studies No. 16", and is analyzed to determine how it might meet or exceed the amino acid requirement for growing test rats.

The Protein Equivalence Ratio or PER is determined relative to a casein baseline (PER=2.5). Feeding tests are performed with rats using a level of 10% Corrected Protein in the diet. The test procedure published in Official Methods of Analysis of the A.O.A.C. p. 800, 11th Edition (1970), is followed. Some tests are performed using unfractionated *C. necator* biomass with no attempt to reduce RNA.

The PER and RNA content of unfractionated biomass versus protein isolate are compared. The isolate made using exclusively the endogenous nuclease is also compared with isolate made using exogenous nuclease, and with the isolates made using a stronger alkali processes.

Example 20

Test of Biostimulant Effect in PH

The effect of PH on the transcriptional pattern of genes coding for the enzymes functioning in the tricarboxylic acid cycle is analyzed via reverse transcription polymerase chain reaction. The transcript accumulation of the genes encoding for the studied enzymes is studied to determine if they are up-regulated by the PH treatment. Enzyme activities are tested as well. The same approach is used to verify the biostimulant effects of a control PH product, such as one derived from hydrolysis of tanning residues.

Example 21

Biostimulant Production and Test

A bacterial cell cream produced from C1 feedstock as described herein is isolated by membrane filtration. The total solids content and total nitrogen content of the cell cream are measured. Targeted amounts are approximately 8% by weight and 0.8% by weight respectively. The viscosity is also measured as well. Sulfuric acid is added to approximately 300 ml of the cell cream to adjust the pH of the cell cream to 3.5. Hydrolysis is carried out by charging the pH-adjusted cell cream into a 500 ml Erlenmeyer flask, covered with foil, and placed in an autoclave at 128° C. for 24 hours under 16 lbs. of pressure. Following hydrolysis, the viscosity of the cell cream (hydrolysate) is measured again. It is expected to be greatly reduced, with a clear separation of solubles and insolubles. After cooling, the hydrolysate is filtered through a 20 micron paper filter and the soluble fraction collected for further analysis. The total solids content and total nitrogen of the soluble fraction are measured. The soluble fraction is tested for its ability to elicit a phytohormone response in turfgrass by measuring shoot density change over time in comparison with control treatments. During a 70 day trial, turfgrass plots in a greenhouse are foliarly treated on a bi-weekly basis with either water, ammonium sulfate, or the soluble fraction. Both the ammonium sulfate and soluble fraction are applied in an amount of 0.05 lbs. nitrogen per 1,000 square feet. Turf shoot densities are measured on day 0, day 44, and day 70. The turfgrass treated with the soluble fraction is tested for a statistically significant ($p<0.05$) increase in shoot density from day 0 to day 70 in comparison with the control treatments.

Example 22

Effect of Industrial Microbial Cell Mass and Hydrolysates Upon the Growth of Radishes A trial is designed to measure the effect of different fertilizer treatments upon the growth and yield of red radishes (*Raphanus salivus*) variety Champion. Seeds are germinated in a misting bed and transplanted into 6 inch diameter pots containing peat moss, perlite and vermiculite in a 20:5:5 ratio, respectively. Pots are watered with 200 ml three day per week. No fertilizer is provided during the germination period. Treatment fertilizers are applied the same day as transplanting. Treatments include a negative control with no fertilizer, positive controls, one with ammonium sulfate, and another with a commercial 9-3-6 fertilizer, and hydrolysates resulting from hydrolysis by protease and papain. The hydrolysates are applied in high and low quantities (e.g. 110 kg N/hectare and 28 kg N/hectare). The positive control is applied in matching high quantities (e.g. 110 kg N/hectare). The high rate of nitrogen, e.g. 110 kg/ha, is expected to meet requirements of radish production. The low rate of nitrogen, e.g. 28 kg/ha is expected to be below the requirement for N. Each treatment is applied to four replicates in a completely randomized block design.

Hydrolysate is obtained from SCP culture broth (ca. 10% total solids) produced from C1 feedstock according to the present invention. The proteinaceous broth is hydrolysed by adjusting the pH to 7 or 9 with 30% potassium hydroxide before adding papain (Liquipanol® T-100, Enzyme Development Corporation, New York, N.Y.) and bacterial protease (Enzeco® Alkaline Protease L660 Enzyme Development Corporation, New York, N.Y.), respectively. Cell creams are hydrolyzed for a total of 24 hours with constant agitation provided by a stirrer and temperature maintained at 60° C. in a water bath. Enzymes are denatured by autoclaving hydrolysates for 5 minutes at 120° C.

Radish weights for all fertilizer treatments are compared with no fertilizer. Comparison of ammonium sulfate and control 9-3-6 tests whether there is any unmet requirement for phosphorous or potassium. A lack of difference supports that levels of P and K are adequate. The low N treatments with Protease and Papain hydrolysate are compared with the high N treatments. The low N cases are tested to see if high yields are possible with less nitrogen, and if the efficiency of nitrogen use for radish production is statistically higher. An improved efficiency is reflective of a biostimulant effect and supports that hydrolyzed cell cream has potential to increase root crop production with lower nutrient inputs.

Example 23

Hydrolysate Test in Hydroponics System

The aim of this experiment is to determine whether the use of microbially-derived PH can enhance the growth and N uptake of lettuce grown in a raft floating hydroponics system Floating Raft or DWC (Deep water culture) is suited to the mass production of certain types of vegetables, in particular lettuce. The lettuce seedlings are placed on a floating raft, usually made of a large polystyrene sheet where a number of holes are cut out to accommodate the roots of the plants.

Clean oxygenated water is essential. The plants roots are heavily oxygenated. The roots themselves are immersed in water all the time. Dirt particles need to be eliminated as the dirt will adhere to the white roots of the plant and block the plants roots from taking up the vital oxygen and minerals that will enable the plant to mature and grow.

The floating raft system uses a number of air stones at regular intervals to heavily oxygenate the plant roots. Water that enters this area should by now be free of most solids. Plant roots should be clean and white looking. Lettuce here should grow rapidly and harvesting carried out easily.

Using full and reduced hydroponic nutrient solution concentrations, weekly foliar applications of PH are tested for impact on the fresh biomass, SPAD index and N uptake. Introduction of the PH to the water is tested as well.

SPAD index is determined using an instrument that measures light transmission through a leaf, at two wavelengths, to determine the greenness and thickness of leaves. Transmission in the infrared range provides a measurement related to leaf thickness, and a wavelength in the red light range is used to determine greenness. The ratio of the transmission of the two wavelengths provides a chlorophyll content index that is referred to as CCI or alternatively as a SPAD index. CCI is a linear scale, and SPAD is a logarithmic scale. These instruments and scales have been shown to correlate to chlorophyll chemical tests for chlorophyll content, except at very high levels. Chlorophyll content meters are commonly used for nutrient plant stress measurement, that includes nitrogen stress, and sulfur stress.

Example 24

Mushroom Growth Enhancer Formulation

A mushroom growth enhancer is produced by a high protein cell as described herein, such as, but not limited to *C. necator*, according to the methods disclosed above. Following growth and harvest, the cell mass is dewatered and dried such that its water content is not more than 13% moisture by weight.

The dried biomass particle size is standardized using methods known to one of average skill in the art. A focused distribution of particle sizes is generated at an optimized average size. The optimal average size is determined so as to provide adequate distribution through the mushroom compost, and nutrient availability, while not making the nutrients too available, which could enable rapid utilization of the particles by competing microorganisms, such as bacteria or foreign molds. At this stage in the manufacturing process, the dry particle product is analyzed to confirm that the product primarily contains particles no larger or smaller than −10+30 US. standard mesh (plus or minus 5%.) The product is also tested for the presence of any viable contaminating organisms.

The carbohydrate content of the product is experimentally tested. A low carbohydrate product is targeted since carbohydrates are generally a key growth stimulant for undesired foreign microorganisms. Low carbohydrates therefore limit the propagation of such organisms. In certain non-limiting embodiments carbohydrates are removed, so as to further increase the protein content and resulting potency of the product per unit weight.

If the product meets the above standards, it is transferred to a mixer unit (Forberg Model C200-SS-2D or equivalent.) In the mixer unit, the product is combined with a preservative agent. Preferred preservative agents include copper-containing, carbamate, phenolic, and antibiotic compounds, specific examples of which are as follows:
1. Copper-Containing Materials—Copper sulfate alone or in combination with lime.
2. Carbamate Materials—Methyl 1-(butylcarbamoyl)-2-benzimidazolecarbamate; zinc ethylenebisdithiocarbamate.
3. Phenolic Materials—o-Phenylphenol; o-BenzyLparachlorophenol, and salts thereof.
4. Antibiotic Materials—Streptomycin; Terramycin.

The selected agents are added in an amount effective to preserve the product from foreign microbial activity while in the compost, but not so much as to prevent utilization of the same by the mushroom mycelium.

The remaining process steps are performed preferably in a continuous mode. The next step involves pasteurizing the product. To accomplish pasteurization, the product is heated in a dryer apparatus (Nara Paddle Dryer Model 1.6W or equivalent.) The dryer is operated to raise the temperature of the product from an ambient level to 220° F. in approximately 5 minutes. Using the Nara Paddle Dryer Model 1.6W, this will occur through the injection of 95 psi of steam at approximately 325° F. Pasteurization is aimed at accomplishing the following objectives: (1) the reduction of vegetative bacteria and mold plate count by at least three logs; (2) the inactivation of mesophilic bacterial spores; and (3) the inactivation of lipoxygenase. However, the above-described amount of heat is intended to be insufficient to substantially denature the product. Pasteurization is intended to reduce the possibility of early and undesired heat generation by foreign microorganisms during the spawn run. The pre- and post-pasteurization levels of living microorganisms are determined.

After pasteurization is completed, the product is transferred to a cooler/evaporator unit consisting of a vibrating fluidized bed conveyor (Jeffrey Dresser Industries, Model IXIO TMV or equivalent.) The cooler/evaporator unit uses ambient, filtered air at 2500 CFM to lower the product temperature from 220° F. to 100° F. in approximately one to two minutes. After cooling in this manner, the moisture level of the product is measured. The targeted moisture level at this stage is approximately 7.5%. The moisture content of the product is measured and tracked during the above-described processes as well as the temperature profile of the product during the pasteurization/cooling phases.

Evaporation of water from the product as described above is intended to prevent spoilage by microorganisms not killed during pasteurization, including bacterial spores. Rapid cooling to 100° F. in 1-2 minutes is intended to prevent protein denaturation—protein denaturation is proportional to the amount of time a product is maintained at a high temperature.

The resulting final mushroom growth enhancer product is intended to be comprised of substantially undenatured protein materials. Denaturation involves a modification of the tertiary or quaternary structure of a protein, with resultant change to the physical and biological properties of the protein. The term "substantially undenatured" as used herein is reflected by an index called "PDI" or "protein dispersibility index." Taking PDI measurements involves extracting the cell product with water and analyzing the extracted portion using Kjeldahl analysis. In conducting Kjeldahl analysis, the product is digested with concentrated $H_2SO_4$ which converts combined nitrogen in the product to ammonium sulfate. The resulting solution is then treated with alkaline materials, causing the liberation of ammonia. The amount of ammonia liberated is determined by titration with standard acid. The results of the titration can then be used to calculate the amount of nitrogen in the product. To calculate PDI, the formula provided in AOCS method Ba 10-65 is used. In the present application, a "substantially undenatured" protein is characterized as that having a PDI not less than 50. PDI analyses is performed on the product and compared with commercially available product using formaldehyde denatured soybean material; reported to have a PDI or approximately 11.4. Proximate analysis of the mushroom growth enhancer is performed including the contents of protein, moisture, fat, ash, crude fiber, carbohydrates. The caloric content is also determined.

The mushroom growth enhancer is used immediately after preparation, or bagged and stored in a dry, cool location for later use. In use, the product is uniformly combined with compost, preferably at the spawning phase of mushroom cultivation. The combined compost/growth enhancer product is maintained within a temperature range of 75°–85° F. during the 14 day spawn run. Temperatures outside of this range, especially above 90° F. may result in substantial losses of yield and quality. The weight percentage of mushroom growth enhancer added to the compost for optimal results is determined through testing. An optimal growth enhancer weight of 3.5% dry weight of the compost is targeted, or more broadly a range of 2 to 5% (dry weight) of the compost.

Example 25

Mushroom Growth Enhancer Test

Compost used in the tests is prepared from wheat straw (46,700 lb.) combined with chicken manure (20,000 lb.), cottonseed hulls (15,000 lb.), potassium sulfate (700 lb.), urea (300 lb.), soybean splits (3,500 lb.), and cottonseed meal (7,000 lb.). The completed compost is placed in 8 inch deep trays with four pounds of cottonseed vegetable oil per tray and pasteurized. After pasteurization, 4.2 pounds per tray of *A. bisporus* mushroom spawn is added to the compost in combination with the supplement materials, prepared as above from proteinaceous cell mass grown on C1 substrate, in additions ranging from 2 to 6% weight percentage. The positive control is a commercial soy protein based formulation. The negative control has no supplement added to the compost. Percent supplementation is based on 6.5 lb. of compost dry matter per square foot. All of the supplements are tested to have similar particle size using standard meshes.

After addition of the supplements, water is then added to the trays to raise the moisture level of the contents to approximately 70%. Next, the trays are placed in a controlled environment room having a relative humidity of 90-95%. The compost temperatures are maintained between 78°–82° F. After 13 days of spawn growth, a 1.75 inch layer of easing soil is applied to the compost surface and watered to capacity. The trays are then maintained in controlled environment rooms (65°-73° F.; 10,000 ppm $CO_2$) for 13 days followed by an abrupt air temperature and $CO_2$ shift to 60° F. and 800 ppm $CO_2$; to cause fruiting of the mushrooms. The trays are then placed in production rooms and harvested for four weekly flushes. The length of time involved is as follows: (a) phase I composting-56 days; (b) phase II composting—6 days; (c) spawn run—13 days; (d) case holding—13 days; and (e) harvesting—32 days. The average total yield in kg/m² of mushrooms is determined for the experiments and controls.

Example 26

Food Processing for Meat Substitute

High protein product (HPP) with reduced nucleic acid content produced as described above is used as a food ingredient.

Preparation:
1. Weigh required amount of HPP and place in a Hobart mixing bowl.
2. Measure water in a ratio of roughly 3:2 to the HPP, and add caramel coloring to the water in a ratio of roughly 1:60. Set mixer on Speed I.
3. Turn Hobart mixer on and add caramel colored water to the HPP in the Hobart mixing bowl very slowly, while mixing. Blend material well.
4. Extrude the blended material through a meat grinder, (e.g., Hobart attachment) and catch the extruded HPP in a dryer tray or pan. The extruded HPP can be cut into the desired length as it emerges from the extruder, or it can be collected as long strands and reduced to the desired size after drying.
5. Dry the extruded material in a convection oven to a moisture content of about 10%. The dried, textured HPP is rehydrated for further use in food product applications by, a) rehydrating in water (excess) at room temperature for I to 2 hours, or by, b) rehydrating in excess warm water (100-140° F.) for I hour. The ratio of water absorption to textured HPP is determined.

Example 27

Test as Growth Enhancer for Tempeh Production and Test Formulations with Okara

Okara is a soy bean based byproduct arising after soy milk/tofu manufacturing. It has relatively high protein content. Okara may be converted to Tempeh by fermenting with the fungus *Rhizopus oligosporus*, using a tempeh starter, or converted to press cake tempehs using ingredients such as brown rice, bulgur wheat, soybeans and other legume and grain combinations.

In this experiment, it is tested whether cells, and/or their extracts and/or hydrolysates of the present invention may be used as a growth enhancer for *R. oligosporus* in combination with okara substrate. It is also tested whether the resultant tempeh produced with the growth enhancer has superior characteristics such as but not limited to nutritional value, over the negative control.

This experiment also tests whether cells, extracts, and/or hydrolysates may be used with okara alone, or in combination with other ingredients such as brown rice, bulgur wheat, soybeans and other legume and grain combinations, in the production of press cake tempehs.

Example 28

Figure 24:
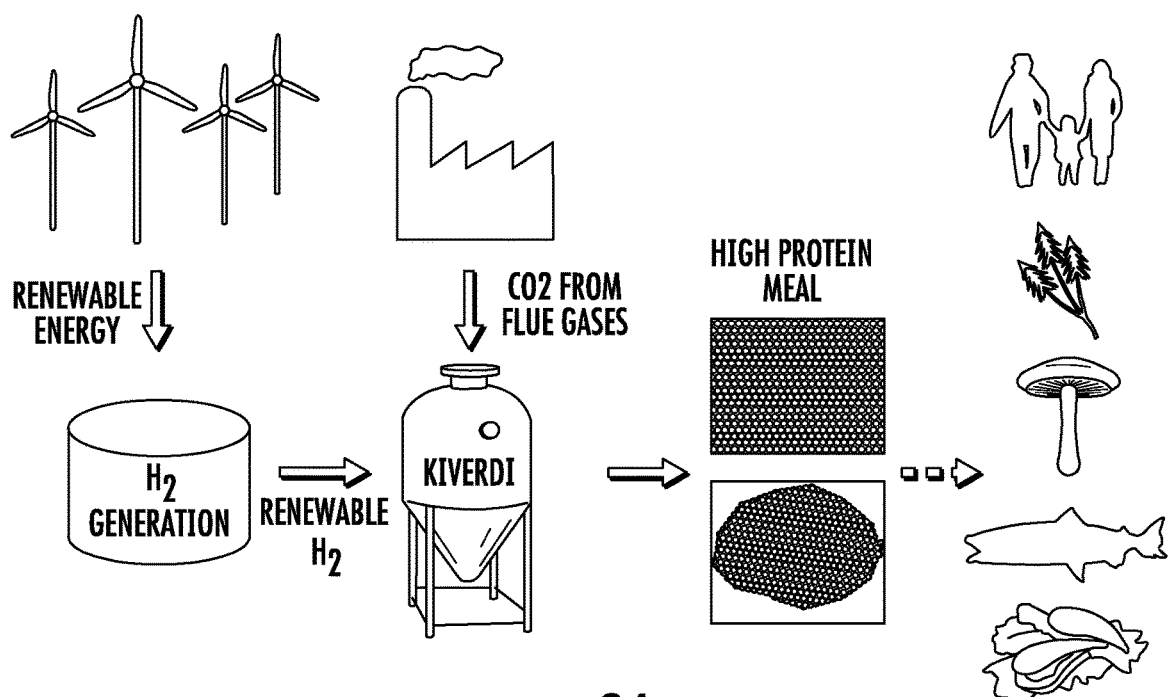
FIG. 24 schematically shows use of $CO_2$+renewable $H_2$ for production of high protein meal, which may be used, for example as a biostimulant, animal feed, or fertilizer, or for direct human nutrition.

Certain embodiments described herein leverage intermittent renewable sources of power, such as solar and wind, to produce the $H_2$ required for carbon fixation. The $CO_2$ source is an industrial source such as a power plant. Electrolyzers generally draw power during periods of low electrical demand and high renewable power supply. During such periods of low demand and high renewable generation, the renewable, $CO_2$-emission free content of the electrical supply can reach up to 95% in regions such as Texas, Scotland and Germany. Thus, in effect the electrolyzer is drawing upon $CO_2$ emissions-free power for the production of $H_2$ from water, and will utilize little if any $CO_2$-intensive power. In such regions, the periods of high renewable power supply and low grid demand occur roughly 50% of the time and thus the electrolyzer is expected to operate roughly 50% of the time. Onsite $H_2$ and $CO_2$ tank storage buffer the difference in timing between $CO_2$ production from the industrial source and $H_2$ production from the electrolyzer, enabling a continuous flow of both of these gases into the $CO_2$-fixing bioprocess. The chemoautotrophic knallgas microbes convert $CO_2$, $H_2$, and mineral nutrients (i.e. NPK) into high protein biomass. This protein-rich biomass can be converted to biostimulants for plants, or growth supplements for mushrooms, or animal feed, or direct nutrition for humans (FIG. 23 and FIG. 24). $O_2$ from the electrolyzer will exceed the requirements of the micro-aerobic knallgas bioprocess. This surplus $O_2$ can be sold as a pure gas co-product (FIG. 25), or else fed back to a fossil combustion or power unit in order to increase thermal efficiency of the unit and increase the concentration of $CO_2$ in the flue gas stream emerging from the unit. Increased concentration of $CO_2$ facilitates the carbon capture step.

Figure 25:
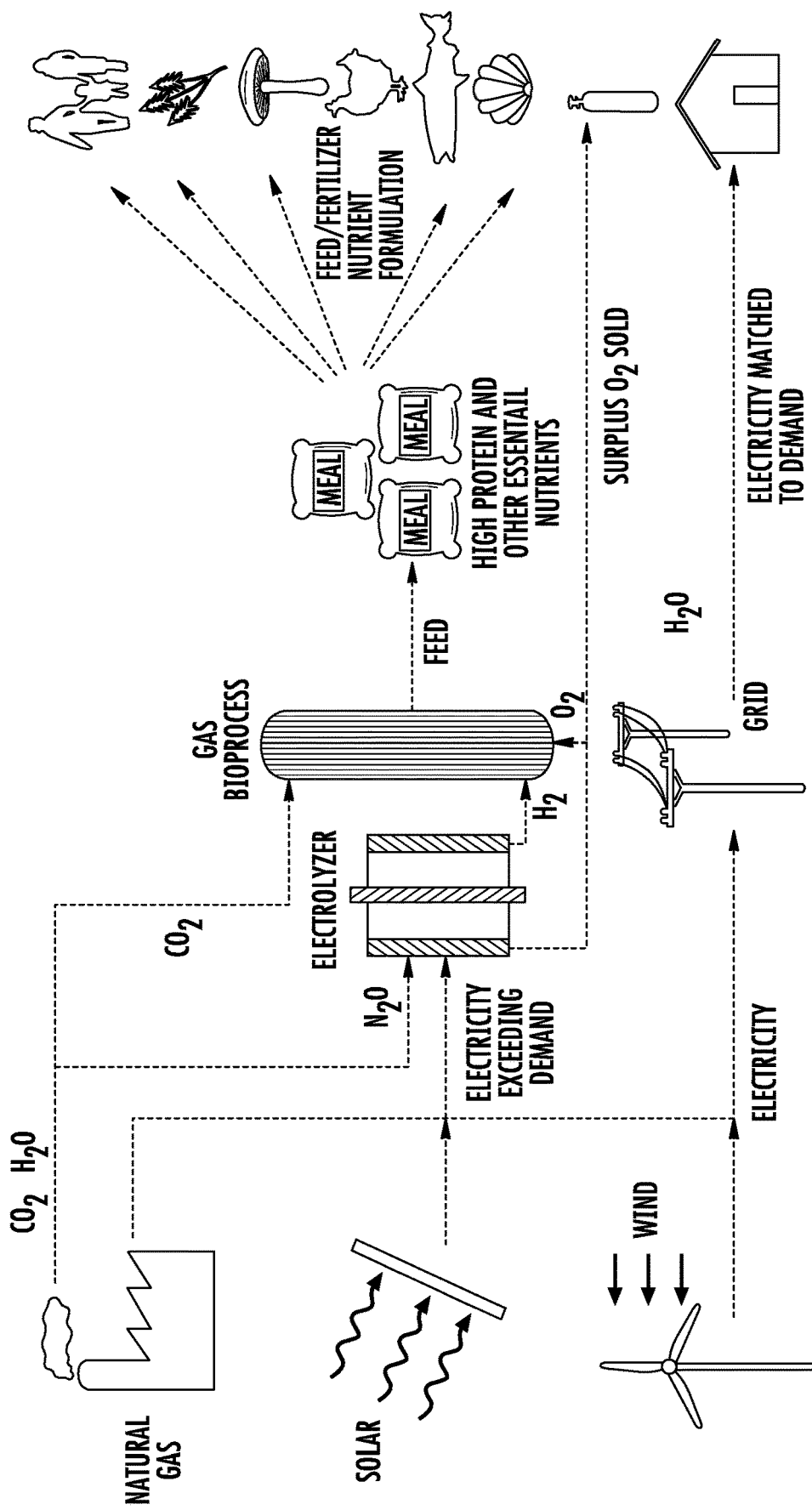
FIG. 25 shows a schematic diagram of an integrated system converting waste $CO_2$ and off-peak, intermittent renewable energy into high protein biostimulant, feed, fertilizer, and/or nutrients. In addition to the capture of $CO_2$ and production of valuable nutrients, the system relieves strain on the grid from excess renewable generation during periods of low demand.

To achieve carbon neutrality, the system is preferably located in regions with high intermittent renewable power generation. The electrolyzer unit only draws power during periods of low electrical demand and renewable power oversupply. This will relieve strain on the electrical grid caused by intermittent renewable energy (FIG. 25). In addition to the capture of $CO_2$, the production of valuable nutrients, and the relief of strain on the grid from excess renewable generation during periods of low demand, the system also enables more complete utilization of renewable capacity by allowing the renewables to keep generating even during periods of low demand. A major current application for electrolyzer technology is to convert the $H_2$ produced during periods of oversupply of renewable power, back into grid electricity during periods of high electrical demand and low renewable power supply—in effect going back down the value chain from $H_2$ to electricity. $H_2$ and $CO_2$ are converted into protein, and from there nutrients for plants, mushrooms, animals, and humans—in effect continuing further up the value chain from $H_2$.

Specific preferred embodiments of the present invention have been described here in sufficient detail to enable those skilled in the art to practice the full scope of invention. However, it is to be understood that these embodiments are illustrative and that many possible variations of the present invention, which have not been specifically described, still fall within the scope of the present invention and the appended claims.

Although the foregoing invention has been described in some detail by way of illustration and examples for purposes of clarity of understanding, it will be apparent to those skilled in the art that certain changes and modifications may be practiced without departing from the spirit and scope of the invention, which are delineated in the appended claims. Therefore, the description should not be construed as limiting the scope of the invention.

The descriptions given herein are added only by way of example and are not intended to limit, in any way, the scope of this invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Where a numerical limit or range is stated herein, the endpoints are included. Also, all values and subranges within a numerical limit or range are specifically included as if explicitly written out. Those skilled in the art will recognize, or be able to ascertain using no more than routine experimentation, many equivalents to the specific embodiments of the invention described herein. Many variations, modifications, additions, and subtractions are possible. Further still, many steps described herein may be permutated in order, and many steps may be added or deleted. It is, therefore, to be understood that the foregoing embodiments are presented by way of example only and that, within the scope of the appended claims and equivalents thereto, the invention may be practiced otherwise than as specifically described and claimed.

The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for the biological conversion of $CO_2$ and/or CO, into a protein containing food product for human consumption, comprising:
   introducing $CO_2$ and/or CO into an environment that comprises knallgas bacterial cells in a liquid culture medium that is suitable for maintaining the bacterial cells;
   growing the bacterial cells by using the $CO_2$ and/or CO as a carbon source, wherein the bacterial cells utilize an oxyhydrogen reaction for growth and production of organic molecules, wherein the oxyhydrogen reaction comprises an energy source comprising $H_2$ as electron donor and $O_2$ as electron acceptor, and wherein the electron donor and/or electron acceptor have been generated chemically and/or electrochemically and/or thermochemically and/or are introduced into the environment from at least one source external to the environment;
   isolating the bacterial cells from the liquid culture medium;
   freeing the organic molecules from the bacterial cells through cellular excretion, secretion or cell lysis, wherein the freed organic molecules comprise proteins and nucleic acids;
   reducing the nucleic acid content of the freed organic molecules to form a protein isolate comprising less than 9% nucleic acid by weight; and
   forming a food product for human consumption that comprises said protein isolate.

2. The method of claim 1, wherein the nucleic acid content of the protein isolate is less than about 5%.

3. The method of claim 1, wherein the nucleic acid content of the protein isolate is less than about 3%.

4. The method of claim 1, wherein the step of freeing the organic molecules from bacterial cells comprises: (i) rupturing the cells to form a cellular debris fraction and a soluble cytoplasmic constituent fraction, and (ii) separating the cellular debris fraction and the soluble cytoplasmic constituent fraction; and wherein the step of reducing the nucleic acid content comprises reducing the nucleic acid content of the cytoplasmic constituent fraction to form the protein isolate.

5. The method of claim 1, wherein the step of reducing the nucleic acid content comprises: (i) hydrolyzing at least a portion of the nucleic acids within the freed organic molecules, and (ii) diffusing the hydrolyzed nucleic acids away from protein contained in the freed organic molecules to form the protein isolate.

6. The method of claim 1, wherein the step of reducing the nucleic acid content comprises using a nuclease to solubilize at least a portion of the nucleic acids within the freed organic molecules.

7. The method of claim 6, wherein the nuclease is an endogenous nuclease.

8. The method of claim 1, wherein the protein isolate has a Protein Equivalence Ratio greater than 1.

9. The method of claim 1, wherein the bacterial cells comprise *Cupriavidus* sp., *Rhodococcus* sp., *Hydrogenovibrio* sp., *Rhodopseudomonas* sp., *Hydrogenobacter* sp., *Gordonia* sp., *Arthrobacter* sp., *Streptomycetes* sp. *Rhodobacter* sp., and/or *Xanthobacter* sp.

10. The method of claim 9, wherein the bacterial cells comprise *Cupriavidus necator*.

11. The method of claim 10, wherein the bacterial cells comprise *Cupriavidus necator* DSM 531.

12. The method of claim 10, wherein the bacterial cells comprise *Cupriavidus necator* DSM 541.

13. The method of claim 1, wherein the food product is a probiotic food product, a prebiotic food product, or a nutritional product.

14. The method of claim 1, wherein the food product is a meat product.

15. The method of claim 1, wherein the food product is a meat substitute product.

16. The composition of claim 1, wherein the food product is a vegetarian or vegan food product.

* * * * *